United States Patent
Gallinari et al.

(10) Patent No.: US 11,643,467 B2
(45) Date of Patent: May 9, 2023

(54) MONOCLONAL ANTIBODY ANTI-FGFR4

(71) Applicant: EXIRIS S.R.L., Rome (IT)

(72) Inventors: Paola Gallinari, Rome (IT); Chantal Paolini, Rome (IT); Gessica Filocamo, Rome (IL); Mirko Brunetti, Rome (IT); Armin Lahm, Rome (IT); Hans-Friedrich Grunert, Freiburg (DE); John Thompson, Sasbach (DE); Lucia Ricci-Vitiani, Rome (IT); Mauro Biffoni, Rome (IT)

(73) Assignee: EXIRIS S.R.L., Rome (IT)

( * ) Notice: Subject to any disclaimer, the term of this patent is extended or adjusted under 35 U.S.C. 154(b) by 152 days.

(21) Appl. No.: 16/637,602

(22) PCT Filed: Aug. 1, 2018

(86) PCT No.: PCT/EP2018/070848
§ 371 (c)(1),
(2) Date: Feb. 7, 2020

(87) PCT Pub. No.: WO2019/034427
PCT Pub. Date: Feb. 21, 2019

(65) Prior Publication Data
US 2021/0230280 A1    Jul. 29, 2021

(30) Foreign Application Priority Data
Aug. 16, 2017 (EP) .................... 17186454

(51) Int. Cl.
*C07K 16/28* (2006.01)
*C07K 16/30* (2006.01)

(52) U.S. Cl.
CPC ...... *C07K 16/2863* (2013.01); *C07K 16/3046* (2013.01); *C07K 2317/24* (2013.01); *C07K 2317/33* (2013.01); *C07K 2317/34* (2013.01); *C07K 2317/73* (2013.01); *C07K 2317/76* (2013.01); *C07K 2317/77* (2013.01); *C07K 2317/92* (2013.01)

(58) Field of Classification Search
CPC ............ C07K 16/2863; C07K 2317/24; C07K 2317/34; C07K 2317/76
See application file for complete search history.

(56) References Cited

U.S. PATENT DOCUMENTS

2014/0037624 A1*  2/2014  Dennis ............... A61P 35/00
424/133.1

FOREIGN PATENT DOCUMENTS

| WO | 03080672 A1 | 10/2003 |
|----|-------------|---------|
| WO | 2008052796 A1 | 5/2008 |
| WO | 2014105849 A1 | 7/2014 |
| WO | 2016023894 A1 | 2/2016 |
| WO | 2016146638 A1 | 9/2016 |
| WO | 2017049296 A1 | 3/2017 |

OTHER PUBLICATIONS

Chen et al., "Generation and characterization of a panel of monoclonal antibodies specific for human fibroblast growth factor receptor 4 (FGFR4)" Hybridoma, 2005, v 24, n 3, p. 152-160.
Product datasheet for Anti-FGFR4 antibody ab41948. Jan. 1, 2017, pp. 1-4.
Page et al., "Induction of Stem Cell Gene Expression in Adult Human Fibroblasts without Transgenes" Cloning and Stem Cells, 2009, v 11, n 3, p. 417-426.
Grabner et al., "Activation of Cardiac Fibroblast Growth Factor Receptor 4 Causes Left Ventricular Hypertrophy" Cell Metab. Dec. 2015, v 22, n 6, p. 1-27.
Dragu et al., "Therapies targeting cancer stem cells: Current trends and future challenges" World Journal of Stem Cells, Oct. 2015, v 7, n 0, p. 1185-1201.
Tamura et al. "Structural Correlates of an Anticarcinoma Antibody: Identification of Specificity-determining residues (SDRs) and development of a minimally immunogenic antibody variant by retention of SDRs only" J Immunol (2000) 164(3): 1432-1441.
Rudikoff et al., "Single amino acid substitution altering antigen-binding specificity" Proc. Nat. Acad. Sci. USA, vol. 79, pp. 1979-1983, Mar. 1982.
Office Action Canadian Patent Application 3,072,284, dated Feb. 2, 2023.

* cited by examiner

*Primary Examiner* — Ruixiang Li
(74) *Attorney, Agent, or Firm* — Greer, Burns & Crain, Ltd.; Gregory P. Einhorn

(57) ABSTRACT

The present disclosure relates to monoclonal antibodies anti-FGFR4 and their use as medicaments and diagnostic agents. In particular, it relates to an antibody which specifically binds to the acid box domain of FGFR4 and to specific portions thereof. Nucleic acids coding for said antibody, vectors and host cells for their expression and production, antibody-drug conjugates and pharmaceutical compositions comprising said antibody are also within the scope of the present disclosure. The present disclosure also relates to antibodies anti-FGFR4 for use for detecting, killing, affecting or inhibiting development and/or differentiation of colon cancer stem cells.

13 Claims, 43 Drawing Sheets
Specification includes a Sequence Listing.

FGFR4

| rank1,1 | CTSC1,1 | FC | rank18 | CTSC18 | FC | rank85 | CTSC85 | FC | rankCRO | CRO | FC | rank1,2 | CTSC1,2 | FC |
|---|---|---|---|---|---|---|---|---|---|---|---|---|---|---|
| 11 | BFG-2F7 | 4,0 | 11 | BFG-2F7 | 3,3 | 14 | BFG-2F7 | 15,1 | 11 | BFG-2F7 | 4,6 | 14 | BFG-2F7 | 5,7 |
| 14 | BFG-5E5 | 7,4 | 13 | BFG-5E5 | 5,5 | 7 | BFG-5E5 | 4,4 | 14 | BFG-5E5 | 6,8 | 11 | BFG-5E5 | 4,0 |
| 12 | BFG-1G9 | 5,2 | 6 | BFG-1G9 | 1,9 | 10 | BFG-1G9 | 5,2 | 13 | BFG-1G9 | 5,6 | 9 | BFG-1G9 | 3,2 |
| 9 | BFG-8E5 | 3,7 | 10 | BFG-8E5 | 3,1 | 9 | BFG-8E5 | 5,1 | 10 | BFG-8E5 | 3,8 | 12 | BFG-8E5 | 4,3 |
| 10 | BFG-7C9 | 3,8 | 9 | BFG-7C9 | 2,8 | 8 | BFG-7C9 | 4,4 | 12 | BFG-7C9 | 4,6 | 8 | BFG-7C9 | 3,0 |
| 6 | BFG-5A5 | 2,3 | 4 | BFG-5A5 | 1,3 | 13 | BFG-5A5 | 11,6 | 5 | BFG-5A5 | 2,1 | 13 | BFG-5A5 | 4,5 |
| 3 | BFG-10F3 | 1,7 | 12 | BFG-10F3 | 3,6 | 12 | BFG-10F3 | 11,5 | 3 | BFG-10F3 | 1,7 | 10 | BFG-10F3 | 3,5 |
| 13 | BFG-5B5 | 7,2 | 7 | BFG-5B5 | 2,0 | 6 | BFG-5B5 | 2,7 | 9 | BFG-5B5 | 3,8 | 3 | BFG-5B5 | 2,1 |
| 7 | BFG-5F7 | 2,6 | 8 | BFG-5F7 | 2,1 | 5 | BFG-5F7 | 2,2 | 7 | BFG-5F7 | 2,4 | 7 | BFG-5F7 | 2,9 |
| 5 | BFG-1E3 | 2,1 | 14 | BFG-1E3 | 9,2 | 3 | BFG-1E3 | 1,5 | 6 | BFG-1E3 | 2,3 | 4 | BFG-1E3 | 2,1 |
| 8 | BFG-6E5 | 2,9 | 1 | BFG-6E5 | 0,8 | 4 | BFG-6E5 | 1,8 | 8 | BFG-6E5 | 2,6 | 6 | BFG-6E5 | 2,3 |
| 2 | BFG-9H7 | 1,3 | 5 | BFG-9H7 | 1,8 | 11 | BFG-9H7 | 5,7 | 1 | BFG-9H7 | 1,2 | 5 | BFG-9H7 | 2,2 |
| 4 | BFG-6D3 | 2,1 | 3 | BFG-6D3 | 1,1 | 2 | BFG-6D3 | 1,5 | 4 | BFG-6D3 | 2,1 | 1 | BFG-6D3 | 1,4 |
| 1 | BFG-7H9 | 1,2 | 2 | BFG-7H9 | 0,9 | 1 | BFG-7H9 | 1,5 | 2 | BFG-7H9 | 1,4 | 2 | BFG-7H9 | 1,5 |

Figure 3A

| FGFR4 14 supers | | | IL17 10 supers |
|---|---|---|---|
| Total rank | super | sum | |
| 14 | BFG-2F7 | 61 | RGMB 12 supers |
| 13 | BFG-5E5 | 59 | |
| 12 | BFG-1G9 | 50 | |
| 11 | BFG-8E5 | 50 | |
| 10 | BFG-7C9 | 47 | EDAR 5 supers |
| 9 | BFG-5A5 | 41 | |
| 8 | BFG-10F3 | 40 | |
| 7 | BFG-5B5 | 38 | |
| 6 | BFG-5F7 | 34 | |
| 5 | BFG-1E3 | 32 | OR51E1 8 supers |
| 4 | BFG-6E5 | 27 | |
| 3 | BFG-9H7 | 24 | |
| 2 | BFG-6D3 | 14 | |
| 1 | BFG-7H9 | 8 | |

Figure 3B

C

FGFR4_human ARGSMIVLQNLTLITGDSLTSSNDDEDPKSHRDPSNRHSYPQQAPYWTHPQRMEKKLHAVPAGNTVKFRCPAAGNPTPTIRWLKDGQAF FGFR4_mouse ARGSMTVVHNLTLLMDDSLTSISNDEDPKTLSSSSSGHVYPQQAPYWTHPQRMEKKLHAVPAGNTVKFRCPAAGNPMPTIHWLKDGQAF ch3B6 epitope DEDPKSHRDPSNRHSYPQQAPYWTHPQR

SEQUENCE LISTING

<160> NUMBER OF SEQ ID NOS: 102

<210> SEQ ID NO 1
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
                20                  25                  30

Tyr Met Ala Trp Val Arg Gln Ala Pro Lys Lys Gly Leu Glu Trp Val
            35                  40                  45

Ala Thr Ile Asn Pro Ser Gly Thr Arg Thr Tyr Pro Asp Ser Val
        50                  55                  60

Lys Gly Arg Phe Thr Leu Ser Arg Asp Ser Ala Lys Ser Ser Leu Tyr
65                  70                  75                  80

Leu Gln Met Asn Ser Leu Lys Ser Glu Asp Thr Ala Thr Phe Tyr Cys
                85                  90                  95

Ala Arg Leu Tyr Asn Asn Tyr Ala Phe Asp Tyr Trp Gly Gln Gly Val
            100                 105                 110

Met Val Thr Val Ser Ser
        115

<210> SEQ ID NO 2
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Tyr Met Ser Trp Val Arg Gln Ala Pro Gly Lys Gly Leu Glu Trp Val
            35                  40                  45

Ala Thr Ile Asn Pro Ser Gly Thr Arg Thr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Asn Tyr Ala Phe Asp Tyr Trp Gly Gln Gly Thr
            100                 105                 110

Leu Val Thr Val Ser Ser
        115

<210> SEQ ID NO 3
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ala Asn Ile Asn Pro Ser Gly Thr Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Asn Tyr Ala Phe Asp Tyr Trp Gly Gln Gly Thr
            100                 105                 110

Leu Val Thr Val Ser Ser
            115

<210> SEQ ID NO 4
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ala Thr Ile Asn Pro Ser Gly Thr Arg Thr Tyr Tyr Pro Asp Ser Val
    50                  55                  60

Lys Gly Arg Phe Thr Ile Ser Arg Asp Ser Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Asn Tyr Ala Phe Asp Tyr Trp Gly Gln Gly Thr
            100                 105                 110

Leu Val Thr Val Ser Ser
            115

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 5

Asn Tyr Tyr Met Ala
1               5

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Asn Tyr Tyr Met Ser
1               5

<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Thr Ile Asn Pro Ser Gly Thr Arg Thr Tyr Tyr Pro Asp Ser Val Lys
1               5                   10                  15

Gly

<210> SEQ ID NO 8
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Asn Ile Asn Pro Ser Gly Thr Arg Thr Tyr Tyr Pro Asp Ser Val Lys
1               5                   10                  15

Gly

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Leu Tyr Asn Asn Tyr Ala Phe Asp Tyr
1               5

<210> SEQ ID NO 10
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 10

Asp Val Gln Met Thr Gln Ser Pro Ala Leu Ala Val Ser Pro Gly Glu
1               5                   10                  15

Arg Val Ser Ile Ser Cys Arg Ala Ser Glu Ser Val Ser Thr Leu Met
            20                  25                  30

His Trp Tyr Gln Gln Lys Pro Gly Gln Gln Pro Lys Leu Leu Ile Tyr
        35                  40                  45

Gly Thr Ser Asn Leu Glu Ser Gly Val Pro Ala Arg Phe Ser Gly Ser
    50                  55                  60

Gly Ser Gly Thr Asp Phe Thr Leu Asn Ile Asp Pro Val Glu Ala Asp
65                  70                  75                  80

Asp Thr Ala Thr Tyr Phe Cys Gln Gln Ser Trp Asn Asp Pro Pro Thr
                85                  90                  95

Phe Gly Gly Gly Thr Lys Leu Glu Val Lys
            100                 105

<210> SEQ ID NO 11
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Val Gln Met Thr Gln Ser Pro Ala Leu Ala Val Ser Pro Gly Glu
1               5                   10                  15

Arg Val Ser Ile Ser Cys Arg Ala Ser Glu Ser Val Ser Thr Leu Met
            20                  25                  30

His Trp Tyr Gln Gln Lys Pro Gly Gln Gln Pro Lys Leu Leu Ile Tyr
        35                  40                  45

Gly Thr Ser Asn Leu Glu Ser Gly Val Pro Ala Arg Phe Ser Gly Ser
    50                  55                  60

Gly Ser Gly Thr Asp Phe Thr Leu Asn Ile Asp Pro Val Glu Ala Asp
65                  70                  75                  80

Asp Thr Ala Thr Tyr Phe Cys Gln Gln Ser Trp Asn Asp Pro Pro Thr
                85                  90                  95

Phe Gly Gly Gly Thr Lys Leu Glu Leu Lys
            100                 105

<210> SEQ ID NO 12
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Ser Thr Leu
            20                  25                  30

Leu His Trp Tyr Gln Gln Lys Pro Gly Lys Ala Pro Lys Leu Leu Ile
        35                  40                  45

Tyr Gly Thr Ser Asn Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Asn Asp Pro Pro
                85                  90                  95

Thr Phe Gly Gly Gly Thr Lys Val Glu Ile Lys
            100                 105

<210> SEQ ID NO 13
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Ser Thr Leu
            20                  25                  30

Met His Trp Tyr Gln Gln Lys Pro Gly Lys Ala Pro Lys Leu Leu Ile
        35                  40                  45

Tyr Gly Thr Ser Asn Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Asn Asp Pro Pro
                85                  90                  95

Thr Phe Gly Gly Gly Thr Lys Val Glu Ile Lys
            100                 105

<210> SEQ ID NO 14
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Arg Ala Ser Glu Ser Val Ser Thr Leu Met His
1               5                   10

<210> SEQ ID NO 15
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Arg Ala Ser Glu Ser Ile Ser Thr Leu Leu His
1               5                   10

<210> SEQ ID NO 16
<211> LENGTH: 7

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Thr Ser Asn Leu Glu Ser
1               5

<210> SEQ ID NO 17
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gln Gln Ser Trp Asn Asp Pro Pro Thr
1               5

<210> SEQ ID NO 18
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
gaggtgcagc tggtggagtc tgggggaggc ctagtgcagc ctggaaggtc cctgaaactc      60
tcctgtgcag cctcaggatt cactttcagt aattattaca tggcctgggt ccgccaggct     120
ccaaagaagg gtctggagtg ggtcgcaacc attaatccca gtggtaccag aacttactat     180
ccagactccg tgaaaggccg attcactctc tccagagata gtgcaaagag cagcctatat     240
ctgcaaatga acagtctgaa gtctgaggac acggccactt tttactgtgc aaggctttat     300
aacaactacg cttttgatta ctggggccag ggagtcatgg tcacagtctc ctca           354

<210> SEQ ID NO 19
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
gaggtgcagc tggtggagtc tgggggaggc ctagtgcagc ctggaaggtc cctgaaactc      60
tcctgtgcag cctcaggatt cactttcagt aattattaca tggcctgggt ccgccaggct     120
ccaaagaagg gtctggagtg ggtcgcaacc attaatccca gtggtaccag aacttactat     180
ccagactccg tgaaaggccg attcactctc tccagagata gtgcaaagag cagcctatat     240
ctgcaaatga acagtctgaa gtctgaggac acggccactt tttactgtgc aaggctttat     300
aacaactacg cttttgatta ctggggccaa ggagtcatgg tcactgtctc ctca           354

<210> SEQ ID NO 20
<211> LENGTH: 354
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
gaggtgcagc tggtggagtc tgggggaggc ttggtccagc ctggggggtc cctgagactc      60
tcctgtgcag cctctggatt cacctttagt aactattaca tgagctgggt ccgccaggct     120
ccagggaagg ggctggagtg ggtggccacc ataaaccctc gcggaaccag aacctactat     180
ccagactctg tgaagggccg attcaccatc tccagagaca cgccaagaa ctcactgtat      240 ctgcaaatga acagcctgag agccgaggac acggctgtgt attactgtgc gagactgtac     300
aacaattacg cctttgacta ctggggccaa ggaaccctgg tcaccgtctc ctca           354

<210> SEQ ID NO 21
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
gaggtgcagc tggtggagtc tgggggaggc ttggtccagc ctggggggtc cctgagactc      60
tcctgtgcag cctctggatt cacctttagt aactattaca tgagctgggt ccgccaggct     120
ccagggaagg ggctggagtg ggtggccaac ataaaccctc gcggaaccag aacctactat     180
ccagactctg tgaagggccg attcaccatc tccagagaca cgccaagaa ctcactgtat      240 ctgcaaatga acagcctgag agccgaggac acggctgtgt attactgtgc gagactgtac     300
aacaattacg cctttgacta ctggggccaa ggaaccctgg tcaccgtctc ctca           354

<210> SEQ ID NO 22
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
gaggtgcagc tggtggagtc tgggggaggc ttggtccagc ctggggggtc cctgagactc      60
tcctgtgcag cctctggatt cacctttagt aactattaca tgagctgggt ccgccaggct     120
ccagggaagg ggctggagtg ggtggccacc ataaaccctc gcggaaccag aacctactat     180
ccagactctg tgaagggccg attcaccatc tccagagaca cgccaagag ctcactgtat      240 ctgcaaatga acagcctgag agccgaggac acggctgtgt attactgtgc gagactgtac     300
aacaattacg cctttgacta ctggggccaa ggaaccctgg tcaccgtctc ctca           354

<210> SEQ ID NO 23
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 23

```
gatgtccaga tgacccagtc tcctgctttg ctgtgtctc caggagagag ggtttccatc    60
tcctgtaggg ccagtgaaag tgtcagtaca cttatgcact ggtaccaaca gaaaccagga   120
cagcaaccca aactcctcat ctacggtaca tccaacctag agtctggagt ccctgccagg   180
ttcagtggca gtgggtctgg gacagacttc accctcaaca tagatcctgt ggaggctgat   240
gacactgcaa cctatttctg tcagcagagt tggaatgatc tccgacgtt cggtggaggc   300
accaagctgg aagtgaaa                                                 318
```

<210> SEQ ID NO 24
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24

```
gatgtccaga tgacccagtc tcctgctttg ctgtgtctc caggagagag ggtttccatc    60
tcctgtaggg ccagtgaaag tgtcagtaca cttatgcact ggtaccaaca gaaaccagga   120
cagcaaccca aactcctcat ctacggtaca tccaacctag agtctggagt ccctgccagg   180
ttcagtggca gtgggtctgg gacagacttc accctcaaca tagatcctgt ggaggctgat   240
gacactgcaa cctatttctg tcagcagagt tggaatgatc tccgacgtt cggtggaggc   300
accaagctgg aattgaaa                                                 318
```

<210> SEQ ID NO 25
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

```
gacatccaga tgacccagtc tccatcctcc ctgtctgcat ctgtaggaga cagagtcacc    60
atcacttgcc gggcaagtga gagcattagc accctgttac actggtatca gcagaaacca   120
gggaaagccc ctaagctcct gatctatggc acctccaact tggagagtgg ggtcccatca   180
aggttcagtg gcagtggatc tgggacagat ttcactctca ccatcagcag tctgcaacct   240
gaagattttg caacttacta ctgtcaacag agttggaacg accctccac tttcggcgga   300
gggaccaagg tggagatcaa a                                             321
```

<210> SEQ ID NO 26
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
gacatccaga tgacccagtc tccatcctcc ctgtctgcat ctgtaggaga cagagtcacc    60
atcacttgcc gggcaagtga gagcgtgagc accctgatgc actggtatca gcagaaacca   120
```

| | |
|---|---|
| gggaaagccc ctaagctcct gatctatggc acctccaact tggagagtgg ggtcccatca | 180 |
| aggttcagtg gcagtggatc tgggacagat ttcactctca ccatcagcag tctgcaacct | 240 |
| gaagattttg caacttacta ctgtcaacag agttggaacg accctcccac tttcggcgga | 300 |
| gggaccaagg tggagatcaa a | 321 |

<210> SEQ ID NO 27
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asp Glu Asp Pro Lys Ser His Arg Asp Pro Ser Asn Arg His Ser Tyr
1               5                   10                  15

Pro Gln Gln Ala Pro Tyr Trp Thr His Pro Gln Arg
            20                  25

<210> SEQ ID NO 28
<211> LENGTH: 1392
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28

| | |
|---|---|
| atgaatctac ttctgatcct tacctttgtt gcggccgctg ttgcggaggt gcagctggtg | 60 |
| gagtctgggg gaggcctagt gcagcctgga aggtccctga actctcctg tgcagcctca | 120 |
| ggattcactt tcagtaatta ttacatggcc tgggtccgcc aggctccaaa gaagggtctg | 180 |
| gagtgggtcg caaccattaa tcccagtggt accagaactt actatccaga ctccgtgaaa | 240 |
| ggccgattca ctctctccag agatagtgca aagagcagcc tatatctgca aatgaacagt | 300 |
| ctgaagtctg aggacacggc cacttttac tgtgcaaggc tttataacaa ctacgctttt | 360 |
| gattactggg gccaaggagt catggtcact gtctcctcag cgtcgaccaa gggcccatcg | 420 |
| gtcttccccc tggcaccctc ctccaagagc acctctgggg gcacagcggc cctgggctgc | 480 |
| ctggtcaagg actacttccc cgaaccggtg acggtgtcgt ggaactcagg cgccctgacc | 540 |
| agcggcgtgc acaccttccc ggctgtccta cagtcctcag gactctactc cctcagcagc | 600 |
| gtggtgaccg tgccctccag cagcttgggc acccagacct acatctgcaa cgtgaatcac | 660 |
| aagcccagca acaccaaggt ggacaagaaa gttgagccca atcttgtga caaaactcac | 720 |
| acatgcccac cgtgcccagc acctgaactc ctggggggac cgtcagtctt cctcttcccc | 780 |
| ccaaaaccca aggacaccct catgatctcc cggacccctg aggtcacatg cgtggtggtg | 840 |
| gacgtgagcc acgaagaccc tgaggtcaag ttcaactggt acgtggacgg cgtggaggtg | 900 |
| cataatgcca agacaaagcc gcgggaggag cagtacaaca gcacgtaccg tgtggtcagc | 960 |
| gtcctcaccg tcctgcacca ggactggctg aatggcaagg agtacaagtg caaggtctcc | 1020 |
| aacaaagccc tcccagcccc catcgagaaa accatctcca aagccaaagg gcagccccga | 1080 |
| gaaccacagg tgtacaccct gcccccatcc cgcgaggaga tgaccaagaa ccaggtcagc | 1140 |
| ctgacctgcc tggtcaaagg cttctatccc agcgacatcg ccgtggagtg ggagagcaat | 1200 |
| gggcagccgg agaacaacta caagaccacg cctcccgtgc tggactccga cggctccttc | 1260 |

<210> SEQ ID NO 29
<211> LENGTH: 1392
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 29

```
atgaatctac ttctgatcct tacctttgtt gcggccgctg ttgcggaggt gcagctggtg      60
gagtctgggg gaggcttggt ccagcctggg gggtccctga gactctcctg tgcagcctct     120
ggattcacct ttagtaacta ttacatgagc tgggtccgcc aggctccagg aaggggctg      180
gagtgggtgg ccaccataaa ccctagcgga accagaacct actatccaga ctctgtgaag     240
ggccgattca ccatctccag agacaacgcc aagaactcac tgtatctgca aatgaacagc     300
ctgagagccg aggacacggc tgtgtattac tgtgcgagac tgtacaacaa ttacgccttt     360
gactactggg gccaaggaac cctggtcacc gtctcctcag cgtcgaccaa gggcccatcg     420
gtcttccccc tggcaccctc ctccaagagc acctctgggg gcacagcggc cctgggctgc     480
ctggtcaagg actacttccc cgaaccggtg acggtgtcgt ggaactcagg cgccctgacc     540
agcggcgtgc acaccttccc ggctgtccta cagtcctcag gactctactc cctcagcagc     600
gtggtgaccg tgccctccag cagcttgggc acccagacct acatctgcaa cgtgaatcac     660
aagcccagca acaccaaggt ggacaagaaa gttgagccca aatcttgtga caaaactcac     720
acatgcccac cgtgcccagc acctgaactc ctggggggac cgtcagtctt cctcttcccc     780
ccaaaaccca aggacaccct catgatctcc cggacccctg aggtcacatg cgtggtggtg     840
gacgtgagcc acgaagaccc tgaggtcaag ttcaactggt acgtggacgg cgtggaggtg     900
cataatgcca agacaaagcc gcgggaggag cagtacaaca gcacgtaccg tgtggtcagc     960
gtcctcaccg tcctgcacca ggactggctg aatggcaagg agtacaagtg caaggtctcc    1020
aacaaagccc tcccagcccc catcgagaaa accatctcca aagccaaagg gcagccccga    1080
gaaccacagg tgtacaccct gcccccatcc cgcgaggaga tgaccaagaa ccaggtcagc    1140
ctgacctgcc tggtcaaagg cttctatccc agcgacatcg ccgtggagtg ggagagcaat    1200
gggcagccgg agaacaacta caagaccacg cctcccgtgc tggactccga cggctccttc    1260
ttcctctaca gcaagctcac cgtggacaag agcaggtggc agcagggaa cgtcttctca    1320
tgctccgtga tgcatgaggc tctgcacaac cactacacgc agaagagcct ctccctgtct    1380
ccgggtaaat ga    1392
```

<210> SEQ ID NO 30
<211> LENGTH: 1392
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

```
atgaatctac ttctgatcct tacctttgtt gcggccgctg ttgcggaggt gcagctggtg      60
gagtctgggg gaggcttggt ccagcctggg gggtccctga gactctcctg tgcagcctct     120
ggattcacct ttagtaacta ttacatgagc tgggtccgcc aggctccagg aaggggctg      180
gagtgggtgg ccaacataaa ccctagcgga accagaacct actatccaga ctctgtgaag     240
ggccgattca ccatctccag agacaacgcc aagaactcac tgtatctgca aatgaacagc     300
ctgagagccg aggacacggc tgtgtattac tgtgcgagac tgtacaacaa ttacgccttt     360
gactactggg gccaaggaac cctggtcacc gtctcctcag cgtcgaccaa gggcccatcg     420
gtcttccccc tggcaccctc ctccaagagc acctctgggg gcacagcggc cctgggctgc     480
ctggtcaagg actacttccc cgaaccggtg acggtgtcgt ggaactcagg cgccctgacc     540
agcggcgtgc acaccttccc ggctgtccta cagtcctcag gactctactc cctcagcagc     600
gtggtgaccg tgccctccag cagcttgggc acccagacct acatctgcaa cgtgaatcac     660
aagcccagca acaccaaggt ggacaagaaa gttgagccca atcttgtga caaaactcac      720
acatgcccac cgtgcccagc acctgaactc ctggggggac cgtcagtctt cctcttcccc     780
ccaaaaccca aggacaccct catgatctcc cggacccctg aggtcacatg cgtggtggtg     840
gacgtgagcc acgaagaccc tgaggtcaag ttcaactggt acgtggacgg cgtggaggtg     900
cataatgcca agacaaagcc gcgggaggag cagtacaaca gcacgtaccg tgtggtcagc     960
gtcctcaccg tcctgcacca ggactggctg aatggcaagg agtacaagtg caaggtctcc    1020
aacaaagccc tcccagcccc catcgagaaa accatctcca aagccaaagg gcagccccga    1080
gaaccacagg tgtacaccct gcccccatcc cgcgaggaga tgaccaagaa ccaggtcagc    1140
ctgacctgcc tggtcaaagg cttctatccc agcgacatcg ccgtggagtg ggagagcaat    1200
gggcagccgg agaacaacta caagaccacg cctcccgtgc tggactccga cggctccttc    1260
ttcctctaca gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaat ga                                                        1392
```

<210> SEQ ID NO 31
<211> LENGTH: 1392
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 31

```
atgaatctac ttctgatcct tacctttgtt gcggccgctg ttgcggaggt gcagctggtg      60
gagtctgggg gaggcttggt ccagcctggg gggtccctga gactctcctg tgcagcctct     120
ggattcacct ttagtaacta ttacatgagc tgggtccgcc aggctccagg aaggggctg      180
gagtgggtgg ccaccataaa ccctagcgga accagaacct actatccaga ctctgtgaag     240
ggccgattca ccatctccag agacagcgcc aagagctcac tgtatctgca aatgaacagc     300
ctgagagccg aggacacggc tgtgtattac tgtgcgagac tgtacaacaa ttacgccttt     360
gactactggg gccaaggaac cctggtcacc gtctcctcag cgtcgaccaa gggcccatcg     420
gtcttccccc tggcaccctc ctccaagagc acctctgggg gcacagcggc cctgggctgc     480
```

-continued

```
ctggtcaagg actacttccc cgaaccggtg acggtgtcgt ggaactcagg cgccctgacc      540
agcggcgtgc acaccttccc ggctgtccta cagtcctcag gactctactc cctcagcagc      600
gtggtgaccg tgccctccag cagcttgggc acccagacct acatctgcaa cgtgaatcac      660
aagcccagca acaccaaggt ggacaagaaa gttgagccca atcttgtgac aaaactcac       720 acatgcccac cgtgcccagc acctgaactc ctgggggac cgtcagtctt cctcttcccc       780
ccaaaaccca aggacaccct catgatctcc cggacccctg aggtcacatg cgtggtggtg      840
gacgtgagcc acgaagaccc tgaggtcaag ttcaactggt acgtggacgg cgtggaggtg      900
cataatgcca agacaaagcc gcgggaggag cagtacaaca gcacgtaccg tgtggtcagc      960
gtcctcaccg tcctgcacca ggactggctg aatggcaagg agtacaagtg caaggtctcc     1020
aacaaagccc tcccagcccc catcgagaaa accatctcca aagccaaagg gcagccccga     1080
gaaccacagg tgtacaccct gcccccatcc cgcgaggaga tgaccaagaa ccaggtcagc     1140
ctgacctgcc tggtcaaagg cttctatccc agcgacatcg ccgtggagtg ggagagcaat     1200
gggcagccgg agaacaacta caagaccacg cctcccgtgc tggactccga cggctccttc     1260
ttcctctaca gcaagctcac cgtggacaag agcaggtggc agcaggggaa cgtcttctca     1320
tgctccgtga tgcatgaggc tctgcacaac cactacacgc agaagagcct ctccctgtct     1380
ccgggtaaat ga                                                          1392
```

<210> SEQ ID NO 32
<211> LENGTH: 687
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32

```
atgaatctac ttctgatcct taccttttgtt gcggccgctg ttgcggatgt ccagatgacc       60
cagtctcctg ctttggctgt gtctccagga gagagggttt ccatctcctg tagggccagt      120
gaaagtgtca gtacacttat gcactggtac aacagaaac caggacagca acccaaactc       180
ctcatctacg gtacatccaa cctagagtct ggagtccctg ccaggttcag tggcagtggg      240
tctgggacag acttcaccct caacatagat cctgtggagg ctgatgacac tgcaacctat      300
ttctgtcagc agagttggaa tgatcctccg acgttcggtg gaggcaccaa gctggaattg      360
aaacgtacgg tggctgcacc atctgtcttc atcttcccgc catctgatga gcagttgaaa      420
tctggaactg cctctgttgt gtgcctgctg aataacttct atcccagaga ggccaaagta      480
cagtggaagg tggataacgc cctccaatcg ggtaactccc aggagagtgt cacagagcag      540
gacagcaagg acagcaccta cagcctcagc agcaccctga cgctgagcaa agcagactac      600
gagaaacaca aagtctacgc ctgcgaagtc acccatcagg gcctgagctc gcccgtcaca      660
aagagcttca caggggaga gtgttga                                            687
```

<210> SEQ ID NO 33
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33

```
atgaatctac ttctgatcct tacctttgtt gcggccgctg ttgcggacat ccagatgacc    60
cagtctccat cctccctgtc tgcatctgta ggagacagag tcaccatcac ttgccgggca   120
agtgagagca ttagcaccct gttacactgg tatcagcaga aaccagggaa agcccctaag   180
ctcctgatct atggcacctc caacttggag agtggggtcc catcaaggtt cagtggcagt   240
ggatctggga cagatttcac tctcaccatc agcagtctgc aacctgaaga ttttgcaact   300
tactactgtc aacagagttg gaacgaccct cccactttcg gcggagggac caaggtggag   360
atcaaacgta cggtggctgc accatctgtc ttcatcttcc cgccatctga tgagcagttg   420
aaatctggaa ctgcctctgt tgtgtgcctg ctgaataact tctatcccag agaggccaaa   480
gtacagtgga aggtggataa cgccctccaa tcgggtaact cccaggagag tgtcacagag   540
caggacagca aggacagcac ctacagcctc agcagcaccc tgacgctgag caaagcagac   600
tacgagaaac acaaagtcta cgcctgcgaa gtcaccccatc agggcctgag ctcgcccgtc   660
acaaagagct tcaacagggg agagtgttga   690
```

<210> SEQ ID NO 34
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 34

```
atgaatctac ttctgatcct tacctttgtt gcggccgctg ttgcggacat ccagatgacc    60
cagtctccat cctccctgtc tgcatctgta ggagacagag tcaccatcac ttgccgggca   120
agtgagagcg tgagcaccct gatgcactgg tatcagcaga aaccagggaa agcccctaag   180
ctcctgatct atggcacctc caacttggag agtggggtcc catcaaggtt cagtggcagt   240
ggatctggga cagatttcac tctcaccatc agcagtctgc aacctgaaga ttttgcaact   300
tactactgtc aacagagttg gaacgaccct cccactttcg gcggagggac caaggtggag   360
atcaaacgta cggtggctgc accatctgtc ttcatcttcc cgccatctga tgagcagttg   420
aaatctggaa ctgcctctgt tgtgtgcctg ctgaataact tctatcccag agaggccaaa   480
gtacagtgga aggtggataa cgccctccaa tcgggtaact cccaggagag tgtcacagag   540
caggacagca aggacagcac ctacagcctc agcagcaccc tgacgctgag caaagcagac   600
tacgagaaac acaaagtcta cgcctgcgaa gtcacccatc agggcctgag ctcgcccgtc    660
acaaagagct tcaacagggg agagtgttga   690
```

<210> SEQ ID NO 35
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 35

```
Ala Pro Tyr Trp Thr His Pro Gln Arg Met Glu Lys Lys Leu His
1               5                   10                  15
```

```
<210> SEQ ID NO 36
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Thr His Pro Gln Arg Met Glu Lys Lys Leu His Ala Val Pro Ala
1               5                   10                  15

<210> SEQ ID NO 37
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Arg Met Glu Lys Lys Leu His Ala Val Pro Ala Gly Asn Thr Val
1               5                   10                  15

<210> SEQ ID NO 38
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Lys Leu His Ala Val Pro Ala Gly Asn Thr Val Lys Phe Arg Cys
1               5                   10                  15

<210> SEQ ID NO 39
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Val Pro Ala Gly Asn Thr Val Lys Phe Arg Cys Pro Ala Ala Gly
1               5                   10                  15

<210> SEQ ID NO 40
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Asn Thr Val Lys Phe Arg Cys Pro Ala Ala Gly Asn Pro Thr Pro
1               5                   10                  15

<210> SEQ ID NO 41
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 41

Phe Arg Cys Pro Ala Ala Gly Asn Pro Thr Pro Thr Ile Arg Trp
1               5                   10                  15

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ala Ala Gly Asn Pro Thr Pro Thr Ile Arg Trp Leu Lys Asp Gly
1               5                   10                  15

<210> SEQ ID NO 43
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Pro Thr Pro Thr Ile Arg Trp Leu Lys Asp Gly Gln Ala Phe His
1               5                   10                  15

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ile Arg Trp Leu Lys Asp Gly Gln Ala Phe His Gly Glu Asn Arg
1               5                   10                  15

<210> SEQ ID NO 45
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Lys Asp Gly Gln Ala Phe His Gly Glu Asn Arg Ile Gly Gly Ile
1               5                   10                  15

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 46

Ala Phe His Gly Glu Asn Arg Ile Gly Gly Ile Arg Leu Arg His
1               5                   10                  15

<210> SEQ ID NO 47
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Glu Asn Arg Ile Gly Gly Ile Arg Leu Arg His Gln His Trp Ser
1               5                   10                  15

<210> SEQ ID NO 48
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Gly Ile Arg Leu Arg His Gln His Trp Ser Leu Val Met Glu
1               5                   10                  15

<210> SEQ ID NO 49
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Leu Arg His Gln His Trp Ser Leu Val Met Glu Ser Val Val Pro
1               5                   10                  15

<210> SEQ ID NO 50
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

His Trp Ser Leu Val Met Glu Ser Val Val Pro Ser Asp Arg Gly
1               5                   10                  15

<210> SEQ ID NO 51
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 51

Val Met Glu Ser Val Val Pro Ser Asp Arg Gly Thr Tyr Thr Cys
1               5                   10                  15

<210> SEQ ID NO 52
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Val Val Pro Ser Asp Arg Gly Thr Tyr Thr Cys Leu Val Glu Asn
1               5                   10                  15

<210> SEQ ID NO 53
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Asp Arg Gly Thr Tyr Thr Cys Leu Val Glu Asn Ala Val Gly Ser
1               5                   10                  15

<210> SEQ ID NO 54
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Tyr Thr Cys Leu Val Glu Asn Ala Val Gly Ser Ile Arg Tyr Asn
1               5                   10                  15

<210> SEQ ID NO 55
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Val Glu Asn Ala Val Gly Ser Ile Arg Tyr Asn Tyr Leu Leu Asp
1               5                   10                  15

<210> SEQ ID NO 56
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Glu Asn Ala Val Gly Ser Ile Arg Tyr Asn Tyr Leu Leu Asp Val
1               5                   10                  15

<210> SEQ ID NO 57
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Phe Arg Cys Pro Ala Ala Gly Asn Pro Thr Pro Thr Ile Arg Trp Leu
1               5                   10                  15

Lys Asp Gly Gln Ala Phe His
            20

<210> SEQ ID NO 58
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Ile Thr Gly Asp Ser Leu Thr Ser Ser Asn Asp Asp Glu Asp Pro
1               5                   10                  15

<210> SEQ ID NO 59
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Thr Gly Asp Ser Leu Thr Ser Ser Asn Asp Asp Glu Asp Pro Lys
1               5                   10                  15

<210> SEQ ID NO 60
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Asp Ser Leu Thr Ser Ser Asn Asp Asp Glu Asp Pro Lys Ser
1               5                   10                  15

<210> SEQ ID NO 61
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 61

Asp Ser Leu Thr Ser Ser Asn Asp Asp Glu Asp Pro Lys Ser His
1               5                   10                  15

<210> SEQ ID NO 62
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ser Leu Thr Ser Ser Asn Asp Asp Glu Asp Pro Lys Ser His Arg
1               5                   10                  15

<210> SEQ ID NO 63
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Leu Thr Ser Ser Asn Asp Asp Glu Asp Pro Lys Ser His Arg Asp
1               5                   10                  15

<210> SEQ ID NO 64
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Thr Ser Ser Asn Asp Asp Glu Asp Pro Lys Ser His Arg Asp Pro
1               5                   10                  15

<210> SEQ ID NO 65
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ser Ser Asn Asp Asp Glu Asp Pro Lys Ser His Arg Asp Pro Ser
1               5                   10                  15

<210> SEQ ID NO 66
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Ser Asn Asp Asp Glu Asp Pro Lys Ser His Arg Asp Pro Ser Asn
1               5                   10                  15
```

```
<210> SEQ ID NO 67
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Asn Asp Asp Glu Asp Pro Lys Ser His Arg Asp Pro Ser Asn Arg
1               5                   10                  15

<210> SEQ ID NO 68
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Asp Asp Glu Asp Pro Lys Ser His Arg Ser Pro Ser Asn Arg His
1               5                   10                  15

<210> SEQ ID NO 69
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Asp Glu Asp Pro Lys Ser His Arg Asp Pro Ser Asn Arg His Ser
1               5                   10                  15

<210> SEQ ID NO 70
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Glu Asp Pro Lys Ser His Arg Asp Pro Ser Asn Arg His Ser Tyr
1               5                   10                  15

<210> SEQ ID NO 71
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Asp Pro Lys Ser His Arg Asp Pro Ser Asn Arg His Ser Tyr Pro
1               5                   10                  15

<210> SEQ ID NO 72
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Pro Lys Ser His Arg Asp Pro Ser Asn Arg His Ser Tyr Pro Gln
1               5                   10                  15

<210> SEQ ID NO 73
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Lys Ser His Arg Asp Pro Ser Asn Arg His Ser Tyr Pro Gln Gln
1               5                   10                  15

<210> SEQ ID NO 74
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Ser His Arg Asp Pro Ser Asn Arg His Ser Tyr Pro Gln Gln Ala
1               5                   10                  15

<210> SEQ ID NO 75
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

His Arg Asp Pro Ser Asn Arg His Ser Tyr Pro Gln Gln Ala Pro
1               5                   10                  15

<210> SEQ ID NO 76
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Arg Asp Pro Ser Asn Arg His Ser Tyr Pro Gln Gln Ala Pro Tyr
1               5                   10                  15

<210> SEQ ID NO 77
<211> LENGTH: 15
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 77

Asp Pro Ser Asn Arg His Ser Tyr Pro Gln Gln Ala Pro Tyr Trp
1               5                   10                  15

<210> SEQ ID NO 78
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Pro Ser Asn Arg His Ser Tyr Pro Gln Gln Ala Pro Tyr Trp Thr
1               5                   10                  15

<210> SEQ ID NO 79
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Ser Asn Arg His Ser Tyr Pro Gln Gln Ala Pro Tyr Trp Thr His
1               5                   10                  15

<210> SEQ ID NO 80
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Asn Arg His Ser Tyr Pro Gln Gln Ala Pro Tyr Trp Thr His Pro
1               5                   10                  15

<210> SEQ ID NO 81
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Arg His Ser Tyr Pro Gln Gln Ala Pro Tyr Trp Thr His Pro Gln
1               5                   10                  15

<210> SEQ ID NO 82
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 82

His Ser Tyr Pro Gln Gln Ala Pro Tyr Trp Thr His Pro Gln Arg
1               5                   10                  15

<210> SEQ ID NO 83
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Ser Tyr Pro Gln Gln Ala Pro Tyr Trp Thr His Pro Gln Arg Met
1               5                   10                  15

<210> SEQ ID NO 84
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ala Thr Ile Asn Pro Ser Gly Thr Arg Thr Tyr Tyr Pro Asp Ser Val
    50                  55                  60

Lys Gly Arg Phe Thr Leu Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Asn Asn Tyr Ala Phe Asp Tyr Trp Gly Gln Gly Thr
            100                 105                 110

Leu Val Thr Val Ser Ser
        115

<210> SEQ ID NO 85
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45
```

```
Ala Thr Ile Asn Pro Ser Gly Thr Arg Thr Tyr Tyr Pro Asp Ser Val
            50                  55                  60

Lys Gly Arg Phe Thr Leu Ser Arg Asp Asn Ala Lys Asn Ser Leu Tyr
 65                  70                  75                  80

Leu Gln Met Asn Ser Leu Arg Ala Glu Asp Thr Ala Thr Phe Tyr Cys
                85                  90                  95

Ala Arg Leu Tyr Asn Asn Tyr Ala Phe Asp Tyr Trp Gly Gln Gly Thr
                100                 105                 110

Leu Val Thr Val Ser Ser
            115

<210> SEQ ID NO 86
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Tyr Met Ala Trp Val Arg Gln Ala Pro Gly Lys Gly Leu Glu Trp Val
            35                  40                  45

Ala Thr Ile Asn Pro Ser Gly Thr Arg Thr Tyr Tyr Pro Asp Ser Val
            50                  55                  60

Lys Gly Arg Phe Thr Leu Ser Arg Asp Ser Ala Lys Ser Ser Leu Tyr
 65                  70                  75                  80

Leu Gln Met Asn Ser Leu Arg Ala Glu Asp Thr Ala Thr Phe Tyr Cys
                85                  90                  95

Ala Arg Leu Tyr Asn Asn Tyr Ala Phe Asp Tyr Trp Gly Gln Gly Thr
                100                 105                 110

Leu Val Thr Val Ser Ser
            115

<210> SEQ ID NO 87
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Tyr Met Ser Trp Val Arg Gln Ala Pro Gly Lys Gly Leu Glu Trp Val
            35                  40                  45

Ala Thr Ile Asn Pro Ser Gly Thr Arg Thr Tyr Tyr Pro Asp Ser Val
            50                  55                  60

Lys Gly Arg Phe Thr Leu Ser Arg Asp Ser Ala Lys Ser Ser Leu Tyr
 65                  70                  75                  80
```

-continued

Leu Gln Met Asn Ser Leu Arg Ala Glu Asp Thr Ala Val Tyr Tyr Cys
                85                  90                  95

Ala Arg Leu Tyr Asn Asn Tyr Ala Phe Asp Tyr Trp Gly Gln Gly Thr
            100                 105                 110

Leu Val Thr Val Ser Ser
        115

<210> SEQ ID NO 88
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ala Thr Ile Asn Pro Ser Gly Thr Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Thr Tyr Tyr Cys
                85                  90                  95

Ala Arg Leu Tyr Asn Asn Tyr Ala Phe Asp Tyr Trp Gly Gln Gly Thr
            100                 105                 110

Leu Val Thr Val Ser Ser
        115

<210> SEQ ID NO 89
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Ser Thr Leu
            20                  25                  30

Leu His Trp Tyr Gln Gln Lys Pro Gly Lys Gln Pro Lys Leu Leu Ile
        35                  40                  45

Tyr Gly Thr Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Trp Asn Asp Pro Pro
                85                  90                  95

Thr Phe Gly Gly Gly Thr Lys Val Glu Ile Lys
            100                 105

<210> SEQ ID NO 90
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Ser Thr Leu
            20                  25                  30

Met His Trp Tyr Gln Gln Lys Pro Gly Lys Gln Pro Lys Leu Leu Ile
        35                  40                  45

Tyr Gly Thr Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Trp Asn Asp Pro Pro
                85                  90                  95

Thr Phe Gly Gly Gly Thr Lys Val Glu Ile Lys
            100                 105
```

<210> SEQ ID NO 91
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 91

```
Asp Val Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Ser Thr Leu
            20                  25                  30

Leu His Trp Tyr Gln Gln Lys Pro Gly Lys Ala Pro Lys Leu Leu Ile
        35                  40                  45

Tyr Gly Thr Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Trp Asn Asp Pro Pro
                85                  90                  95

Thr Phe Gly Gly Gly Thr Lys Val Glu Ile Lys
            100                 105
```

<210> SEQ ID NO 92
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

```
gaggtgcagc tggtggagtc tgggggaggc ttggtccagc ctgggggtc cctgagactc      60
tcctgtgcag cctctggatt cacctttagt aactattaca tgagctgggt ccgccaggct    120
ccagggaagg ggctggagtg ggtggccacc ataaaccta gcggaaccag aacctactat    180
ccagactctg tgaagggccg attcaccctc tccagagaca acgccaagaa ctcactgtat    240
ctgcaaatga acagcctgag agccgaggac acggctgtgt attactgtgc gagactgtac    300
aacaattacg cctttgacta ctggggccaa ggaaccctgg tcaccgtctc ctca          354
```

<210> SEQ ID NO 93
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
gaggtgcagc tggtggagtc tgggggaggc ttggtccagc ctgggggtc cctgagactc      60
tcctgtgcag cctctggatt cacctttagt aactattaca tggcctgggt ccgccaggct    120
ccagggaagg ggctggagtg ggtggccacc ataaaccta gcggaaccag aacctactat    180
ccagactctg tgaagggccg attcaccctc tccagagaca acgccaagaa ctcactgtat    240
ctgcaaatga acagcctgag agccgaggac acggctacct tctactgtgc gagactgtac    300
aacaattacg cctttgacta ctggggccaa ggaaccctgg tcaccgtctc ctca          354
```

<210> SEQ ID NO 94
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94

```
gaggtgcagc tggtggagtc tgggggaggc ttggtccagc ctgggggtc cctgagactc      60
tcctgtgcag cctctggatt cacctttagt aactattaca tggcctgggt ccgccaggct    120
ccagggaagg ggctggagtg ggtggccacc ataaaccta gcggaaccag aacctactat    180
ccagactctg tgaagggccg attcaccctc tccagagaca cgccaagag ctcactgtat    240
ctgcaaatga acagcctgag agccgaggac acggctacct tctactgtgc gagactgtac    300
aacaattacg cctttgacta ctggggccaa ggaaccctgg tcaccgtctc ctca          354
```

<210> SEQ ID NO 95
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 95

```
gaggtgcagc tggtggagtc tgggggaggc ttggtccagc ctgggggtc cctgagactc      60
tcctgtgcag cctctggatt cacctttagt aactattaca tgagctgggt ccgccaggct    120
```

| | |
|---|---|
| ccagggaagg ggctggagtg ggtggccacc ataaaccctc gcggaaccag aacctactat | 180 |
| ccagactctg tgaagggccg attcaccctc tccagagaca gcgccaagag ctcactgtat | 240 |
| ctgcaaatga acagcctgag agccgaggac acggctgtgt attactgtgc gagactgtac | 300 |
| aacaattacg cctttgacta ctggggccaa ggaaccctgg tcaccgtctc ctca | 354 |

<210> SEQ ID NO 96
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 96

| | |
|---|---|
| gaggtgcagc tggtggagtc tgggggaggc ttggtccagc ctgggggtc cctgagactc | 60 |
| tcctgtgcag cctctggatt cacctttagt aactattaca tggcctgggt ccgccaggct | 120 |
| ccagggaagg ggctggagtg gtggccacc ataaaccctc gcggaaccag aacctactat | 180 |
| ccagactctg tgaagggccg attcaccatc tccagagaca acgccaagaa ctcactgtat | 240 |
| ctgcaaatga acagcctgag agccgaggac acggctacct attactgtgc gagactgtac | 300 |
| aacaattacg cctttgacta ctggggccaa ggaaccctgg tcaccgtctc ctca | 354 |

<210> SEQ ID NO 97
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 97

| | |
|---|---|
| gacatccaga tgacccagtc tccatcctcc ctgtctgcat ctgtaggaga cagagtcacc | 60 |
| atcacttgcc gggcaagtga gagcattagc accctgttac actggtatca gcagaaacca | 120 |
| gggaaacagc ctaagctcct gatctatggc acctccaact tggagagtgg ggtcccatca | 180 |
| aggttcagtg gcagtggatc tgggacagat ttcactctca ccatcagcag tctgcaacct | 240 |
| gaagattttg caacttactt ctgtcaacag agttggaacg accctcccac tttcggcgga | 300 |
| gggaccaagg tggagatcaa a | 321 |

<210> SEQ ID NO 98
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 98

| | |
|---|---|
| gacatccaga tgacccagtc tccatcctcc ctgtctgcat ctgtaggaga cagagtcacc | 60 |
| atcacttgcc gggcaagtga gagcgtgagc accctgatgc actggtatca gcagaaacca | 120 |
| gggaaacagc ctaagctcct gatctatggc acctccaact tggagagtgg ggtcccatca | 180 |
| aggttcagtg gcagtggatc tgggacagat ttcactctca ccatcagcag tctgcaacct | 240 |
| gaagattttg caacttactt ctgtcaacag agttggaacg accctcccac tttcggcgga | 300 |
| gggaccaagg tggagatcaa a | 321 |

<210> SEQ ID NO 99
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99

```
gacgtgcaga tgacccagtc tccatcctcc ctgtctgcat ctgtaggaga cagagtcacc      60
atcacttgcc gggcaagtga gagcattagc accctgttac actggtatca gcagaaacca     120
gggaaagccc ctaagctcct gatctatggc acctccaact tggagagtgg ggtcccatca     180
aggttcagtg gcagtggatc tgggacagat ttcactctca ccatcagcag tctgcaacct     240
gaagattttg caacttactt ctgtcaacag agttggaacg accctcccac tttcggcgga     300
gggaccaagg tggagatcaa a                                                321
```

<210> SEQ ID NO 100
<211> LENGTH: 89
<212> TYPE: PRT
<213> ORGANISM: Homo sapiens

<400> SEQUENCE: 100

```
Ala Arg Gly Ser Met Ile Val Leu Gln Asn Leu Thr Leu Ile Thr Gly
1               5                   10                  15

Asp Ser Leu Thr Ser Ser Asn Asp Asp Glu Asp Pro Lys Ser His Arg
            20                  25                  30

Asp Pro Ser Asn Arg His Ser Tyr Pro Gln Gln Ala Pro Tyr Trp Thr
        35                  40                  45

His Pro Gln Arg Met Glu Lys Lys Leu His Ala Val Pro Ala Gly Asn
    50                  55                  60

Thr Val Lys Phe Arg Cys Pro Ala Ala Gly Asn Pro Thr Pro Thr Ile
65                  70                  75                  80

Arg Trp Leu Lys Asp Gly Gln Ala Phe
                85
```

<210> SEQ ID NO 101
<211> LENGTH: 89
<212> TYPE: PRT
<213> ORGANISM: Mus musculus

<400> SEQUENCE: 101

```
Ala Arg Gly Ser Met Thr Val Val His Asn Leu Thr Leu Leu Met Asp
1               5                   10                  15

Asp Ser Leu Thr Ser Ile Ser Asn Asp Glu Asp Pro Lys Thr Leu Ser
            20                  25                  30

Ser Ser Ser Ser Gly His Val Tyr Pro Gln Gln Ala Pro Tyr Trp Thr
        35                  40                  45

His Pro Gln Arg Met Glu Lys Lys Leu His Ala Val Pro Ala Gly Asn
    50                  55                  60

Thr Val Lys Phe Arg Cys Pro Ala Ala Gly Asn Pro Met Pro Thr Ile
65                  70                  75                  80

His Trp Leu Lys Asp Gly Gln Ala Phe
                85
```

<210> SEQ ID NO 102

```
<211> LENGTH: 28
<212> TYPE: PRT
<213> ORGANISM: Homo sapiens

<400> SEQUENCE: 102

Asp Glu Asp Pro Lys Ser His Arg Asp Pro Ser Asn Arg His Ser Tyr
1               5                   10                  15

Pro Gln Gln Ala Pro Tyr Trp Thr His Pro Gln Arg
            20                  25
```

MONOCLONAL ANTIBODY ANTI-FGFR4

This application is a national phase application claiming benefit of priority under 35 U.S.C. § 371 to Patent Convention Treaty (PCT) International Application serial number PCT/EP2018/070848, filed Aug. 1, 2018, now pending, which claims the benefit of priority to European patent No. 17186454.9 filed on Aug. 16, 2017. The aforementioned applications are expressly incorporated herein by reference in their entirety and for all purposes.

The present invention relates to the field of monoclonal antibodies, in particular to monoclonal antibodies anti-FGFR4 and their use as medicaments and diagnostic agents.

BACKGROUND OF THE INVENTION

Cancer is one of the most common diseases in the Western world with ever-increasing numbers and it represents a mounting socio-economic burden worldwide. Despite a considerable improvement in our understanding of cancer biology, patients with solid metastatic tumors are essentially incurable and their quality of life is often significantly affected as a consequence of treatment. With 14.1 million new cancer cases and 8.2 million deaths worldwide in 2012 and with estimated 24 million new cases each year by 2035, cancer remains an important public health problem in the world (Ferlay et al. 2015).

Our inability to efficiently address advanced cancer therapeutically has recently received a new theoretical underpinning. Compelling evidence supported the existence, in different hematological and solid tumors, as well as in many normal tissues, of a cellular hierarchical organization at the base of which is a unique subset of undifferentiated cells with high tumorigenic potential, capable of generating a differentiated cancer cell progeny and of efficiently propagating the tumor in its original and in distant locations (Bonnet & Dick, 1997; Brittan & Wright, 2004; Barker et al., 2007; Lapidot et al., 1994; Reya et al., 2001; Singh et al., 2003; Al-Haj et al., 2003). These commonly termed cancer stem cells (CSC) are identified based on the expression of specific surface markers and defined based on their capability of self-renewal and of dividing asymmetrically generating two different daughter cells, one retaining sternness features and one progressively differentiating from transiently amplifying progenitors to terminally differentiated cancer cells (Valent et al., 2012). In addition, isolated CSCs proved to be highly resistant to conventional chemotherapy and radiotherapy (Maugeri-Sacca et al., 2011; Bao et al., 2006; Diehn et al., 2009). Defined as the primary source for all tumor cells, they are essential for sustained primary tumor growth, relapse and metastasis, and represent a key mechanism of therapeutic resistance. As a direct clinical consequence, an effective therapy should also target CSCs, since the elimination of the bulk of the tumor by acting on differentiated progenitors without affecting the stem cell compartment would produce only temporary success followed by relapse and/or metastasis.

Colorectal cancer (CRC) is a major cause of morbidity and mortality throughout the world. It accounts for over 13% of all cancer incidence and is the third most commonly diagnosed malignancy and the fourth leading cause of cancer-related death, with an incidence of about 1.4 million new cases and 700,000 deaths each year worldwide. Furthermore, its global burden is expected to increase by 60% to more than 2.2 million new cases and 1.1 million cancer deaths by 2030 (Arnold et al., 2017). While early stage CRC can be cured by surgery alone or by a combination of surgery and chemotherapy, metastatic disease is almost always incurable and represents a considerable medical challenge as well as a burden to the healthcare system. About 30% of patients present with metastatic disease at their first diagnosis, whereas 25% of those diagnosed with localized disease will develop metastases several years later (American Cancer Society). Therefore, developing new therapeutic strategies to eliminate tumor is ultimately critical.

Some of the present inventors were among the first to isolate CSCs from CRC tumor specimens (Ricci-Vitiani et al. 2007; Dalerba et al., 2007) and developed standard protocols for their isolation and in vitro culture, characterization and in vivo propagation. In particular, these cells show the ability to form xenografts in immunodeficient mice that histologically and genetically phenocopy the tumors from which they were originally isolated (Baiocchi et al., 2010).

At present there are no drugs selectively targeting colon CSCs, nor are there robust assays that would allow their detection in clinical samples (Zeuner et al. 2014).

We now discovered that colon CSCs express the tyrosine kinase fibroblast growth factor receptor 4 (FGFR4) and that this protein controls several important functions of colon CSCs. Subsequently, the present inventors generated monoclonal antibodies against this antigen using a known technology for genetic immunization (see for example the following references: Bioprocessing—Genetic Immunization for Antibody Production. Tutorial: Genovac's Technological Shortcut From Gene to Antibody. By John Thompson, Ph.D., and Stefan Lang, Ph.D., published in Genetic Engineering News, Vol. 22, No. 17, Oct. 1, 2002; Custom-made antibodies produced by genetic immunisation: Applications in drug development, therapy and diagnosis. By Stefan Lang and John Thompson, published in Global Outsourcing Review, Vol. 5, No. 1, Spring 2003; A shortcut from genomics to drug development. By Jens Lohrmann, Stefan Lang and John Thompson, published in Current Drug Discovery, October 2003).

These antibodies are useful to detect colon CSCs in patient specimens and find applications in clinical grade assays aimed at measuring the effects of novel CRC treatments on the CSC populations.

More importantly, antibodies have been found that are able to affect CSC survival and proliferation, therefore having therapeutic value.

Within the growth factor signalling pathways that emerged as critical players in tumorigenesis, FGF has recently gained high attention in tumor development, progression and metastasis (Dienstmann et al. 2014; Hierro et al., 2015). There are 22 human FGFs and 4 types of FGF receptors (FGFRs) that functions as receptor tyrosine kinases (RTKs) (Goetz & Mohammadi, 2013). Once activated, the FGF/FGFR signalling proceeds through multiple downstream pathways, such as RAS-MAPK, which regulates cellular proliferation, or PI3K-AKT, which controls cellular survival (Beenken & Mohammadi, 2009).

The extracellular region of a prototypical FGFR consists of three immunoglobulin (Ig)-like domains (Ig I, Ig II, and IgIII) connected by flexible linkers. A unique characteristic of FGFRs is a stretch of glutamate-, aspartate-, and serine-rich sequence situated in the Ig I-Ig II linker, termed the acid box (AB). Loss of the AB/linker enhances the affinity of FGFR for FGF and increases the signalling capacity of FGFR, demonstrating that this portion of the receptor controls FGFR autoinhibition (Kalinina et al., 2012). The flexible nature of the acid box facilitates intramolecular interactions that keep FGFR in a "closed" low-activity state, in which the affinity of FGFR for its ligands is reduced (Olsen et al., 2004). The loss of this region has been implicated in cancer (Onwuazor et al., 2003).

An increasing number of recently published data has suggested a role for FGFR4 in a large panel of neoplasms, showing overexpression of this receptor and/or of its ligand FGF19 in subsets of different solid neoplasms including hepatocellular carcinoma (HCC), rhabdomyosarcoma, and colorectal, prostate, breast, pituitary, lung (NSCLC), gastric and ovary tumors (Lin & Desnoyers, 2012; Wu & Li, 2012; Katoh & Nakagama, 2014; Crose et al., 2012; Li et al. 2014; Sahadevan et al., 2007; Andre & Cortes, 2015; Abbass et al., 1997; Huang et al., 2015; Chen H et al., 2015; Zaid et al., 2013). In some of these tumor types, FGFR4 has been identified as an unfavorable prognostic biomarker and several polymorphisms in its gene, the most studied of which being rs351855 (Gly388Arg), positively correlate both with tumor progression and a poor prognosis (Spinola et al., 2005a, 2005b; Taylor et al., 2009; Cho et al., 2016; Xu et al., 2011; Streit et al., 2004; Yang et al., 2012; Frullanti et al., 2011). Pre-clinical studies have highlighted a tumor promoter role for the FGF19-FGFR4 axis in the induction of cell proliferation (liver, colorectal, ovary and prostate carcinoma) (Ho et al., 2009; Wu et al., 2010; Desnoyers et al., 2008; Pai et al. 2008; Pelaez-Garcia et al., 2013; Zaid et al., 2013; Yu et al., 2011), of cell survival (rhabdomyosarcoma and liver, colorectal, breast, gastric carcinoma), and of cellular multidrug resistance (colorectal and breast carcinoma) (Ho et al., 2009; Turkington et al., 2014; Zaid et al., 2013; Ye et al., 2013; Roidl et al. 2009). Moreover, a role for FGFR4 in promoting cellular motility, invasiveness and epithelial-to-mesenchymal transition (EMT) has also been highlighted in CRC (Pelaez-Garcia et al., 2013; Liu et al., 2013).

Based on this evidence, the inhibition of the FGF19-FGFR4 axis has been recently taken into consideration as a new therapeutic strategy against different tumor types and in particular against hepatocellular carcinoma (HCC).

Liver cancer is the fifth most common malignance in the world, but ranks second as cause of death because of the high case fatality (Ferlay et al. 2015). HCC is difficult to treat because it is usually asymptomatic in the early stages, and when it causes symptoms it usually already reached an advanced stage (Fong et al., 2001; Bruix & Sherman 2005). Although surgical resection and liver transplantation have been implemented, the 5-year survival rate has not shown any significant improvement, partially due to the fact that most patients are in the late stage at diagnosis (Trovato et al., 2015). Additionally, many HCC patients exhibit low sensitivity to standard radiotherapy and chemotherapy (Llovet et al., 2015; Worns & Galle, 2014).

Therefore, it is a shared opinion that non-cytotoxic agents targeting molecular pathways that are aberrantly activated in HCC are urgently needed (Hoofnagle 2004).

The molecular basis of HCC progression is highly heterogeneous, even within the same tumor (El-Serag & Rudolph, 2007; Thorgeirsson & Grisham, 2002). In recent years, several pieces of evidence have defined that some genes and cellular signalling pathways play a key role in the development and progression of HCC (Chen & Wang, 2015). Moreover, some growth factor signalling pathways such as epidermal growth factor (EGF), hepatocyte growth factor (HGF), insulin-like growth factor (IGF), transforming growth factor (TGF), platelet-derived growth factor (PDGF) and fibroblast growth factor (FGF) emerged as critical players in tumorigenesis including liver carcinogenesis (Enguita-German & Fortes, 2014; Yoshida et al., 2014; Hopfner et al., 2008). Among the FGF receptors, FGFR4 is the prevailing isoform in human hepatocytes and it is overexpressed in human HCCs and HCC cell lines (Lin et al., 2007; Ho et al., 2009). Furthermore, it has been demonstrated that FGFR4 is required for hepatocarcinogenesis, since FGF19 transgenic mice that are prone to developing spontaneous HCCs, failed to develop liver tumors after they were crossed with FGFR4 knockout mice (French et al., 2012). In addition, it was shown that endogenous ileal FGF15 contributes to fibrosis-associated hepatocellular carcinogenesis in a clinically relevant mouse model (Uriarte et al., 2015).

In normal hepatocytes, FGF19 regulates hepatic bile acid metabolism through repression of the gene encoding Cyp7a1, the first rate-limiting step in the synthesis of bile acids (Inagaki et al., 2005; Chiang et al., 2009). FGF19 (and its murine homolog FGF15) secreted by the gut acts as an endocrine hormone by binding to FGFR4 on hepatocytes, thus preventing activation of Cyp7a1 and thereby inhibiting bile acid synthesis. FGFR4 KO mice have a larger bile acid pool, increased excretion of bile acids, and bile acid-depleted gall bladders, indicating negative regulation of cholesterol and bile acid synthesis (Xie et al., 1999; Yu et al., 2000). Klotho beta (KLB), a transmembrane protein with no predicted kinase activity, has been identified as a cofactor required for liver-specific activities of FGF19 (Lin et al., 2007), and impaired negative feedback suppression of bile acid synthesis has been described in klotho beta-deficient mice (Ito et al., 2005).

Previous studies have shown that treatment with an anti-FGF19 antibody reduced growth of colon tumor xenografts and prevented hepatocellular carcinomas in FGF19 transgenic mice (Desnoyers et al., 2008). However, in a repeat dose safety study in cynomolgus monkeys, anti-FGF19 treatment (3-100 mg/kg) demonstrated dose-related liver toxicity accompanied by severe diarrhea and low food consumption (Pai et al. 2012).

Accordingly, there is still the need of an antibody or a therapeutic agent capable of effectively inhibiting the interaction of FGFR4 with its ligand, which is effective and with a good therapeutic index, i.e. with a low or at least acceptable toxicity.

More recent studies on the anti-tumor effects of therapeutic antibodies and small molecules targeting FGFR4 have proven efficacy against HCC and other tumor isotypes in animal models and some are currently being evaluated in clinical trials.

A problem underlying the present invention was to provide anti-FGFR4 antibodies which can be used in diagnosing, preventing and/or treating diseases associated with FGFR4 expression, overexpression and/or hyperactivity.

A number of anti-FGFR4 monoclonal antibodies showed therapeutic efficacy in mouse models of HCC and other tumor types with an activated FGFR4 pathway (French et al., 2012; Bumbaca et al., 2011; Bartz et al., 2016; U.S. Pat. No. 9,266,955 B2; WO 2014/105849 A1; WO 2016/023894 A1). In addition, a phase I study of one of these antibodies (U3-1784, U3/Daiichi Sankyo, NCT02690350) is ongoing in patients with advanced solid tumours and liver cancer.

Furthermore, new-generation tyrosine kinase receptor inhibitors, highly specific for FGFR4, have being validated in mouse models of HCC (Hagel et al., 2015; WO 2014/011900 A2; WO 2016/151499 A1; US 2016/0244450 A1) and two of them are being currently evaluated in clinic phase I/II for their tolerability and efficacy in HCC and cholangiocarcinoma patients (BLU-554, Blueprint, NCT02508467), and in HCC and solid tumors characterized by positive FGFR4 and KLB Expression (FGF401, Novartis, NCT02325739).

Further patent literature related to the targeting of FGF receptors is the following: US20050147612, US20070248605, U.S. Pat. No. 8,263,074, US20140301946, US20110212091, US20160017027, U.S. Pat. No. 9,284,379, US20100143386, U.S. Pat. No. 7,531,304, WO2010004204, WO2015107171.

However, for none of the antibodies or inhibitors disclosed in the above mentioned literature an activity on colon cancer stem cells has been shown.

Accordingly, there is the strongly felt need of an agent capable of targeting colon cancer stem cells (colon CSC) and to kill them or at least substantially inhibit their growth, multiplication and differentiation.

There is also a strongly felt need of an agent capable of detecting colon CSCs in order to reveal them in a diagnostic assay.

It has now been found and validated both in vitro and in vivo that FGFR4 is a therapeutic target for the colon cancer stem cells, and the presence of FGFR4 in CSCs has been correlated to higher proliferation rates and clonogenic efficiencies and higher migration propensity.

Therefore, agents directed against FGFR4 and able to inhibit its activity can be advantageously used in colon cancer for killing or inhibiting the activity of colon cancer stem cells. Since it has been found that FGFR4 is present on colon CSC, agents directed against this antigen can also be advantageously used for detecting and recognizing said cells.

There is also a strong need of a monoclonal antibody which is selective against FGFR4, capable of effectively inhibiting its interaction with the ligand and acting as an effective antitumor agent.

There is also a need of a monoclonal antibody anti-FGFR4, which is effective on colon CSCs.

Another particular strongly felt need is of a monoclonal antibody anti-FGFR4, for the treatment of FGFR4-dependent tumors such as, but not limited to, hepatocellular carcinoma (HCC).

It has now been found a monoclonal antibody, herein also named BMK-3B6-E4 and its chimeric (ch3B6) and humanized (hu3B6) forms, showing a high anti-proliferative activity on cultured cells and in vivo, paralleled by a high efficiency in modulating FGFR4 signalling components in the same cells.

This antibody has been shown to inhibit ligand binding to FGFR4 in vitro.

It has been surprisingly found that said antibody of the invention binds to an epitope within the auto-inhibitory acid box domain of the FGFR4, an extracellular region that is known not to be involved in ligand binding (Kalilina et al., 2012). On the contrary, this domain is known to have an auto-inhibitory action on FGFR4, indeed it is known that loss of this region enhances the binding of the receptor to its ligand. Therefore, it has been found that the antibody of the invention binds to the FGFR in a unique mode that conformationally affects ligand interaction and receptor activation.

It has also been found that an antibody able to specifically recognize and bind to the domain named "acid box" of FGFR4 inhibits the interaction of the receptor with the ligand and has an anti-tumor effect.

These unexpected features are valuable in the clinical development of humanized antibodies, glycoengineered antibodies and antibody-drug conjugates against colon CSCs and for the treatment of FGFR4 dependent cancers.

SUMMARY OF THE INVENTION

It is an object of the present invention a monoclonal antibody anti-FGFR4 for use for detecting and/or killing and/or affecting and/or inhibiting development and/or differentiation of colon cancer stem cells.

It is an object of the present invention a monoclonal antibody which specifically binds to an epitope between amino acid 119 and 156 of human FGFR4, preferably between amino acid 127 and 154 of human FGFR4 and which inhibits FGF19 binding to FGFR4.

In particular, said antibody specifically binds to the acid box domain of FGFR4.

Preferably, the antibody specifically recognizes as an epitope an amino acid sequence with SEQ ID N. 27.

In a particular embodiment, the antibody specifically recognizes the following amino acids within the amino acid sequence with SEQ ID N. 27: D127, P130, K131, P136, S137, R139, H140, S141, Q144, Y148, W149, T150, Q153, R154. Amino acid numbering refers to human FGFR4 precursor, including the signal peptide (NCBI accession number NP_001341913).

Particularly preferred antibodies of the present invention are capable of blocking binding of FGF19 ligand to human FGFR4 by at least 60%, preferably at least 70% and more preferably at least 80% or 87%. Particularly preferred are those antibodies of the invention, which block binding of FGF19 to human FGFR4 by at least 80%, more preferably at least 85% or at least 90%. Blocking of ligand binding to human FGFR4 results in inhibition of FGFR4 signalling.

In a preferred embodiment, the antibodies of the invention are also capable of blocking binding of further FGFR4 ligands including, for example, FGF1, FGF8, FGF17, FGF18, FGF21, FGF23 (Zhang et al., 2006) by at least 60%, preferably at least 70% and more preferably at least 80% or 87%.

It is an object of the present invention an antibody or antigen-binding fragment thereof comprising the amino acids of the hypervariable region of the antibody herein disclosed necessary for specifically binding to the epitope to which the monoclonal antibody herein disclosed binds.

In this context, for "hypervariable region" it is intended tertiary structures derived from triplets of non-contiguous variable regions of amino acid sequence (CDRs).

It is an object of the present invention an antibody that binds to the antigen or epitope, in particular expressed by colon cancer stem cells, recognized by the monoclonal antibody herein disclosed. For example, in certain embodiments, an antibody is provided that binds to the same epitope as an anti-FGFR4 antibody comprising a heavy chain variable region (VH) sequence of SEQ ID NO: 1-4 and a light chain variable region (VL) sequence of SEQ ID NO: 10-13 or one or more CDRs as below disclosed.

It is an object of the present invention an antibody, or antigen-binding fragment thereof, that binds to the acid box of FGFR4, or a portion thereof, and comprises: (i) a heavy chain CDR1 comprising the amino acid sequence of SEQ ID NO: 5-6, and/or (ii) a heavy chain CDR2 comprising the amino acid sequence of SEQ ID NO:7-8, and/or (iii) a heavy chain CDR3 comprising the amino acid sequence of SEQ ID NO:9, and/or (iv) a light chain CDR1 comprising the amino acid sequence of SEQ ID NO: 14-15, and/or (v) a light chain CDR2 comprising the amino acid sequence of SEQ ID NO: 16, and/or (vi) a light chain CDR3 comprising the amino acid sequence of SEQ ID NO: 17, wherein anyone of said CDRs may differ by one or two amino acids compared with at least one of the sequences mentioned above, provided that the antibody keeps its binding specificity.

It is an object of the present invention an antibody, or antigen-binding fragment thereof, that binds to the acid box of FGFR4 wherein the variable region of its heavy chain is coded by a nucleotide sequence having at least 80% identity with the sequence SEQ ID NO: 18-22 or SEQ ID NO: 92-96 and the variable region of its light chain is coded by a nucleotide sequence having at least 80% identity with the sequence SEQ ID NO: 23-26, or SEQ ID NO: 97-99 provided that the antibody keeps its binding specificity.

In a preferred embodiment of the application, the antibody of the invention is able to recognize and bind to the "acid box" domain of FGFR4 and at the same time inhibit the interaction of the receptor with the ligand FGF19 and impair ligand-dependent FGFR4 signalling.

It has been found that the anti-FGFR4 antibody of the invention is able to efficiently inhibit the binding of FGF ligands, in particular FGF19, to FGFR4 and is able to interfere with the FGFR4-dependent signalling pathway, in particular in HCC cell lines.

This renders it particularly advantageous for the treatment of tumors dependent on FGFR4, such as hepatocellular carcinoma.

In particular the antibody of the invention shows an effective tumor cell inhibition, in particular in tumors expressing FGFR4.

Furthermore, the antibody of the invention shows a high binding activity on colon CSCs therefore being particularly useful for the treatment of colon cancer.

Also, the antibody of the invention has a high and specific binding affinity for FGFR4, while it does not bind to other FGF receptors. This is advantageous because it reduces the possibility of side effects due to the activity on other FGF receptors not involved in the cancer pathology.

In a particular embodiment of the invention, the antibody is the antibody herein indicated as BMK-3B6-E4, and its chimeric (ch3B6) and humanized (hu3B6) forms. This antibody shows a high, dose-dependent reactivity on both cancer stem cells and tumor cell lines with high FGFR4 expression levels, particularly on hepatocellular carcinoma (HCC) cell lines.

A reduction of the tumor volume is observed in mice treated with this antibody relative to the control group.

In addition, the antibody of the invention binds efficiently also to the FGFR4 Y367C mutant overexpressed in the MDA-MB453 cells. This mutant receptor has been described as a dominant, ligand-independent, constitutive activated variant, insensitive to the inhibition with a known antagonistic antibody (Roidl et al., 2010). This provides the advantage that an antibody according to the invention can be used also in subjects having said mutation which do not respond to therapies with known antagonistic antibodies.

In an additional embodiment of the invention, the antibody is a humanized antibody.

In an additional embodiment of the invention the antibody is a human antibody.

The antibody of the invention shows a binding specificity for FGFR4 acid box and inhibits the binding of the ligand to the receptor. This was unexpected due to the fact already mentioned above that the acid box is known for not being involved in the binding of the ligand. On the contrary, the acid box is known to be involved in auto inhibition of the receptor.

The invention also provides conjugates including an antibody as herein described. In particular, antibody drug conjugates are a preferred subject-matter of the invention.

A further object of the invention is a nucleic acid molecule encoding the antibody, optionally in operative linkage to an expression control sequence.

Said isolated nucleic acid typically comprises a sequence encoding the heavy chain and a sequence encoding the light chain, both comprising the variable and the constant region. Said sequence encoding the heavy chain is preferably selected from the group consisting of the sequences of SEQ ID N. 28-31 or a sequence having at least 80% identity with said sequences and said sequence encoding the light chain is preferably selected from the group consisting of the sequences of SEQ ID N. 32-34 or a sequence having at least 80% identity with said sequences.

A further object of the invention is a vector comprising one or more nucleic acid sequences as disclosed herein, preferably it is an expression vector. For example, said vector can comprise nucleic acid sequences coding for the antibody or for its light and/or heavy chains, constant and/or variable regions, or for its CDRs.

A further aspect of the invention is a host, in particular a recombinant cell which comprises the nucleic acid molecule. The cell may be used for the preparation of the antibody.

A further aspect of the invention is the antibody of the invention for use for the diagnosis, prevention and/or treatment of a disease associated with FGFR4 expression, overexpression and/or hyperactivity.

Preferably said disease is a cancer disease, more preferably it is colon cancer or hepatocellular carcinoma (HCC).

In a more preferred embodiment, the antibody of the invention is used for killing or affecting or inhibiting development and/or differentiation of colon cancer stem cells.

It is an object of the present invention a pharmaceutical composition comprising the monoclonal antibody anti-FGFR4 herein disclosed.

It is an object of the present invention an antibody-drug conjugate (ADC) comprising the monoclonal antibody herein disclosed, a pharmaceutical composition comprising it and their use as medicaments, in particular for the treatment of tumors.

These and other objects of the present invention will be described in detail herein below, also with reference to Figures and Examples.

BRIEF DESCRIPTION OF THE FIGURES

FIG. 3. Summary of the FACS analysis data obtained with all supernatants on 5 different CSC lines. Fold change (FC) is the ratio of the mean fluorescence intensity (MFI) measured with each supernatant to the negative control (myeloma cells conditioned medium). A score was assigned based on FC values on each CSC line (3A) and the final rank was calculated by summing the individual scores (3B). For simplicity, only data obtained with the anti-FGFR4 supernatants are shown.

DETAILED DESCRIPTION OF THE INVENTION

Definitions

Figure 1:
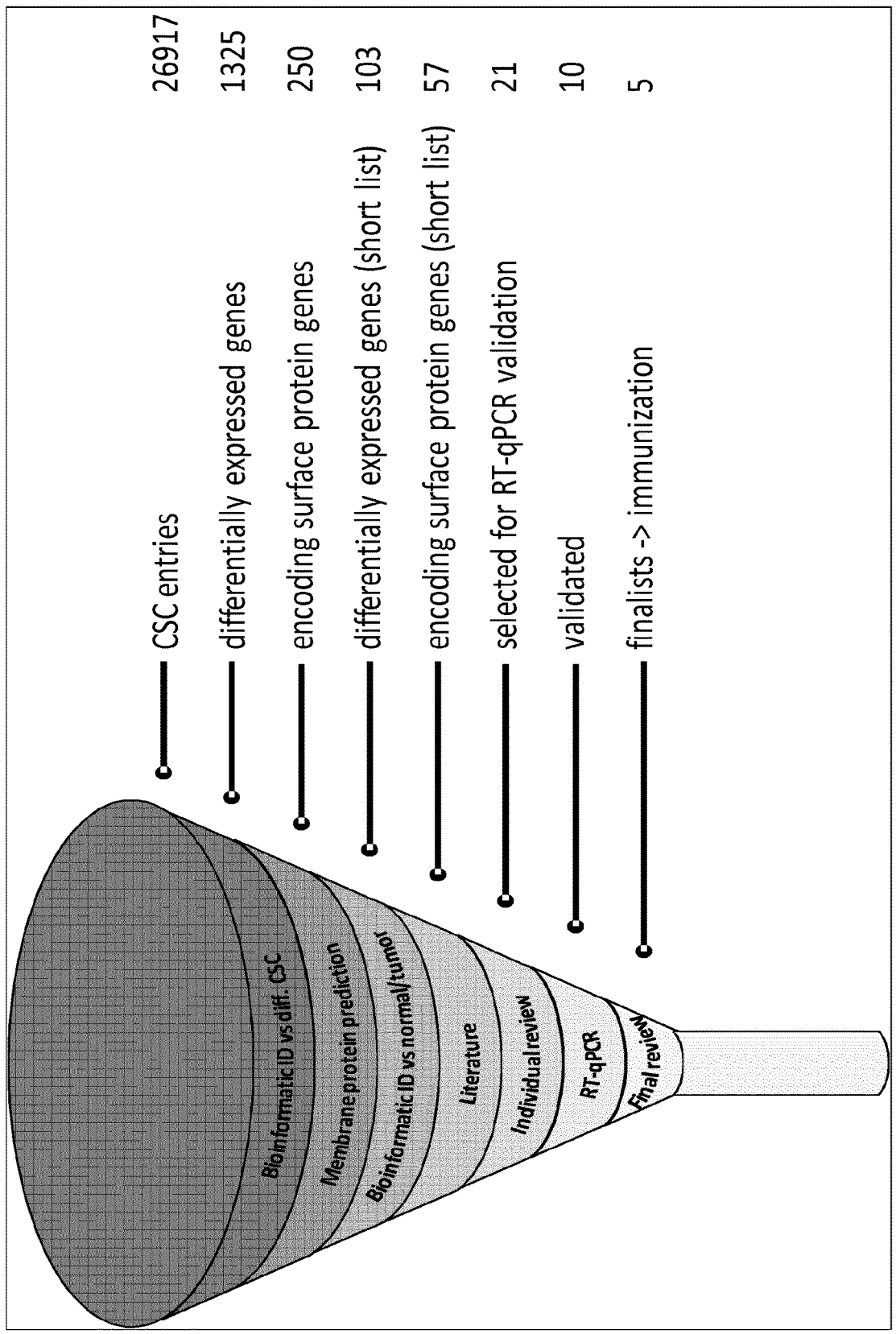
FIG. 1. Gene selection funnel

Within the meanings of the present invention for "antibody" is intended generally a molecule that contains at least one antigen binding site that immunospecifically binds to a particular antigenic target of interest. The term "antibody" thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term "antibody," thus, includes full length antibodies and/or their variants, as well as fragments thereof. Binding of an antibody to at least one target antigen can cause a variety of effects, such as but not limited to where such binding modulates, decreases, increases, antagonizes, agonizes, mitigates, alleviates, blocks, inhibits, abrogates and/or interferes with at least one target antigen activity, in particular with a target receptor activity, in vitro, in situ, and/or in vivo. The present invention, thus, encompasses antibody fragments capable of binding to a biological molecule (such as an antigen or receptor) or portions thereof, including but not limited to Fab, Fab' and F(ab')2, facb, pFc', Fd, Fv or scFv fragments (See, e.g., Colligan et al. eds., John Wiley & Sons, Inc., NY, 1994-2001); diabodies; linear antibodies (Zapata et al. (1995) Protein Eng. 8(10): 1057); single-chain antibody molecules; and multispecific antibodies formed from antibody fragments. Accordingly, antibody is used in the broadest sense and specifically covers, for example, single anti-FGFR4 monoclonal antibodies (including agonist, antagonist, and neutralizing antibodies), anti-FGFR4 antibody compositions with polyepitopic specificity, single chain anti-FGFR4 antibodies, and fragments of anti-FGFR4 antibodies. The present invention also encompasses antibody derivatives. Derivatives of monoclonal antibodies of this invention are e.g. antibody fragments, radioactively labeled monoclonal antibodies, and conjugates of the monoclonal antibodies with enzymes, with fluorescent markers, with cytotoxic drugs, or the like. The term "derivative" further encompasses any mutants of the antibody construct differing by the addition, deletion, and/or substitution of at least one amino acid. The capacity of the fragment or derivative of the antibody to bind to the epitope can be determined by direct ELISA, for example, as described in the following sections.

Within the meaning of the present invention for "monoconal antibody" is intended an antibody obtained from a population of substantially homogeneous antibodies, i.e., the individual antibodies comprising the population are identical except for possible naturally-occurring mutations that may be present in minor amounts. Monoclonal antibody may be abbreviated as "mAb."

Within the meaning of the present invention, the term "chimeric antibody" refers to an antibody in which the constant region, or a portion thereof, is altered, replaced or exchanged, such that the variable region is linked to a constant region of a different species, or belongs to another antibody class or subclass. The term "chimeric antibody" also refers to an antibody in which the variable region, or a portion thereof, is altered, replaced or exchanged, such that the constant region is linked to a variable region of a different species, or belongs to another antibody class or subclass. The methods of producing chimeric antibodies are known to those skilled in the art. See, for example, Morrison, 1985, Science, 229: 1202; Oi and al., 1986, Bio Techniques, 4: 214; Gillies and al., 1989, J. Immunol. Methods, 125:191-202; U.S. Pat. Nos. 5,807,715; 4,816,567; and 4,816,397. These chimeric versions of the antibody may comprise the fusion of the murine VL and VH variable regions to the CL (kappa) and the CH (IgGI) constant domains of human origin in order to generate a chimeric monoclonal antibody.

Within the meaning of the present invention for "humanized antibodies" is intended an antibody from non-human species whose protein sequences have been modified to increase their similarity to antibody variants produced naturally in humans. The process of "humanization" is usually applied to monoclonal antibodies developed for administration to humans.

Within the meaning of the present invention for "human antibody" is intended an antibody that may naturally occur in human beings. The term "human antibody" generally encompasses fully human or humanized antibodies.

Within the meaning of the present invention the term "bind" or "binding" of an antibody means an at least temporary interaction or association with or to a target antigen.

Within the meaning of the present invention, for "inhibit" or "inhibition" it is intended to limit, prevent and/or block the action or function of a biologic agent. "Blocking" is also herein used as a synonym.

Within the meaning of the present invention, cancer stem cells (CSCs) are cancer cells that possess characteristics associated with normal stem cells, in particular the ability to differentiate into all cell types found in a particular cancer sample and to self-renew indefinitely.

Within the meaning of the present invention, for "treatment", "treating" it is intended obtaining a desired pharmacologic, and/or physiologic effect. The effect may be therapeutic in terms of a partial or complete cure for a disease and/or adverse effect attributable to the disease. "Treatment," as used herein, includes administration of a compound of the present invention for treatment of a disease or condition in a mammal, particularly in a human, and includes: (a) inhibiting the disease, i.e., arresting its development; (b) providing palliative care, i.e., reducing and preventing the suffering of a patient; and (c) relieving the disease, i.e., causing regression of the disease or disorder or alleviating symptoms or complications thereof. Dosage regimens may be adjusted to provide the optimum desired response.

Within the meaning of the present invention for "epitope" it is intended a portion of an antigenic molecule to which an antibody is produced and to which the antibody will bind. A "FGFR4 epitope" comprises the part of the FGFR4 protein to which an anti-FGFR4 monoclonal antibody specifically binds. Epitopes can comprise linear amino acid residues (i.e., residues within the epitope are arranged sequentially one after another in a linear fashion), nonlinear amino acid residues, or both linear and nonlinear amino acid residues.

Typically linear epitopes are generally short amino acid sequences (e.g. about five amino acids in length).

Within the meaning of the present invention for "pharmaceutical composition" it is intended a composition wherein an effective amount of the antibody of the invention is admixed with at least one pharmaceutically acceptable vehicle and/or at least one pharmaceutically acceptable excipient in order to be suitable for administration to a subject.

Within the meaning of the present invention for "substantially" it is intended to a large and/or significant extent.

Within the meaning of the present invention for "antibody drug conjugate" or "ADC" it is intended a compound wherein a monoclonal antibody is linked to a drug, generally a highly cytotoxic drug.

The present invention refers to an antibody, in particular a human antibody, directed against FGFR4 or a functional fragment or functional derivative thereof.

The term "antibody" particularly refers to molecules comprising at least one immunoglobulin heavy chain and at least one immunoglobulin light chain. Each heavy and light chain may comprise a variable and a constant domain. The antigen binding site may be formed from the variable domains of a heavy and light chain. A variable region (also referred to as variable domain) comprises complementarity determining regions (CDRs), e.g. a CDR1, a CDR2 and a CDR3 region and framework regions (FRs) flanking the CDRs. The term "complementarity determining region" is readily understood by the skilled person (see for example Harlow and Lane (eds.), Antibodies: A Laboratory Manual, CSHL press, Cold Spring Harbor, N.Y., 1988) and refers to the stretches of amino acids within the variable domain of an antibody that primarily make contact with the antigen and determine antibody specificity. The tertiary structure derived from triplets of non-contiguous CDRs is also known as the hypervariable region.

It is an object of the present invention an antibody against FGFR4 for use for detecting and/or killing and/or affecting and/or inhibiting development and/or differentiation of colon cancer stem cells.

Monoclonal antibodies anti-FGFR4 are known in the art and can be purchased or synthetized by common methods. See for example the references cited in the above introduction, such as French et al., 2012; Bumbaca et al., 2011; Bartz et al., 2016; U.S. Pat. No. 9,266,955 B2; WO 2014/105849 A1; WO 2016/023894 A1, U3-1784 (U3/Daiichi Sankyo, NCT02690350). Monoclonal antibodies against FGFR4 can also be obtained using known technologies for genetic immunization; genetic immunization is well-known in the art and commonly used by those of ordinary skill in the art. Reference for this technique can be found in Tang D C, DeVit M, Johnston S A. Nature. 1992, 356(6365): 152-154.

According to the present invention antibodies against FGFR4 can be used for detecting and recognizing colon cancer stem cells. In particular, they can be advantageously used for the detection of colon cancer stem cells in clinical samples therefore finding applications in a diagnostic assay. More in particular, they can be advantageously used in clinical grade assays aimed at measuring the effects of novel CRC treatments on the CSC populations.

According to the present invention, antibodies against FGFR4 can also be used for killing colon cancer stem cells or for affecting or inhibiting their development or their differentiation.

In particular, an antibody against FGFR4 can be administered to a subject in need thereof in the form of a pharmaceutical composition for killing colon cancer stem cells in order to treat colon cancer. Also it can be administered to a subject in need thereof to inhibit the development or the differentiation of said cells in order to prevent or improve a colon cancer condition.

Pharmaceutical compositions and administration modes are conventional and within the abilities and knowledge of a skilled person in the field, for example a physician.

Further details regarding therapeutic applications can be found hereinafter in the paragraph "Pharmaceutical compositions and medical treatments".

The inventors of the present application also found that antibodies directed against an epitope between amino acids 119-156 of human FGFR4 or functional fragments or functional derivatives thereof are particularly useful for therapeutic and diagnostic applications. This epitope of FGFR4 is also known as "acid box" domain.

In a preferred embodiment, the antibody of the invention is directed against an epitope between amino acid 127 and 154 of human FGFR4. Indeed, it has been found that the binding to this particular epitope is advantageous to inhibit FGFR4 activity.

According to a particularly preferred embodiment, the antibody of the invention is directed against an epitope comprising, essentially consisting of or consisting of the amino acid sequence comprised between amino acids 119 and 156 of human FGFR4, preferably between amino acid 127 and 154 of human FGFR4. Preferably, said amino acid sequence has the sequence with SEQ ID N.27 (DEDPK-SHRDPSNRHSYPQQAPYWTHPQR).

In another embodiment of the invention, the antibody binds to the antigen or epitope recognized by the monoclonal antibody disclosed in the following.

In another embodiment, the antibody of the invention comprises the amino acids of the hypervariable region of the antibody disclosed in the following necessary for specifically binding to the epitope to which a monoclonal antibody as disclosed in the following binds.

Such antibody may be obtained by cloning the DNA which encodes said hypervariable region and expressing the DNA, using standard recombinant DNA procedures, in a suitable unicellular or other host. Further, the polypeptide may be synthesized using well known techniques for synthesizing polypeptides, by chemical procedures.

The subject of the invention is not limited to the antibody having variable light and heavy chains and CDRs as herein disclosed. The invention also embraces polypeptides which comprise or consist essentially of an amino acid sequence capable of specifically binding to the same epitope to which the antibody herein disclosed binds. One way to obtain such a polypeptide is to substitute amino acids of the hypervariable region of said antibody selectively so as to identify amino acids which when substituted affect, or do not affect, binding of the polypeptide to the antigen.

All these techniques are well known in the art and within the knowledge of the skilled person.

Figure 26A:
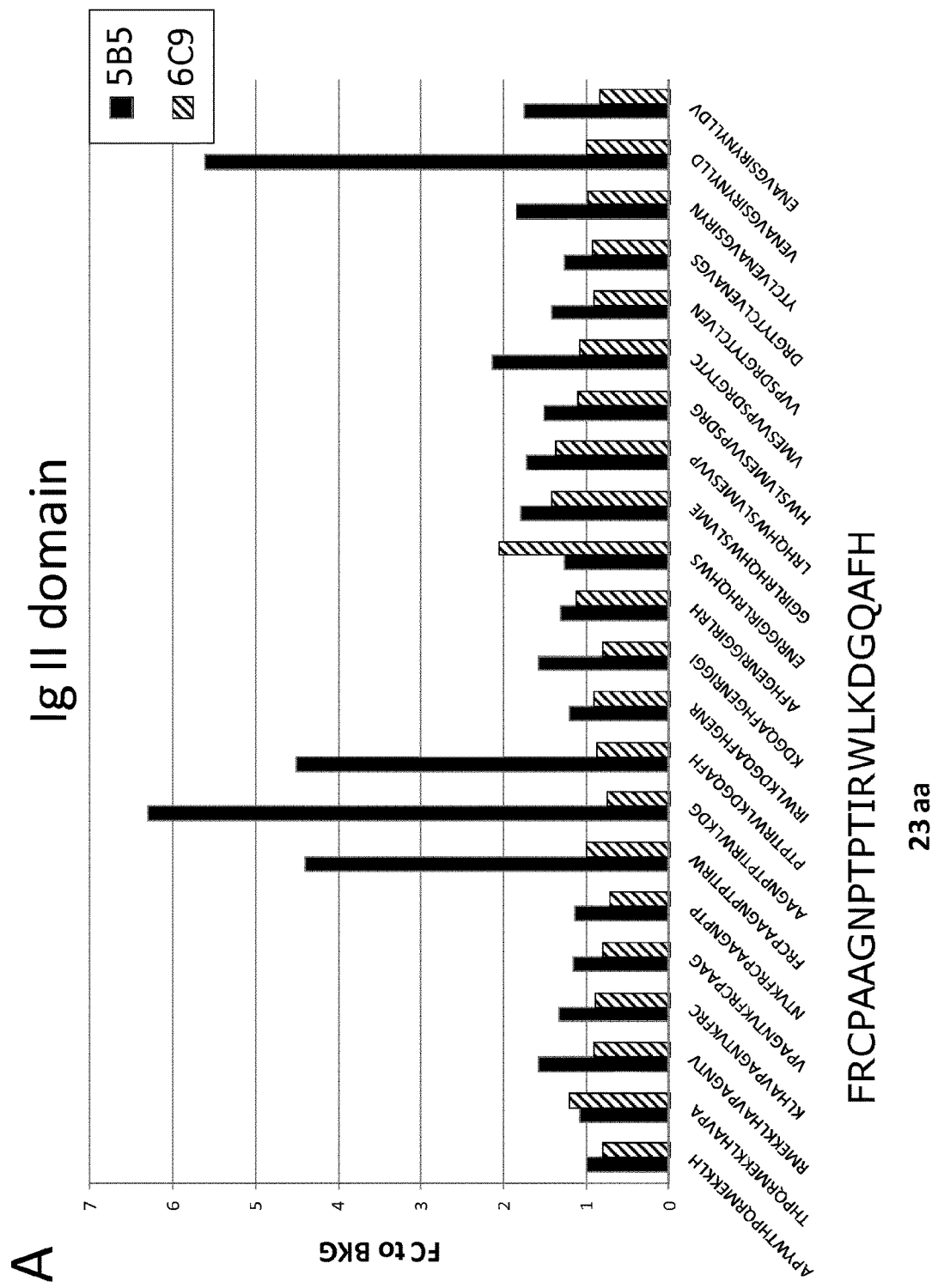
FIG. 26. Epitope mapping for the different anti-FGFR4 antibodies. In panel A, a histogram representative of 2 independent ELISA experiments is shown, where binding of the antibodies ch5B5 (positive, filled bars) and ch6C9 (negative, dash bars) to the Ig II domain peptide collection was analyzed. The ch5B5 binding sequence inferred from this analysis is also shown. In panel A, FIG. 26 discloses SEQ ID NOS 35-57, respectively, in order of appearance. In panel B, a histogram representative of 3 independent ELISA experiments is shown, where binding of the antibodies ch3B6 (positive, filled bars) and ch6C9 (negative, dash bars) to the acid box peptide collection was analyzed. The ch3B6 binding sequence inferred from this analysis is also shown. Underlined are the residues that contribute to the binding; in bold are residues corresponding to the highest peaks. In panel B, FIG. 26 discloses SEQ ID NOS 58-83 and 27, respectively, in order of appearance. In panel C, the alignment of the human FGFR4 protein sequence (SEQ ID NO: 100) (NCBI accession number NP_001341913) and the mouse orthologous sequence (SEQ ID NO: 101) (NCBI accession number NP_032037) within the acid box region is shown and the experimentally identified ch3B6 binding region on the human receptor is indicated (SEQ ID NO: 102). Underlined are the residues that contribute to the binding; in bold are conserved residues between human and mouse.
Figure 26B:
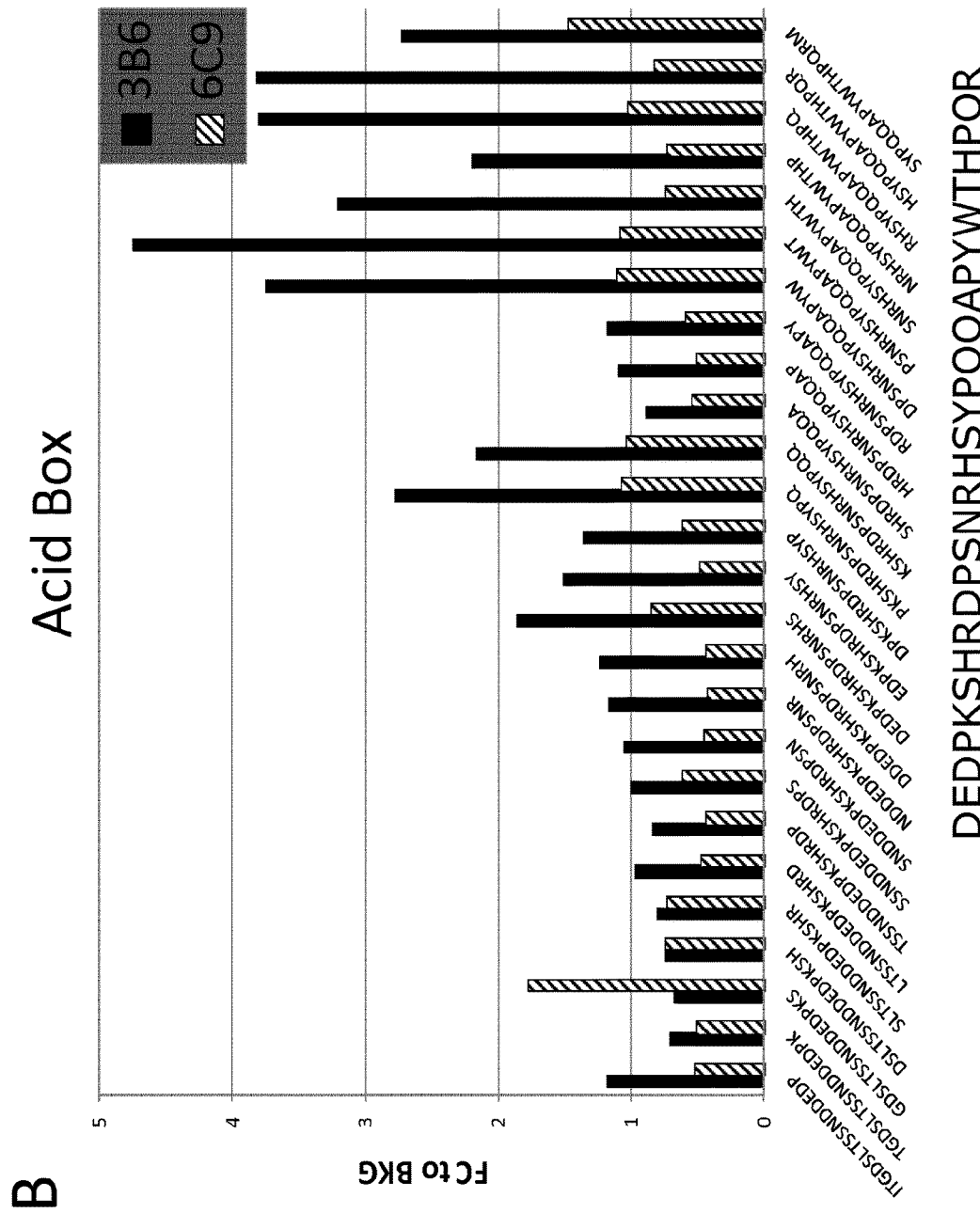

For example, reference can be made to the binding site within the acid box comprising amino acids between 127 and 154 shown in FIG. 26B. Based on this binding site, it is possible for a skilled person to identify the amino acids of the hypervariable region of the antibody disclosed in the following necessary for specifically binding to the epitope.

The antibodies of the invention may be of various immunoglobulin (Ig) types, for example of the IgA-, IgD-, IgE-, IgG- or IgM-type, preferably of the IgG- or IgM-type including but not limited to the IgGI-, IgG2-, IgG3-, IgG4-, IgM I and IgM2-type. In one preferred embodiment the antibody is of the IgGI type.

Also, the constant portion of the light chain can be of the kappa type or of the lambda type, preferably it is of the kappa type.

In some embodiments, the antibody of the invention is a monoclonal antibody.

In some embodiments, it is a human, humanized, or chimeric antibody.

In certain embodiments of the present invention, the antibody comprises specific heavy chain complementarity determining regions CDRH 1, CDRH2 and/or CDRH3 as described herein below.

In one embodiment, the antibody comprises a heavy chain complementarity determining region 1 (CDRH 1) having the amino acid sequence as shown in any one of SEQ ID NOs: 5-6, or an amino acid sequence differing in 1 or 2 amino acids therefrom.

In a further embodiment, the antibody comprises a heavy chain complementarity determining region 2 (CDRH2) having the amino acid sequence as shown in any one of SEQ ID NOs: 7-8, or an amino acid sequence differing in 1 or 2 amino acids therefrom.

In yet a further embodiment, the antibody comprises a heavy chain complementarity determining region 3 (CDRH3) having the amino acid sequence as shown in SEQ ID NO:9, or an amino acid sequence differing in 1 or 2 amino acids therefrom.

The antibody according to the invention may also comprise specific light chain complementarity determining regions CDRLI, CDRL2 and/or CDRL3.

Accordingly, in one embodiment, the antibody comprises a light chain complementarity determining region 1 (CDRLI) having the amino acid sequence as shown in any one of SEQ ID NOs: 14-15, or an amino acid sequence differing in 1 or 2 amino acids therefrom.

In a further embodiment, the antibody comprises a light chain complementarity determining region 2 (CDRL2) having the amino acid sequence as shown in SEQ ID NO: 16, or an amino acid sequence differing in 1 or 2 amino acids therefrom.

In yet a further embodiment, the antibody comprises a light chain complementarity determining region 3 (CDRL3) having the amino acid sequence as shown in SEQ ID NO: 17, or an amino acid sequence differing in 1 or 2 amino acids therefrom.

The antibody of the present invention preferably comprises a specific combination of CDRs (i.e. of CDRH 1, CDRH2 and CDRH3) within one heavy chain.

Accordingly, in one preferred embodiment, the antibody comprises a heavy chain comprising complementarity determining regions CDRH 1, CDRH2 and CDRH3, wherein CDRH 1 is selected from the sequences as shown in SEQ ID NOs: 5-6, or an amino acid sequence differing in 1 or 2 amino acids therefrom, CDRH2 is selected from the sequences shown in SEQ ID NOs: 7-8, or an amino acid sequence differing in 1 or 2 amino acids therefrom, and CDRH3 is shown in SEQ ID NOs: 9, or an amino acid sequence differing in 1 or 2 amino acids therefrom.

Most preferably, the antibody of the invention comprises a heavy chain comprising three CDRs, wherein the combination of CDRH 1, CDRH2 and CDRH3 is selected from those shown in table 1. It is understood that each line of this table represents one specific combination of a CDRH 1, a CDRH2 and a CDRH3.

TABLE 1

| CDRH1 | CDRH2 | CDRH3 |
| --- | --- | --- |
| (NYYM)<br>SEQ ID N. 5 | (TINPSGTRTYYPDSVKG)<br>SEQ ID N. 7 | (LYNNYAFDYT)<br>SEQ ID N. 9 |
| (NYYMS)<br>SEQ ID N. 6 | (TINPSGTRTYYPDSVKG)<br>SEQ ID N. 7 | (LYNNYAFDY)<br>SEQ ID N. 9 |

TABLE 1-continued

| CDRH1 | CDRH2 | CDRH3 |
| --- | --- | --- |
| (NYYMS)<br>SEQ ID N. 6 | (NINPSGTRTYYPDSVKG)<br>SEQ ID N. 8 | (LYNNYAFDY)<br>SEQ ID N. 9 |

According to the present invention, it is further preferred that the antibody comprises a specific combination of CDRs within one light chain (i.e. of CDRLI, CDRL2 and CDRL3). Thus, in one preferred embodiment, the antibody comprises a light chain comprising complementarity determining regions CDRLI, CDRL2 and CDRL3, wherein CDRLI has the amino acid sequence as shown in any of SEQ ID NOs: 14-15, or an amino acid sequence differing in 1 or 2 amino acids therefrom, CDRL2 has the amino acid sequence as shown in SEQ ID NO: 16, or an amino acid sequence differing in 1 or 2 amino acids therefrom, and CDRL3 has the amino acid sequence as shown in SEQ ID NOs: 17, or an amino acid sequence differing in 1 or 2 amino acids therefrom.

Most preferably, the antibody of the invention comprises a light chain comprising three CDRs, wherein the combination of CDRLI, CDRL2 and CDRL3 is selected from those shown in table 2. It is understood that each line of this table represents one specific combination of a CDRLI, a CDRL2 and a CDRL3.

TABLE 2

| CDRL1 | CDRL2 | CDRL3 |
| --- | --- | --- |
| (RASESVSTLMH)<br>SEQ ID N. 14 | (GTSNLES)<br>SEQ ID N. 16 | (QSSWNDPPT)<br>SEQ ID N. 17 |
| (RASESISTLLH)<br>SEQ ID N. 15 | (GTSNLES)<br>SEQ ID N. 16 | (QQSWNDPPT)<br>SEQ IQ N. 17 |

As described above, the complementarity determining regions (CDRs) of an antibody may be flanked by framework regions. A heavy or light chain of an antibody containing three CDRs contains e.g. four framework regions.

Functional fragments and functional derivatives of those antibodies are also within the scope of the invention.

Additionally, the present invention also encompasses those antibodies that recognize the same epitope on human FGFR4 as a specific antibody characterized by the above heavy and/or light chain CDRs.

To determine the epitope on FGFR4 recognized by the antibody, chemically prepared arrays of short peptides derived from the amino acid sequence of the extracellular domain of human FGFR4 can be used to locate and identify antibody epitopes (Reinicke W., Methods Mol. Biol. 2004, 248: 443-63). A further method to map the epitopes in the FGFR4 extracellular domain bound by the antibodies of the invention comprises Snaps/SELDI (Wang et al, Int. J. Cancer, 2001, June 15; 92 (6): 871-6) or a routine cross-blocking assay such as described in Antibodies, A Laboratory Manual, Cold Spring Harbor Laboratory, Ed Harlow and David Lane (1988) can be performed.

According to a particularly preferred embodiment, the antibody of the invention comprises a heavy chain comprising at least one CDR selected from the group consisting of
(a) a CDRH 1 as shown in SEQ ID NO: 5-6, or a CDRH 1 sequence differing in 1 or 2 amino acids therefrom,
(b) a CDRH2 as shown in SEQ ID NO: 7-8, or a CDRH2 sequence differing in 1 or 2 amino acids therefrom, and (c) a CDRH3 as shown in SEQ ID NO: 9, or a CDRH3 sequence differing in 1 or 2 amino acids therefrom, and/or a light chain comprising at least one CDR selected from the group consisting of (d) a CDRL1 as shown in SEQ ID NO: 14-15, or a CDRL1 sequence differing in 1 or 2 amino acids therefrom, (e) a CDRL2 as shown in SEQ ID NO: 16, or a CDRL2 sequence differing in one or two amino acids therefrom, and (f) a CDRL3 as shown in SEQ ID NO: 17, or a CDRL3 sequence differing in 1 or 2 amino acids therefrom.

In a preferred embodiment of the invention, the antibody comprises a heavy chain variable region (VH) as shown in any one of SEQ ID N.1-4 or SEQ ID N.84-88 or a sequence having at least 85% identity with said sequences. Furthermore, the human antibody of the invention preferably comprises a light chain variable region (VL) as shown in any one of SEQ ID N. 10-13 or SEQ ID N.89-91 or a sequence having at least 85% identity with said sequences. At least 85% identity means an amino acid identity percentage comprised between 85 and 100%, preferably being 90, 95 or 99%.

Above mentioned sequences with SEQ ID N.1-4 are herein disclosed; in each sequence the positions of the CDRs within the variable chain are underlined:

-variable heavy chain
SEQ ID N. 1
EVQLVESGGGLVQPGRSLKLSCAASGFTFSNYYMAWVRQAPKKGLEWVA
TINPSGTRTYYPDSVKGRFTLSRDSAKSSLYLQMNSLKSEDTATFYCAR
LYNNYAFDYWGQGVMVTVSS -variable heavy chain
SEQ ID N. 2
EVQLVESGGGLVQPGGSLRLSCAASGFTFSNYYMSWVRQAPGKGLEWVA
TINPSGTRTYYPDSVKGRFTISRDNA KNSLYLQMNSLRAEDTAVYYCA
RLYNNYAFDYWGQGTLVTVSS -variable heavy chain
SEQ ID N. 3
EVQLVESGGGLVQPGGSLRLSCAASGFTFSNYYMSWVRQAPGKGLEWVA
NINPSGTRTYYPDSVKGRFTISRDNA KNSLYLQMNSLRAEDTAVYYCA
RLYNNYAFDYWGQGTLVTVSS -variable heavy chain
SEQ ID N. 4
EVQLVESGGGLVQPGGSLRLSCAASGFTFSNYYMSWVRQAPGKGLEWVA
TINPSGTRTYYPDSVKGRFTISRDSA KSSLYLQMNSLRAEDTAVYYCA
RLYNNYAFDYWGQGTLVTVSS Above mentioned sequences with SEQ ID N.84-88 are herein disclosed; in each sequence the positions of the CDRs within the variable chain are underlined:

-variable heavy chain
SEQ ID N. 84
EVQLVESGGGLVQPGGSLRLSCAASGFTFSNYYMSWVRQAPGKGLEWVA
TINPSGTRTYYPDSVKGRFTLSRDNA KNSLYLQMNSLRAEDTAVYYCA
RLYNNYAFDYWGQGTLVTVSS -variable heavy chain
SEQ ID N. 85
EVQLVESGGGLVQPGGSLRLSCAASGFTFSNYYMAWVRQAPGKGLEWVA
TINPSGTRTYYPDSVKGRFTLSRDNA KNSLYLQMNSLRAEDTATFYCA
RLYNNYAFDYWGQGTLVTVSS -variable heavy chain
SEQ ID N. 86
EVQLVESGGGLVQPGGSLRLSCAASGFTFSNYYMAWVRQAPGKGLEWVA
TINPSGTRTYYPDSVKGRFTLSRDSA KSSLYLQMNSLRAEDTATFYCA
RLYNNYAFDYWGQGTLVTVSS -variable heavy chain
SEQ ID N. 87
EVQLVESGGGLVQPGGSLRLSCAASGFTFSNYYMSWVRQAPGKGLEWVA
TINPSGTRTYYPDSVKGRFTLSRDSA KSSLYLQMNSLRAEDTAVYYCA
RLYNNYAFDYWGQGTLVTVSS -variable heavy chain
SEQ ID N. 88
EVQLVESGGGLVQPGGSLRLSCAASGFTFSNYYMAWVRQAPGKGLEWVA
TINPSGTRTYYPDSVKGRFTISRDNA KNSLYLQMNSLRAEDTATYYCA
RLYNNYAFDYWGQGTLVTVSS Above mentioned sequences with SEQ ID N.10-13 are herein disclosed; in each sequence the positions of the CDRs within the variable chain are underlined:

-variable light chain
SEQ ID N. 10
DVQMTQSPALAVSPGERVSISCRASESVSTLMHWYQQKPGQQPKLLIYG
TSNLESGVPARFSGSGSGTDFTLNID PVEADDTATYFCQQSWNDPPTF
GGGTKLEVK -variable light chain
SEQ ID N. 11
DVQMTQSPALAVSPGERVSISCRASESVSTLMHWYQQKPGQQPKLLIYG
TSNLESGVPARFSGSGSGTDFTLNID PVEADDTATYFCQQSWNDPPTF
GGGTKLELK variable light chain
SEQ ID N. 12
DIQMTQSPSSLSASVGDRVTITCRASESISTLLHWYQQKPGKAPKLLIY
GTSNLESGVPSRFSGSGSGTDFTLTI SSLQPEDFAYYCQQSWNDPPFG
GGTKVEIK -variable light chain
SEQ ID N. 13
DIQMTQSPSSLSASVGDRVTITCRASESVSTLMHWYQQKPGKAPKLLIY
GTSNLESGVPSRFSGSGSGTDFTLTI SSLQPEDFATYYCQQSWNDPPT
FGGGTKVEIK Above mentioned sequences with SEQ ID N. 89-91 are herein disclosed; in each sequence the positions of the CDRs within the variable chain are underlined:

-variable light chain
SEQ ID N. 89
DIQMTQSPSSLSASVGDRVTITCRASESISTLLHWYQQKPGKQPKLLIY
GTSNLESGVPSRFSGSGSGTDFTLTI SSLQPEDFATYFCQQSWNDPPT
FGGGTKVEIK -variable light chain
SEQ ID N. 90
DIQMTQSPSSLSASVGDRVTITCRASESVSTLMHWYQQKPGKQPKLLIY
GTSNLESGVPSRFSGSGSGTDFTLTI SSLQPEDFATYFCQQSWNDPPT
FGGGTKVEIK -variable light chain
SEQ ID N. 91
DVQMTQSPSSLSASVGDRVTITCRASESISTLLHWYQQKPGKAPKLLIY
GTSNLESGVPSRFSGSGSGTDFTLTI SSLQPEDFATYFCQQSWNDPPT
FGGGTKVEIK Particularly preferred are human antibodies comprising a heavy chain variable region as shown in any one of SEQ ID NOs. 2-4 and a light chain variable region as shown in any one of SEQ ID NOs. 12-13.

An antibody, or antigen-binding fragment thereof, that binds to the acid box of FGFR4 wherein the variable region of its heavy chain is coded by a nucleotide sequence having at least 80% identity with the sequence SEQ ID NO: 18-22 or SEQ ID NO: 92-96 and the variable region of its light chain is coded by a nucleotide sequence having at least 80% identity with the sequence SEQ ID NO: 23-26 or SEQ ID NO: 97-99 is still within the scope of the present invention, provided that the antibody keeps its binding specificity. At least 80% identity means a nucleotide identity percentage comprised between 80 and 100%, preferably being 90, 95 or 99%.

Particularly preferred are human antibodies (hu3B6a and hu36Bc) comprising a heavy chain comprising a CDRH 1 as shown in SEQ ID NO: 6, a CDRH2 as shown in SEQ ID NO: 7 and a CDRH3 as shown in SEQ ID NO: 9 and a light chain comprising a CDRL1 as shown in SEQ ID NO: 15, a CDRL2 as shown in SEQ ID NO: 16 and a CDRL3 as shown in SEQ ID NO: 17. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 2 and a light chain variable region according to SEQ ID NO: 12 (hu3B6a). In another particularly preferred embodiment, the human antibody comprises a heavy chain variable region according to SEQ ID NO: 4 and a light chain variable region according to SEQ ID NO: 12 (hu3B6c). Also encompassed are human antibodies wherein the sequences of the variable region of the heavy chain and/or the light chain have at least 85% identity with the sequences shown in SEQ ID NOs. 2, 4 and 12.

Particularly preferred is a human antibody (hu3B6b) comprising a heavy chain comprising a CDRH 1 as shown in SEQ ID NO: 6, a CDRH2 as shown in SEQ ID NO: 8 and a CDRH3 as shown in SEQ ID NO: 9 and a light chain comprising a CDRL1 as shown in SEQ ID NO: 15, a CDRL2 as shown in SEQ ID NO: 16 and a CDRL3 as shown in SEQ ID NO: 17. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 3 and a light chain variable region according to SEQ ID NO: 12. Also encompassed are human antibodies wherein the sequences of the variable region of the heavy chain and/or the light chain have at least 85% identity with the sequences shown in SEQ ID NOs. 3 and 12.

Particularly preferred are human antibody (hu3B6d and hu3B6f) comprising a heavy chain comprising a CDRH 1 as shown in SEQ ID NO: 6, a CDRH2 as shown in SEQ ID NO: 7 and a CDRH3 as shown in SEQ ID NO: 9 and a light chain comprising a CDRL1 as shown in SEQ ID NO: 14, a CDRL2 as shown in SEQ ID NO: 16 and a CDRL3 as shown in SEQ ID NO: 17. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 2 and a light chain variable region according to SEQ ID NO: 13 (hu3B6d). In another particularly preferred embodiment, the human antibody comprises a heavy chain variable region according to SEQ ID NO: 4 and a light chain variable region according to SEQ ID NO: 13 (hu3B6f). Also encompassed are human antibodies wherein the sequences of the variable region of the heavy chain and/or the light chain have at least 85% identity with the sequences shown in SEQ ID NOs. 2, 4 and 13.

Particularly preferred is a human antibody (hu3B6e) comprising a heavy chain comprising a CDRH 1 as shown in SEQ ID NO: 6, a CDRH2 as shown in SEQ ID NO: 8 and a CDRH3 as shown in SEQ ID NO: 9 and a light chain comprising a CDRL1 as shown in SEQ ID NO: 14, a CDRL2 as shown in SEQ ID NO: 16 and a CDRL3 as shown in SEQ ID NO: 17. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 3 and a light chain variable region according to SEQ ID NO: 13. Also encompassed are human antibodies wherein the sequences of the variable region of the heavy chain and/or the light chain have at least 85% identity with the sequences shown in SEQ ID NOs. 3 and 13.

Another preferred antibody is a rat monoclonal antibody (BMK-3B6-E4-C3) comprising a heavy chain comprising a CDRH 1 as shown in SEQ ID NO: 5, a CDRH2 as shown in SEQ ID NO: 7 and a CDRH3 as shown in SEQ ID NO: 9 and a light chain comprising a CDRL1 as shown in SEQ ID NO: 14, a CDRL2 as shown in SEQ ID NO: 16 and a CDRL3 as shown in SEQ ID NO: 17. Also encompassed are antibodies, wherein one or more of the CDRs differ in 1 or 2 amino acids or antibodies recognizing the same epitope on human FGFR4. In a particularly preferred embodiment, the antibody comprises a heavy chain variable region according to SEQ ID NO: 1 and a light chain variable region according to SEQ ID NO: 10. Also encompassed are antibodies wherein the sequences of the variable region of the heavy chain and/or the light chain have at least 85% identity with the sequences shown in SEQ ID NOs. 1 and 10.

Another preferred antibody is a chimeric antibody (ch3B6) comprising a heavy chain comprising a CDRH 1 as shown in SEQ ID NO: 5, a CDRH2 as shown in SEQ ID NO: 7 and a CDRH3 as shown in SEQ ID NO: 9 and a light chain comprising a CDRL1 as shown in SEQ ID NO: 14, a CDRL2 as shown in SEQ ID NO: 16 and a CDRL3 as shown in SEQ ID NO: 17. Also encompassed are antibodies, wherein one or more of the CDRs differ in 1 or 2 amino acids or antibodies recognizing the same epitope on human FGFR4. In a particularly preferred embodiment, the antibody comprises a heavy chain variable region according to SEQ ID NO: 1 and a light chain variable region according to SEQ ID NO: 11. Also encompassed are antibodies wherein the sequences of the variable region of the heavy chain and/or the light chain have at least 85% identity with the sequences shown in SEQ ID NOs. 1 and 11.

In embodiments of the invention, the antibody of the invention comprises a light chain and a heavy chain wherein the variable region of the heavy chain has a sequence selected from anyone of sequences with SEQ ID N. 1-4, 84-88, and the variable region of the light chain has a sequence selected from anyone of sequences with SEQ ID N. 10-13, 89-91.

In embodiments of the invention, the antibody of the invention comprises a light chain and a heavy chain wherein the variable region of the heavy chain is coded by a nucleotide sequence selected from anyone of sequences with SEQ ID N. 18-22, 92-96, and the variable region of the light chain is coded by a nucleotide sequence selected from anyone of sequences with SEQ ID N. 23-26, 97-99.

In preferred embodiments of the invention, the antibody of the invention comprises a light chain and a heavy chain wherein the combination of variable light chain (VL) and variable heavy chain (VH) is selected from those shown in table 3 below. Also the antibody comprises a combination of CDRH and CDRL preferably selected from those shown in following table 3. It is understood that each line of this table represents one specific combination of a CDRL1, a CDRL2, a CDRL3, a CDRH 1, a CDRH2 and a CDRH3 and a specific combination of variable light chain and variable heavy chain.

TABLE 3

The numbers indicate the SEQ ID N.
as per the enclosed sequence listing.

| Antibody | VH | VL | CDRH 1 | CDRH2 | CDRH3 | CDRL1 | CDRL2 | CDRL3 | internal code |
|---|---|---|---|---|---|---|---|---|---|
| Hu3B6a | 2 | 12 | 6 | 7 | 9 | 15 | 16 | 17 | |
| Hu3B6b | 3 | 12 | 6 | 8 | 9 | 15 | 16 | 17 | |
| Hu3B6c | 4 | 12 | 6 | 7 | 9 | 15 | 16 | 17 | |
| Hu3B6d | 2 | 13 | 6 | 7 | 9 | 14 | 16 | 17 | |
| Hu3B6e | 3 | 13 | 6 | 8 | 9 | 14 | 16 | 17 | |
| Hu3B6f | 4 | 13 | 6 | 7 | 9 | 14 | 16 | 17 | |

As mentioned above, the antibodies of the invention show advantageous properties with respect to their binding specificity and biological activity, in particular with respect to their capability to recognize a specific epitope of FGFR4 and to decrease cell growth and cell migration.

In particular, the antibodies of the invention hu3B6, ch3B6 and BMK-3B6-E4-C3 have anti-tumor activity.

Also, they specifically bind to FGFR4 and preferably show no cross-reactivity to other FGF receptors FGFR1-3.

The antibodies of the invention are capable of inhibiting FGF19 binding to FGFR4.

The effect of the antibody on ligand binding to FGFR4 can be determined using a solid phase receptor-binding assay. Those antibodies which reduce the binding affinity of ligand for the FGFR4 receptor or which block binding of ligand to FGFR4 can be identified.

Particularly preferred antibodies of the present invention are capable of blocking binding to the receptor of further FGFR4 ligands including, for example, FGF1, FGF8, FGF17, FGF18, FGF21, FGF23 (Zhang et al., 2006) by at least 60%, preferably at least 70% and more preferably at least 80% or 87%.

Blocking of ligand binding to human FGFR4 results in inhibition of FGFR4 signalling. FGFR4 activation involves the inhibition of Cyp7Al and the induction of CTGF gene transcription, and also the stimulation of the phosphorylation of the receptor itself and of downstream effector proteins such as FRS2 and ErkI/2. To select for blocking antibodies, cells can be pre-incubated with buffer (control) or antibody, then treated with ligand or a control buffer. The cells are then lysed and cell lysates can be processed either for gene expression analysis by RT-PCR using Cyp7Al and CTGF specific probes, or analyzed by SDS-PAGE and Western blots probed with anti-phospho FGFR4, anti-phospho FRS2, and/or anti-phospho ErkI/2 antibodies. Those antibodies which relieve Cyp7Al inhibition, repress CTGF expression, and/or reduce FGFR4, FRS2, and ErkI/2 phosphorylation relative to control (untreated cells) are selected.

In vitro experiments can be conducted in order to determine the ability of the antibodies of the invention to inhibit FGFR4-dependent cell proliferation. Clonogenic assays and soft agar colony formation assays can be conducted. An appropriate number of single cells of interest are seeded and treated or not with antibodies diluted in appropriate medium. Antibodies are replaced twice weekly for the duration of the experiment (10-15 days) and then colonies produced are counted. To select for those antibodies which reduce FGFR4-mediated cell migration, transmigration experiments can be performed. Cells are incubated with antibody. An appropriate number of cells may be placed in the top chamber of coated transwell plates with 8 $\mu\eta_{JT}$ pores (BD Biosciences, San Jose, Calif.; U.S.A.). In the case of stimulation medium alone or containing a chemotactic agent is used in the bottom chamber. Cells are left to migrate and are subsequently stained. Stained cells are counted; percent inhibition is expressed as inhibition relative to a control antibody.

It was found that the antibodies of the invention have an anti-tumor activity.

The anti-tumor efficacy of therapeutic antibodies may be evaluated in human xenograft tumor studies. In these studies, human tumors grow as xenografts in immunocompromised mice and therapeutic efficacy is measured by the degree of tumor growth inhibition. In order to determine if the FGFR4 antibodies of the invention interfere with tumor growth of human cancer cells in immunocompromised mice, cells are implanted in mice. Tumors are subcutaneously grown on the back or in the flanks of the animal. Treatment may be started immediately or when tumors reach a certain mean volume. Prior to the first treatment, mice are randomized and statistical tests are performed to assure uniformity in starting tumor volumes (mean, median and standard deviation) across treatment groups. Treatment is started with a loading dose of 25 mg/kg followed by 25 mg/kg injections twice a week by intraperitoneal injection.

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81: 6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In an exemplary embodiment, chimeric antibodies can be prepared by cloning the cDNAs encoding for the rat variable heavy chain regions in frame with the coding sequence for the human IgGI constant regions and the cDNAs encoding for the rat variable light chain regions in frame with the coding sequence for the human kappa chain constant region into the same expression vector. The expression vectors encoding the hybrid heavy and light chains are then co-transfected into suitable cell lines and the desired antibodies are obtained.

In certain embodiments, the antibody is a humanized antibody. Typically, a non-human antibody is humanized to reduce immunogenicity to humans, while retaining the specificity and affinity of the parental non-human antibody. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies may be prepared by humanization of monoclonal antibodies according to known techniques. Typically, a non-human antibody is humanized to reduce immunogenicity to humans, while retaining the specificity and affinity of the parental non-human antibody. Humanized antibodies and methods of making them are reviewed, e.g. in Alamagro and Fransson, Front. Biosci. 13: 1619-1633 (2008) and are further described, e.g., in Riechmann et al., Nature 332: 323-329 (1988); Queen et al., Proc. Nat'l Acad. Sci. USA 86: 10029-10033 (1989); U.S. Pat. Nos. 5,821, 337, 7,527,791, 6,982,321, and 7,087,409; Kashmiri et al., Methods 36: 25-34 (2005) (describing SDR (a-CDR) grafting); Padlan, Mol. Immunol. 28:489-498 (1991) (describing "resurfacing"); Dal!' Acqua et al., Methods 36:43-60 (2005) (describing "FR shuffling"); and Osbourn et al., Methods 36:

61-68 (2005) and Klimka et al., Br. J. Cancer, 83: 252-260 (2000) (describing the "guided selection" approach to FR shuffling).

Human framework regions that may be used for humanization include but are not limited to: framework regions selected using the "best-fit" method (see, e.g., Sims et al. J. Immunol. 151: 2296 (1993)); framework regions derived from the consensus sequence of human antibodies of a particular subgroup of light or heavy chain variable regions (see, e.g., Carter et al. Proc. Na. Acad. Sci. USA, 89:4285 (1992); and Presta et al. J. Immunol., 151: 2623 (1993)); human mature (somatically mutated) framework regions or human germline framework regions (see, e.g., Almagro and Fransson, Front. Biosci.

13: 1619-1633 (2008)); and framework regions derived from screening FR libraries (see, e.g., Baca et al., J. Biol. Chem. 272: 10678-10684 (1997) and Rosok et al., J. Biol. Chem. 271:22611-22618 (1996)).

In an exemplary embodiment of the invention, fully humanized antibody are obtained using humanized expression vectors generated starting from a chimeric expression vector and replacing the original rat variable heavy chain coding sequence with the humanized variable heavy chain coding sequence and the original rat variable light chain coding sequence with the humanized variable light chain coding sequence. The expression vectors so obtained are then co-transfected in suitable cell lines to produce the humanized antibodies.

Human antibodies may be prepared from genetically engineered animals, e.g. animals comprising a xenogenic immune system or from antibody display libraries according to known techniques. Human antibodies are described generally in van Dijk and van de Winkel (Curr. Opin. Pharmacol. 5: 368-74 (2001)) and Lonberg (Curr. Opin. Immunol. 20: 450-459 (2008)). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see for example Lonberg, Nat. Biotech. 23: 1117-1125 (2005). Human variable regions from intact antibodies generated by such animals may be further modified, e.g. by combining with a different human constant region.

Human antibodies can also be made by hybridoma-based methods. Human myeloma and mouse-human heteromyeloma cell lines for the production of human monoclonal antibodies have been described (see e.g. Kozbor J. Immunol. 133: 3001 (1984); Brodeur et al., Monoclonal Antibody Production Techniques and Applications, pp. 51-63). Human antibodies generated via human B-cell hybridoma technology are also described in Li et al, Proc. Natl. Acad. Sci., USA 103: 3557-3562 (2006).

Human antibodies may also be generated by phage display methods (see e.g., U.S. Pat. Nos. 6,248,516, 5,403,484, 5,969,108, 5,885,793, 6,696,248, 5,849,500). Techniques for selecting human antibodies from antibody libraries are known in the art. (see e.g., Carmen, S. et al., Briefings in Functional Genomics and Proteomics (2002), 1 (2), p. 189-203; and Siriwardena, D. et al., Ophthalmology (2002) 109 (3), p. 427-431). For example, a phage display method can be used, which involves causing human antibody variable regions to be expressed as a single-chain antibody (scFv) on phage surface and selecting phages binding to antigens (Nature (1991), 352, (6336), p. 624-628, Journal of Molecular Biology (1992), 227, (2), p 381-388, and Nature Biotechnology (2005), 23, (9), p. 1105-1116). Likewise, another phage display method can also be used, which involves causing human antibody Fab (antigen-binding fragment) to be expressed on the surface of phage and selecting phages binding to antigens (WO 97/08320 and WO 01/05950). Genes of the phages selected based on antigen binding can be analyzed to thereby determine DNA sequences encoding human antibody variable regions binding to the antigens. When the DNA sequence of scFv or Fab binding to the antigens is clarified, CDR sequences are extracted therefrom, and expression vectors having the sequences can be prepared and introduced into appropriate hosts, followed by gene expression to obtain human antibodies (WO 92/01047, WO 92/20791, WO 93/06213, WO 93/11236, WO 93/19172, WO 95/01438, WO 95/15388, Annu. Rev. Immunol (1994) 12, p. 433-455, and Nature Biotechnology (2005) 23 (9), p. 1105-1116). Human antibodies may also be generated by isolating Fv clone variable domain sequences selected from human-derived phage display libraries. Such variable domain sequences may then be combined with a desired human constant domain. Techniques for selecting human antibodies from antibody libraries are known in the art.

In a particular embodiment of the present invention, humanization of the antibody ch3B6 was obtained by grafting the original hybridoma rat CDR sequences into selected human immunoglobulin variable regions. To optimize the humanized variants, the human germline immunoglobulin variable sequences most similar to those of the original rat antibody 3B6 were identified and selected. Based on the homology with known immunoglobulin crystal structures, a 3D model of the selected human germline variable regions was generated both for the heavy chain variable region (VH), and for the light chain variable region (VL). Each amino acid position within the 3D model was evaluated in order to decide which additional amino acid residues within the human frameworks needed to be substituted by the corresponding original murine residues, with particular attention for the amino acids potentially affecting the antigen binding or the VH/VL orientation. Slightly different versions of the humanized sequences were designed, three for VH and two for VL, respectively, whose combination produces six different antibodies (hu3B6a, hu3B6b, hu3B6c, hu3B6d, hu3B6e, hu3B6f).

The invention also encompasses fragments of human antibodies, e.g. portions of the above-mentioned antibodies which comprise at least one antigen binding site. Examples of antibody fragments include Fab fragments, Fab' fragments, F(ab')2 fragments, Fv fragments, diabodies or single chain antibody molecules and other fragments as long as they exhibit the desired capability of binding to human FGFR4. For a review of certain antibody fragments see Hudson et al., Nat. Met. 9: 129-134 (2003).

In certain embodiments, amino acid sequence variants of the antibodies provided herein are contemplated as long as they exhibit the desired capability of binding to human FGFR4. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from and/or insertions into and/or substitutions of residues within the amino acid sequences of the antibody. Any combination of deletion, insertion and substitution can be made to arrive at the final construct, provided that the final construct possesses the desired characteristics, e.g. antigen binding.

The antibody according to the present invention can be obtained by means of preparation methods which are part of the common general knowledge in this field.

For example, reference can be made to the last edition of "Current protocols in immunology" Colligan et al. eds., John Wiley & Sons, Inc., NY.

In an embodiment, the monoclonal antibody according to present invention is prepared by genetic immunization, as shown in Example 3. Genetic immunization is well-known in the art and commonly used by those of ordinary skill in the art. Reference for this technique can be found for example in Tang D C, DeVit M, Johnston S A. Nature. 1992, 356(6365): 152-154.

The antibody of the present invention may be coupled to a heterologous group, e.g. an effector group. Such an antibody conjugate is especially suitable for therapeutic applications. The term "effector group" may refer to a cytotoxic group, such as a radioisotope or a radionuclide, a toxin, a therapeutic group or another effector group known in the art.

Conjugates wherein the antibody is coupled to a therapeutic group, so-called antibody-drug-conjugates (ADCs) are particularly preferred.

The antibody of the present invention, due to its properties of targeting FGFR4 selectively, is particularly useful in building antibody-drug conjugates (ADC). In preferred embodiments, in said ADC the drug component to be attached to the antibody is a toxin, preferably selected from the group consisting of: auristatins, maytansinoids, calicheamycins, tubulysins, duocarmycins, camptothecin analogs, benzodiazepines, doxorubicins, α-amanitin derivatives, anthracyclins, rhizoxins, thailanstatins, spliceostatins, cryptophycins and histone deacetylase inhibitors. For a review on this topic reference can be made to Beck et al., Nat Rev Drug Discov. 16: 315-337 (2017).

According to an embodiment of the present invention the conjugate (ADC) with the monoclonal antibody disclosed herein comprises a cryptophycin, in particular a cryptophycin of the following formula:

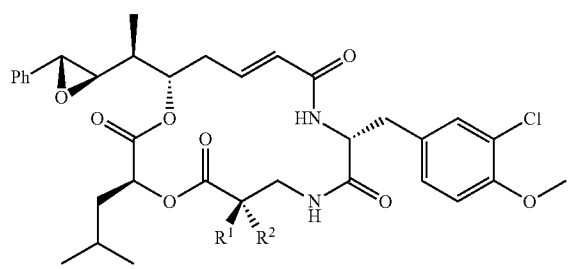

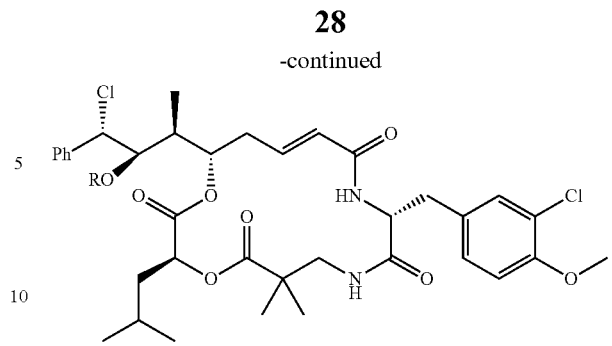

Cryptophycin-1: R=R=H Cryptophycin-55: R=H

Cryptophycin-52: $R^1$=CH$_3$, $R^2$=H Cryptophycin-55-Glycinate: R=CO—CH$_2$NH

According to an embodiment of the present invention the conjugate has formula (I)

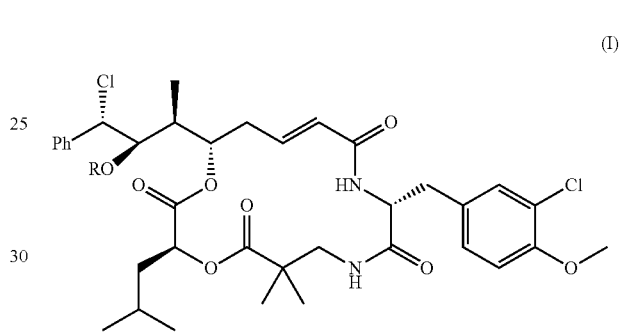

(I)

wherein R is —CO—CH$_2$—X-(A)$_n$-B wherein X is selected from the group consisting of NR$^a$, wherein R$^a$ is selected from a group consisting of H and C$_1$-C$_{10}$ alkyl, and O;

A, which can be present or absent, is a self-immolative linker, n is 0 or 1;

B is an antibody as disclosed in the present invention;

and the pharmaceutically acceptable salts thereof.

In an embodiment of the present invention, in the conjugate of formula (I) the linker A is a moiety of formula (II)

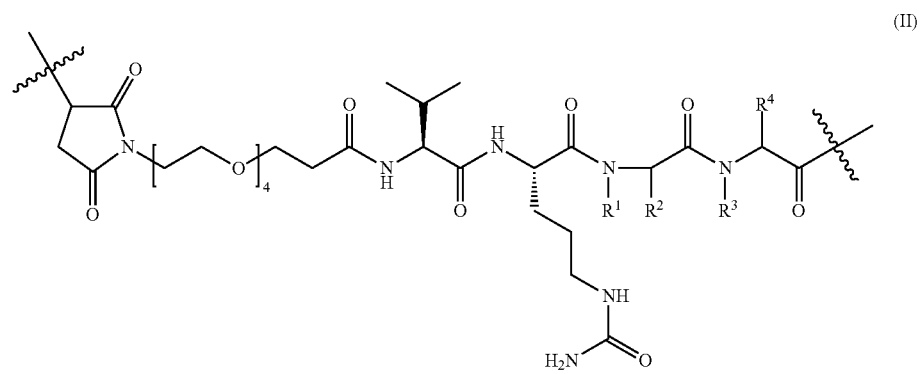

(II)

wherein $R^1$ is selected from the group consisting of H, $(C_1-C_{10})$ alkyl, $R^2$, optionally together with $R^1$, is the residue of an amino acid side chain, $R^3$ is selected from the group consisting of H, $(C_1-C_{10})$ alkyl, $R^4$, optionally together with $R^3$, is the residue of an amino acid side chain.

In an embodiment of the present invention, in the conjugate of formula (I) the linker A is selected from the group consisting of

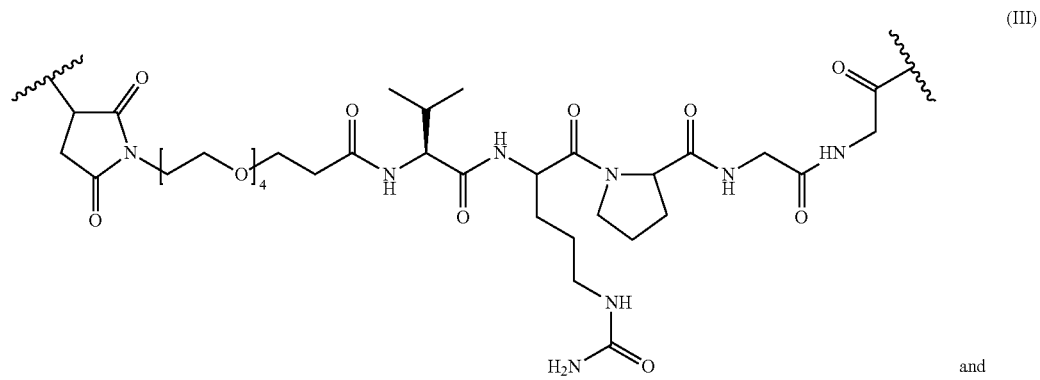

(III)

and

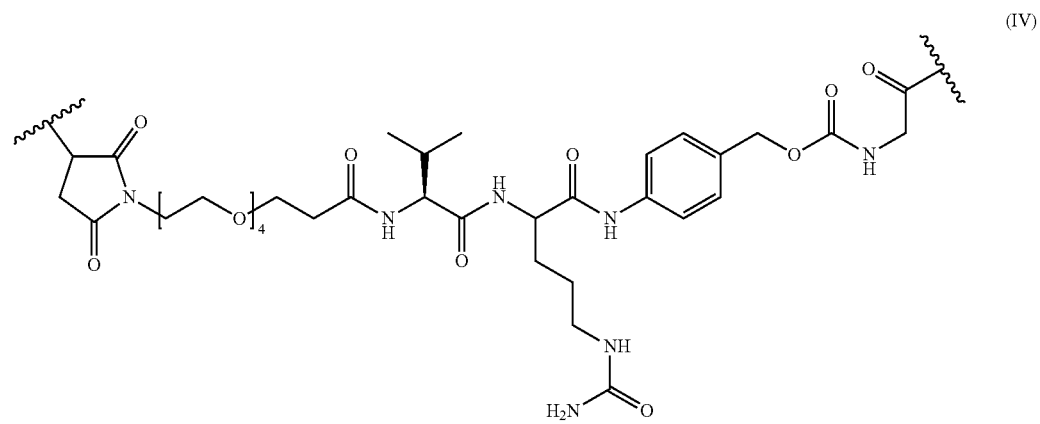

(IV)

In an embodiment of the present invention, the above conjugate has formula (V)

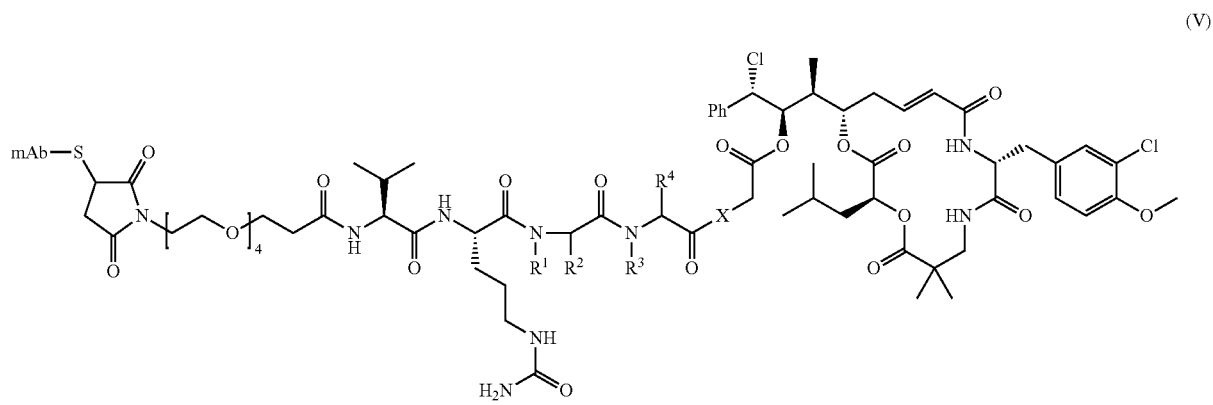

(V)

wherein $R^1$, $R^2$, $R^3$ and $R^4$ are as defined above, X is selected from the group consisting of NH, N—($C_1$-$C_{10}$)-Alkyl, O; mAb represents a monoclonal antibody as disclosed in the present invention.

In an embodiment of the present invention, the above conjugate has formula (VI), suitable for diagnostic applications. As used herein, the term "labeling group" refers to a detectable marker, e.g. a radiolabeled amino acid or biotin moiety, a fluorescent marker, an enzyme or any other type of marker which is known in the art. The linking of antibodies or antibody fragments of the invention to radioisotopes e.g. provides advantages to tumor (VI)

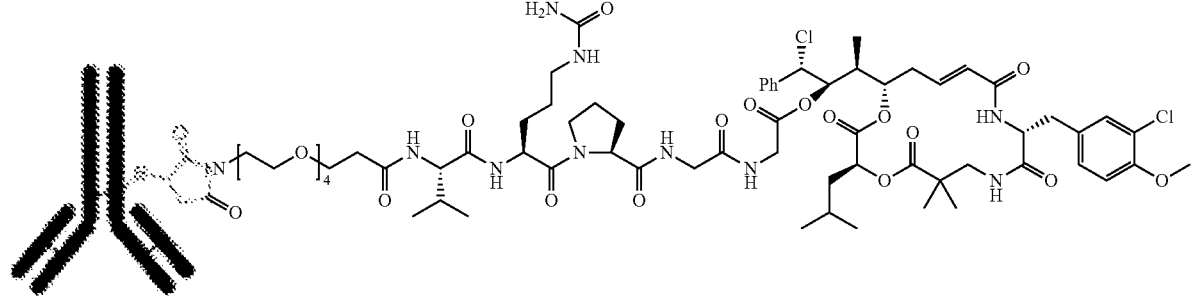

wherein the symbol at the left end of the formula represents a monoclonal antibody as disclosed in the present invention.

In an embodiment of the present invention, the above conjugate has formula (VII)

treatments. Unlike chemotherapy and other forms of cancer treatment, radioimmunotherapy or the administration of a radioisotope-antibody combination targets the cancer cells with minimal damage to surrounding normal healthy tissue.

(VII)

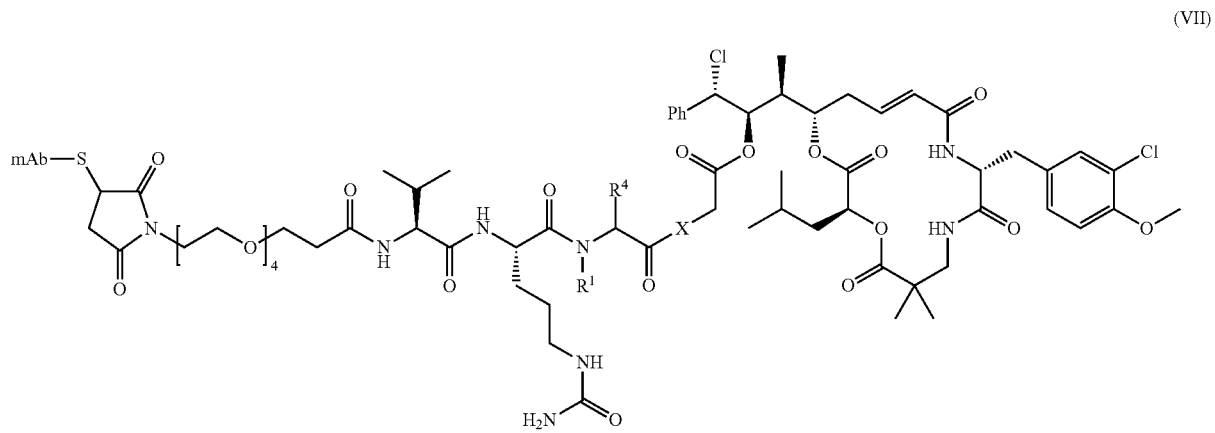

wherein $R^1$ is selected from the group consisting of H, ($C_1$-$C_{10}$) alkyl, $R^4$, optionally together with $R^1$, is the residue of an amino acid side chain; X is selected from the group consisting of NH, N—($C_1$-$C_{10}$), Alkyl O; mAb represents a monoclonal antibody as disclosed in the present invention.

All the above embodiments also comprise the respective pharmaceutically acceptable salts.

In a preferred embodiment, the antibody of the present invention is comprised in an ADC, wherein the drug moiety is a cryptophycin as disclosed in WO2016146638.

In another preferred embodiment, the antibody of the present invention is comprised in an ADC, wherein the drug moiety is a cryptophycin and the linkers are as disclosed in WO2016146638.

In another preferred embodiment, the antibody of the present invention corresponds to the group B in the compound of formula (I) disclosed in WO2016146638.

Also, the antibody of the invention may be coupled to a labeling group. Such an antibody conjugate is particularly In some embodiments, the antibody of the invention can be engineered in order to improve, for example, antigen binding properties, effector functions, pharmacokinetics, pharmaceutical properties and safety issues. In particular, the variable regions of the antibody can be engineered. Engineering antibodies, in particular for obtaining the above mentioned effects, is a common activity in the immunology field. Reference can be made, for example, to the review of Igawa T, Tsunoda H, Kuramochi T, Sampei Z, Ishii S, Hattori K. MAbs. 2011 May-June; 3(3): 243-52, "Engineering the variable region of therapeutic IgG antibodies". In particular, glycoengineered versions of the antibody of the invention are within the scope of the present invention and they can be obtained by the skilled person according to the general knowledge in the field.

The invention also refers to a nucleic acid molecule encoding the antibody as described above.

The term "nucleic acid molecule" encompasses DNA, e.g. single- or double-stranded DNA or RNA. The DNA may be of genomic, cDNA or synthetic origin, or a combination thereof. The nucleic acid molecule of the invention may be in operative linkage to an expression control sequence, i.e. to a sequence which is necessary to effect the expression of coding nucleic acid sequences. Such expression control sequences may include promoters, enhancers, ribosomal binding sites and/or transcription termination sequences. Specific examples of suitable expression control sequences are known in the art.

According to a preferred embodiment, the invention is directed to an isolated nucleic acid molecule selected from the group consisting of
(a) a nucleic acid sequence encoding an antibody, a fragment or a derivative thereof as defined above,
(b) a nucleic acid sequence as shown in any one of SEQ ID NOs: 18-22, 92-96 and SEQ ID NOs. 23-26, 97-99 or in SEQ ID N.28-31 and SEQ ID NOs 32-34,
a nucleic acid sequence complementary to any one of the sequences in (a) or (b), and
a nucleic acid sequence capable of hybridizing to (a) or (b) under stringent conditions.

According to a particularly preferred embodiment of the invention, a nucleic acid molecule comprises a sequence encoding the variable region of the heavy chain and a sequence encoding the variable region of the light chain of the antibody.

In an alternative embodiment, a combination of two nucleic acid molecules is provided, wherein one nucleic acid molecule encodes the light chain of the antibody and the other nucleic acid molecule encodes the heavy chain of the antibody.

The nucleic acid sequence encoding the variable region of the heavy chain is preferably selected from the sequences as shown in any one of SEQ ID NOs. 18-22. The nucleic acid sequence encoding the variable region of the light chain of the antibody is preferably selected from the sequences as shown in any one of SEQ ID NOs. 23-26.

Above mentioned nucleic acid sequences with SEQ ID N.18-22 coding for the variable region of the heavy chain are herein reported:

```
-Nucleic acid coding for variable heavy chain
                                                     SEQ ID N. 18
GAGGTGCAGCTGGTGGAGTCTGGGGGAGGCCTAGTGCAGCCTGGAAGGTCCCTGAAACTCTC

CTGTGCAGCCTCA

GGATTCACTTTCAGTAATTATTACATGGCCTGGGTCCGCCAGGCTCCAAAGAAGGGTCTGGAGT

GGGTCGCAACC

ATTAATCCCAGTGGTACCAGAACTTACTATCCAGACTCCGTGAAAGGCCGATTCACTCTCTCCA

GAGATAGTGCA

AAGAGCAGCCTATATCTGCAAATGAACAGTCTGAAGTCTGAGGACACGGCCACTTTTTACTGTG

CAAGGCTTTAT

AACAACTACGCTTTTGATTACTGGGGCCAGGGAGTCATGGTCACAGTCTCCTCA

-Nucleic acid coding for variable heavy chain
                                                     SEQ ID N. 19
GAGGTGCAGCTGGTGGAGTCTGGGGGAGGCCTAGTGCAGCCTGGAAGGTCCCTGAAACTCTC

CTGTGCAGCCTCA

GGATTCACTTTCAGTAATTATTACATGGCCTGGGTCCGCCAGGCTCCAAAGAAGGGTCTGGAGT

GGGTCGCAACC

ATTAATCCCAGTGGTACCAGAACTTACTATCCAGACTCCGTGAAAGGCCGATTCACTCTCTCCA

GAGATAGTGCA

AAGAGCAGCCTATATCTGCAAATGAACAGTCTGAAGTCTGAGGACACGGCCACTTTTTACTGTG

CAAGGCTTTAT

AACAACTACGCTTTTGATTACTGGGGCCAAGGAGTCATGGTCACTGTCTCCTCA

-Nucleic acid coding for variable heavy chain
                                                     SEQ ID N. 20
GAGGTGCAGCTGGTGGAGTCTGGGGGAGGCTTGGTCCAGCCTGGGGGGTCCCTGAGACTCTC

CTGTGCAGCCTCT

GGATTCACCTTTAGTAACTATTACATGAGCTGGGTCCGCCAGGCTCCAGGGAAGGGGCTGGAG

TGGGTGGCCACC

ATAAACCCTAGCGGAACCAGAACCTACTATCCAGACTCTGTGAAGGGCCGATTCACCATCTCCA

GAGACAACGCC
```

```
-continued
AAGAACTCACTGTATCTGCAAATGAACAGCCTGAGAGCCGAGGACACGGCTGTGTATTACTGTG

CGAGACTGTAC

AACAATTACGCCTTTGACTACTGGGGCCAAGGAACCCTGGTCACCGTCTCCTCA

-Nucleic acid coding for variable heavy chain
                                          SEQ ID N. 21
GAGGTGCAGCTGGTGGAGTCTGGGGGAGGCTTGGTCCAGCCTGGGGGGTCCCTGAGACTCTC

CTGTGCAGCCTCT

GGATTCACCTTTAGTAACTATTACATGAGCTGGGTCCGCCAGGCTCCAGGGAAGGGGCTGGAG

TGGGTGGCCAAC

ATAAACCCTAGCGGAACCAGAACCTACTATCCAGACTCTGTGAAGGGCCGATTCACCATCTCCA

GAGACAACGCC

AAGAACTCACTGTATCTGCAAATGAACAGCCTGAGAGCCGAGGACACGGCTGTGTATTACTGTG

CGAGACTGTAC

AACAATTACGCCTTTGACTACTGGGGCCAAGGAACCCTGGTCACCGTCTCCTCA

-Nucleic acid coding for variable heavy chain
                                          SEQ ID N. 22
GAGGTGCAGCTGGTGGAGTCTGGGGGAGGCTTGGTCCAGCCTGGGGGGTCCCTGAGACTCTC

CTGTGCAGCCTCT

GGATTCACCTTTAGTAACTATTACATGAGCTGGGTCCGCCAGGCTCCAGGGAAGGGGCTGGAG

TGGGTGGCCACC

ATAAACCCTAGCGGAACCAGAACCTACTATCCAGACTCTGTGAAGGGCCGATTCACCATCTCCA

GAGACAGCGCC

AAGAGCTCACTGTATCTGCAAATGAACAGCCTGAGAGCCGAGGACACGGCTGTGTATTACTGT

GCGAGACTGTAC

AACAATTACGCCTTTGACTACTGGGGCCAAGGAACCCTGGTCACCGTCTCCTCA
```

Above mentioned nucleic acid sequences with SEQ ID N.92-96 coding for the variable region of the heavy chain are herein reported:

```
-Nucleic acid coding for variable heavy chain
                                          SEQ ID N. 92
GAGGTGCAGCTGGTGGAGTCTGGGGGAGGCTTGGTCCAGCCTGGGGGGTCCCTGAGACTCTC

CTGTGCAGCCTCT

GGATTCACCTTTAGTAACTATTACATGAGCTGGGTCCGCCAGGCTCCAGGGAAGGGGCTGGAG

TGGGTGGCCACC

ATAAACCCTAGCGGAACCAGAACCTACTATCCAGACTCTGTGAAGGGCCGATTCACCCTCTCCA

GAGACAACGCC

AAGAACTCACTGTATCTGCAAATGAACAGCCTGAGAGCCGAGGACACGGCTGTGTATTACTGTG

CGAGACTGTAC

AACAATTACGCCTTTGACTACTGGGGCCAAGGAACCCTGGTCACCGTCTCCTCA

-Nucleic acid coding for variable heavy chain
                                          SEQ ID N. 93
GAGGTGCAGCTGGTGGAGTCTGGGGGAGGCTTGGTCCAGCCTGGGGGGTCCCTGAGACTCTC

CTGTGCAGCCTCT
```

-continued

```
GGATTCACCTTTAGTAACTATTACATGGCCTGGGTCCGCCAGGCTCCAGGGAAGGGGCTGGAG

TGGGTGGCCACC

ATAAACCCTAGCGGAACCAGAACCTACTATCCAGACTCTGTGAAGGGCCGATTCACCCTCTCCA

GAGACAACGCC

AAGAACTCACTGTATCTGCAAATGAACAGCCTGAGAGCCGAGGACACGGCTACCTTCTACTGTG

CGAGACTGTAC

AACAATTACGCCTTTGACTACTGGGGCCAAGGAACCCTGGTCACCGTCTCCTCA
```

-Nucleic acid coding for variable heavy chain
SEQ ID N. 94

```
GAGGTGCAGCTGGTGGAGTCTGGGGGAGGCTTGGTCCAGCCTGGGGGGTCCCTGAGACTCTC

CTGTGCAGCCTCT

GGATTCACCTTTAGTAACTATTACATGGCCTGGGTCCGCCAGGCTCCAGGGAAGGGGCTGGAG

TGGGTGGCCACC

ATAAACCCTAGCGGAACCAGAACCTACTATCCAGACTCTGTGAAGGGCCGATTCACCCTCTCCA

GAGACAGCGCC

AAGAGCTCACTGTATCTGCAAATGAACAGCCTGAGAGCCGAGGACACGGCTACCTTCTACTGT

GCGAGACTGTAC

AACAATTACGCCTTTGACTACTGGGGCCAAGGAACCCTGGTCACCGTCTCCTCA
```

-Nucleic acid coding for variable heavy chain
SEQ ID N. 95

```
GAGGTGCAGCTGGTGGAGTCTGGGGGAGGCTTGGTCCAGCCTGGGGGGTCCCTGAGACTCTC

CTGTGCAGCCTCT

GGATTCACCTTTAGTAACTATTACATGAGCTGGGTCCGCCAGGCTCCAGGGAAGGGGCTGGAG

TGGGTGGCCACC

ATAAACCCTAGCGGAACCAGAACCTACTATCCAGACTCTGTGAAGGGCCGATTCACCCTCTCCA

GAGACAGCGCC

AAGAGCTCACTGTATCTGCAAATGAACAGCCTGAGAGCCGAGGACACGGCTGTGTATTACTGT

GCGAGACTGTAC

AACAATTACGCCTTTGACTACTGGGGCCAAGGAACCCTGGTCACCGTCTCCTCA
```

-Nucleic acid coding for variable heavy chain
SEQ ID N. 96

```
GAGGTGCAGCTGGTGGAGTCTGGGGGAGGCTTGGTCCAGCCTGGGGGGTCCCTGAGACTCTC

CTGTGCAGCCTCT

GGATTCACCTTTAGTAACTATTACATGGCCTGGGTCCGCCAGGCTCCAGGGAAGGGGCTGGAG

TGGGTGGCCACC

ATAAACCCTAGCGGAACCAGAACCTACTATCCAGACTCTGTGAAGGGCCGATTCACCATCTCCA

GAGACAACGCC

AAGAACTCACTGTATCTGCAAATGAACAGCCTGAGAGCCGAGGACACGGCTACCTATTACTGTG

CGAGACTGTAC

AACAATTACGCCTTTGACTACTGGGGCCAAGGAACCCTGGTCACCGTCTCCTCA
```

Above mentioned nucleic acid sequences with SEQ ID N.23-26 coding for the variable region of the light chain are herein reported:

```
-Nucleic acid coding for variable light chain
                                            SEQ ID N. 23
GATGTCCAGATGACCCAGTCTCCTGCTTTGGCTGTGTCTCCAGGAGAGAGGGTTTCCATCTCCT

GTAGGGCCAGT

GAAAGTGTCAGTACACTTATGCACTGGTACCAACAGAAACCAGGACAGCAACCCAAACTCCTCA

TCTACGGTACA

TCCAACCTAGAGTCTGGAGTCCCTGCCAGGTTCAGTGGCAGTGGGTCTGGGACAGACTTCACC

CTCAACATAGAT

CCTGTGGAGGCTGATGACACTGCAACCTATTTCTGTCAGCAGAGTTGGAATGATCCTCCGACGT

TCGGTGGAGGC ACCAAGCTGGAAGTGAAA

-Nucleic acid coding for variable light chain
                                            SEQ ID N. 24
GATGTCCAGATGACCCAGTCTCCTGCTTTGGCTGTGTCTCCAGGAGAGAGGGTTTCCATCTCCT

GTAGGGCCAGT

GAAAGTGTCAGTACACTTATGCACTGGTACCAACAGAAACCAGGACAGCAACCCAAACTCCTCA

TCTACGGTACA

TCCAACCTAGAGTCTGGAGTCCCTGCCAGGTTCAGTGGCAGTGGGTCTGGGACAGACTTCACC

CTCAACATAGAT

CCTGTGGAGGCTGATGACACTGCAACCTATTTCTGTCAGCAGAGTTGGAATGATCCTCCGACGT

TCGGTGGAGGC ACCAAGCTGGAATTGAAA

-Nucleic acid coding for variable light chain
                                            SEQ ID N. 25
GACATCCAGATGACCCAGTCTCCATCCTCCCTGTCTGCATCTGTAGGAGACAGAGTCACCATCA

CTTGCCGGGCA

AGTGAGAGCATTAGCACCCTGTTACACTGGTATCAGCAGAAACCAGGGAAAGCCCCTAAGCTC

CTGATCTATGGC

ACCTCCAACTTGGAGAGTGGGGTCCCATCAAGGTTCAGTGGCAGTGGATCTGGGACAGATTTC

ACTCTCACCATC

AGCAGTCTGCAACCTGAAGATTTTGCAACTTACTACTGTCAACAGAGTTGGAACGACCCTCCCA

CTTTCGGCGGA GGGACCAAGGTGGAGATCAAA

-Nucleic acid coding for variable light chain
                                            SEQ ID N. 26
GACATCCAGATGACCCAGTCTCCATCCTCCCTGTCTGCATCTGTAGGAGACAGAGTCACCATCA

CTTGCCGGGCA

AGTGAGAGCGTGAGCACCCTGATGCACTGGTATCAGCAGAAACCAGGGAAAGCCCCTAAGCTC

CTGATCTATGGC

ACCTCCAACTTGGAGAGTGGGGTCCCATCAAGGTTCAGTGGCAGTGGATCTGGGACAGATTTC

ACTCTCACCATC

AGCAGTCTGCAACCTGAAGATTTTGCAACTTACTACTGTCAACAGAGTTGGAACGACCCTCCCA

CTTTCGGCGGA GGGACCAAGGTGGAGATCAAA
```

Above mentioned nucleic acid sequences with SEQ ID N.97-99 coding for the variable region of the light chain are herein reported:

-Nucleic acid coding for variable light chain
SEQ ID N. 97
GACATCCAGATGACCCAGTCTCCATCCTCCCTGTCTGCATCTGTAGGAGACAGAGTCACCATCA

CTTGCCGGGCA

AGTGAGAGCATTAGCACCCTGTTACACTGGTATCAGCAGAAACCAGGGAAACAGCCTAAGCTC

CTGATCTATGGC

ACCTCCAACTTGGAGAGTGGGGTCCCATCAAGGTTCAGTGGCAGTGGATCTGGGACAGATTTC

ACTCTCACCATC

AGCAGTCTGCAACCTGAAGATTTTGCAACTTACTTCTGTCAACAGAGTTGGAACGACCCTCCCA

CTTTCGGCGGA GGGACCAAGGTGGAGATCAAA

-Nucleic acid coding for variable light chain
SEQ ID N. 98
GACATCCAGATGACCCAGTCTCCATCCTCCCTGTCTGCATCTGTAGGAGACAGAGTCACCATCA

CTTGCCGGGCA

AGTGAGAGCGTGAGCACCCTGATGCACTGGTATCAGCAGAAACCAGGGAAACAGCCTAAGCTC

CTGATCTATGGC

ACCTCCAACTTGGAGAGTGGGGTCCCATCAAGGTTCAGTGGCAGTGGATCTGGGACAGATTTC

ACTCTCACCATC

AGCAGTCTGCAACCTGAAGATTTTGCAACTTACTTCTGTCAACAGAGTTGGAACGACCCTCCCA

CTTTCGGCGGA GGGACCAAGGTGGAGATCAAA

-Nucleic acid coding for variable light chain
SEQ ID N. 99
GACGTGCAGATGACCCAGTCTCCATCCTCCCTGTCTGCATCTGTAGGAGACAGAGTCACCATC

ACTTGCCGGGCA

AGTGAGAGCATTAGCACCCTGTTACACTGGTATCAGCAGAAACCAGGGAAAGCCCCTAAGCTC

CTGATCTATGGC

ACCTCCAACTTGGAGAGTGGGGTCCCATCAAGGTTCAGTGGCAGTGGATCTGGGACAGATTTC

ACTCTCACCATC

AGCAGTCTGCAACCTGAAGATTTTGCAACTTACTTCTGTCAACAGAGTTGGAACGACCCTCCCA

CTTTCGGCGGA GGGACCAAGGTGGAGATCAAA

A nucleic acid comprising at least one of the sequences as shown in SEQ ID NOs. 18-22, 92-96 and at least one of the sequences shown in SEQ ID NOs. 23-26, 97-99 is within the scope of the invention.

Particularly preferred is a combination of nucleic acid sequences comprising at least one of the sequences as shown in SEQ ID NOs. 18-22 and at least one of the sequences shown in SEQ ID NOs. 23-26. The nucleic acid sequences may be present within one isolated nucleic acid molecule or in a combination of two isolated nucleic acid molecules.

In a preferred embodiment (rat antibody BMK-3B6-E4-C3), said isolated nucleic acid molecule comprises as sequence encoding the variable region of the heavy chain the sequence of SEQ ID NO 18 (encoding amino acid sequence with SEQ ID NO 1) and as sequence encoding the variable region of the light chain the sequence of SEQ ID NO. 23 (encoding amino acid sequence with SEQ ID NO 10).

In another preferred embodiment (chimeric antibody ch3B6), said isolated nucleic acid molecule comprises as sequence encoding the variable region of the heavy chain the sequence of SEQ ID NO 19 (encoding amino acid sequence with SEQ ID NO 1) and as sequence encoding the variable region of the light chain the sequence of SEQ ID NO. 24 (encoding amino acid sequence with SEQ ID NO 11).

Particularly preferred is a combination of nucleic acid sequences wherein the nucleic acid sequence encoding the variable region of the heavy chain is selected from the sequences as shown in any one of SEQ ID NOs. 20-22 and the nucleic acid sequence encoding the variable region of the light chain of the antibody is selected from the sequences as shown in any one of SEQ ID NOs. 25-26. The nucleic acid sequences may be present within one isolated nucleic acid molecule or in a combination of two isolated nucleic acid molecules.

In a preferred embodiment (human antibody Hu3B6a), said isolated nucleic acid molecule comprises as sequence encoding the variable region of the heavy chain the sequence of SEQ ID NO 20 (encoding amino acid sequence with SEQ ID NO 2) and as sequence encoding the variable region of the light chain the sequence of SEQ ID NO. 25 (encoding amino acid sequence with SEQ ID NO 12).

In a preferred embodiment (human antibody Hu3B6d), said isolated nucleic acid molecule comprises as sequence encoding the variable region of the heavy chain the sequence of SEQ ID NO 20 (encoding amino acid sequence with SEQ ID NO 2) and as sequence encoding the variable region of the light chain the sequence of SEQ ID NO. 26 (encoding amino acid sequence with SEQ ID NO 13).

In a preferred embodiment (human antibody Hu3B6b), said isolated nucleic acid molecule comprises as sequence encoding the variable region of the heavy chain the sequence of SEQ ID NO 21 (encoding amino acid sequence with SEQ ID NO 3) and as sequence encoding the variable region of the light chain the sequence of SEQ ID NO. 25 (encoding amino acid sequence with SEQ ID NO 12).

In a preferred embodiment (human antibody Hu3B6e), said isolated nucleic acid molecule comprises as sequence encoding the variable region of the heavy chain the sequence of SEQ ID NO 21 (encoding amino acid sequence with SEQ ID NO 3) and as sequence encoding the variable region of the light chain the sequence of SEQ ID NO. 26 (encoding amino acid sequence with SEQ ID NO 13).

In a preferred embodiment (human antibody Hu3B6c), said isolated nucleic acid molecule comprises as sequence encoding the variable region of the heavy chain the sequence of SEQ ID NO 22 (encoding amino acid sequence with SEQ ID NO 4) and as sequence encoding the variable region of the light chain the sequence of SEQ ID NO. 25 (encoding amino acid sequence with SEQ ID NO 12).

In a preferred embodiment (human antibody Hu3B6f), said isolated nucleic acid molecule comprises as sequence encoding the variable region of the heavy chain the sequence of SEQ ID NO 22 (encoding amino acid sequence with SEQ ID NO 4) and as sequence encoding the variable region of the light chain the sequence of SEQ ID NO. 26 (encoding amino acid sequence with SEQ ID NO 13).

In further embodiments, said isolated nucleic acid comprises a sequence encoding the heavy chain and a sequence encoding the light chain, both comprising the variable and the constant region.

In an embodiment, said isolated nucleic acid is for the production of a chimeric antibody and said sequence encoding the heavy chain is the sequence of SEQ ID N.28 and the sequence encoding the light chain is the sequence of SEQ ID N.32, as shown below:

```
-Nucleic acid coding for heavy chain
                                                    SEQ ID N. 28
ATGAATCTACTTCTGATCCTTACCTTTGTTGCGGCCGCTGTTGCGGAGGTGCAGCTGGTGGAGT

CTGGGGGAGGC

CTAGTGCAGCCTGGAAGGTCCCTGAAACTCTCCTGTGCAGCCTCAGGATTCACTTTCAGTAATT

ATTACATGGCC

TGGGTCCGCCAGGCTCCAAAGAAGGGTCTGGAGTGGGTCGCAACCATTAATCCCAGTGGTACC

AGAACTTACTAT

CCAGACTCCGTGAAAGGCCGATTCACTCTCTCCAGAGATAGTGCAAAGAGCAGCCTATATCTGC

AAATGAACAGT

CTGAAGTCTGAGGACACGGCCACTTTTTACTGTGCAAGGCTTTATAACAACTACGCTTTTGATTA

CTGGGGCCAA

GGAGTCATGGTCACTGTCTCCTCAGCGTCGACCAAGGGCCCATCGGTCTTCCCCCTGGCACCC

TCCTCCAAGAGC

ACCTCTGGGGGCACAGCGGCCCTGGGCTGCCTGGTCAAGGACTACTTCCCCGAACCGGTGAC

GGTGTCGTGGAAC

TCAGGCGCCCTGACCAGCGGCGTGCACACCTTCCCGGCTGTCCTACAGTCCTCAGGACTCTAC

TCCCTCAGCAGC

GTGGTGACCGTGCCCTCCAGCAGCTTGGGCACCCAGACCTACATCTGCAACGTGAATCACAAG

CCCAGCAACACC

AAGGTGGACAAGAAAGTTGAGCCCAAATCTTGTGACAAAACTCACACATGCCCACCGTGCCCA

GCACCTGAACTC

CTGGGGGGACCGTCAGTCTTCCTCTTCCCCCCAAAACCCAAGGACACCCTCATGATCTCCCGG

ACCCCTGAGGTC

ACATGCGTGGTGGTGGACGTGAGCCACGAAGACCCTGAGGTCAAGTTCAACTGGTACGTGGAC

GGCGTGGAGGTG
```

```
CATAATGCCAAGACAAAGCCGCGGGAGGAGCAGTACAACAGCACGTACCGTGTGGTCAGCGT

CCTCACCGTCCTG

CACCAGGACTGGCTGAATGGCAAGGAGTACAAGTGCAAGGTCTCCAACAAAGCCCTCCCAGCC

CCCATCGAGAAA

ACCATCTCCAAAGCCAAAGGGCAGCCCCGAGAACCACAGGTGTACACCCTGCCCCCATCCCGC

GAGGAGATGACC

AAGAACCAGGTCAGCCTGACCTGCCTGGTCAAAGGCTTCTATCCCAGCGACATCGCCGTGGAG

TGGGAGAGCAAT

GGGCAGCCGGAGAACAACTACAAGACCACGCCTCCCGTGCTGGACTCCGACGGCTCCTTCTTC

CTCTACAGCAAG

CTCACCGTGGACAAGAGCAGGTGGCAGCAGGGGAACGTCTTCTCATGCTCCGTGATGCATGAG

GCTCTGCACAAC CACTACACGCAGAAGAGCCTCTCCCTGTCTCCGGGTAAATGA

-Nucleic acid coding for light chain
                                               SEQ ID N. 32
ATGAATCTACTTCTGATCCTTACCTTTGTTGCGGCCGCTGTTGCGGATGTCCAGATGACCCAGT

CTCCTGCTTTG

GCTGTGTCTCCAGGAGAGAGGGTTTCCATCTCCTGTAGGGCCAGTGAAAGTGTCAGTACACTT

ATGCACTGGTAC

CAACAGAAACCAGGACAGCAACCCAAACTCCTCATCTACGGTACATCCAACCTAGAGTCTGGAG

TCCCTGCCAGG

TTCAGTGGCAGTGGGTCTGGGACAGACTTCACCCTCAACATAGATCCTGTGGAGGCTGATGAC

ACTGCAACCTAT

TTCTGTCAGCAGAGTTGGAATGATCCTCCGACGTTCGGTGGAGGCACCAAGCTGGAATTGAAA

CGTACGGTGGCT

GCACCATCTGTCTTCATCTTCCCGCCATCTGATGAGCAGTTGAAATCTGGAACTGCCTCTGTTG

TGTGCCTGCTG

AATAACTTCTATCCCAGAGAGGCCAAAGTACAGTGGAAGGTGGATAACGCCCTCCAATCGGGT

AACTCCCAGGAG

AGTGTCACAGAGCAGGACAGCAAGGACAGCACCTACAGCCTCAGCAGCACCCTGACGCTGAG

CAAAGCAGACTAC

GAGAAACACAAAGTCTACGCCTGCGAAGTCACCCATCAGGGCCTGAGCTCGCCCGTCACAAAG

AGCTTCAACAGG GGAGAGTGTTGA
```

In another embodiment, said isolated nucleic acid is for the production of a humanized antibody and said sequence encoding the heavy chain is selected from the sequences of SEQ ID N.29-31 and the sequence encoding the light chain is selected from the sequences of SEQ ID N.33-34, as shown below.

```
-Nucleic acid coding for heavy chain
                                               SEQ ID N. 29
ATGAATCTACTTCTGATCCTTACCTTTGTTGCGGCCGCTGTTGCGGAGGTGCAGCTGGTGGAGT

CTGGGGAGGC

TTGGTCCAGCCTGGGGGGTCCCTGAGACTCTCCTGTGCAGCCTCTGGATTCACCTTTAGTAACT

ATTACATGAGC
```

TGGGTCCGCCAGGCTCCAGGGAAGGGGCTGGAGTGGGTGGCCACCATAAACCCTAGCGGAAC

CAGAACCTACTAT

CCAGACTCTGTGAAGGGCCGATTCACCATCTCCAGAGACAACGCCAAGAACTCACTGTATCTG

CAAATGAACAGC

CTGAGAGCCGAGGACACGGCTGTGTATTACTGTGCGAGACTGTACAACAATTACGCCTTTGACT

ACTGGGGCCAA

GGAACCCTGGTCACCGTCTCCTCAGCGTCGACCAAGGGCCCATCGGTCTTCCCCCTGGCACC

CTCCTCCAAGAGC

ACCTCTGGGGGCACAGCGGCCCTGGGCTGCCTGGTCAAGGACTACTTCCCCGAACCGGTGAC

GGTGTCGTGGAAC

TCAGGCGCCCTGACCAGCGGCGTGCACACCTTCCCGGCTGTCCTACAGTCCTCAGGACTCTAC

TCCCTCAGCAGC

GTGGTGACCGTGCCCTCCAGCAGCTTGGGCACCCAGACCTACATCTGCAACGTGAATCACAAG

CCCAGCAACACC

AAGGTGGACAAGAAAGTTGAGCCCAAATCTTGTGACAAAACTCACACATGCCCACCGTGCCCA

GCACCTGAACTC

CTGGGGGGACCGTCAGTCTTCCTCTTCCCCCCAAAACCCAAGGACACCCTCATGATCTCCCGG

ACCCCTGAGGTC

ACATGCGTGGTGGTGGACGTGAGCCACGAAGACCCTGAGGTCAAGTTCAACTGGTACGTGGAC

GGCGTGGAGGTG

CATAATGCCAAGACAAAGCCGCGGGAGGAGCAGTACAACAGCACGTACCGTGTGGTCAGCGT

CCTCACCGTCCTG

CACCAGGACTGGCTGAATGGCAAGGAGTACAAGTGCAAGGTCTCCAACAAAGCCCTCCCAGCC

CCCATCGAGAAA

ACCATCTCCAAAGCCAAAGGGCAGCCCCGAGAACCACAGGTGTACACCCTGCCCCCATCCCGC

GAGGAGATGACC

AAGAACCAGGTCAGCCTGACCTGCCTGGTCAAAGGCTTCTATCCCAGCGACATCGCCGTGGAG

TGGGAGAGCAAT

GGGCAGCCGGAGAACAACTACAAGACCACGCCTCCCGTGCTGGACTCCGACGGCTCCTTCTTC

CTCTACAGCAAG

CTCACCGTGGACAAGAGCAGGTGGCAGCAGGGGAACGTCTTCTCATGCTCCGTGATGCATGAG

GCTCTGCACAAC CACTACACGCAGAAGAGCCTCTCCCTGTCTCCGGGTAAATGA

-Nucleic acid coding for heavy chain

SEQ ID N. 30

ATGAATCTACTTCTGATCCTTACCTTTGTTGCGGCCGCTGTTGCGGAGGTGCAGCTGGTGGAGT

CTGGGGGAGGC

TTGGTCCAGCCTGGGGGGTCCCTGAGACTCTCCTGTGCAGCCTCTGGATTCACCTTTAGTAACT

ATTACATGAGC

TGGGTCCGCCAGGCTCCAGGGAAGGGGCTGGAGTGGGTGGCCAACATAAACCCTAGCGGAAC

CAGAACCTACTAT

```
CCAGACTCTGTGAAGGGCCGATTCACCATCTCCAGAGACAACGCCAAGAACTCACTGTATCTG

CAAATGAACAGC

CTGAGAGCCGAGGACACGGCTGTGTATTACTGTGCGAGACTGTACAACAATTACGCCTTTGACT

ACTGGGGCCAA

GGAACCCTGGTCACCGTCTCCTCAGCGTCGACCAAGGGCCCATCGGTCTTCCCCCTGGCACC

CTCCTCCAAGAGC

ACCTCTGGGGGCACAGCGGCCCTGGGCTGCCTGGTCAAGGACTACTTCCCCGAACCGGTGAC

GGTGTCGTGGAAC

TCAGGCGCCCTGACCAGCGGCGTGCACACCTTCCCGGCTGTCCTACAGTCCTCAGGACTCTAC

TCCCTCAGCAGC

GTGGTGACCGTGCCCTCCAGCAGCTTGGGCACCCAGACCTACATCTGCAACGTGAATCACAAG

CCCAGCAACACC

AAGGTGGACAAGAAAGTTGAGCCCAAATCTTGTGACAAAACTCACACATGCCCACCGTGCCCA

GCACCTGAACTC

CTGGGGGGACCGTCAGTCTTCCTCTTCCCCCCAAAACCCAAGGACACCCTCATGATCTCCCGG

ACCCCTGAGGTC

ACATGCGTGGTGGTGGACGTGAGCCACGAAGACCCTGAGGTCAAGTTCAACTGGTACGTGGAC

GGCGTGGAGGTG

CATAATGCCAAGACAAAGCCGCGGGAGGAGCAGTACAACAGCACGTACCGTGTGGTCAGCGT

CCTCACCGTCCTG

CACCAGGACTGGCTGAATGGCAAGGAGTACAAGTGCAAGGTCTCCAACAAAGCCCTCCCAGCC

CCCATCGAGAAA

ACCATCTCCAAAGCCAAAGGGCAGCCCCGAGAACCACAGGTGTACACCCTGCCCCCATCCCGC

GAGGAGATGACC

AAGAACCAGGTCAGCCTGACCTGCCTGGTCAAAGGCTTCTATCCCAGCGACATCGCCGTGGAG

TGGGAGAGCAAT

GGGCAGCCGGAGAACAACTACAAGACCACGCCTCCCGTGCTGGACTCCGACGGCTCCTTCTTC

CTCTACAGCAAG

CTCACCGTGGACAAGAGCAGGTGGCAGCAGGGGAACGTCTTCTCATGCTCCGTGATGCATGAG

GCTCTGCACAAC CACTACACGCAGAAGAGCCTCTCCCTGTCTCCGGGTAAATGA
-Nucleic acid coding for heavy chain
                                                        SEQ ID N. 31
ATGAATCTACTTCTGATCCTTACCTTTGTTGCGGCCGCTGTTGCGGAGGTGCAGCTGGTGGAGT

CTGGGGGAGGC

TTGGTCCAGCCTGGGGGGTCCCTGAGACTCTCCTGTGCAGCCTCTGGATTCACCTTTAGTAACT

ATTACATGAGC

TGGGTCCGCCAGGCTCCAGGGAAGGGGCTGGAGTGGGTGGCCACCATAAACCCTAGCGGAAC

CAGAACCTACTAT

CCAGACTCTGTGAAGGGCCGATTCACCATCTCCAGAGACAGCGCCAAGAGCTCACTGTATCTG

CAAATGAACAGC
```

CTGAGAGCCGAGGACACGGCTGTGTATTACTGTGCGAGACTGTACAACAATTACGCCTTTGACT

ACTGGGGCCAA

GGAACCCTGGTCACCGTCTCCTCAGCGTCGACCAAGGGCCCATCGGTCTTCCCCCTGGCACC

CTCCTCCAAGAGC

ACCTCTGGGGGCACAGCGGCCCTGGGCTGCCTGGTCAAGGACTACTTCCCCGAACCGGTGAC

GGTGTCGTGGAAC

TCAGGCGCCCTGACCAGCGGCGTGCACACCTTCCCGGCTGTCCTACAGTCCTCAGGACTCTAC

TCCCTCAGCAGC

GTGGTGACCGTGCCCTCCAGCAGCTTGGGCACCCAGACCTACATCTGCAACGTGAATCACAAG

CCCAGCAACACC

AAGGTGGACAAGAAAGTTGAGCCCAAATCTTGTGACAAAACTCACACATGCCCACCGTGCCCA

GCACCTGAACTC

CTGGGGGACCGTCAGTCTTCCTCTTCCCCCCAAAACCCAAGGACACCCTCATGATCTCCCGG

ACCCCTGAGGTC

ACATGCGTGGTGGTGGACGTGAGCCACGAAGACCCTGAGGTCAAGTTCAACTGGTACGTGGAC

GGCGTGGAGGTG

CATAATGCCAAGACAAAGCCGCGGGAGGAGCAGTACAACAGCACGTACCGTGTGGTCAGCGT

CCTCACCGTCCTG

CACCAGGACTGGCTGAATGGCAAGGAGTACAAGTGCAAGGTCTCCAACAAAGCCCTCCCAGCC

CCCATCGAGAAA

ACCATCTCCAAAGCCAAAGGGCAGCCCCGAGAACCACAGGTGTACACCCTGCCCCCATCCCGC

GAGGAGATGACC

AAGAACCAGGTCAGCCTGACCTGCCTGGTCAAAGGCTTCTATCCCAGCGACATCGCCGTGGAG

TGGGAGAGCAAT

GGGCAGCCGGAGAACAACTACAAGACCACGCCTCCCGTGCTGGACTCCGACGGCTCCTTCTTC

CTCTACAGCAAG

CTCACCGTGGACAAGAGCAGGTGGCAGCAGGGGAACGTCTTCTCATGCTCCGTGATGCATGAG

GCTCTGCACAAC CACTACACGCAGAAGAGCCTCTCCCTGTCTCCGGGTAAATGA

-Nucleic acid coding for light chain

SEQ ID N. 33

ATGAATCTACTTCTGATCCTTACCTTTGTTGCGGCCGCTGTTGCGGACATCCAGATGACCCAGT

CTCCATCCTCC

CTGTCTGCATCTGTAGGAGACAGAGTCACCATCACTTGCCGGGCAAGTGAGAGCATTAGCACC

CTGTTACACTGG

TATCAGCAGAAACCAGGGAAAGCCCCTAAGCTCCTGATCTATGGCACCTCCAACTTGGAGAGT

GGGGTCCCATCA

AGGTTCAGTGGCAGTGGATCTGGGACAGATTTCACTCTCACCATCAGCAGTCTGCAACCTGAA

GATTTTGCAACT

TACTACTGTCAACAGAGTTGGAACGACCCTCCCACTTTCGGCGGAGGGACCAAGGTGGAGATC

AAACGTACGGTG

```
GCTGCACCATCTGTCTTCATCTTCCCGCCATCTGATGAGCAGTTGAAATCTGGAACTGCCTCTG

TTGTGTGCCTG

CTGAATAACTTCTATCCCAGAGAGGCCAAAGTACAGTGGAAGGTGGATAACGCCCTCCAATCG

GGTAACTCCCAG

GAGAGTGTCACAGAGCAGGACAGCAAGGACAGCACCTACAGCCTCAGCAGCACCCTGACGCT

GAGCAAAGCAGAC

TACGAGAAACACAAAGTCTACGCCTGCGAAGTCACCCATCAGGGCCTGAGCTCGCCCGTCACA

AAGAGCTTCAAC AGGGGAGAGTGTTGA

-Nucleic acid coding for light chain
                                                SEQ ID N. 34
ATGAATCTACTTCTGATCCTTACCTTTGTTGCGGCCGCTGTTGCGGACATCCAGATGACCCAGT

CTCCATCCTCC

CTGTCTGCATCTGTAGGAGACAGAGTCACCATCACTTGCCGGGCAAGTGAGAGCGTGAGCACC

CTGATGCACTGG

TATCAGCAGAAACCAGGGAAAGCCCCTAAGCTCCTGATCTATGGCACCTCCAACTTGGAGAGT

GGGGTCCCATCA

AGGTTCAGTGGCAGTGGATCTGGGACAGATTTCACTCTCACCATCAGCAGTCTGCAACCTGAA

GATTTTGCAACT

TACTACTGTCAACAGAGTTGGAACGACCCTCCCACTTTCGGCGGAGGGACCAAGGTGGAGATC

AAACGTACGGTG

GCTGCACCATCTGTCTTCATCTTCCCGCCATCTGATGAGCAGTTGAAATCTGGAACTGCCTCTG

TTGTGTGCCTG

CTGAATAACTTCTATCCCAGAGAGGCCAAAGTACAGTGGAAGGTGGATAACGCCCTCCAATCG

GGTAACTCCCAG

GAGAGTGTCACAGAGCAGGACAGCAAGGACAGCACCTACAGCCTCAGCAGCACCCTGACGCT

GAGCAAAGCAGAC

TACGAGAAACACAAAGTCTACGCCTGCGAAGTCACCCATCAGGGCCTGAGCTCGCCCGTCACA

AAGAGCTTCAAC AGGGGAGAGTGTTGA
```

Preferably, said isolated nucleic acid molecule comprises as sequence encoding the heavy chain the sequence of SEQ ID NO 29 and as sequence encoding the light chain the sequence of SEQ ID NO. 33.

Preferably, said isolated nucleic acid molecule comprises as sequence encoding the heavy chain the sequence of SEQ ID NO 30 and as sequence encoding the light chain the sequence of SEQ ID NO. 33.

Preferably, said isolated nucleic acid molecule comprises as sequence encoding the heavy chain the sequence of SEQ ID NO 31 and as sequence encoding the light chain the sequence of SEQ ID NO. 33.

Preferably, said isolated nucleic acid molecule comprises as sequence encoding the heavy chain the sequence of SEQ ID NO 29 and as sequence encoding the light chain the sequence of SEQ ID NO. 34.

Preferably, said isolated nucleic acid molecule comprises as sequence encoding the heavy chain the sequence of SEQ ID NO 30 and as sequence encoding the light chain the sequence of SEQ ID NO. 34.

Preferably, said isolated nucleic acid molecule comprises as sequence encoding the heavy chain the sequence of SEQ ID NO 31 and as sequence encoding the light chain the sequence of SEQ ID NO. 34.

The term "hybridizing under stringent conditions" means that two nucleic acid fragments hybridize with one another under standardized hybridization conditions as described, for example in Sambrook et al., "Expression of cloned Genes in E. coli" in Molecular Cloning: A Laboratory Manual (1989), Cold Spring Harbor Laboratory Press, New York, USA. Such conditions are, for example, hybridization in 6.0×SSC (Saline Sodium Citrate) at about 45° C. followed by a washing step with 2.0×SSC at 50° C., preferably 2.0×SSC at 65° C. or 0.2×SSC at 50° C., preferably 0.2×SSC at 65° C. A further example of hybridization under stringent conditions is hybridization to filter-bound DNA in 0.5M NaHPO$_4$, 7% sodium dodecyl sulfate (SDS), 1 mM EDTA at 65° C., and washing in 0.1×SSC/0.1% SDS at 68° C. (Ausubel F M et al. eds., 2003, Current Protocol in Molecular Biology, Vol. I, Green Publishing Associates, Inc., and John Wiley & sons, Inc., New York, at p. 2.20.3).

Nucleotide sequences having at least 80% identity with any of the sequences above disclosed are still within the scope of the present invention, provided that the coded antibody keeps its binding specificity.

In particular, nucleotide sequences coding for the variable heavy chain having at least 80% identity with sequences SEQ ID NO: 18-22 and nucleotide sequences coding for the variable light chain having at least 80% identity with the sequence SEQ ID NO:23-26 are still within the scope of the present invention. At least 80% identity means a nucleotide identity percentage comprised between 80 and 100%, preferably being 90, 95 or 99%.

The nucleic acid molecule of the invention may be located on a vector which may additionally contain a replication origin and/or a selection marker gene. Examples of vectors are e.g. plasmids, cosmids, phages, viruses etc. Thus, a further embodiment of the invention is a vector comprising a nucleic acid sequence as disclosed herein. Preferably, the vector is an expression vector.

Said vector may, for example, be a phage, plasmid, viral or retro viral vector.

Retro viral vectors may be replication competent or replication defective. In the latter case, viral propagation generally will occur only in complementing hosts/cells.

The nucleic acid molecules of the invention may be joined to a vector containing selectable markers for propagation in a host. Generally, a plasmid vector is introduced in a precipitate such as a calcium phosphate precipitate or rubidium chloride precipitate or in a complex with a charged lipid or in carbon-based clusters such as fullerenes. Should the vector be a virus, it may be packed in vitro using an appropriate packaging cell line prior to application to host cells.

Preferably, the vector of the invention is an expression vector, wherein the nucleic acid molecule is operatively linked to one or more control sequences allowing the transcription and optionally expression in prokaryotic and/or eukaryotic host cells. Expression of said nucleic acid molecule comprises transcription of the nucleic acid molecule, preferably into a translatable mRNA. Regulatory elements ensuring expression in eukaryotic cells, preferably mammalian cells, are well-known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g. the lac, trp or tac promoter in *E. coli*, and examples for regulatory elements permitting expression in eukaryotic host cells are the AOXI or GAL-1 promoter in yeast or the CMV (Cytomegalovirus)-, SV40 (Simian Virus 40)-, RSV-promoter (Rous sarcoma virus), CMV-enhancer, SV40-enhancer or a globin intron in mammalian and other animal cells. Beside elements which are responsible for the initiation of transcription, such regulatory elements may also comprise transcription termination signals such as the SV40-poly-A site or the tk-poly-A site, downstream of the polynucleotide. In this context, suitable expression vectors are known in the art such as Okayama-Berg cDNA expression vector pcDVI (Pharmacia), pCDM8, pRc/CMV, pcDNAI, pcDNA3 or pSPORTI (Thermo Fisher Scientific). Preferably, said vector is an expression vector and/or a gene transfer or targeting vector. Expression vectors derived from viruses such as retrovirus, vaccina virus, adeno-associated virus, herpes virus or bovine papilloma virus may be used for delivery of the polynucleotides or vector of the invention into targeted cell population.

Methods which are well-known to those skilled in the art can be used to construct recombinant viral vectors; see for example the techniques described in Sambrook, Molecular Cloning, A Laboratory Manual, Cold Spring Harbor Laboratory Press (2001, 3<rd>edition), N.Y. and Ausubel, Current Protocols in Molecular Biology, Green Publishing Associates and Wiley Interscience, N.Y. (1994). Alternatively, the nucleic acid molecules of the invention can be reconstituted into liposomes for delivery to target cells. Further, the invention refers to a host which comprises the nucleic acid molecule or the vector as described above. The nucleic acid molecule or the vector may be introduced into the host by transformation, transfection or transduction according to any method known in the art.

Said host may be a prokaryotic or eukaryotic cell or a non-human transgenic animal. The polynucleotide or vector of the invention which is present in the host may either be integrated into the genome of the host or it may be maintained extrachromosomally. In this respect, it is also to be understood that the nucleic acid molecule of the invention can be used for "gene targeting" and/or "gene replacement", for restoring a mutant gene or for creating a mutant gene via homologous recombination; see for example Mouellic, Proc. Natl. Acad. Sci. USA, 87 (1990), 4712-4716; Joyner, Gene Targeting, A Practical Approach, Oxford University Press.

The host can be any prokaryotic or eukaryotic cell such as a bacterial, insect, fungal, plant, animal, mammalian or preferably a human cell. Preferred fungal cells are, for example those of the genus *Saccharomyces*, in particular those of the species *S. cerevisiae*. The term "prokaryotic" is meant to include all bacteria which can be transformed or transfected with a polynucleotide for the expression of a variant polypeptide of the invention. Prokaryotic hosts may include gram negative as well as gram positive bacteria such as for example *E. coli, Salmonella typhimurium, Serratia marcescens* and *Bacillus subtilis*. A polynucleotide coding for a mutant form of variant polypeptides of the invention can be used to transform or transfect the host using any of the techniques commonly known to those of ordinary skill in the art. Methods for preparing fused operably linked genes and expression them in bacteria or animal cells are well-known in the art (Sambrook, Molecular Cloning, A Laboratory Manual, Cold Spring Harbor Laboratory Press (2001, 3<rd>edition). The genetic constructs and methods described therein can be utilized for expression of variant antibodies, antibody fragments or derivatives thereof of the invention in e.g. prokaryotic hosts. In general, expression vectors containing promoter sequences, which facilitate the efficient transcription of the inserted nucleic acid molecule, are used in connection with the host. The expression vector typically contains an origin of replication, a promoter and a terminator as well as specific genes which are capable of providing phenotypic selection of the transformed cells. The transformed prokaryotic hosts can be grown in fermentors and cultured according to techniques known in the art to achieve optimal cell growth. The antibodies, antibody fragments or derivatives thereof of the invention can then be isolated from the growth medium, cellular lysates or cellular membrane fractions. The isolation and purification of the microbially or otherwise expressed antibodies, antibody fragments or derivatives thereof of the invention may be by any conventional means, such as for example preparative chromatographic separations and immunological separations such as those involving the use of monoclonal or polyclonal antibodies.

According to one embodiment of the invention, the host is a human, bacteria, animal, fungal, amphibian or plant cell.

Preferred animal cells include but are not limited to Chinese hamster ovary (CHO) cells, baby hamster kidney (BHK) cells, monkey kidney cells (COS), mouse embryonic fibroblast cells (NIH-3T3) and a number of other cell lines, including human cells.

In another preferred embodiment, said animal cell is an insect cell. Preferred insect cells include but are not limited to cells from the SF9 cell lines.

Preferably, the cell is a mammalian cell, e.g. a hamster, rabbit or human cell. Most preferably, the cell is a human cell. Said human cells include but are not limited to human embryonic kidney cells (HEK293, 293T, 293 freestyle). Furthermore, said human cell lines include but are not limited to HeLa cells, human hepatocellular carcinoma cells (e.g. HEPG2, Huh-7), A549 cells. According to another embodiment, the host of the present invention is a nonhuman transgenic animal. The invention provides transgenic nonhuman animals comprising one or more nucleic acid molecules of the invention that may be used to produce antibodies of the invention. Antibodies can be produced in and recovered from tissue or body fluids, such as milk, blood or urine of goats, cows, horses, pigs, rats, mice, rabbits, hamsters or other mammals. See for example U.S. Pat. Nos. 5,827,690; 5,756,687; 5,750,172; and 5,741,957. As described above, non-human transgenic animals that comprise human immunoglobulin loci can be produced by immunizing with FGFR4 or a portion thereof. The antibody of the invention may be prepared by a method, wherein said antibody is obtained from a host as described herein above. Thus, a further embodiment of the present invention is a method for the preparation of an antibody comprising culturing the host of the invention under conditions that allow synthesis of said antibody and recovering said antibody from said culture.

The transformed hosts can be grown in fermentors and cultured according to techniques known in the art to achieve optimal cell growth. Once expressed, the whole antibodies, their dinners, individual light and heavy chains, or other immunoglobulin forms of the present invention can be purified according to standard procedures of the art, including ammonium sulfate precipitation, affinity columns, column chromatography, gel electrophoresis and the like; see Scopes, "Protein Purification", Springer-Verlag, N.Y. (1982). The antibody or its corresponding immunoglobulin chain(s) of the invention can then be isolated from the growth medium, cellular lysates or cellular membrane fractions. The isolation and purification of the e.g. microbially expressed antibodies or immunoglobulin chains of the invention may be by any conventional means, such as for example preparative chromatographic separations and immunological separations such as those involving the use of monoclonal or polyclonal antibodies directed e.g. against the constant region of the antibody of the invention. It will be apparent to those skilled in the art that the antibodies of the invention can be further coupled to other moieties, e.g. drug targeting and imaging applications. Such coupling may be conducted chemically after expression of the antibody or antigen to side of attachment or the coupling product may be engineered into the antibody or antigen of the invention at the DNA level. The DNAs are then expressed in a suitable host system, and the expressed proteins are collected and renatured if necessary.

According to one embodiment, a recombinant cell as described above is cultured under conditions which allow expression of the antibody encoding nucleic acid molecules. The antibody may be collected from the cultured cell or the culture supernatant. Preferably, the antibody is prepared from a mammalian, particularly from a human cell.

Pharmaceutical Compositions and Medical Treatments

Still a further aspect of the present invention relates to a pharmaceutical composition comprising the antibody, the conjugate, the fusion protein, the nucleic acid molecule, the vector or the host as described above, optionally together with a pharmaceutically acceptable carrier.

The term "carrier" includes agents, e.g. diluents, stabilizers, adjuvants or other types of excipients that are non-toxic to the cell or mammal to be exposed thereto at the dosages and concentrations employed. Examples of pharmaceutically acceptable carriers are well-known in the art and include phosphate-buffered saline solutions, water, emulsions such as oil/water emulsions, various types of wetting agents, sterile solutions, etc. Often, the pharmaceutically acceptable carrier is an aqueous pH-buffered solution which is useful for drug delivery, particularly for the delivery of antibody molecules. The pharmaceutical composition may be formulated by well known conventional methods, i.e. by mixing the active agent with carriers and optionally other agents that are usually incorporated into the formulation. For example, the composition may be formulated in the form of lyophilized formulations, aqueous solutions, dispersions or solid preparations. Administration of the suitable compositions may be effected by different ways, e.g. by intravenous, intraperitoneal, subcutaneous, intramuscular, topical, intradermal, intranasal or intrabronchial administration. The compositions of the invention may also be administered directly to the target site, e.g. by biolistic delivery to an external or internal target site, like the brain. The dosage regimen will be determined by the attending physician and clinical factors.

The present invention also encompasses the administration of the pharmaceutical composition to a subject in need thereof, particularly a human patient suffering from a disorder associated with FGFR4 expression, overexpression and/or hyperactivity.

As is well-known in the medical arts, dosages for any one patient depend upon many factors including the patient's size, body surface and area, age, the particular compound to be administered, sex, time and route of administration, general health and other drugs being administered concurrently. Depending on the type and severity of the condition to be treated, about 1 pg/kg to 15 mg/kg of the active ingredient may be administered to a patient in need thereof, e.g. by one or more separate administrations or by continuous infusion. A typical daily dosage might range from about 1 pg/kg to about 100 mg/kg, depending on the factors mentioned above. For repeated administrations over several days or longer, depending on the condition to be treated, the treatment is sustained until a desired suppression of the disease or the symptoms occurs. The composition may be administered by any suitable route, for example by parental, subcutaneous, intranasal, intravascular, intravenous, intraarterial or intrathecal injection or infusion. Progress can be monitored by periodic assessment.

The compositions of the inventions may be administered locally or systemically. Preparations for parental administration include sterile aqueous or non-aqueous solutions, suspensions and emulsions. Examples of non-aqueous solvents are propylenes, glycol, polyethylene glycol, vegetable oils such as olive oil, and injectable organic esters such as ethyl-oleate. Aqueous carriers include water, alcoholic/aqueous solutions, emulsions or suspensions, including saline and buffered media. Parental vehicles include sodium chloride solution, Ringers dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present, such as for example antimicrobials, antioxidants, chelating agents and inert gases, and the like.

The active agent according to the present invention may be administered together with other active agents. The additional active agent(s) may be administered separately or as a part of the pharmaceutical composition of the present invention.

According to a preferred embodiment of the invention, the pharmaceutical composition of the invention may comprise further agents depending on the intended use of the pharmaceutical composition.

It is particularly preferred that the pharmaceutical composition comprises further active agents like e.g. an additional antineoplastic agent, small-molecule inhibitor, anti-tumor agent or chemotherapeutic agent. The invention also relates to a pharmaceutical composition comprising the antibody of the invention in combination with at least one further antineoplastic agent. Such combination is effective for example in inhibiting abnormal cell growth.

Many antineoplastic agents are presently known in the art. In one embodiment, the antineoplastic agent is selected from the group of therapeutic proteins including but not limited to antibodies or immunomodulatory proteins.

In another embodiment, the antineoplastic agent is selected from the group of small-molecule inhibitors or chemotherapeutic agents consisting of mitotic inhibitors, kinase inhibitors, alkylating agents, antimetabolites, intercalating antibodies, growth factor inhibitors, cell cycle inhibitors, enzymes, topoisomerase inhibitors, histone deacetylase inhibitors, anti-survival agents, biological response modifiers, anti-hormones, e.g. anti-androgens and antiangiogenesis agents.

The above-mentioned additional active agents can, of course, not only be administered together with the antibody of the invention within a mutual pharmaceutical composition, but they can also be administered separately.

Once formulated, the compositions of the invention can be administered directly to the subject. The subjects to be treated can be animals; in particular, human subjects can be treated.

The medicament of this invention may be administered by any number of mutes including, but not limited to, oral, intravenous, intramuscular, intra-arteral, intramedullary, intrathecal, intraventricular, transdermal or transcutaneous applications, subcutaneous, intraperitoneal, intranasal, enteral, topical, sublingual, intravaginal or rectal means.

All these methods and formulations are conventional and well known in the art and do not need further explanations.

In yet another embodiment, the present invention relates to a diagnostic method comprising determining the amount and/or localization of FGFR4 in the patient tissue or in a patient sample. In this embodiment, it is particularly preferred to use an antibody carrying a labeling group as described above. A comparison of the result obtained for the patient tissue or patient sample to reference data allows for the diagnosis of diseases associated with FGFR4 expression, overexpression and/or hyperactivity. The diagnostic method of the invention is useful for detecting an undesired expression, overexpression or hyperactivity of human FGFR4 in different cells, tissues or other suitable samples. Accordingly, the onset or the disease state of diseases associated with FGFR4 expression, overexpression and/or hyperactivity can be assessed. The diagnostic method of the invention may also include a step of establishing a treatment regimen for the patient on the basis of the obtained results.

In another embodiment, the present invention relates to a method of assessing for the presence of FGFR4 expressing cells comprising contacting the antibody of the invention with cells or tissue suspected of carrying FGFR4 on their/its surface. Suitable methods for detecting FGFR4 expression in a sample may be an enzyme-linked immunosorbent assay (ELISA) or immunohistochemistry (IHC). An ELISA assay may be carried out in a microtiter plate format, wherein e.g. wells of a microtiter plate are adsorbed with an anti-FGFR4 antibody. The wells are rinsed and treated with a blocking agent such as milk protein or albumin to prevent non-specific adsorption of the analyte. Subsequently, the wells are treated with a test sample. After rinsing away the test sample or standard, the wells are treated with a second anti-FGFR4 antibody that is labeled, e.g. by conjugation with biotin. After washing away excess secondary antibody, the label is detected, e.g. with avidin-conjugated horseradish peroxidase (HRP) and a suitable chromogenic substrate. A concentration of the FGFR4 antigen in the test sample is determined by comparison with a standard curve developed from standard samples. For IHC, paraffin-embedded tissues may be used, wherein the tissues are e.g. first deparaffinized in xylene and then dehydrated e.g. with ethanol and rinsed in distilled water. Antigenic epitopes masked by formalin fixation and paraffin embedding may be exposed by epitope unmasking, enzymatic digestion or saponin. For epitope unmasking, paraffin sections may be heated in a steamer, water bath or microwave oven for 20-40 minutes in an epitope-retrieval solution as for example 2 N HCL solution (pH 1.0). In the case of enzyme digestion, tissue sections may be incubated at 37° C. for 1030 minutes in different enzyme solutions such as proteinase K, trypsin, pronase, pepsin, etc. After rinsing away the epitope-retrieval solution or excess enzyme, tissue sections are treated with a blocking buffer to prevent unspecific interactions. The primary anti-FGFR4 antibody is added at appropriate concentrations. Excess primary antibody is rinsed away and sections are incubated in peroxidase blocking solution for 10 minutes at room temperature. After another washing step, tissue sections are incubated with a secondary labeled antibody, e.g. labeled with a group that might serve as an anchor for an enzyme. Examples therefore are biotin-labeled secondary antibodies that are recognized by streptavidin-coupled horseradish peroxidase. Detection of the antibody/enzyme complex is achieved by incubating with a suitable chromogenic substrate.

In an additional embodiment, the present invention relates to a method of blocking FGFR4 function comprising contacting the antibody of the invention with cells or a tissue suspected of carrying FGFR4 on their/its surface under conditions, wherein the antibody is capable of blocking FGFR4 function. The contacting may be in vitro or in vivo.

Furthermore, the present invention relates to kits for the diagnosis or treatment of diseases associated with FGFR4 expression, overexpression and/or hyperactivity. A kit of the invention comprises at least one antibody, nucleic acid molecule and/or vector as described above. In addition, the kit may further comprise at least one other active agent or further components. It is particularly preferred that the kit further comprises one or more further therapeutic agents useful for cancer combination therapy, like e.g. an additional antineoplastic agent, small-molecule inhibitor, anti-tumor agent or chemotherapeutic agent. Many antineoplastic agents are presently known in the art. In one embodiment, the antineoplastic agent is selected from the group of therapeutic proteins including but not limited to antibodies or immunomodulatory proteins. In another embodiment, the antineoplastic agent is selected from the group of small-molecule inhibitors or chemotherapeutic agents consisting of mitotic inhibitors, kinase inhibitors, such as tyrosin-kinase inhibitors, alkylating agents, antimetabolites, intercalating antibodies, growth factor inhibitors, cell cycle inhibitors, enzymes, topoisomerase inhibitors, histone deacetylase inhibitors, anti-survival agents, biological response modifiers, anti-hormones, e.g. anti-androgens and antiangiogenesis agents.

A diagnostic kit of the present invention preferably comprises a labeled antibody as described herein above. Further, the diagnostic kit may comprise reference data about the amount and/or localization of FGFR4 in the same type of tissue or sample. The reference data may be obtained from one or more healthy subjects and/or from one or more subjects with a known disease state. A comparison to said reference data allows for the diagnosis of diseases associated with FGFR4 expression, overexpression and/or hyperactivity. Based on the obtained results, a treatment regimen for the patient may be established.

Another object of the invention is the antibody of the invention for use for prevention and/or treatment of a disease associated with FGFR4 expression, overexpression and/or hyperactivity.

According to the present invention, diseases associated with FGFR4 expression, overexpression and/or hyperactivity are for example hyperproliferative diseases such as cancer. Cancer that can be diagnosed, prevented and/or treated according to the invention may be selected from the group consisting of hepatocellular carcinoma, breast cancer, gastric cancer, colon cancer, rhabdomyosarcoma, colorectal cancer, prostate cancer, breast cancer, pituitary cancer, ovarian cancer, soft tissue sarcoma, melanoma, head and neck squamous carcinoma and lung adenocarcinoma and other FGFR4-expressing or -overexpressing cancers and formation of tumor metastases.

The skilled person can easily identify according to the general knowledge in the field if a disease is associated with FGFR4 expression, overexpression or hyperactivity.

Reference can be made, for example, to the references mentioned in the introductory part (for example, Lin & Desnoyers, 2012; Wu & Li, 2012; Katoh & Nakagama, 2014; Crose et al., 2012; Li et al. 2014; Sahadevan et al., 2007; Andre & Cortes, 2015; Abbass et al., 1997; Huang et al., 2015; Chen H et al., 2015; Zaid et al., 2013).

According to a particular embodiment of the present invention, the antibody herein disclosed is for use in the treatment of colon cancer, in particular for killing or substantially affecting growth and/or differentiation of colon cancer stem cells.

According to another particular embodiment of the present invention, the antibody herein disclosed is for use in the treatment of liver cancer.

In a particular embodiment, the antibody of the invention is used in colon cancer, in particular for specifically targeting colon cancer stem cells.

In a preferred embodiment, the antibody of the invention is for use for detecting and/or killing and/or affecting and/or inhibiting development and/or differentiation of colon cancer stem cells.

According to another embodiment, the disease associated with FGFR4 expression, overexpression and/or hyperactivity is a metabolic disease, in particular metabolic syndrome or obesity.

According to a still further embodiment of the invention, the disease associated with FGFR4 expression, overexpression and/or hyperactivity is ventricular hypertrophy, heart hypertrophy or chronic kidney disease.

Chronic kidney disease (CKD) increases risk of premature death, and cardiovascular disease is the leading cause at all stages of CKD (Go et al. N. Engl. J. Med., 351(13): 1296-1305, 2004). Left ventricular hypertrophy (LVH) is an important mechanism of cardiovascular disease in CKD that contributes to diastolic dysfunction, congestive heart failure, arhythmia, and sudden death. Due to its role in LVH, it is known that inhibition of FGFR4 is beneficial to prevent cardiovascular diseases (see for example US20160039936 and references cited therein).

Therefore, it is also within the invention, the treatment or prevention of a cardiovascular disease (e.g., primary cardiac disease, secondary cardiac disease, cardiac hypertrophy, heart failure, left ventricular hypertrophy), CKD, diabetes, obesity, in a subject comprising the use of the antibody of the invention to inhibit activation of FGFR4, in particular in cardiac cells (e.g., myocytes, fibroblasts, endothelial cells, smooth muscle cells). In specific embodiments, the cardiovascular disease is hypertension, congestive heart failure, left ventricular hypertrophy, uremic cardiomyopathy, diabetic cardiomyopathy, or primary cardiomyopathy.

The following examples further illustrate the present invention.

EXAMPLES

Example 1

Bioinformatic Identification of Genes Encoding Membrane Proteins Selectively Expressed in Colon Cancer Stem Cells In order to identify novel colon cancer stem cells (CSC) membrane antigens, a computational analysis has been performed by mining a proprietary CSC-specific Affymetrix microarray and cross-querying available public expression databases.

This analysis took advantage of the availability of a genome-wide gene expression data bank (Affymetrix microarray, Human Gene 1.0 ST platform), including data obtained from eight colon CSC lines isolated from primary tumor samples and metastases that were propagated as spheroids in defined serum-free media complemented with EGF and bFGF, or differentiated in vitro in the presence of 10% serum (Ricci-Vitiani et al., 2007). This dataset contains distinct probesets for 26917 different human genes.

In order to define a list of potential target genes the following overall workflow was adopted. Using the reference colon CSC dataset, a first list of genes (1325) differentially up-regulated in the undifferentiated colon CSCs with respect to their in vitro differentiated counterparts was generated using the Bioconductor RankProd algorithm (Hong et al., 2006 & 2008); only genes with a statistically significant differential expression (p-value<0.1) were included. The target gene list was then reduced to 250 entries annotated as genes encoding potential trans-membrane proteins or glycosylphosphatidylinositol (GPI)-anchored proteins, according to two different sources (http://www.uniprot.org/ and Sallman Almen et al., 2009). Within this gene list it was evident that the up-regulation levels in the undifferentiated cell samples were generally low and often <2, a value regarded as the minimum limit for a gene to be considered up-regulated in a biological contest. Therefore, as an additional prioritization strategy, the undifferentiated colon CSC samples were compared to colon normal tissue samples, colon tumor tissue samples and commercial tumor cell line samples as a further selection criteria towards CSC specificity.

Public gene expression data repositories (NCBI GEO and EBI ArrayExpress) were searched for datasets containing human colon tissue samples (normal or tumor) or data for commercially available colon cancer cell lines. An initial examination of the found datasets revealed that very few of them were based on the same microarray platform (Human Gene ST 1.0) or the closely related platform Human Exon ST 1.0. In particular the majority of datasets containing normal or tumor colon samples were based on the Affynnetix platform U 133 plus 2.0. It was therefore necessary to include, as the basis for the comparison with the colon CSCs, also the U 133plus 2.0 platform data. No sub-selection was performed with respect to the exact anatomic localization of the tumor samples (where available) used to generate the available data. For the tumor category, only carcinoma samples were accepted excluding all identifiable adenoma samples or other clearly distinct samples, e.g. samples from inflammatory bowel disease patients (Table 4).

by LCM) from 16 different datasets and 145 colon tumor cell line samples (74 unique cell lines) from 8 different datasets. In addition, 6 additional datasets containing human normal and tumor stem cell samples were also included. Only two datasets have the same microarray architecture (HuGene ST 1.0) as the reference colon CSC dataset, all other datasets were based on the Affymetrix U 133 plus 2.0 platform. Raw expression data files for all datasets were downloaded from the NCBI website "Gene Expression Omnibus" (GEO) ( ) and processed with the standard "Robust Multi-array Average" (RMA) procedure using methods available within the R Bioconductor program suite (Gentleman et al., 2004; http://www.bioconductor.org/; http://www.r-project.org/).

To correct for technical effects arising from the use of two different microarray platforms, the following strategy was applied. Data in the normal and tumor colon datasets were initially pre-processed with the ComBat algorithm (Johnson & Rabinovic, 2007) correcting for evident batch effects. The same procedure was applied to the colon tumor cell line dataset. A second ComBat correction applied to the overall combined dataset then removed the bias due to the two different microarray architectures.

TABLE 4

Datasets within the public NCBI GEO database included in this analysis

| GEO Accession number | Platform | Colon normal | Colon Normal microdis. | Colon tumor | Colon tumor microdis. | Colon Cancer Cell lines | Stem cells (SCs) | Comments |
|---|---|---|---|---|---|---|---|---|
| GSE2109 | U133plus2.0 | | | 315 | | | | |
| GSE4107 | U133plus2.0 | 10 | | 12 | | | | |
| GSE4183 | U133plus2.0 | 8 | | 15 | | | | |
| GSE8671 | U133plus2.0 | 32 | | 32 | | | | Matched pairs |
| GSE9254 | U133plus2.0 | 19 | | | | | | |
| GSE9348 | U133plus2.0 | 12 | | 70 | | | | |
| GSE11381 | U133plus2.0 | 17 | | | | | | |
| GSE17536 | U133plus2.0 | | | 177 | | | | |
| GSE17537 | U133plus2.0 | | | 55 | | | | |
| GSE18088 | U133plus2.0 | | | 53 | | | | |
| GSE18105 | U133plus2.0 | 34 | | 77 | | | | |
| GSE20916 | U133plus2.0 | 24 | 20 | 36 | 10 | | | |
| GSE22598 | U133plus2.0 | 17 | | 17 | | | | |
| GSE23878 | U133plus2.0 | 24 | | 35 | | | | |
| GSE26906 | U133plus2.0 | | | 90 | | | | |
| GSE33113 | U133plus2.0 | | | 90 | | | | |
| GSE14733 | U133plus2.0 | | | | | 8 | | |
| GSE23295 | U133plus2.0 | | | | | 4 | | |
| GSE24795 | U133plus2.0 | | | | | 30 | | |
| GSE28214 | HuGene ST 1.0 | | | | | 2 | | HCT116 cells |
| GSE34211 | U133plus2.0 | | | | | 14 | | |
| GSE35478 | U133plus2.0 | | | | | 16 | | |
| GSE35566 | U133plus2.0 | | | | | 18 | | |
| GSE36155 | U133plus2.0 | | | | | 70 | | |
| GSE17375 | U133plus2.0 | | | | | | 4 | Colon CSCs |
| GSE21243 | U133plus2.0 | | | | | | 4 | Undiff. Induced pluripotent SCs |
| GSE21244 | HuGene ST 1.0 | | | | | | 7 | Various human SCs |
| GSE31255 | U133plus2.0 | | | | | | 10 | Colonic SCs (EP HB2-purified) |
| GSE33112 | U133plus2.0 | | | | | | 12 | Colon CSCs |
| GSE34053 | U133plus2.0 | | | | | | 9 | CD133 ± colon CSCs |

Overall the global dataset comprised a total of 200 normal samples [20 of which obtained by laser capture microdissection (LCM)], 1100 tumor samples (87 of which obtained Due to the large number of samples present in the normal and tumor colon datasets, a selection procedure was applied during the pre-processing reducing the total data number and making the number of normal and tumor colon samples approximately equal. Based on an average median distance between the samples, the selection procedure successfully removed samples farthest from the center of the sample cluster (normal or tumor) until the desired number of remaining samples was reached. Applying this procedure 105 normal and 176 tumor samples were sub-selected. An equivalent procedure reduced the number of LCM samples within dataset GSE18105 from 77 to 19. No selection was instead applied to the LCM samples from dataset GSE20916.

The ComBat algorithm was also applied to the colon tumor cell lines data to eliminate the batch effects (not shown).

These batch-corrected sub-datasets were then combined with the reference colon CSC dataset (only the undifferentiated samples) adding also the additional 6 stem-cell related datasets. In particular the addition of dataset GSE33112 (colon CSC culture samples) was essential since it provided samples measured with the Affymetrix U 133 plus 2.0 platform and closely related to the reference CSC samples. This allowed to apply ComBat as a final global scaling step correcting the architecture-specific differences between the two Affymetrix platforms (HuGene ST 1.0 and U 133 plus 2.0). Before applying the ComBat correction the global dataset displayed a clear pattern of microarray platform-specific sample clustering. Following the ComBat correction this effect was strongly reduced with the colon CSC samples now clustering close to the equivalent samples from GSE33112.

Within the global dataset the undifferentiated CSC samples were then compared using the algorithm RankProd to the different subsets: macro-dissected colon normal and tumor datasets, micro-dissected colon normal and tumor datasets, and colon tumor cell line dataset. Average fold-change (FC) differences between the colon CSC samples and each dataset were calculated by RankProd at a p-value cutoff of 0.05. No FC value was assigned to pro besets/genes above this p-value cutoff.

The number of potential target genes was then further reduced accepting only genes for which a positive FC difference was observed to the normal colon dataset. The resulting list of 104 genes was then examined in detail (membrane localization prediction and literature data) in order to confirm or reject their status as trans-membrane or GPI-anchored plasma membrane proteins, thus restricting the selection to 57 genes. Then these potential targets have been individually analyzed and prioritized according to the following criteria: (i) FC difference>2 to the colon tumor tissues and cell lines (p<0.05); (ii) absent/low expression in normal tissues derived from vital organs, relevant to anticipate the potential toxicity of the corresponding antibodies, by comparison with data extracted from the "BioGPS" (http://biogps.org/) and the "Body Atlas" dataset GSE14938, within the NCBI GEO repository (http://www.ncbi.nlm.nih.gov/geo/query/acc.cgi7acc=GSE14938); (iii) absence, for each gene product, of soluble protein variants generated either by alternative splicing or shedding and of short extracellular domains; (iv) biological function, associated signalling pathways, protein interaction networks and the expression and role in different tumor types of each gene product based on two online resources (http://www.uniprot.org/, http://www.genecards.org/, http://www.ncbi.nlm.nih.gov/gene/) and scientific publications. A number of additional immunological criteria led to counter screen genes encoding proteins similar to poorly immunogenic ones, or with ectopic low expression, or too similar to human paralogs and murine orthologs, thus generating a restricted list of 21 candidate genes.

Example 2

Confirmation of the Specificity of the Selected Gene Expression in Colon CSC

The differential expression of the 21 selected genes have been confirmed and quantified by qRT-PCR. The eight different colon CSC lines used to generate microarray data were propagated as spheroids in defined serum-free media complemented with EGF and bFGF. For comparison, eleven different commercial colon tumor cell lines (ATCC), selected among those included in the dataset used in the bioinformatic analysis, were cultured following ATCC recommendations (Table 5).

TABLE 5

Colon tumor cell lines analyzed by qRT-PCR.

| Colon CSC line | Colon tumor cell line | Code |
|---|---|---|
| 1.1 | Caco-2 | cl1 |
| 1.2 | DLD-1 | cl2 |
| 18 HCT 1 | 16 | cl3 |
| 85 HCT | 15 | cl4 |
| CR01 | HT-29 | cl5 |
| CC1 | LoVo | cl6 |
| CC2 | SNU-C2B | cl7 |
| CC5 | SW48 | cl8 |
|  | SW480 | cl9 |
|  | SW620 | cl10 |
|  | WiDr | cl1 1 |

Total RNA was prepared using the RNAeasy mini kit (Qiagen) following the manufacturer's recommendations. RNA samples were collected in RNase-free water, quantified by measuring the absorbance at 260 nm using an Eppendorf BioPhotometer and qualitatively controlled using an Agilent 2100 bioanalyzer. mRNA levels of each selected gene were compared in undifferentiated CSCs and in the colon tumor cell lines by quantitative reverse transcription-PCR (qRT-PCR). In addition, the expression of the 21 selected genes in the colon CSCs has been compared to that measured by q RT-PCR in an RNA sample from human normal colon tissue (FirstChoice Human Colon Total RNA, Life Technologies).

Two colon CSC-specific markers, OLFM-4 and Lgr5 (van der Flier et al., 2009; Barker et al. 2007) were also included as positive controls. Two genes, whose expression does not vary significantly in the analyzed cell lines (Affymetrix dataset), encoding the glyceradehyde-3-phosphate dehydrogenase (GAPDH) and the heterogeneous nuclear ribonucleoprotein K (HNRNPK), respectively, have been included as normalizers. Assays have been performed in triplicate in MicroAmp 96-well plates using gene-specific probes and primers (TaqMan® Gene Expression Assays, Applied Biosystems/Thermo Fisher Scientific): 40 uL of a reaction mix were dispensed in each well containing 25 uL of 2× Master Mix/0.5 uL of 100× RT (Qiagen), 2.5 uL of each TaqMan Assay and 12 uL of $H_2O$. 10 uL of total RNA at concentrations of 5 ng/uL were then added in a final reaction volume of 50 uL, and qRT-PCR was performed using a Perkin Elmer ABI 7900 HT real time thermal cycler (50° C. 30 min, 95° C. IO min, followed by 40 cycles: 95° C. 15 sec, 60° C. I min). Quantitative calculations were performed by using the 2^ (-AA$_{c\_j}$) method.

The top-eight qRT-PCR validated genes (>3-fold CSC selectivity over normal colon and at least 4 different tumor cell lines in at least 3 independent CSC lines) were reduced to five based on their predicted immunogenicity (Table 6).

TABLE 6

Colon cancer stem cell candidate antigens selected for genetic immunization.
Growth factor receptors Cytokine receptors
Repulsive guidance molecules
Tumor necrosis factors Olfactory receptors

|   | Gene | Protein type | Protein type |
|---|------|--------------|--------------|
| 1 | FGFR4 | Fibroblast growth factor receptor 4 | Type I membrane protein |
| 2 | IL17RB | Interleukin 17 receptor B | Type I membrane protein |
| 3 | RGMB | RGM domain family, member B (Dragon) | GPI-anchored protein |
| 4 | EDAR | Ectodysplasin A receptor | Type I membrane protein |
| 5 | OR51E1 | Olfactory receptor, family 51, subfamily, member 1 | G-protein coupled receptor 1 family |

The complete selection process is summarized in FIG. 1.

Additional experiments have been performed in order to confirm, at the protein level, the preferential expression in colon CSCs of the five selected genes.

Figure 2A:
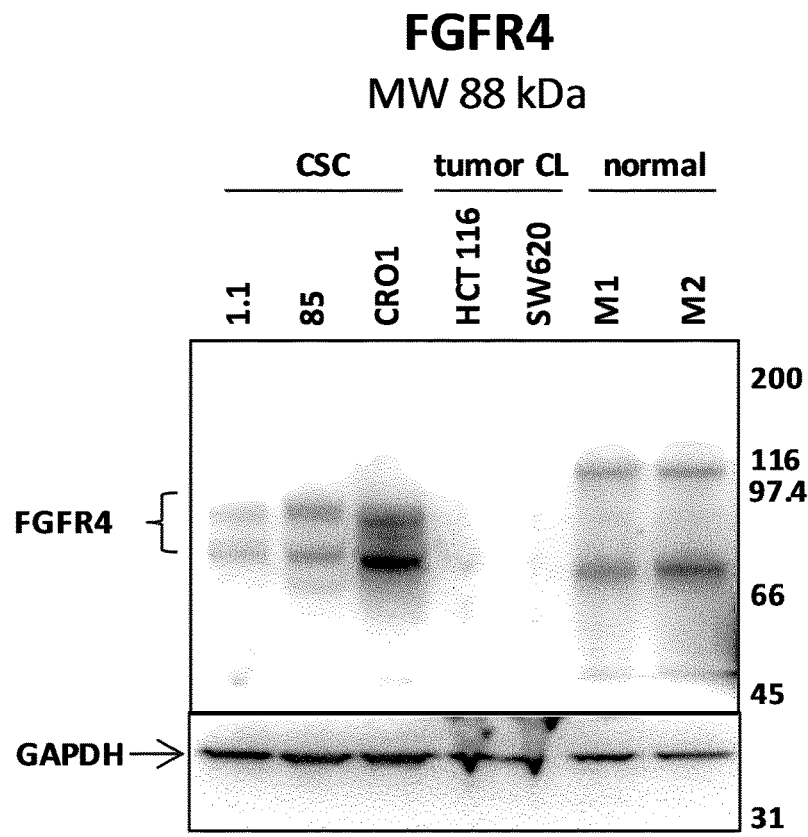
FIG. 2 (A-B). Preferential expression of the selected protein antigens in CSCs relative to ATCC tumor cell lines and normal colon tissues analyzed by Western Blot using specific commercial primary antibodies.
Figure 2A:
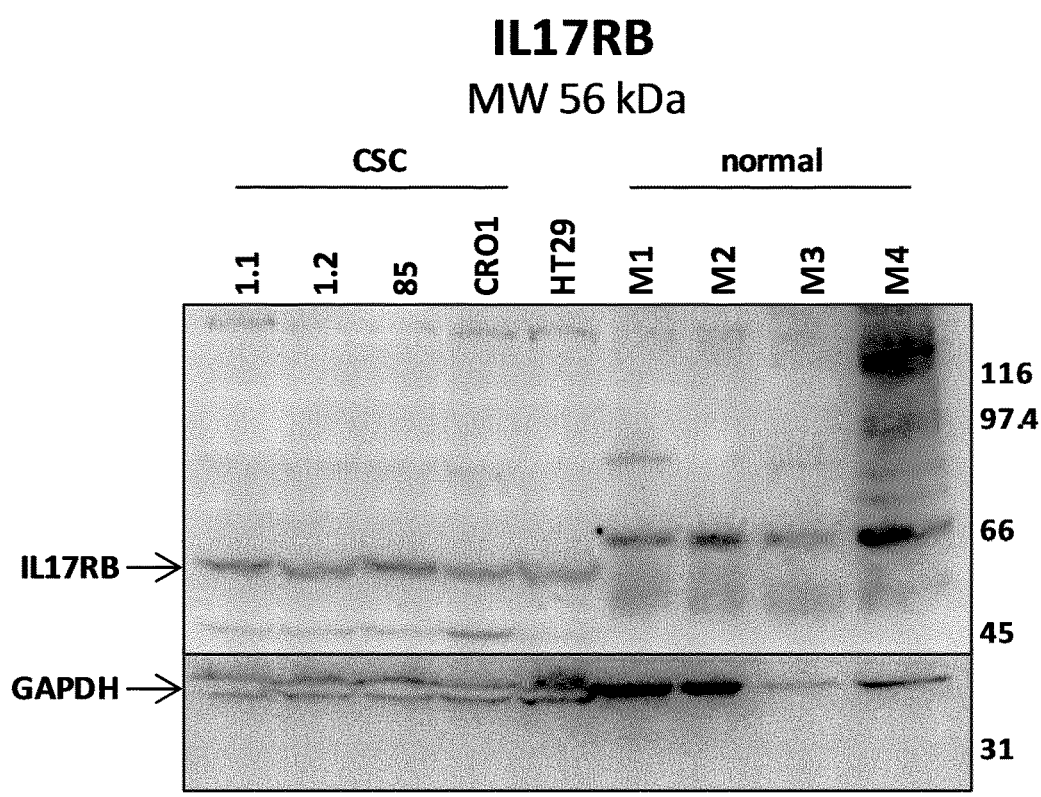
Figure 2B:
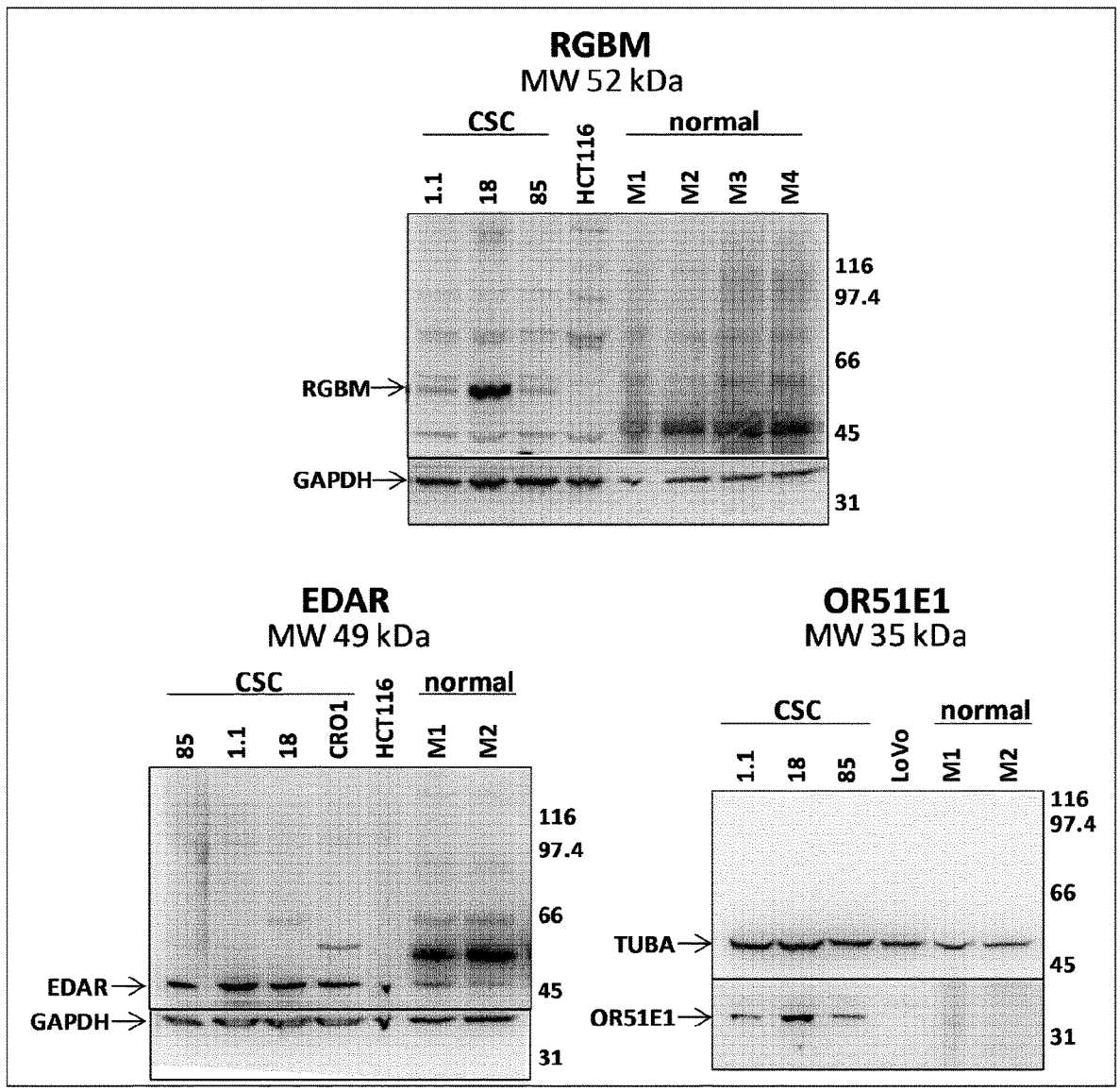

Total protein extracts have been prepared from the colon CSC lines expressing high mRNA levels of each gene and from the ATCC colon tumor cell lines expressing low mRNA levels of the same gene. In addition protein extracts were prepared from human normal colonic mucosa. Samples were then analyzed by SDS-PAGE and Western Blot (FIG. 2). This analysis confirmed also at the protein level the preferential expression in the CSCs of the five genes that have been selected based on their differential mRNA expression levels.

Example 3

Generation of Monoclonal Antibodies Against the Colon CSC Membrane Antigens

Monoclonal antibodies (mAbs) against the five selected antigens have been generated by genetic immunizations of rats using the Aldevron/GENOVAC core technology platform that enables the development of antibodies against protein targets directly using the corresponding DNA coding-sequences (http://www.aldevron.com/services/antibody-development/genetic-immunization, see for example the following references:

Bioprocessing—Genetic Immunization for Antibody Production. Tutorial: Genovac's Technological Shortcut From Gene to Antibody. By John Thompson, Ph.D., and Stefan Lang, Ph.D., published in Genetic Engineering News, Vol. 22, No. 17, Oct. 1, 2002; Custom-made antibodies produced by genetic immunisation: Applications in drug development, therapy and diagnosis. By Stefan Lang and John Thompson, published in Global Outsourcing Review, Vol. 5, No. 1, Spring 2003; A shortcut from genomics to drug development. By Jens Lohrmann, Stefan Lang and John Thompson, published in Current Drug Discovery, October 2003). Genetic immunization has several advantages relative to conventional immunization techniques, especially because the expression of a properly folded and glycosylated antigen, or of specific antigen domains, increases the probability of generating mAbs that recognize with high affinity native epitopes, with a higher propensity to functional activity.

Target cDNA sequences have been cloned into Aldevron (Freiburg, Germany) proprietary immunization vector (pB8-HA) and detection vector (pBI-myc) engineered to ensure ectopic expression of the corresponding proteins at the cell surface in frame with a hemagglutinin (HA) tag and a myc tag, respectively. For FGFR4, IL17RB and RGMB the constructs contained the full-length sequences, while for EDAR and OR51E1 distinct extracellular domains were inserted.

HEK293-derivative BOSC23 cells were transiently cotransfected with the selected antigen expression vectors (either pB8-HA or pBI-myc derivatives) and the reciprocal empty vectors as internal negative controls. FACS analysis using both anti-HA and anti-myc antibodies confirmed a significant and specific plasma membrane expression for all five antigens.

Rats were immunized with the immunization vectors pB8-FGFR4, pB8-IL17RB, pB8-RGMB, pB8-EDAR-h-ecd pB8-EDAR-h-ecd+TM, or pB8-OR51E1-h-syn, by performing 4-6 genetic applications of the corresponding DNAs absorbed on gold particles and administered intradermal^ for direct delivery into cells in the living animals. To control whether this procedure had elicited an immune response, rat sera were collected 24-60 days after immunization, diluted 1:1000 in PBS/1% BSA, and tested by FACS using BOSC23 cells transiently transfected with the corresponding antigen cDNA cloned in the pBI-myc detection vector. A goat anti-rat IgG R-phycoerythrin conjugate (Southern Biotech) was used at 10 µg/mL as secondary antibody. As a negative control, BOSC23 cells, transfected with an irrelevant cDNA cloned in the same expression vector, were incubated with immune sera of each animal and submitted to FACS analysis. In addition, cell surface expression of the detection vectors pBI-FGFR4, pBI-IL17RB, pBI-RGMB, pBI-EDAR-h-ecd pBI-EDAR-h-ecd+TM or pBI-OR51El-h-syn was controlled by FACS using an anti-myc primary antibody and a goat anti-mouse IgG R-phycoerythrin conjugate (Southern Biotech) at 10 pg/mL as secondary antibody.

Specific reactivity of the immune sera of all cohorts of rats immunized with the different antigens could be detected against cells expressing the corresponding antigens at their surface, when compared to cells transfected with an irrelevant cDNA. The plasma membrane expression of the different antigens was confirmed in a parallel experiment (data not shown).

The next step consisted in the isolation of splenic B cells from the rats immunoresponsive to each antigen and their fusion with suitable myeloma cells to generate hybridomas. After the selection and clonal expansion of the hybridomas, those producing antibodies with the appropriate specificity were identified by flow cytometric evaluation of the corresponding supernatants immunoreactivity towards their antigens ectopically expressed on the surface of the reporter cell line BOSC 23 transiently transfected with the pBI-antigen-encoding constructs (Table 7).

TABLE 7

Yield of fusions with lymphocytes taken from rats immunized pB8-immunization vectors expressing the different antigens.

| Antigen | Fusion | Nr. plated lymphocytes (*10^6) | Nr. Hybridoma colonies 96 w/1. | Nr. specific Hybridoma 96 w/1 | Selected clones limited to Nr. | Nr. specific stable clones | Nr. specific positive Hybridoma T25 |
|---|---|---|---|---|---|---|---|
| FGFR4 | BFG | 132 | 7100 | 477 | 108 | 20 | 14 |
| IL17RB | BFI | 132 | 6540 | 503 | 108 | 20 | 16 |
| RGMB | BGH | 132 | 6540 | 394 | 108 | 20 | 17 |
| EDAR-hum-ecd | BGG | 132 | 3860 | 130 | 108 | 63 | 11 |
| EDAR-hum-ecd-TM | BGC | 132 | 1810 | 37 | 37 | 24 | 11 |
| OR51E1-hum-synth | BGG | 132 | 3570 | 170 | 108 | 68 | 24 |

From the isolated hybridoma stable parental clones, supernatants were obtained (14-24/target, last column of Table 7) containing antibodies that resulted positive and antigen-specific according to the FACS analysis.

Example 4

Selection of the Hybridoma Parental Clones by Flow Cytometric Evaluation of the Corresponding Supernatant Immunoreactivity Towards Colon CSC Endogenous Antigens The positive supernatants against the five antigens were analyzed for their ability to bind the colon CSC surface, by evaluating their immunoreactivity by FACS on five different cell lines. A commercial colon tumor cell line at low expression for the correspondent transcript has been included as a negative control for each antigen. The assay has been performed in 96 well-microplates with $3\lambda10^4$ cells/well in 50 uL of cell medium to which 100 uL of the tested supernatant were added. Conditioned medium of the murine myeloma cells used in hybridomas (DMEM/10% FBS) was included as negative control. After Ih at 4° C., an anti-rat fluorescent secondary antibody (Alexa FluorR 647 goat anti-Rat IgG [H+L], Thermo Fisher Scientific) was added and the cells were treated with 7-aminoactinomicin D (7-AAD) at 5 ug/mL to control cell viability. Samples incubated only with the secondary antibody were also included as an additional negative control. The flow cytometric evaluation has been performed using the cytofluorimeter FACS LSR II (Becton Dickinson).

In most cases the differences of the selected antigen mRNA expression between the colon CSCs and the commercial colon tumor cell lines have been confirmed at the protein level.

For each of the five colon CSC lines analyzed by FACS (Signore et al., 2016) the mean fluorescence intensity (MFI) of viable cells was used as evaluation parameter. For each supernatant this value was divided by the MFI of the negative control, thus obtaining a fold change (FC) value with respect to control. For each CSC line the supernatants were ranked according to their FC value, assigning the highest score to the supernatants with the highest reactivity. By adding the individual ratings assigned to each supernatant on each CSC line, a final rank was obtained (FIG. 3).

On this basis the best performing supernatants were prioritized (5-12/antigens, FIG. 3), affinity purified on protein G-Sepharose, and analyzed in a cell viability assay on five colon CSC lines.

For the affinity purification, 5 mL of each supernatant were incubated for 2 h at room temperature (RT) with 0.5 mL of protein G-Sepharose resin (GammaBind Plus Protein G Sepharose, GE) in 0.1M sodium phosphate pH 7.0, 1.5M NaCl, 0.1M EDTA (IX BB). After the binding step, the samples were transferred into empty chromatography columns (Poly-Prep® columns, Bio-Rad), the resin was allow to settle by gravity and washed with 20 volumes of IX BB. Bound antibodies were eluted in two steps with 1 mL/each of 0.1 M Glycine-HCl, pH 2.3 collected in tubes containing 100 uL of 1M Tris pH 9 for pH neutralization. Purified mAbs were then quantified and controlled by SDS-PAGE.

The purified mAbs were evaluated in cell viability assays performed with two to four colon CSCs for each antibody. Briefly, after enzymatic disaggregation of cell spheroids, 4000 viable single cells were plated in each well of 96-well microplates in 100 uL of culture medium, in triplicate. After 24 h incubation at 37° C., 5% $CO_2$, 10 uL of each antibody solution, or of a 1: 5-1:10 dilution in Tris-Glycine pH 7 were added. 10 uL of a rat IgG solution at 30 ug/mL in Tris-Glycine pH 7 were included as negative control. After 96 h incubation with the antibodies at 37° C., 5% $CO_2$, cell viability was measured using the chemiluminescent CellTiter-Glo™ (Promega) reagent, following the manufacturer's recommendations. The luminescent intensity, proportional to the cellular ATP content and therefore to cell viability, was measured using the microplate reader Beckman Coulter DTX 880 Multidetector.

Two to eight antibodies/antigen showed an anti-proliferative/cytotoxic activity and the most effective ones were selected for the subcloning of the corresponding hybridomas (4 subclones/antigen at most).

Example 5

Characterization of the Antibodies Purified from the Supernatants Obtained from Selected Hybridoma Subclones Four parental hybridomas, producing the best specific antibodies against each antigen, have been subcloned to maintain the stability and monoclonal character of the cell lines.

The evaluation of the positivity of the antibodies produced by the stable subclone cultures was performed by FACS analysis of their immunoreactivity against the antigens ectopically expressed on the surface of the BOSC 23 reporter cell line, as described in Example 3.

On this basis, three to four subclones were selected for each of the antigens FGFR4, IL17RB, RGMB and EDAR, while for the fifth antigen OR51E1 the subclone supernatants showed reactivity only against the extracellular domain (used for immunization) and not against the full-length protein, being therefore set aside (Table 8).

TABLE 8

Positive subclones

| antigen | FGFR4 | IL17RB | RGMB | EDAR |
|---|---|---|---|---|
| | BFG-2F7-B9 | BFI-6G10-E7 | BFH-5C9-C1 | BGC-6F6-C10 |
| | BFG-5E5-B5 | BFI-7C7-G3 | BFH-9H5-C11 | BGB-6F7-B5 |
| subclones | BFG-5F7-D5 | BFI-8B8-D3 | BFH-10F2-H2 | BGC-10B7-E3 |
| | | BFI-8E1-B2 | | |

The corresponding monoclonal antibodies were purified from 200 mL of each of the thirteen positive supernatants (in serum free medium) using a Protein G-Sepharose Fast Flow affinity column (HiTrap™ Protein G HP, GE Healthcare) and the fast protein liquid chromatography AKTA system (GE Healthcare). 1 mL-peak fractions eluted in 0.1 M Glycine-HCl pH 2.5 and neutralized with 100 uL of 1 M Tris pH 9 were pooled and the purified IgGs were quantified and controlled by SDS-PAGE.

The binding of the purified antibodies to their specific surface antigens was analyzed by FACS on five colon CSC lines in dose-response assays. Dissociation constants and maximum binding values were inferred from FACS analysis using the GraphPad Prism software. These values were obtained by fitting the experimental FC values, defined in the Example 4, as a function of the mAb concentration, to the "one site binding" (hyperbole) equation: $Y=B_{max}*X/(K_d+X)$, where $B_{max}$ is the maximum binding value and Kd (dissociation constant) is the antibody concentration required to reach half maximum binding. The anti-FGFR4 and anti-EDAR mAbs showed a significant, dose-dependent reactivity on at least two cell lines with $K_d$ values in the sub/low nanomolar range (0.2-1.3 nM), while the anti-IL17RB mAbs resulted less reactive ($K_d$ values between 40 and 125 nM), and only one anti-RGMB mAb was positive (Table 9).

TABLE 9

Dissociation constants and maximum binding values of the anti-FGFR4, anti-EDAR, anti-IL17RB and anti-RGMB mAbs on the colon CSCs.

anti-FGFR4 mAbs

| Cell clone | CTSC85 | | | CTSC1.2 | | |
|---|---|---|---|---|---|---|
| mAb | BFG-2F7-B9 | BFG-5E5-B5 | BFG-5F7-D5 | BFG-2F7-B9 | BFG-5E5-B5 | BFG-5F7-D5 |
| Bmax | 5.2 (±0.5) | 4.1 (±0.3) | 4 (±0.1) | 3.9 (±0.3) | 4.2 (±0.1) | 3.9 (±0.2) |
| Kd (ug/mL) | 0.12 (±0.06) | 0.15 (±0.05) | 0.07 (±0.015) | 0.09 (±0.03) | 0.23 (±0.03) | 0.065 (±0.02) |
| Kd (nM) | 0.8 (±0.4) | 1 (±0.4) | 0.5 (±0.1) | 0.6 (±0.2) | 1.6 (+0.2) | 0.4 (±0.16) | anti-EDAR mAbs

| Cell clone | CTSC1.2 | | | CTSC1.2 | | |
|---|---|---|---|---|---|---|
| mAb | BGC-6F6-C10 | BGB-6F7-B5 | BGC-10B7-E3 | BGC-6F6-C10 | BGB-6F7-B5 | BGC-10B7-E3 |
| Bmax | 5.9 (±0.4) | 8 (±1.7) | 7.2 (±0.6) | 5.2 (±0.8) | 4.7 (±1.1) | 6.5 (±1) |
| Kd (ug/mL) | 0.03 (±0.02) | 3.2 (±2) | 0.09 (±0.04) | 0.06 (±0.06) | 2.6 (±2) | 0.06 (±0.06) |
| Kd (nM) | 0.18 (±0.1) | 21 (±14.5) | 0.6 (±0.27) | 0.4 (±0.4) | 17.5 (±13.5) | 0.4 (±0.4) | anti-IL17RB mAbs

| Cell clone | CTSC85 | | | CTSC1.1 | | | CTSC18 | | |
|---|---|---|---|---|---|---|---|---|---|
| mAb | BFI-6G10-E7 | BFI-8B8-D3 | BFI-8E1-B2 | BFI-6G10-E7 | BFI-8B8-D3 | BFI-8E1-B2 | BFI-6G10-E7 | BFI-8B8-D3 | BFI-8E1-B2 |
| Bmax | 6.9 (±1.1) | 2.7 (±0.5) | 2.65 (±0.4) | 7.9 (±3.5) | 6 (±1.5) | 4.3 (±0.5) | 11 (±3.5) | — | — |
| Kd (ug/mL) | 6 (±2.5) | 2 (±1.3) | 0.7 (±0.45) | 18.8 (±14) | 8.9 (±4.8) | 4.3 (±1.4) | 12.7 (±7.7) | — | — |
| Kd (nM) | 40 (±17) | 13 (±9) | 4.7 (±0.1) | 125.6 (±93) | 59 (±32) | 28.7 (±9) | 80.5 (±51) | — | — | anti-RGMB mAbs

| Cell clone | CTSC1.2 | CTSC18 | CTSC1.1 |
|---|---|---|---|
| mAb | | BFH-10F2-H2 | |
| Bmax | 1.8 (±0.2) | 2.8 (±0.5) | 9.4 (±3.5) |
| Kd (ug/mL) | 0.6 (±0.35) | 2.6 (±1.5) | 10.45 (±8) |
| Kd (nM) | 4 (±2.3) | 17.4 (±10.2) | 70 (±0.54) |

The antigen binding specificity of some selected antibodies was confirmed with commercial colon tumor cell lines transduced with suitable lentiviral vectors (GIPZ Lentiviral shRNA, Thermo Fisher Scientific) encoding short hairpin RNAs (shRNA) to silence antigen expression. Three cell lines, HCT116, SW48 and SW480, which showed relatively high expression levels of FGFR4, IL17RB and RGMB, respectively, were used for lentiviral-based knockdown of the corresponding transcripts. FACS analysis of FGFR4-IL17RB- and RGMB-silenced cells, controlled by qRT-PCR, demonstrated the specificity on the antibodies for the corresponding antigens.

Example 6

Evaluation of the Proliferative Potential, Cell Motility and Tumorigenicity of Colon CSCs Enriched for and Depleted of FGFR4

It has been observed that selected antibodies against different targets showed by FACS a bimodal distribution reactivity when tested on the colon CSC line CTSC85 (Signore et al., 2016).

Figure 4:
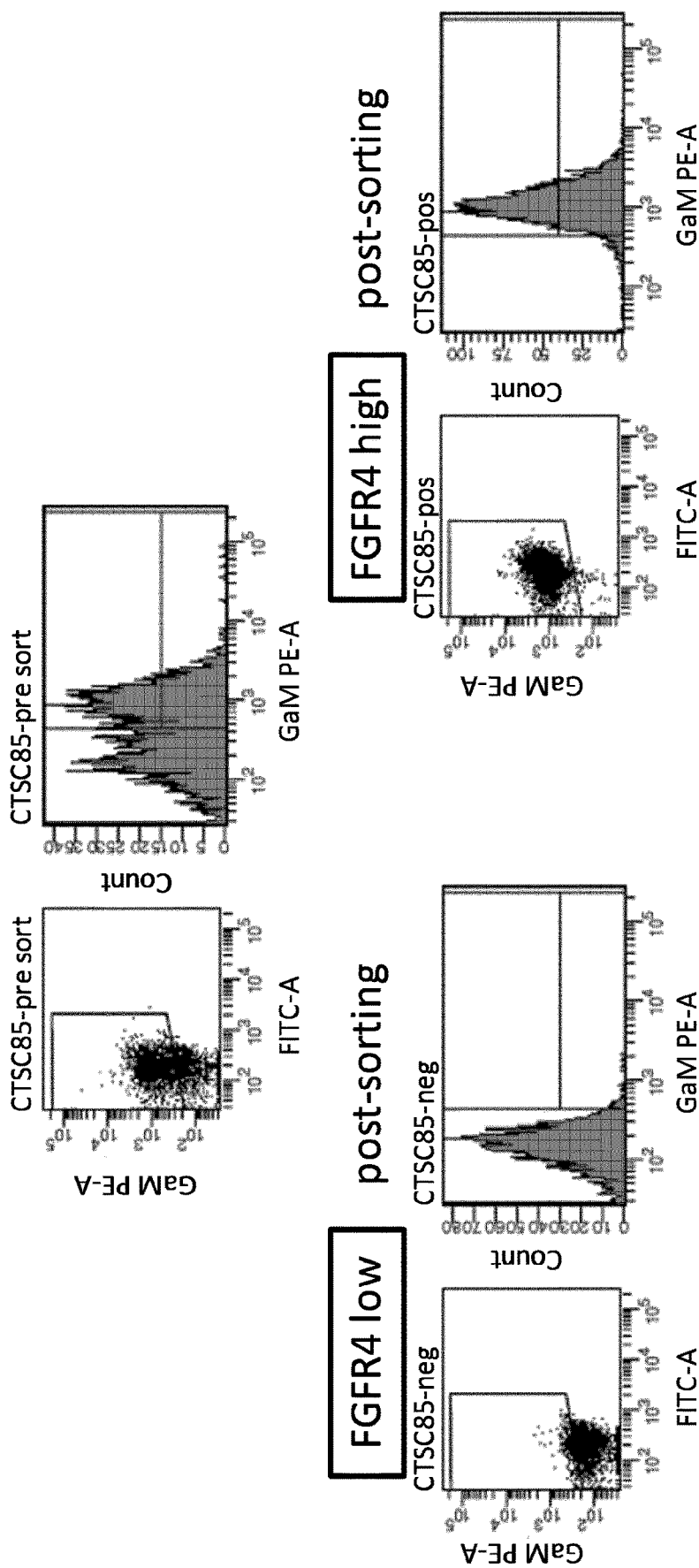
FIG. 4. FACS analysis of the CSC line CTSC85 before and after flow cytometry cell sorting performed to separate the two subpopulations with different FGFR4 surface expression levels.

In order to experimentally validate FGFR4 as a potential therapeutic target for the colon CSCs, the CSC line CTSC85 was submitted to flow cytometry cell sorting to separate two subpopulations, FGFR4$^{High}$ and FGFR4$^{Low}$ respectively, based on the bimodal binding profile with the anti-FGFR4 antibody BFG-5F7-D5 (FIG. 4).

Directly after isolation, the two cell populations were evaluated in a number of in vitro assays in order to highlight possible functional differences. The assays were performed in parallel together with the parental heterogeneous cell population (mock-sorted cells), used as a reference for the two separated subpopulations.

Figure 5:
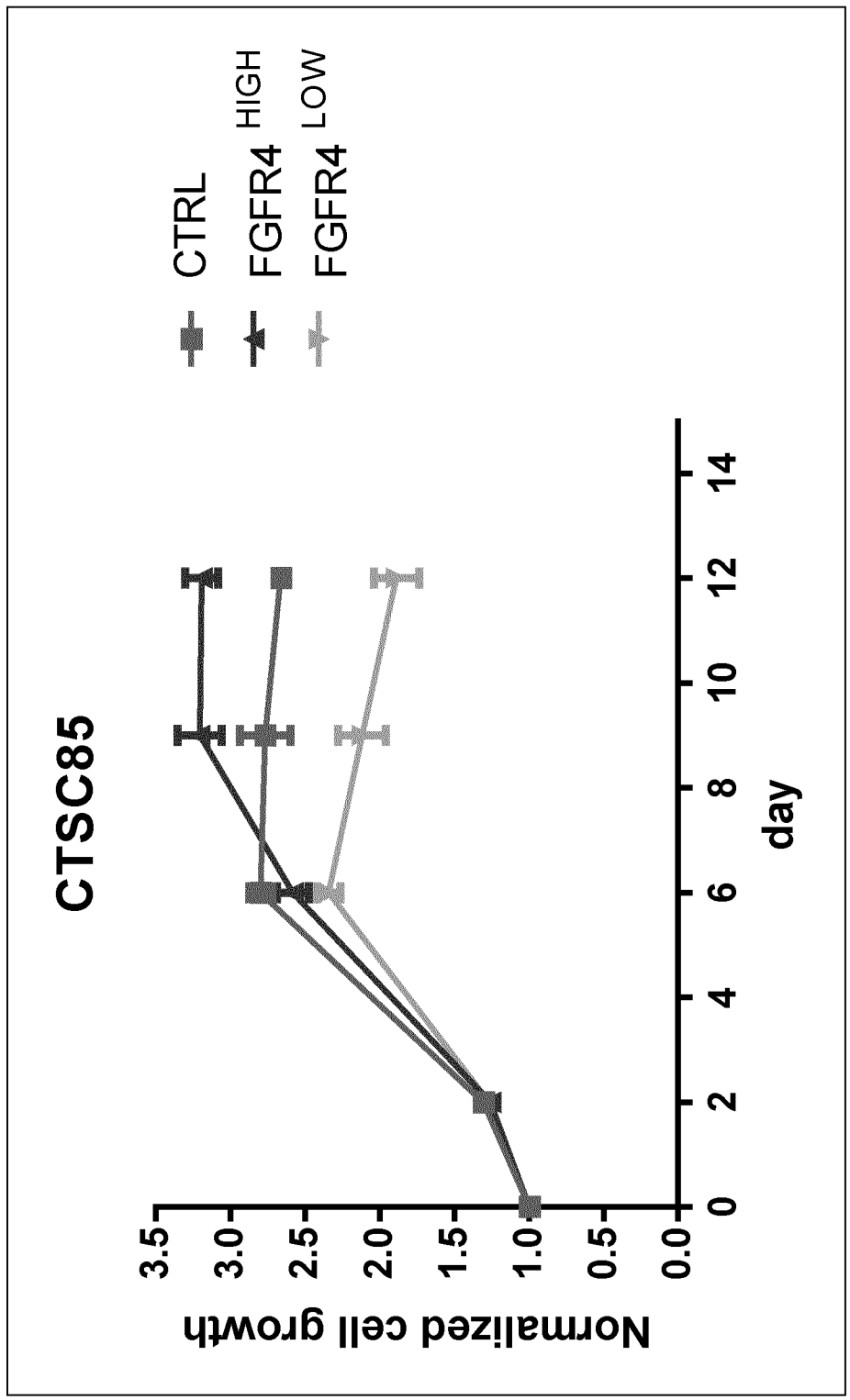
FIG. 5. Growth curves of control (mock sorted, square), FGFR4High (triangle) and FGFR4Low (inverted triangle) CTSC85 cell populations evaluated by CellTiter-Blue™ assay (n=3). Data are normalized to day 0.

To measure cell proliferation, 2000 cells were seeded in each well of a 96 well-microplate in 100 uL of culture medium, setting eight experimental points in triplicate. The cell proliferation rate was monitored for fourteen days, measuring the number of viable cells every two days, using the cell viability fluorometric assay CellTiter-Blue™ (Promega), following the manufacturer's protocol. Fluorescence intensity, proportional to cell viability, was measured with the microplate reader Victor 2™ (Wallac, Perkin Elmer). Means of the triplicate fluorescence intensity values corresponding to the different time-points were normalized to the mean value measured on the cell plating day (day 0) (FIG. 5).

In addition, the two FGFR4$^{High}$ and FGFR4$^{Low}$ subpopulations and the control population (mock-sorted) of CTSC85 cells, have been analyzed for their colony forming efficiency, both in limiting dilution experiments and in soft agar.

For the clonogenic assay in liquid culture, 1, 5, or 25 single cells were seeded in each well of 96 well-microplates in 100 uL of growth medium. After fourteen days the number of wells containing colonies relative to the total number of wells was calculated for each cell dilution condition, thus obtaining the colony-forming frequency.

For the colony formation assay in soft agar, 24 well-plates were used. Briefly, 500 uL of a 0.9% low-melting agarose (low-melting point Sea Plaque Agarose, Cambrex Bioscience) solution in growth medium were dispensed into each well and allow to solidify at 4° C. for at least Ih (bottom layer). For the top layer, equal volumes of a 1% low-melting agarose solution in growth medium and a cell suspension of 5.2×10+ cells/mL were mixed and 500 uL of the mixture were transferred to each well (1.3×10$^4$ cells/well) and allowed to solidify at room temperature. 100 uL of culture medium were then added to each well.

Figure 6:
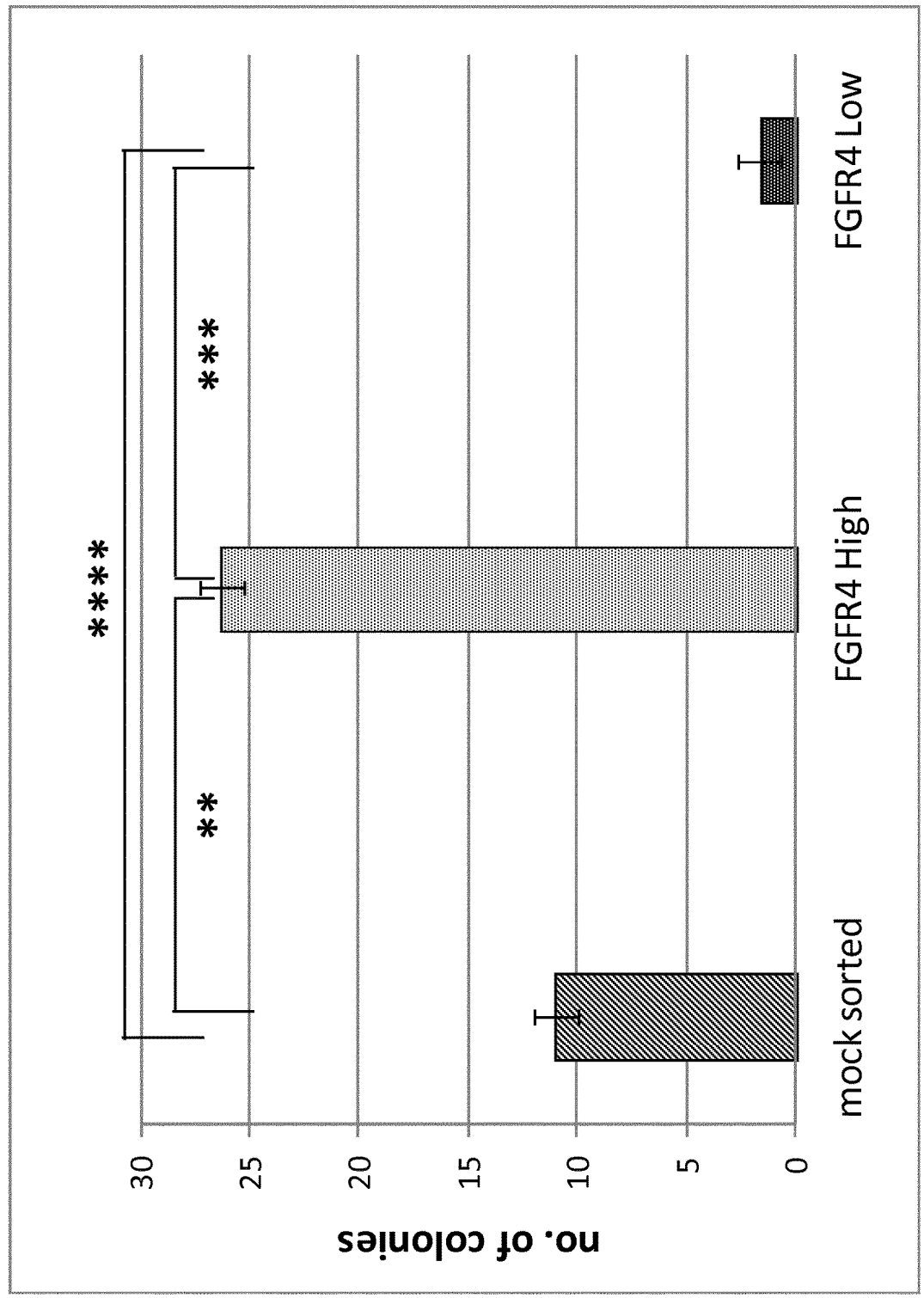
FIG. 6. Number of colonies in soft agar counted for the three CTSC85 cell populations. Mean values of three different experiments are shown ±StDev. The differences of colony number between the FGFR4High and FGFR4Low cell subpopulations were statistically significant (*p=0.001), as well as the differences between the FGFR4High and mock-sorted populations (p=0.007) and between the FGFR4Low and mock-sorted populations (****p=0.00015).

Triplicates of each cell subpopulation were plated and incubated at 37° C., 5% $CO_2$, adding fresh medium to the cultures every two days. Cell colony formation was monitored under an inverted light microscope and after 12 days of incubation colonies were counted. Colonies were scored that contained 30 or more cells (FIG. 6).

Overall the FGFR4$^{High}$ CTSC85 cell subpopulation showed higher proliferation rates and clonogenic efficiencies compared to the FGFR4$^{Low}$ cell subpopulation.

The migration efficiency of the three CTSC85 cell populations was also evaluated. The transwell migration assay was performed using the Corning® FluoroBlock 96 well-microplates, seeding 3000 cells in the upper chamber (insert) of each well in quadruplicate and adding 200 uL of complete growth medium in the lower chamber. Following a 48 h incubation at 37° C., 5% $CO_2$, cells were stained with 4 µM Calcein AM fluorescent dye (Thermo Fisher Scientific) added to the lower chamber for 30 min at RT. The fluorescence associated with the viable cells migrated through the membrane was measured on the bottom microplate reader Multimode Detector DTX 880 (Beckman Coulter) at 485/535 nm (Ex/Em). Images were captured using an inverted fluorescence microscope with a digital microscope camera (Nikon) and stained cells were counted using the ImageJ software.

Figure 7:
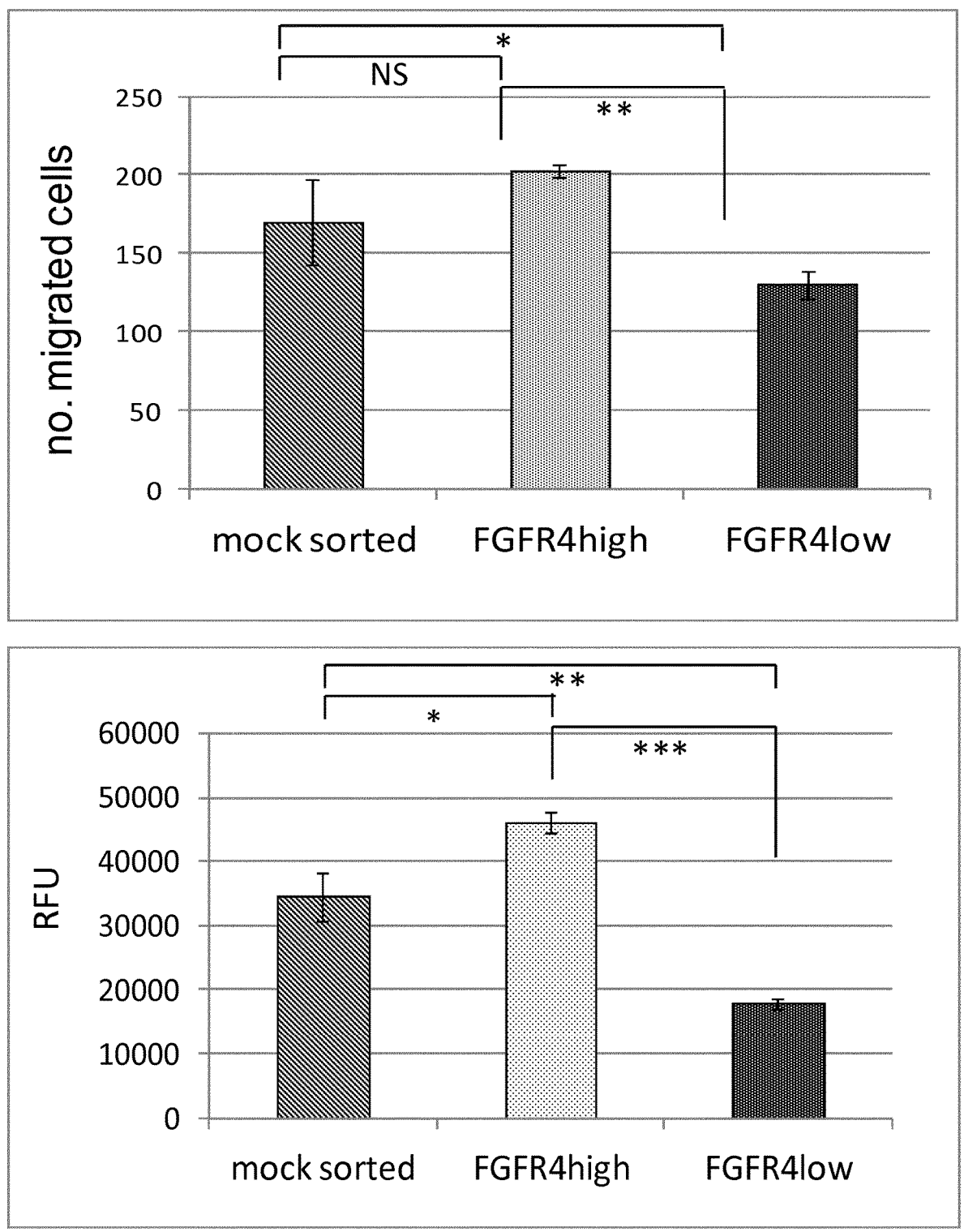
FIG. 7. Migration efficiencies of the FGFR4High, FGFR-Low and mock-sorted CTSC85 cell populations (n=3) evaluated by a transwell migration assay and Calcein AM fluorescent staining after 48 h. Upper panel, mean fluorescent cell numbers for each of the three populations counted with the help of the ImageJ software. Lower panel, mean fluorescence intensity values associated to migrated cells for each of the three populations, expressed in relative fluorescence units (RLU). (*) $p<0.04$; () $p<0.004$; (*) $p<0.001$.

In FIG. 7 representative results of three independent experiments are shown, indicating that the FGFR$^{High}$ CTSC85 cells have a higher migration propensity compared to the FGFR4$^{Low}$ cells.

On the basis of the experimental evidence obtained in the in vitro assays, the two FGFR4$^{High}$ and FGFR4$^{Low}$ CTSC85 cell subpopulations were injected into immunodeficient mice to evaluate their tumorigenic potential in vivo.

The experiment was performed on six NOD/SCID mice (Charles River), inoculated subcutaneously in the right and left flanks with the same number of the two cell subpopulations. Tumor growth was evaluated by measuring with a vernier caliper the tumor size (major and minor axis) twice a week for three weeks after the first appearance of the tumors. Tumor volumes were calculated using the formula: TV (mm$^3$)=d2×D/2 where d and D refer to the shortest and the longest diameter, respectively.

Figure 8:
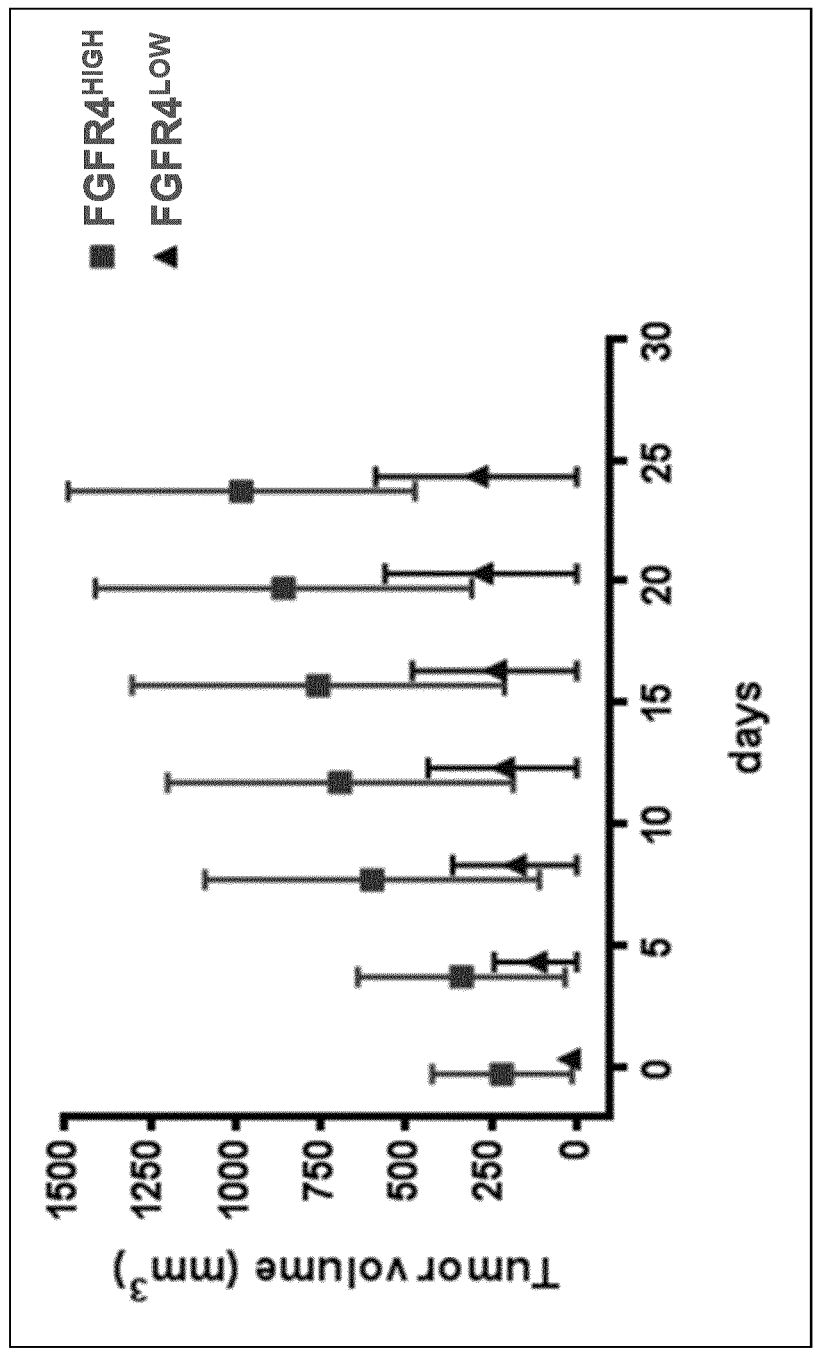
FIG. 8. Different tumor growth of xenografts derived from the two CTSC85 cell subpopulations collected after sorting. FGFR4High (squares) and FGFR4Low (triangles) tumor growth curves are shown. Data are expressed as medium tumor volumes±StDev.

The results of the in vivo experiment (FIG. 8) showed that the CSC cell subpopulation enriched for FGFR4 expression appears to have an increased tumorigenic potential compared to the FGFR4-depleted cell subpopulation, in agreement with the functional in vitro data.

Example 7

Characterization of the Anti-FGFR4 Monoclonal Antibodies

We have prioritized FGFR4 as an oncology target and further characterized the novel monoclonal antibodies generated against this antigen.

The cytofluorimetric analysis of the three anti-FGFR4 purified antibodies BFG-2F7-B9, BFG-5E5-B5 and BFG-5F7-D5 has been extended to all five colon CSC lines (1.1, 1.2, 18, 85, CROI) and to a panel of colon (HCT116, SW48, SW620, HT29, DLD1) and liver (Huh7, HepG2) ATCC tumor cell lines. Each antibody was tested at increasing concentrations to evaluate the dose-dependency of its binding to the endogenous surface receptor. The assay has been performed in 96 well-microplates with 10$^5$ cells/well in 200 uL of cell medium in which the tested antibody was serially diluted. After incubation at 4° C. for Ih, an anti-rat fluorescent secondary antibody (Goat Anti-Rat IgG R-phycoerythrin [R-PE] Conjugate, Southern Biotech) was added and the cells were treated with DAPI (4',6-Diamidino-2-Phenylindole, Dihydrochloride) at 1 ug/mL to control cell viability. Samples incubated only with the secondary antibody were included as the negative control. The flow cytometric evaluation was performed using the cytofluori meter MACSQuan® VYB (Miltenyi Biotec).

Based on the obtained experimental data, the binding affinity of each antibody was determined using as parameter the ratio of the mean fluorescence intensity of each experimental point to that of the control sample (fold change, FC). FC values were plotted as a function of the mAb concentration, expressed in ug/mL, and $B_{max}$ and $K_d$ constants were calculated using the GraphPad Prism software as described in Example 5.

As summarized in Table 10, the anti-FGFR4 antibodies showed a high, dose-dependent reactivity on both CSC and tumor cell lines with high FGFR4 expression levels, particularly on the two hepatocellular carcinoma (HCC) cell lines HepG2 and Huh7, with $K_d$ values in the sub/low nanomolar range (0.4-12 nM). On the contrary, the CTSC18 and DLD1 cell lines resulted much less responsive, consistent with their FGFR4 low expression levels.

TABLE 10

Dissociation constants and maximum binding values of the anti-FGFR4 mAbs on the colon CSC and on colon (CRC) and liver (HCC) ATCC tumor cell lines. $K_d$ values have been considered reliable only if interpolated from curves with Bmax > 2.

Cell line BFG-2F7-B9 BFG-5E5-B5 BFG-5F7-D5
Bmax 2 2.7 1.8
CTSC1.I Kd (ug/mL) 0.3 1 0.06
Kd (nM) 2 6.7 0.4
Bmax 3.9 4.2 3.9
CTSC1.2 Kd (ug/mL) 0.1 0.2 0.07
Kd (nM) 0.7 1.3 0.5
Bmax 1.2 1.6 1.4
CTSC18
Kd (ug/mL) — — —
Kd (nM) — — —
Bmax 5.2 4.1 4
CTSC85
Kd (ug/mL) 0.1 0.15 0.06
Kd (nM) 0.7 1 0.4
Bmax 3.9 3.2 3.5
CTSC CR01 Kd (ug/mL) 0.4 0.6 0.2
Kd (nM) 2.8 4 1.3
Bmax 4.1 3.5 4.4
HCT116 Kd (ug/mL) 0.25 0.3 0.3
Kd (nM) 1.7 2 2
Bmax 5.3 ND 5.4
SW48 Kd (ug/mL) 0.3 ND 0.3
Kd (nM) 2 ND 2
Bmax 1.6 1.5 1.6
DLD1 Kd (ug/mL) — — —
Kd (nM) — — —
Bmax 18.2 ND ND
SW620
Kd (ug/mL) 0.2 ND ND
Kd (nM) 1.4 ND ND
Bmax 8.6 ND ND
HT29 Kd (ug/mL) 0.3 ND ND
Kd (nM) 2 ND ND
Bmax 56 58 52.6
HepG2 Kd (ug/mL) 0.4 1.8 0.3
Kd (nM) 2.5 12 2
Bmax 36.4 ND 35.5
Huh7 Kd (ug/mL) 0.35 ND 0.33
Kd (nM) 2.3 ND 2.2

The binding affinity and specificity of the anti-FGFR4 antibodies have been tested in in vitro binding assays on recombinant human FGFR4 extracellular domain fused to the human IgG Fc (solid phase receptor binding assay). Briefly, 96 well-microplates (Nunc MaxiSorp® ELISA plates) were coated overnight at 4° C. with 50 uL of an anti-human IgG Fc (Bethyl Laboratories) diluted in PBS pH7 at 2 ug/mL. Non specific binding sites were then saturated with 200 uL of PBS/3% BSA for h, followed by five washes in PBS. Next the human chimeric receptor FGFR4-Fc (R&D Systems) was added in PBS/0.3% BSA at 1 ug/mL for Ih. Microplates were then washed five times in PBS and incubated for Ih with 1:3 serial dilutions of the anti-FGFR4 antibodies or of an isotypic control (Rat IgG2a/e, Southern Biotech) in 50 uL of PBS/0.3% BSA. Triplicates of each experimental point were included.

After five washes in PBS, bound antibodies were detected using a HRP-conjugated anti-rat IgG secondary antibody (Southern Biotech) diluted 1:4000 and incubated for Ih, followed by the addition of the chromogenic substrate TMB (Thermo Fisher Scientific) for 3-10 min. The reaction was terminated by the addition of 100 uL of 2M sulfuric acid and the absorbance at 450 nm was measured using the microplate reader Multimode Detector DTX 880 (Beckman Coulter).

In this assay, both anti-FGFR4 antibodies BFG-2F7-B9 and BFG-5F7-D5 showed a high and identical binding affinity for the chimeric receptor (5 ng/mL, 0.03 nM), while no binding was detected with the control immunoglobulin to the maximal concentration tested.

Potential therapeutic antitumor effects of the antibody BFG-2F7-B9 were evaluated in two different colon cancer in vivo models, using immunodeficient mice transplanted either with the ATCC cell line HCT116, or with the CSC line CTSC85.

For the first xenograft model, a suspension of 1.8×10 HCT116 cells in 50% Matrigel (Corning) was inoculated subcutaneously in the flank of each of twenty CD-1 nude mice (Charles River) of 5 weeks of age. Nine days after the transplant, mice that showed measurable tumors were randomly assigned to two groups (n=7), namely the antibody and control groups, with mean tumor volumes of 110 mm³ in both groups. Mice were treated via intraperitoneal (IP) injection with 50 mg/Kg of BFG-2F7-B9 antibody in PBS administered once a week for three weeks. The control group received corresponding volumes of blank injection (PBS). Mice weight was controlled twice a week and tumor size (major and minor axis) was measured with a vernier caliper twice a week. Tumor volumes were calculated using the formula: TV (mm³)=d2×D/2 where d and D refer to the shortest and the longest diameter, respectively.

Figure 9:
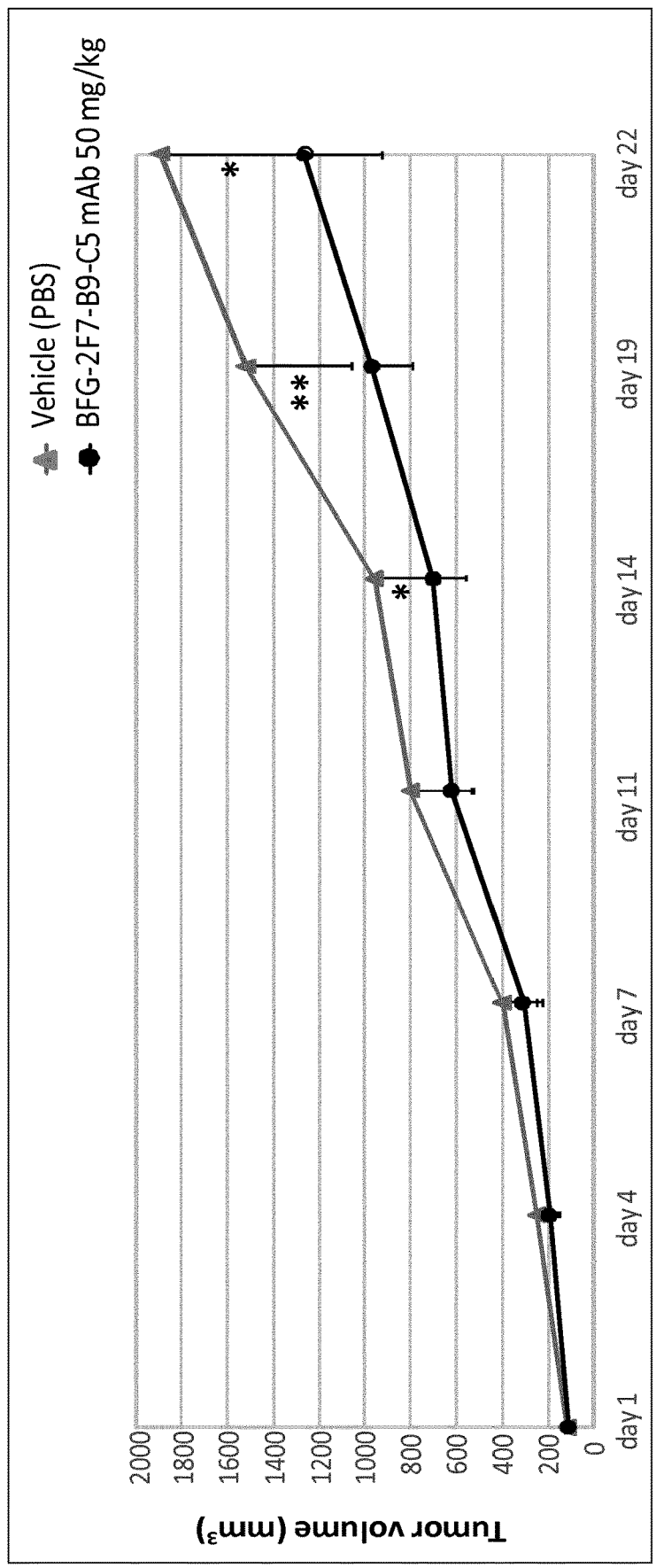
FIG. 9. Anti-tumor effects by the BFG-2F7-B9 antibody on xenografts of HCT116 colon tumor cells. Data are expressed as mean tumor volume±StDev; (*) $p<0.05$; (**) $p<0.01$ relative to vehicle control.

A reduction of the tumor volume was observed in mice treated with the antibody relative to the control group, a difference that became statistically significant starting from the 14th day of treatment (FIG. 9). On the contrary, body weight loss or clinical adverse effects were not observed (not shown).

For the second xenograft model, a suspension of I×IO⁵ CTSC85 cells was inoculated subcutaneously in the flank of each of twenty two NOD/SCID mice (Charles River). About three weeks after the transplant, mice that showed measurable tumors were randomly assigned to three groups (n=7), namely the anti-FGFR4 antibody BFG-2F7-B9, the unrelated antibody 1H4 (isotype control) and the vehicle control groups, with mean tumor volumes of 70 mm, in each group. Mice were treated via IP injection with 50 mg/Kg of BFG-2F7-B9 or 1H4 antibody in PBS, administered once a week for five weeks. The control group received corresponding volumes of blank injection (PBS). Mice weight was controlled twice a week and tumor size (major and minor axis) was measured with a vernier caliper twice a week. Tumor volumes were calculated using the formula: TV (mm³)=d2×D/2 where d and D refer to the shortest and the longest diameter, respectively.

Figure 10:
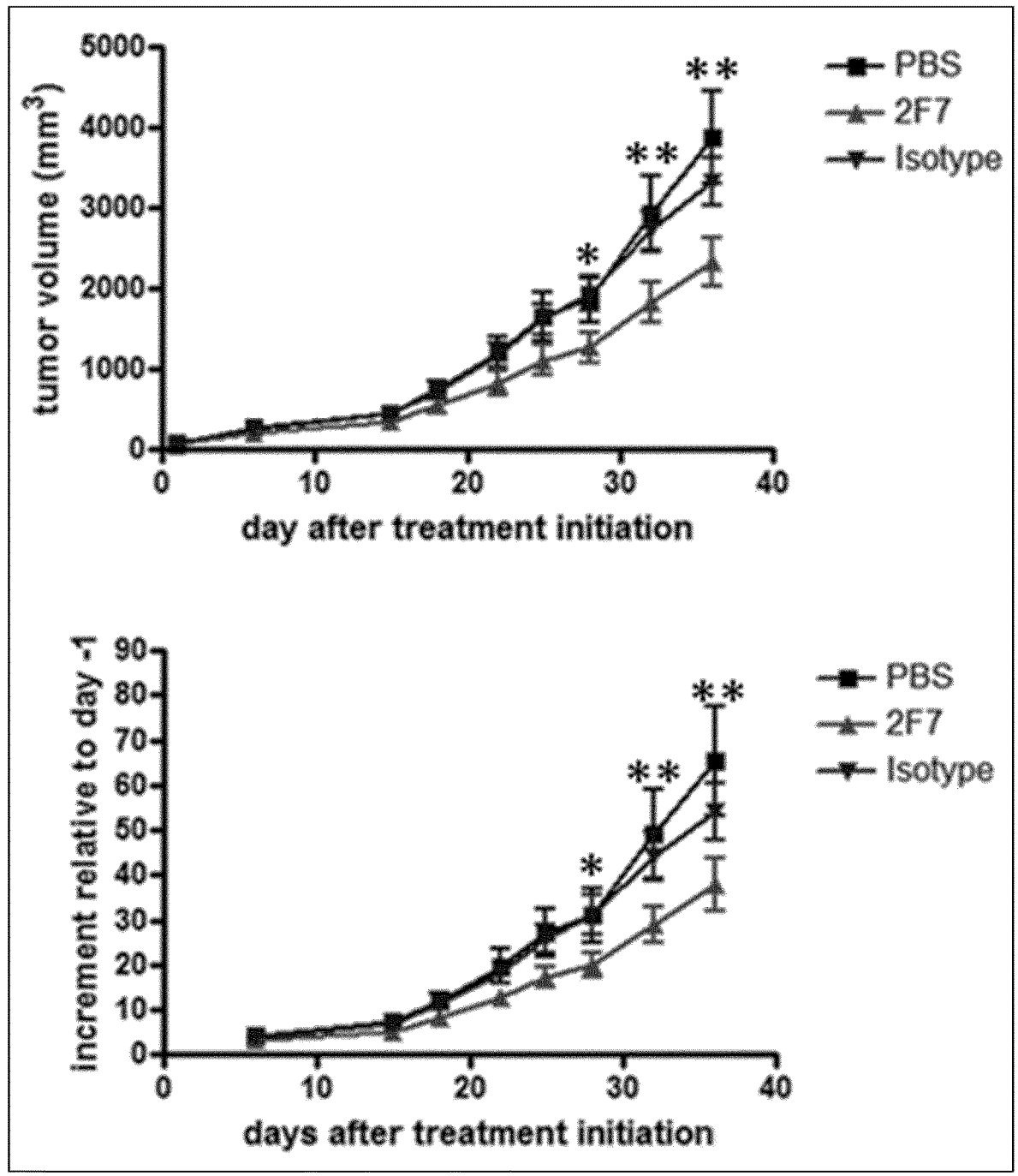
FIG. 10. Anti-tumor effects by the BFG-2F7-B9 antibody on xenografts of colon CTSC85. In the upper panel, curves represent the increase of the mean tumor volumes±StDev during the treatment period; in the lower panel, the increment of the mean tumor volumes relative to day −1 is shown t StDev. (*) $p<0.05$; (**) $p<0.01$ with respect to the vehicle control.

The result of this experiment, shown in FIG. 10, confirmed the capability of the anti-FGFR4 antibody BFG-2F7-B9 to inhibit the growth of colon cancer cells observed in other in vitro and in vivo models. Comparing the tumor growth rate of the BFG-2F7-B9-treated group to that of the control groups the difference resulted statistically significant. Body weight loss or clinical adverse effects were not observed during the treatment (not shown).

Example 8

Selection and Characterization of Additional Anti-FGFR4 Monoclonal Antibodies that Cross-React with the Murine FGFR4 Receptor and Inhibit the Ligand-Receptor Interaction With the aim of identifying novel anti-FGFR4 antibodies able to inhibit the binding of FGF to the receptor, and therefore with better biologic effects in blocking the interaction ligand-receptor than those previously described, two different strategies were followed.

First Strategy:

The first strategy consisted in re-examining the original fourteen parental hybridoma supernatants that had shown positivity in the first screening both by identifying the antibody binding domain on the extracellular region of the receptor and by testing their cross-reactivity on the murine receptor. In fact FGFR4 Ig II and Ig III domains, necessary and sufficient for the interaction with the ligand and the heparan sulfate (Goetz & Mohammadi, 2013), are the most conserved across different species. In addition, the amino acid residues that differ between the human and murine receptor in Ig II and Ill are located on the surface opposite to the FGF binding pocket. As a consequence, cross-reactivity with the murine receptor and binding to domains Ig II and III could be distinctive features of antibodies that can interfere with the ligand-receptor interaction.

Three deletion mutants (d I, d2, d3) of the extracellular region of the human FGFR4 receptor were generated. In d I the region comprising amino acids 1-118, corresponding to the Ig I domain was deleted; in d2 the region comprising amino acids 1-151, corresponding to both Ig I and the acid box was deleted; in d3 the region comprising amino acids 1-248 corresponding to Ig I, acid box and Ig II was deleted (amino acid numbering refers to the full-length (FL) receptor, including the signal peptide). The cDNAs encoding the FGFR4 FL and truncated forms have been cloned in frame with a myc-tag in the pBI-myc expression vector (described in the Example 3). FACS analysis of the reporter cells BOSC23 transiently transfected with pBI-FGFR4 FL, d I, d2 and d3 and tested with the fourteen parental hybridoma supernatants confirmed their reactivity towards the full-length receptor. Ten of them retained full reactivity on the d I mutant, among which BFG-5A5 and BFG 7H9 completely lost positivity on the d2 mutant. Finally, all eight remaining supernatants, including the previously described BFG-2F7, BFG-5E5 and BFG-5F7, resulted negative on the d3 mutant, thus showing a binding specificity for the domain Ig II.

The same supernatants were analyzed by FACS on transiently-transfected BOSC23 cells ectopically expressing human, monkey, or murine FL FGFR4 upon transfection with the corresponding pBI-myc constructs. Thirteen supernatants showed cross-reactivity towards the monkey receptor, while only three of them resulted positive also on the murine receptor. Interestingly, the supernatants from which the previously described antibodies BFG-2F7-B9, BFG-5E5-B5 and BFG-5F7-D5 were isolated resulted instead specific for the human FGFR4.

BFG-5B5 supernatant, one of the most cross-reactive on the murine receptor and positive on the Ig II domain, was selected for subcloning of the corresponding hybridoma, thus obtaining a cell subclone producing the antibody BFG-5B5-G7 that was purified by protein G-Sepharose affinity chromatography as described in the Example 5.

The reactivity of the antibody BFG-5B5-G7 to five different colon CSC lines (1.1, 1.2, 18, 85, CROI) and to the HCC cell line Huh7 was evaluated by FACS analysis in dose-response experiments as described in the Example 7. The previously described BFG-2F7-B9 anti-FGFR4 antibody and the unrelated antibody 1H4 were included as references. Fold change (FC) values with respect to the control (secondary antibody only) were plotted as a function of the mAb concentration, expressed in ug/mL, and $B_{max}$ and $K_d$ constants were calculated using the GraphPad Prism software and applying the "one site binding equation" as described in the Example 5.

As summarized in Table 11, the antibody BFG-5B5-G7 showed a high binding activity similar to that measured with BFG-2F7-B9 on all cell lines expressing high FGFR4 levels, while the CTSC18 cell line, with low FGFR4 expression, confirmed to be much less responsive. On the contrary, the unrelated antibody 1H4 resulted negative on all cell lines tested. The $K_d$ values calculated for BFG-5B5-G7 were all in the subnanomolar range and comparable or slightly lower than those calculated for BFG-2F7-B9.

TABLE 11

Dissociation constants and maximum binding values of the anti-FGFR4 mAbs BFG-5B5-G7 and BFG-2F7-B9 on five colon CSC lines and on the HCC cell line Huh7.

| Cell line | BFG-5B5-G7 | BFG-2F7-B9 | 1H4 |
|---|---|---|---|
| Bmax | 9.8 | 11 | 1.3 |
| CTSCl.I Kd (ug/mL) | 0.07 | 0.17 | — |
| Kd (nM) | 0.5 | 1.1 | — |
| Bmax | 8.2 | 9.2 | 1.1 |
| CTSC1.2 Kd (ug/mL) | 0.09 | 0.2 | — |
| Kd (nM) | 0.6 | 1.4 | — |
| Bmax | 2.2 | 3 | 1 |
| CTSC18 | | | |
| Kd (ug/mL) | 0.04 | 0.07 | — |
| Kd (nM) | 0.3 | 0.5 | — |
| Bmax | 6.6 | 7.6 | 0.3 |
| CTSC85 | | | |
| Kd (ug/mL) | 0.04 | 0.08 | — |
| Kd (nM) | 0.3 | 0.5 | — |
| Bmax | 10.6 | 11.7 | 1 |
| CTSC CROI Kd (ug/mL) | 0.09 | 0.2 | — |
| Kd (nM) | 0.6 | 0.1 | — |
| Bmax | 12.8 | 15.1 | 0.9 |
| Huh7 Kd (ug/mL) | 0.1 | 0.3 | — |
| Kd (nM) | 0.65 | 2 | — |

The binding affinity and specificity of BFG-5B5-G7 for FGFR4 was then measured in vitro using the solid phase receptor binding assay described in the Example 7 and the human chimeric receptors FGFRI-Fc, FGFR2-Fc, FGFR3-Fc FGFR4-Fc (R&D Systems). Microplates coated with the different FGFR-Fcs have been incubated with increasing concentrations of BFG-5B5-G7 or of the isotype control (rat IgG2a). In this assay, the antibody BFG-5B5-G7 showed a high and specific binding affinity ($K_d$=0.02 ug/mL, 0.1 nM) for FGFR4, while no binding was detected on the other FGF receptors or with the isotype control.

The ability of the antibody BFG-5B5-G7 to prevent/compete the formation of the FGF19-FGFR4 complex was then analyzed in the FGFR4-Fc-dependent solid phase binding assay described in the Example 7, in which the following modifications have been introduced. Following the Ih incubation with 1:3 serial dilutions of the antibody in triplicate, recombinant FGF19 (Peprotech) and low molecular weight heparin (Clexane, mean MW 4.5 kDa, Sigma-Aldrich) were added at an equimolar concentration of 23 nM (corresponding to the $k_d$ value inferred from a previous dose-response binding experiment, not shown). Following a 2 h incubation, microplates were washed 5 times in PBS and incubated for Ih with an anti-FGF19 biotinylated antibody (R&D Systems) diluted 1:1000 in PBS/0.3% BSA. After 5 washes in PBS, the residual FGF19 bound to the immobilized receptor was detected by adding 50 uL of HRP-conjugated streptavidin (Thermo Fisher Scientific/Pierce) in PBS containing 3% BSA and 0.02% Tween-20. After 30 minutes incubation, excess streptavidin was removed with 3 washes in PBS/ 0.02% Tween-20 and 2 more washes in PBS, followed by the addition of the chromogenic substrate TMB (Thermo Fisher Scientific) for 12 minutes. The reaction was terminated by the addition of 100 uL of 2M sulfuric acid and the absorbance at 450 nm was measured using the microplate reader Multimode Detector DTX 880 (Beckman Coulter).

The assay had been previously validated by testing both the FGF19 binding selectivity for FGFR4 with respect to the other FGFRs and the ability of FGF1, another FGFR4 high affinity ligand, to inhibit the FGF19-FGFR4 interaction.

Subsequently, eleven 1:2 serial dilutions of the antibody BFG-5B5-G7 (from 0.015 ug/mL to 15 ug/mL) were tested in triplicate, under the previously described experimental conditions. The unrelated antibody 1H4 was also tested at the same concentrations as a negative control.

This result indicates that, different from the previously described anti-FGFR4 mAbs BFG-2F7-B9 and the unrelated antibody 1H4 (not shown), the antibody BFG-5B5-G7 was able to efficiently inhibit the binding of FGF19 to FGFR4, in agreement with its reactivity towards the murine receptor and its binding specificity for the FGFR domain Ig II.

The expression of the cholesterol 7a-hydroxylase (CYP7A1) and the connective tissue growth factor (CTGF) are modulated, at the transcriptional level, by FGF19-dependent activation of the FGFR4 signalling pathway both in normal and tumor liver cells (Inagaki et al., 2005; Chiang et al., 2009; Uriarte et al., 2015). The ability of the antibodies BFG-5B5-G7 and BFG-2F7-B9 to inhibit FGF19-mediated gene modulation was evaluated on HepG2 cells that have been pre-incubated, after eight hours of serum starvation, with the anti-FGFR4 mAbs overnight in serum free-medium. FGF19 was then added at a concentration of 100 ng/mL (4.6 nM) together with equimolar heparin amounts, six hours before cell lysis. Negative control samples treated with PBS were included. As a positive control, an FGFR4 tyrosine kinase specific inhibitor, BLU9931 (Hagel et al., 2015), was added at concentrations of 0.1 uM, 0.3 uM or 1 uM seven hours before cell lysis. Total RNA was extracted from HepG2 cells and qRT-PCR assays were performed in triplicate as described in the Example 2, using gene-specific probes and primers (Applied Biosystems/Thermo Fisher Scientific TaqMan® Gene Expression Assays) and GAPDH as a normalizer.

In agreement with published data, the addition of FGF19 reduced CYP7A1 expression (about 5 fold) and increased CTGF expression (about 2.5 fold). The treatment with BFG-5B5-G7 partially reverted these effects already at a concentration of 30 ug/mL (0.2 uM) causing an increase of Cyp7Al mRNA and a decrease of CTGF mRNA at levels comparable to those observed with similar concentrations of the compound BLU9931.

These data indicate that BFG-5B5-G7, different from BFG-2F7-B9 (not shown), is able to interfere with the FGFR4-dependent signalling pathway in hepatocellular carcinoma cells that showed high positivity by FACS with this antibody.

Subsequently, BFG-5B5-G7 and BFG-2F7-B9 were evaluated for their ability of inhibiting the FGFR4-dependent phosphorylation of the fibroblast growth factor receptor substrate 2 (FRS2), induced by the treatment with FGF19 of Huh7 and Hep3B hepatocellular carcinoma cell lines.

After 8 h serum starvation, cells were incubated overnight in serum-free medium with BFG-5B5-G7, BFG-2F7-B9 or the control antibody 1H4 at concentrations of 7.5 ug/mL, 15 ug/mL and 30 ug/mL, while FGF19 and heparin were added at equimolar concentrations (4.6 nM) 10 min before cell lysis. BLU9931 was included as positive control Ih before cell lysis at concentrations of 100 or 300 nM. Total protein lysates in SDS were prepared and analyzed by Western Blot using an anti-phospho-FRS2 antibody (Tyrl96, Cell Signalling), an anti-FRS2 antibody (LSBio) and an anti-GAPDH antibody (Sigma-Aldrich).

The antibody BFG-5B5-G7 was significantly more efficient than BFG-2F7-B9 in inhibiting the FGF19-induced FRS2 phosphorylation, in a dose-dependent manner and in both cell lines, while the negative control antibody 1H4 was completely inactive.

The antibody BFG-5B5-G7 was then tested for its capability of decreasing colony forming efficiency in soft agar of two FGFR4-positive colon CSC lines (CTSC1.2 and CROI). The experimental procedure is that described in detail in the Example 6, with the following modifications. BFG-5B5-G7 or the unrelated antibody 1H4 were included both in the top soft agar layer and in the overlying culture medium at a final concentration of 7.5, 15 or 30 ug/mL. As positive control, the FGFR4 inhibitor BLU9931 was tested in parallel at a concentration of 100 nM. Quadruplicates of each experimental point were plated and incubated at 37° C., 5% $CO_2$, adding fresh medium containing antibodies or compound every two days.

Cell colony formation was monitored under an inverted light microscope and after 14 days of incubation the number of colonies containing 30 or more cells was determined. The continuous treatment of the two CSC lines with BFG-5B5-G7 caused a decrease of the number of colonies with respect to control that reached statistical significance at all concentrations on CTSC1.2 and at the highest concentrations tested on CTSC CROI.

Second Strategy:

In order to identify novel anti-FGFR4 antibodies with a potentially higher anti-tumor activity than BFG-2F7-B9, new hybridoma cell lines were generated from cryopreserved lymphocytes isolated from rats originally immunized with the pB8-HA-FGFR4 expression vector described in the Example 3. For this second screening two new selection criteria have been introduced consisting in the early evaluation (i) of the cross-reactivity with the murine receptor and (ii) of the ability of interfering with the FGF19-FGFR4 interaction by the correspondent supernatants.

As in the Example 3, new hybridoma cell lines have been generated and after the hybridoma selection and expansion steps, the reactivity of the corresponding supernatants to both the human and the murine receptor was evaluated by FACS analysis of BOSC23 cells transfected with either expression vector.

On this basis, 70 hybridoma cell lines producing antibodies that resulted positive on human FGFR4 were selected (BMK fusions), among which 50 were also reactive towards the murine receptor and 20 were specific for human FGFR4.

As for the first screening (Example 4), the 70 selected supernatants have been analyzed by FACS for their efficiency of binding to the colon CSCs surface. The experiments were performed both on the four colon CSC lines with high reactivity towards the previously identified anti-FGFR4 antibodies (CTSC1.1, CTSC 1.2, CTSC85 and CTSC CROI), and on the CSC line CTSC18 with low reactivity for the same antibodies. The assay was performed in a 96-well microplate by seeding $10^5$ cells/well to which 200 uL of each supernatant were added. Conditioned medium of the murine myeloma cells used for hybridoma fusions (DMEM/10% FBS) was added to each plate as a negative control, while the anti-FGFR4 BFG-2F7-B9 antibody was included as positive control at a concentration of 3 ug/mL. After incubation at 4° C. for Ih, an anti-rat fluorescent secondary antibody (Goat Anti-Rat IgG R-phycoerythrin [R-PE] Conjugate, Southern Biotech) was added and the cells were treated with DAPI (4',6-Diamidino-2-Phenylindole, Dihydrochloride) at 0.25 ug/mL (1 uM) to control cell viability. The flow cytometric evaluation has been performed using the cytofluorimeter MACSQuant® VYB (Miltenyi Biotec).

All supernatants but two resulted negative on the CTSC18 cell line and were ranked on the basis of their positivity, according to their FC values, on the other CSC lines, as described in the Example 4. By adding the individual ratings assigned to each supernatant on each of the four CSC lines with high FGFR4 expression, a final rank was obtained (Table 12) where the lowest number corresponds to the highest reactivity.

TABLE 12

Summary of the FACS analysis data obtained with the 70 supernatants on 5 different CSC lines. Fold change (FC) is the ratio of the mean fluorescence intensity (MFI) measured with each supernatant to the negative control (myeloma cells conditioned medium). A score was assigned based on FC values on each FGFR4-positive CSC line and the final rank was calculated by adding the individual scores (total ranking). Supernatants that did not show cross-reactivity with the murine receptor are underlined.

Binding parental sups to CSC cells by FACS
1.1 1.2 85 C O TOTAL RANKING 18
[Parental sup FC RAN FC RAN FC RAN FC RANK | FC |
1 B9 14.2 7 5.3 10 7.7 19 12.8 11 47 1.8
1.D.2 2.0 16 3.8 11 12.9 15 2.7 18 60 1.3
1 E 7 13.7 7 9.5 6 24.4 10 17.1 7 30 2.3
1 F3 13.6 7 5.0 10 7.6 20 11.3 11 48 1.9
1 H 10 53.6 1 29.2 1 15.3 13 42.1 1 16 28.8
2A8 7.7 12 7.4 8 15.2 13 11.2 12 45 1.5
2A11 2.1 16 2.5 12 2.2 23 3.5 17 68 1.1
2E6 4.7 13 2.0 13 8.7 18 7.5 14 58 1.4
2E10 3.0 15 4.2 11 14.1 14 11.3 12 52 2.2
2G2 10.1 10 6.8 8 11.8 16 15.1 9 43 1.6
2H 1 1 1.3 .17 1.4 13 1.3 24 1.5 19 73 1.3
3A9 4.6 14 2.5 12 2.7 23 6.0 15 64 1.1
3A10 1.3 17 1.3 13 1.2 24 1.1 19 73 1.3
3B6 11.5 9 7.5 8 13.6 14 16.5 8 39 2.1
3D1 3.2 15 2.3 13 1.3 24 3.5 17 69 2.5
3D8 17.8 4 7.5 8 9.2 18 20.3 5 35 2.4
3F3 1.2 17 3.4 12 3.1 23 5.0 16 68 1.5
3P5 2.0 16 3.7 11 11.1 16 3.3 17 60 1.4
3C39 1.6 16 3.2 12 2.4 23 4.8 16 67 1.3
4A5 1.4 16 2.2 13 2.6 23 3.5 17 69 1.5
4A11 3.6 11 12.9 4 9.7 18 16.4 8 41 11.4
481 10.3 10 6.8 8 12.7 15 14.8 9 42 1.9
4D7 2.7 15 4.8 10 4.1 22 13.8 10 57 1.2
4E10 3.2 15 4.5 11 7.3 20 5.7 15 61 1.3
4F8 2.3 16 2.5 12 2.1 23 3.3 17 68 1.1
5A5 1.8 16 1.7 13 1.6 24 2.3 18 71 1.2
5B9 16.9 5 7.2 8 10.4 17 16.7 8 38 1.9
5C9 14.5 6 7.1 8 8.2 19 1.63 8 41 2.0
5D3 16.3 5 6.9 8 7.5 20 16.2 8 41 2.2
5D6 3.5 15 7.5 8 11.8 16 16.0 8 47 2.2
5E1 1.3 17 3.7 11 11.1 16 1.8 18 62 1.3
5H6 2.1 16 3.8 11 11.9 15 2.5 18 60 1.3
5H9 25.3 2 8.2 7 26.2 9 15.5 9 27 2.1
6A11 9.8 10 6.0 9 6.5 21 15.8 8 48 1.7
685 13.2 8 6.6 9 12.3 15 14.7 9 41 2.0
6C9 18.0 4 7.6 8 10.8 17 13.0 6 35 2.4
8C1 1 16.3 5 11.4 5 20.9 11 27.6 2 23 2.9
8D11 18.7 3 12.2 4 49.2 7 20.6 5 19 2.1

TABLE 12-continued

Summary of the FACS analysis data obtained with the 70 supernatants on 5 different CSC lines. Fold change (FC) is the ratio of the mean fluorescence intensity (MFI) measured with each supernatant to the negative control (myeloma cells conditioned medium). A score was assigned based on FC values on each FGFR4-positive CSC line and the final rank was calculated by adding the individual scores (total ranking). Supernatants that did not show cross-reactivity with the murine receptor are underlined.

6E2 11.1 9 4.3 11 6.7 20 11.1 12 52 1.8
6E7 3.4 15 11.3 5 63.3 4 2.2 18 42 1.5
6F4 2.5 15 1.8 13 1.3 24 2.6 18 70 1.5
6G5 12.6 8 17.1 3 87.5 2 3.6 13 26 1.5
6H3 13.0 8 5.4 10 7.7 19 14.4 10 47 1.7
6H5 11.8 9 4.4 11 10.4 17 12.8 11 48 1.8
7B5 10.2 10 10.6 5 55.2 6 8.8 13 34 1.7
7B7 16.3 5 7.1 8 8.8 18 20.1 5 36 2.2
7B11 3.9 14 6.7 8 8.8 18 22.9 4 44 1.6
7E4 7.4 12 4.5 11 15.6 13 5.7 15 51 1.6
7H 1 4.3 14 10.2 6 61.5 5 3.2 17 42 1.4
8A4 3.4 15 5.2 10 28.0 8 2.1 18 51 1.3
8D4 10.9 9 7.2 8 3.7 18 23.9 4 39 1.8
8E3 13.1 3 8.4 7 11.3 16 25.3 3 29 2.3
8F 1 0 16.1 5 22.4 2 107.2 1 18.3 6 14 1.9
8H5 5.6 13 5.6 10 8.2 19 17.2 7 49 2.0
8H9 2.3 16 1.5 13 1.7 24 2.0 18 71 1.3
8H 10 15.4 6 6.2 9 10.3 16 16.7 8 39 1.9
9B 1 13.0 8 5.6 10 8.7 19 16.6 8 45 1.8
9C5 8.1 12 3.8 11 13.7 14 7.0 14 51 1.3
9C6 10.5 10 10.3 6 84.5 3 4.5 16 35 1.8
9F7 9.4 11 5.5 10 19.2 12 7.6 14 47 1.4
9H4 4.1 14 3.1 12 3.7 22 7.1 14 62 1.4
9H5 3.6 14 2.6 12 2.6 23 6.3 15 64 1.4
1 QA1 1 2.2 16 13 1.6 24 2.4 18 71 1.4
10D4 8.1 12 3.3 12 4.3 22 6.4 15 61 1.5
10D9 6.2 13 4.9 10 20.4 11 4.9 16 50 1.4
1 (TC¾? 10.7 10 4.2 11 5.6 21 11.7 12 54 1.4
10G5 13.6 7 5.7 9 9.5 18 17.3 7 41 2.1
10G1 1 13.1 8 8.9 7 43.2 7 14.4 10 32 1.7
|2F7 3 ug/ml 118.0 8.0 10.0 22.0|

In parallel, the reactivity of the 70 supernatants has been measured in the previously described solid phase receptor binding assay. Microplate wells coated with FGFR4-Fc were incubated with increasing volumes, from 0.08 uL to 10 uL, of each supernatant bringing the final volume to 50 uL with myeloma cells conditioned medium. An antibody generated against a different target (BGC-6H7) was added to each plate as a negative control, while the anti-FGFR4 BFG-2F7-B9 antibody was included as positive control at a concentration of 6 ug/mL. The absorbance values at 450 nm were obtained by subtracting the conditioned medium background value. As summarized in Table 13, all supernatants but BMK-7E4, BMK-8H9 and BMK-8H 10 showed dose-dependent receptor binding activity, albeit to different extents. 14 supernatants, for which a decrease in the absorbance at 450 nm was not observed even at the minimum tested volume, have been evaluated in a second test using a lower volume range where all supernatants showed dose-response activity. Also in this case a final rank was assigned to each supernatant on the basis of data obtained with 2 uL and 0.08 uL supernatant volumes as summarized in Table 13.

TABLE 13

Summary of the binding data obtained with the 70 supernatants in the solid phase FGFR4-dependent assay (n = 3). The lowest number corresponds to highest reactivity. The best 18 supernatants are indicated with a (+) sign.

| volume (uL) | OD450 | | | | OD450 | | | | | rank uL | rank 0.08 uL | final rank | |
|---|---|---|---|---|---|---|---|---|---|---|---|---|---|
| | 10 | 2 | 0.4 | 0.08 | 0.4 | 0.08 | 0.016 | 0.0032 | 0.00064 | | | | |
| BMK-1B9 | 1.27 | 0.48 | 0.16 | 0.08 | | | | | | 7 | 12 | 19 | |
| BMK-1D2 | 1.38 | 0.70 | 0.25 | 0.08 | | | | | | 6 | 12 | 18 | |
| BMK-1E7 | 1.31 | 1.39 | 1.20 | 0.52 | | | | | | 1 | 7 | 8 | + |
| BMK-1F9 | 0.53 | 0.15 | 0.06 | 0.04 | | | | | | 10 | 12 | 22 | |
| BMK-1H10 | 1.34 | 1.34 | 1.45 | 0.96 | 0.84 | 0.57 | 0.22 | 0.06 | | 1 | 2 | 3 | + |
| BMK-2A8 | 1.34 | 0.66 | 0.24 | 0.07 | | | | | | 6 | 12 | 18 | |
| BMK-2A11 | 1.25 | 1.03 | 0.40 | 0.12 | | | | | | 3 | 11 | 14 | |
| BMK-2E6 | 1.15 | 1.30 | 1.19 | 0.57 | | | | | | 1 | 6 | 7 | + |
| BMK-2E10 | 1.27 | 1.26 | 1.31 | 1.33 | | 0.90 | 0.56 | 0.21 | 0.06 | 2 | 1 | 3 | + |
| BMK-2G2 | 1.22 | 0.51 | 0.13 | 0.05 | | | | | | 7 | 12 | 19 | |
| BMK-2H11 | 0.31 | 0.17 | 0.05 | 0.05 | | | | | | 10 | 12 | 22 | |
| BMK-3A9 | 1.08 | 0.47 | 0.12 | 0.06 | | | | | | 7 | 12 | 19 | |
| BMK-3A10 | 1.29 | 0.71 | 0.33 | 0.04 | | | | | | 6 | 12 | 18 | |
| BMK-3B6 | 1.22 | 1.35 | 1.17 | 0.71 | 0.78 | 0.55 | 0.20 | 0.07 | | 1 | 5 | 6 | + |
| BMK-3D1 | 0.81 | 0.84 | 0.83 | 0.78 | | 0.89 | 0.50 | 0.18 | 0.04 | 5 | 4 | 9 | + |
| BMK-3D8 | 0.72 | 0.66 | 0.35 | 0.18 | | | | | | 6 | 11 | 17 | |
| BMK-3F3 | 0.69 | 0.69 | 0.68 | 0.70 | | 0.82 | 0.84 | 0.50 | 0.16 | 6 | 5 | 11 | + |
| BMK-3F5 | 0.46 | 0.21 | 0.14 | 0.01 | | | | | | 9 | 13 | 22 | |
| BMK-3G9 | 0.77 | 0.70 | 0.71 | 0.72 | | 0.77 | 0.34 | 0.09 | 0.02 | 6 | 5 | 11 | + |
| BMK-4A5 | 0.50 | 0.24 | 0.15 | 0.03 | | | | | | 9 | 12 | 21 | |
| BMK-4A11 | 0.74 | 0.71 | 0.43 | 0.18 | | | | | | 6 | 11 | 17 | |
| BMK-4B1 | 0.54 | 0.45 | 0.27 | 0.20 | | | | | | 7 | 10 | 17 | |
| BMK-4D7 | 0.51 | 0.50 | 0.49 | 0.51 | | 0.76 | 0.60 | 0.22 | 0.05 | 7 | 7 | 14 | |
| BMK-4E10 | 0.56 | 0.52 | 0.32 | 0.18 | | | | | | 7 | 11 | 18 | |
| BMK-4F8 | 0.38 | 0.19 | 0.14 | 0.05 | | | | | | 10 | 12 | 22 | |
| BMK-5A5 | 0.49 | 0.27 | 0.16 | 0.05 | | | | | | 9 | 12 | 21 | |
| BMK-5B6 | 0.78 | 0.63 | 0.32 | 0.17 | | | | | | 6 | 11 | 17 | |
| BMK-5B9 | 0.57 | 0.45 | 0.22 | 0.06 | | | | | | 7 | 12 | 19 | |
| BMK-5C9 | 1.17 | 0.80 | 0.32 | 0.08 | | | | | | 5 | 12 | 17 | |
| BMK-5D3 | 1.14 | 0.79 | 0.32 | 0.09 | | | | | | 5 | 12 | 17 | |
| BMK-5D6 | 1.05 | 1.06 | 1.00 | 0.97 | | 0.81 | 0.63 | 0.23 | 0.06 | 3 | 2 | 5 | + |
| BMK-5E1 | 1.04 | 0.50 | 0.13 | 0.02 | | | | | | 7 | 12 | 19 | |
| BMK-5H6 | 0.96 | 0.44 | 0.12 | 0.02 | | | | | | 7 | 12 | 19 | |
| BMK-5H9 | 1.06 | 1.02 | 0.63 | 0.25 | | | | | | 3 | 9 | 12 | |
| BMK-6A11 | 1.13 | 0.68 | 0.21 | 0.06 | | | | | | 6 | 12 | 18 | |
| BMK-6B5 | 1.09 | 0.66 | 0.24 | 0.06 | | | | | | 6 | 12 | 18 | |
| BMK-6C9 | 0.99 | 0.98 | 0.90 | 0.50 | 0.79 | 0.41 | 0.14 | 0.00 | | 3 | 7 | 10 | + |
| BMK-6C11 | 1.03 | 1.03 | 0.69 | 0.23 | | | | | | 3 | 10 | 13 | + |
| BMK-6D11 | 1.01 | 0.76 | 0.27 | 0.06 | | | | | | 5 | 12 | 17 | |
| BMK-6E2 | 0.42 | 0.09 | 0.01 | 0.00 | | | | | | 11 | 14 | 25 | |
| BMK-6E7 | 0.78 | 0.28 | 0.05 | 0.00 | | | | | | 9 | 14 | 23 | |
| BMK-6F4 | 0.70 | 0.18 | 0.01 | 0.00 | | | | | | 10 | 14 | 24 | |
| BMK-6G5 | 0.94 | 0.31 | 0.07 | 0.01 | | | | | | 8 | 13 | 21 | |
| BMK-6H3 | 0.57 | 0.16 | 0.03 | 0.00 | | | | | | 10 | 14 | 24 | |
| BMK-6H5 | 0.92 | 0.88 | 0.88 | 0.76 | | 0.74 | 0.36 | 0.11 | 0.03 | 4 | 4 | 8 | + |
| BMK-7B5 | 0.62 | 0.19 | 0.04 | 0.01 | | | | | | 10 | 13 | 23 | |
| BMK-7B7 | 0.87 | 0.81 | 0.48 | 0.17 | | | | | | 5 | 11 | 16 | |
| BMK-7B11 | 0.90 | 0.89 | 0.90 | 0.86 | | 0.72 | 0.79 | 0.44 | 0.14 | 4 | 3 | 7 | + |
| BMK-7C1 | 0.66 | 0.22 | 0.04 | 0.00 | | | | | | 9 | 14 | 23 | |
| BMK-7E4 | 0.19 | 0.05 | 0.03 | 0.02 | | | | | | 11 | 12 | 23 | |
| BMK-7H1 | 0.91 | 0.64 | 0.26 | 0.07 | | | | | | 6 | 12 | 18 | |
| BMK-8A4 | 1.55 | 0.99 | 0.40 | 0.11 | | | | | | 3 | 11 | 14 | |
| BMK-8D4 | 0.98 | 0.92 | 0.83 | 0.47 | | | | | | 4 | 7 | 11 | + |
| BMK-8E3 | 1.01 | 0.95 | 0.92 | 0.82 | | 0.70 | 0.36 | 0.12 | 0.04 | 4 | 4 | 8 | + |
| BMK-8F10 | 0.91 | 0.65 | 0.26 | 0.07 | | | | | | 6 | 12 | 18 | |
| BMK-8H5 | 0.87 | 0.85 | 0.56 | 0.22 | | | | | | 5 | 10 | 15 | |
| BMK-8H9 | 0.12 | 0.00 | 0.00 | 0.00 | | | | | | 11 | 14 | 25 | |
| BMK-8H10 | 0.60 | 0.16 | 0.00 | 0.00 | | | | | | 10 | 14 | 24 | |
| BMK-9B1 | 0.90 | 0.77 | 0.34 | 0.04 | | | | | | 5 | 12 | 17 | |
| BMK-9C5 | 0.55 | 0.14 | 0.00 | 0.00 | | | | | | 10 | 14 | 24 | |
| BMK-9C6 | 1.00 | 0.94 | 0.52 | 0.18 | | | | | | 4 | 11 | 15 | |
| BMK-9F7 | 0.58 | 0.24 | 0.06 | 0.00 | | | | | | 9 | 14 | 23 | |
| BMK-9H4 | 1.19 | 0.86 | 0.52 | 0.15 | | | | | | 4 | 11 | 15 | |
| BMK-9H5 | 1.02 | 0.43 | 0.01 | 0.00 | | | | | | 7 | 14 | 21 | |
| BMK-10A11 | 0.98 | 0.50 | 0.32 | 0.29 | | | | | | 7 | 9 | 16 | |
| BMK-10D4 | 1.22 | 0.69 | 0.38 | 0.30 | | | | | | 6 | 9 | 15 | |
| BMK-10D9 | 0.77 | 0.39 | 0.29 | 0.27 | | | | | | 8 | 9 | 17 | |
| BMK-10G2 | 1.38 | 1.33 | 0.78 | 0.44 | | | | | | 1 | 8 | 9 | + |
| BMK-10G5 | 1.30 | 1.30 | 1.17 | 0.75 | 0.82 | 0.49 | 0.15 | 0.00 | | 1 | 4 | 5 | + |
| BMK-10G11 | 1.22 | 1.23 | 0.99 | 0.63 | 0.72 | 0.31 | 0.09 | 0.00 | | 2 | 6 | 8 | + |

The overall data were evaluated in order to select a number of supernatants to be further characterized. The best 17 supernatants derived from FACS analysis on colon CSCs were prioritized, among which 13 were also reactive towards the murine receptor, while the other 4 were specific for human FGFR4. These supernatants resulted among the best ones in at least one of the two binding assays on the recombinant receptor, namely in the FGFR4-dependent solid phase assay and on BOSC23 cells ectopically expressing the receptor on their surface.

The 17 supernatants were evaluated in dose-response experiments for their ability of inhibiting the binding of FGF19 to the immobilized receptor in the previously described solid phase assay. Immobilized FGFR4-Fc was pre-incubated with increasing volumes (from 0.185 uL to 16.6 uL) of each supernatant prior of the addition of FGF19 and heparin, bringing the final volume to 50 uL with myeloma cells conditioned medium. A supernatant that resulted non reactive in all three binding assays was included as a negative control, while FGF1 was used as positive control at a concentration of 5 nM.

Figure 11A:
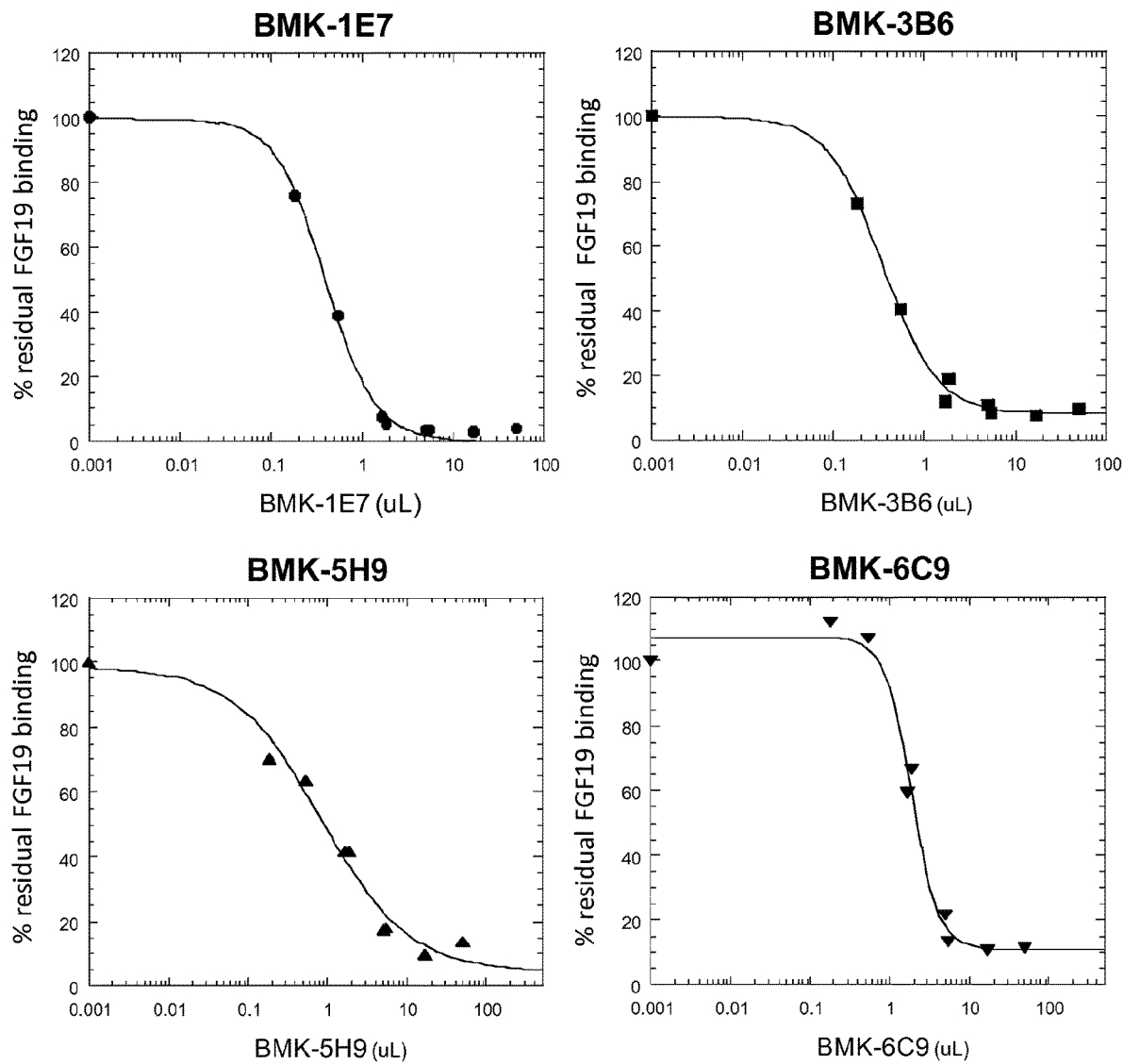
FIG. 11. Dose-response curves of the residual binding of FGF19 to FGFR4 as a function of the volume of each of the indicated supernatants, derived from the absorbance values at 450 nm obtained from a solid phase FGF19-FGFR4 binding assay (n=3). Inhibition curves were obtained by 4P logistic fitting of the experimental data with the KaleidaGraph software based on the residual absorbance at 450 nm (% of conditioned medium control) at increasing supernatant volumes.
Figure 11B:
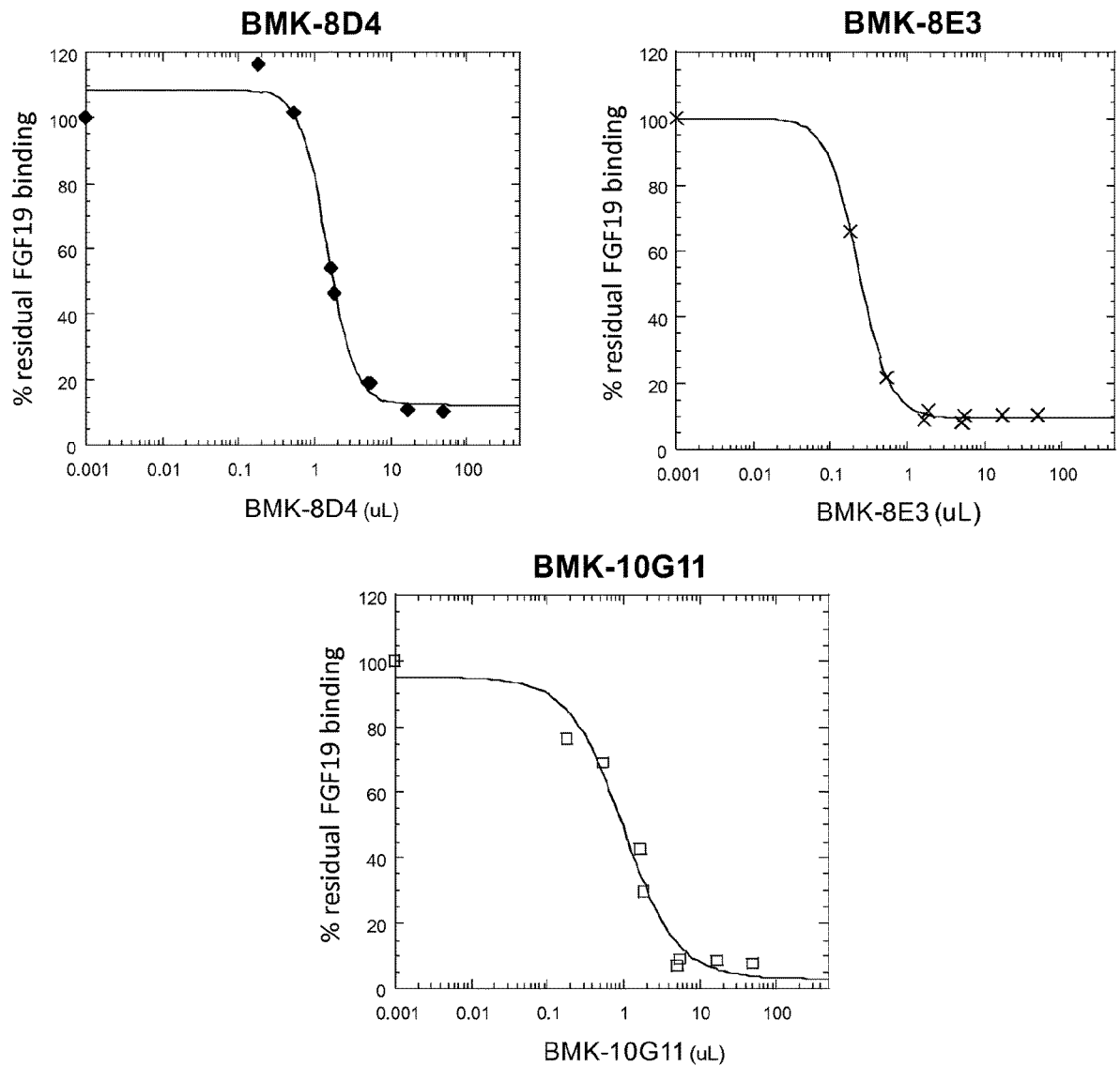

As shown in FIG. 11, seven out of the seventeen analyzed supernatants caused a clear dose-dependent inhibition of the FGF19-FGFR4 binding. Among those, five were cross-reactive with the murine receptor (BMK-1E7, 3B6, 5H9, 6C9, 10G11), while only two were specific for human FGFR4 (BMK-8D4 and BMK-8E3). Interestingly, these seven supernatants resulted to be among the most efficient ones in binding both to the endogenous and to the recombinant receptor.

Example 9

Characterization of the Anti-FGFR4 Monoclonal Antibodies

The parental hybridoma cell lines producing the seven selected supernatants were subcloned, and a stable subclone was obtained for each of them that produced antibodies reactive towards BOSC23 cells ectopically expressing FGFR4 (detailed in the Example 3). The corresponding monoclonal antibodies have been purified by protein G-Sepharose affinity chromatography as described in the Example 5.

The reactivity of the seven antibodies to three different colon CSC lines (CTSC1.2, CTSC85 and CTSC CROI) and to the HCC cell line Huh7 was evaluated by FACS analysis in dose-response experiments as described in the Example 7. As reference, the previously described BFG-5B5-G7 antibody was also tested. Fold change (FC) values with respect to the control (secondary antibody only) were plotted as a function of the mAb concentration, expressed in ug/mL, and $B_{max}$ and K, constants were calculated using the GraphPad Prism software and applying the "one site binding equation" as described in the Example 5.

As summarized in Table 14, BFG-5B5-G7 confirmed the high binding efficiency shown in previous experiments. Among the novel mAbs, BMK-3B6-E4 and BMK-6C9-C11 showed a high binding efficiency similar to that measured with BFG-5B5-G7 on all cell lines. On the contrary, the antibodies BMK-1E7-C4, BMK-5H9-D1, BMK-8D4-E2, BMK-8E3-E4 and BMK-10G11-F3 resulted significantly less reactive and, for BMK-8E3-E4, curves did not reach saturation on some of the analyzed cell lines, thus suggesting a certain degree of unspecific off-target binding.

TABLE 14

Dissociation constants and maximum binding values of the seven anti-FGFR4 mAbs and of BFG-5B5-G7 on three colon CSC lines and on the HCC cell line Huh7.

Parameters: 5B5-G7 1E7-C4 3B6-E4 5H9-D1 6C9-C11 8D4-E2 8E3-E4B 10G11-F3
CTSC1.2 Bmax 5.6 4.9 4.5 7.5 4.7 5.1 4.5 3.2
Kd (ug/mL) 0.18 0.2 0.2 1.3 0.135 0.78 1.1 0.03
Kd (n) 1.2 1.3 1.3 8.7 0.9 5.2 7.3 0.2
Parameters: 5B5-G7 1E7-C4 3B6-E4 5H9-D1 6C9-C11 8D4-E2 8E3-E4 10G11-F3
CTSC85 Bmax 4.6 6 3.9 7.7 3.9 4.6 8.4 4
Kd (ug/mL) 0.07 0.55 0.14 1.2 0.05 0.5 2.7 0.04
Kd (nM) 0.45 3.7 0.9 8 0.3 3.3 18 0.27
Parameters: 5B5-G7 1E7-C4 3B6-E4 5H9-D1 6C9-C11 8D4-E2 8E3-E4 10G11-F3
CTSC C OI Bmax 5 6.6 4.46 7.9 4.3 5 9.6 2.4
Kd (ug/mL) 0.07 0.57 0.16 1 0.05 0.5 3.2 0.03
Kd (nM) 0.5 3.8 1.1 6.7 0.3 3.3 21.3 0.2
Parameters: 5B5-G7 1E7-C4 3B6-E4 5H9-D1 6C9-C11 8D4-E2 8E3-E4 10611-F3
Huh 7 Bmax 63.5 34.3 27.5 21.1 30.6 33.4 not converge 8.3
Kd(ug/mL) 0.16 0.49 0.26 2.36 0.12 1.44 — 0.06
Kd (nM) 1.1 3.3 1.7 15.7 0.8 9.6 — 0.4

The novel mAbs have also confirmed the ability of preventing/compete the formation of the FGF19-FGFR4 complex in the receptor-dependent solid phase assay described in the Example 8. As the antibody BFG-5B5-G7, included as reference, the additional mAbs showed low nanomolar inhibition constants (Table 15).

TABLE 15

$IC_{50}$ values were calculated by 4P logistic fitting of the experimental data with the KaleidaGraph software based on the residual absorbance at 450 nm (% of PBS control) at increasing antibody concentrations (1:3 serial dilutions from 0.014 to 30 ug/mL; n = 3).

mAb IC50 (ug/mL) !C50 (nM)
5B5-G7 0.2 1.7
1E7-C4 0.1 0.7
3B6-E4 0.17 1.1
5H9-D1 0.17 1.1
6C9-C11 0.25 1.65
8D4-E2 0.26 1.7
8E3-E4 0.8 5.5
10G11-F3 0.13 0.9 qRT-PCR assays with total RNA from the HCC cell line HepG2 were then performed to evaluate the ability of the antibodies of modulating the FGF19/FGFR4-dependent expression of Cyp7Al and CTGF genes. Cells were treated with 60 ug/mL of each antibody or with PBS prior of the addition of FGF19 (100 ug/mL) under the experimental conditions described in the Example 8 for the antibody BFG-5B5-G7 that was included as reference. The RNA extraction and qRT-PCR protocols were the same as previously described.

Figure 12:
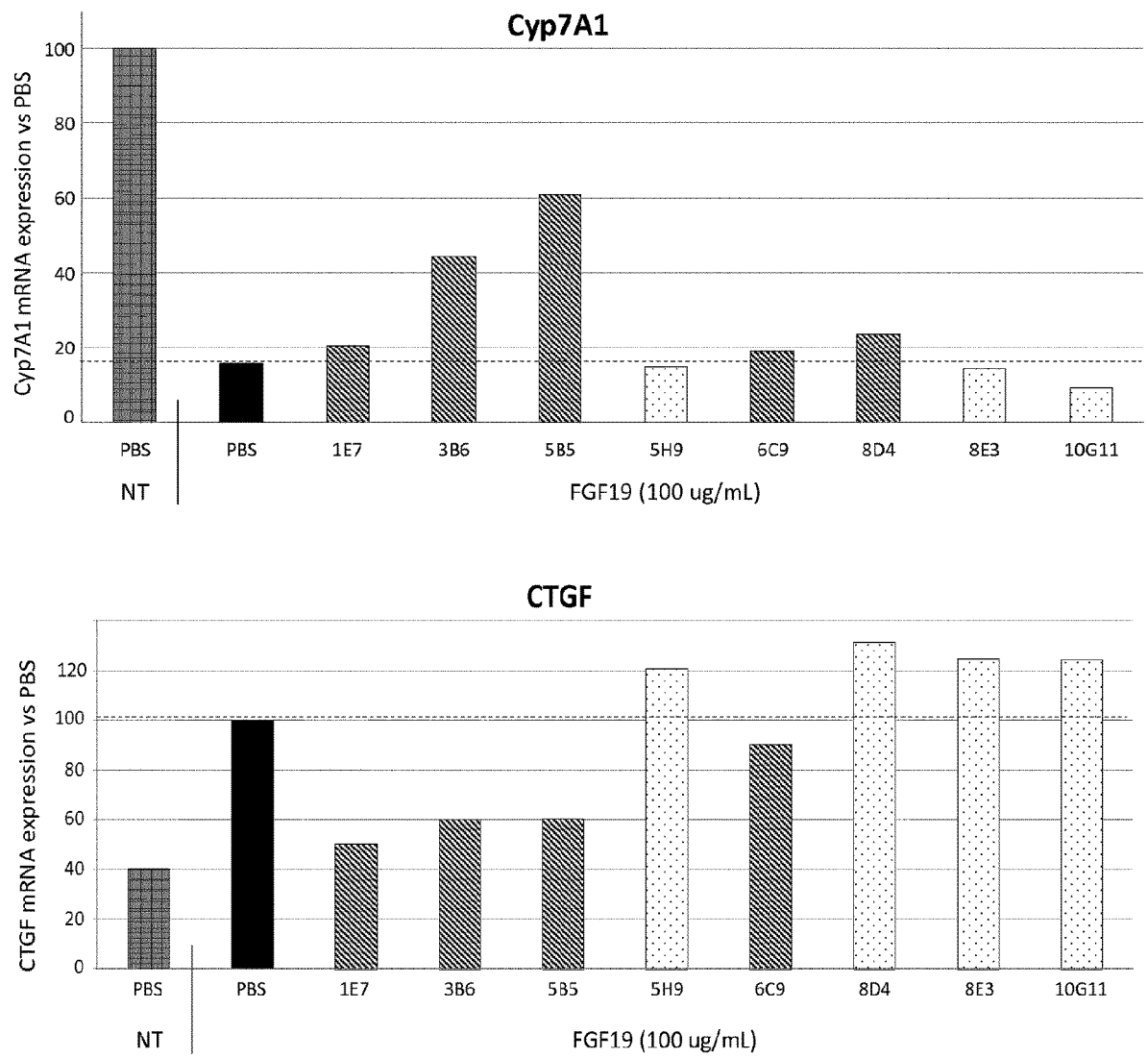
FIG. 12. qRT-PCR assays of HCC HepG2 cells treated with different anti-FGFR4 antibodies. Some of the new antibodies inhibit the repression of CYP7A1 expression (upper panel) and the induction of CTGF expression (lower panel), both dependent on FGF19-mediated FGFR4 activation, in HepG2 cells. mRNA levels of the two genes are expressed as percentage of the PBS control values in the absence (CYP7A1) or in the presence (CTGF) of FGF19, respectively. Dashed bars represent active mAbs; dotted bars represent inactive mAbs.

The results of this analysis, obtained with the $2^{\wedge}(-AA_{c\_j})$ calculation method, are shown in FIG. 12. As in previous experiments, the addition of FGF19 reduced CYP7A1 expression (about 5 fold) and increased CTGF expression (about 2.5 fold). BFG-5B5-G7 confirmed to be able to partially revert these effects, as well as the new antibodies BMK-1E7-C4, BMK-3B6-E4, and BMK-6C9-C11, causing an increase of Cyp7Al mRNA levels and a decrease of CTGF mRNA levels, respectively.

Subsequently, the antibodies were evaluated for their ability of inhibiting the FGFR4-dependent phosphorylation of FRS2, induced by the treatment with FGF19 of the HCC cell line Hep3B. Cells were treated with 60 ug/mL of each antibody or with PBS prior of the addition of FGF19/heparin under the experimental conditions described in the Example 8 for the antibody BFG-5B5-G7 that was included as reference.

Figure 13:
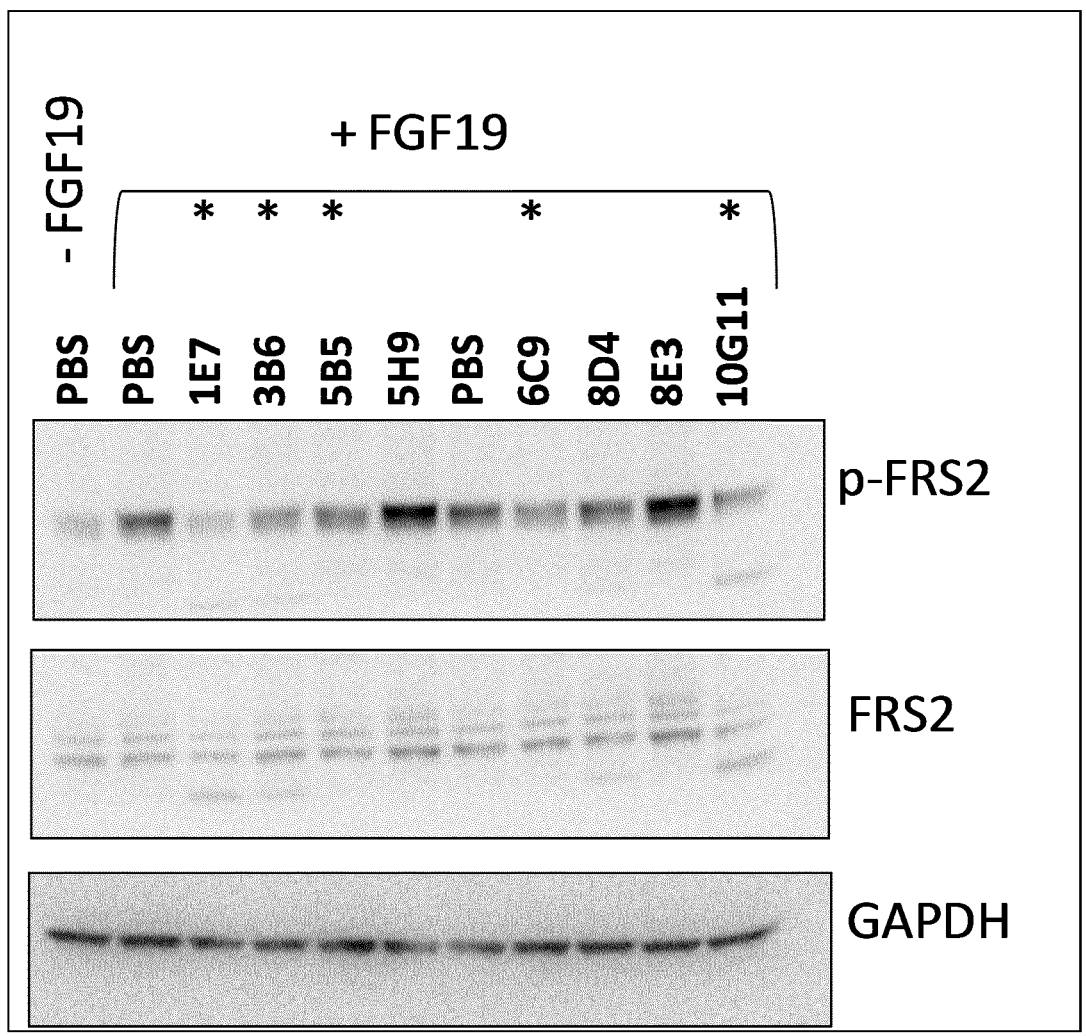
FIG. 13. Inhibition of FGF19-dependent FRS2 phosphorylation in Hep3B cells treated with different anti-FGFR4 antibodies analyzed by Western Blot. (*) Active antibodies.

The results of this analysis are shown in FIG. 13. The antibodies BMK-1E7-C4, BMK-3B6-E4, BMK-6C9-C11 and BMK-10G11-F3, as well as the positive control BFG-5B5-G7, could inhibit FGF19-induced FRS2 phosphorylation, albeit to different extents.

Finally, the anti-proliferative activity of the antibodies on the HCC cell line Huh7 was evaluated in a clonogenic assay in liquid. The antibody BFG-5B5-G7 and the FGFR4 inhibitor BLU9931 were included as references.

Figure 14:
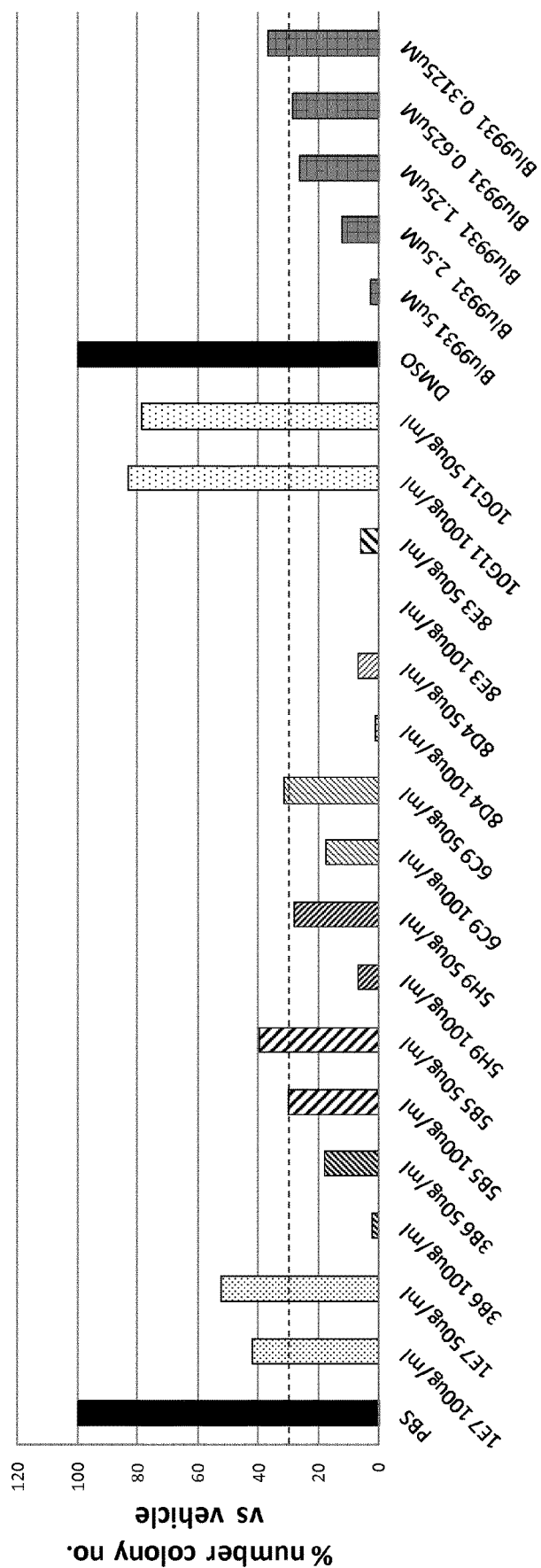
FIG. 14. Inhibitory effects of the anti-FGFR4 antibodies on the colony formation efficiency by HCC Huh7 cells. 300 cells/well of a 24-well plate were incubated at 37° C., 5% CO2 for ten days in the presence or absence (negative controls in PBS or DMSO) of the indicated antibodies at concentrations of 50 ug/mL and 100 ug/mL, or with the compound BLU9931 at the indicated increasing concentrations. Cultures were supplemented with fresh medium containing antibodies, BLU9931, or vehicles every two days. Colonies were monitored under an inverted light microscope and at the end of the experiment were stained with a 0.5% Crystal Violet solution in 20% methanol. The number of colonies in each of the experimental quadruplicates was determined and the replicate means were expressed as percentage of those of the vehicle controls (PBS for the antibodies and DMSO for BLU9931).
Figure 15A:
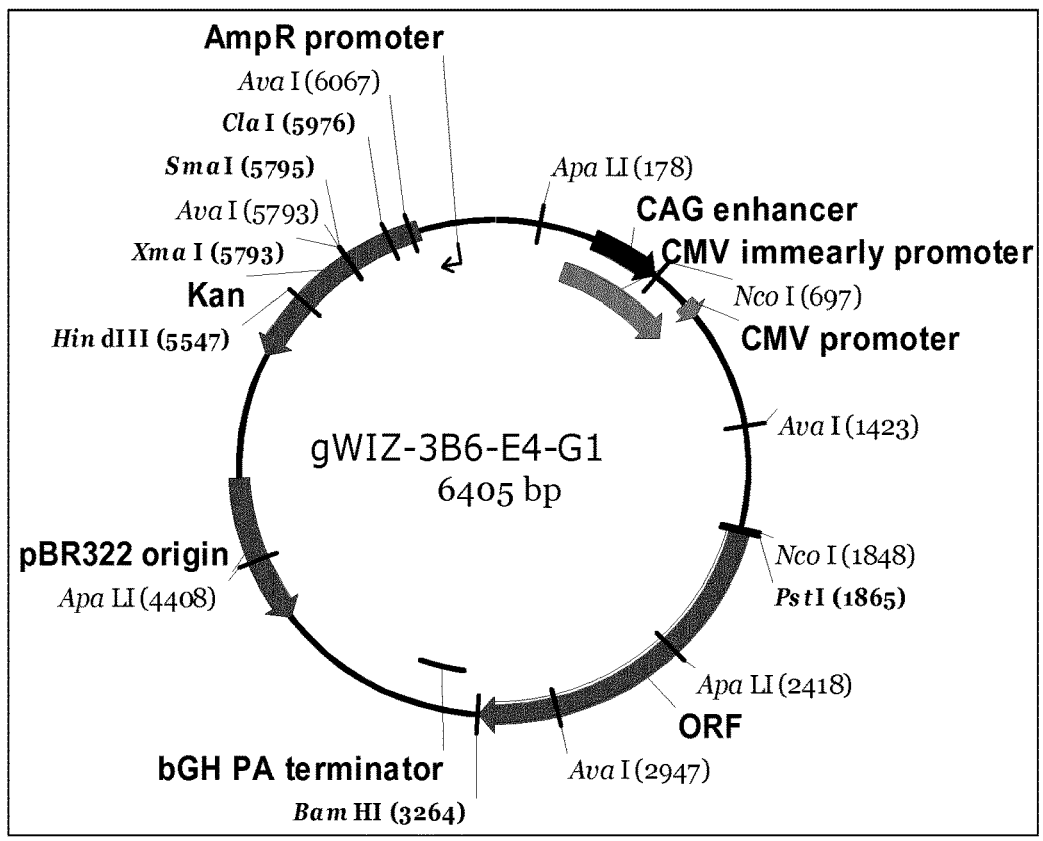
FIG. 15 (A-C). Expression vectors encoding the heavy and light chains of the human-rat chimeric antibodies ch3B6, ch6C9 and ch5B5. Similar expression vectors were obtained for the other antibodies.
Figure 15A:
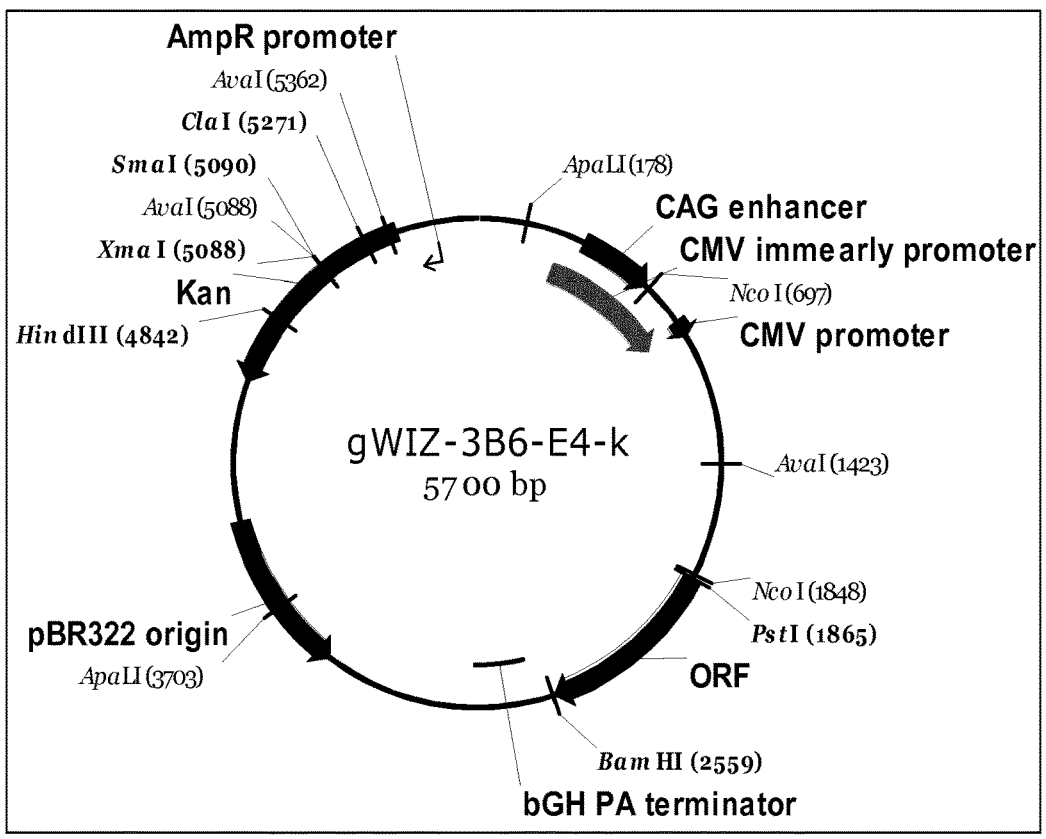
Figure 15B:
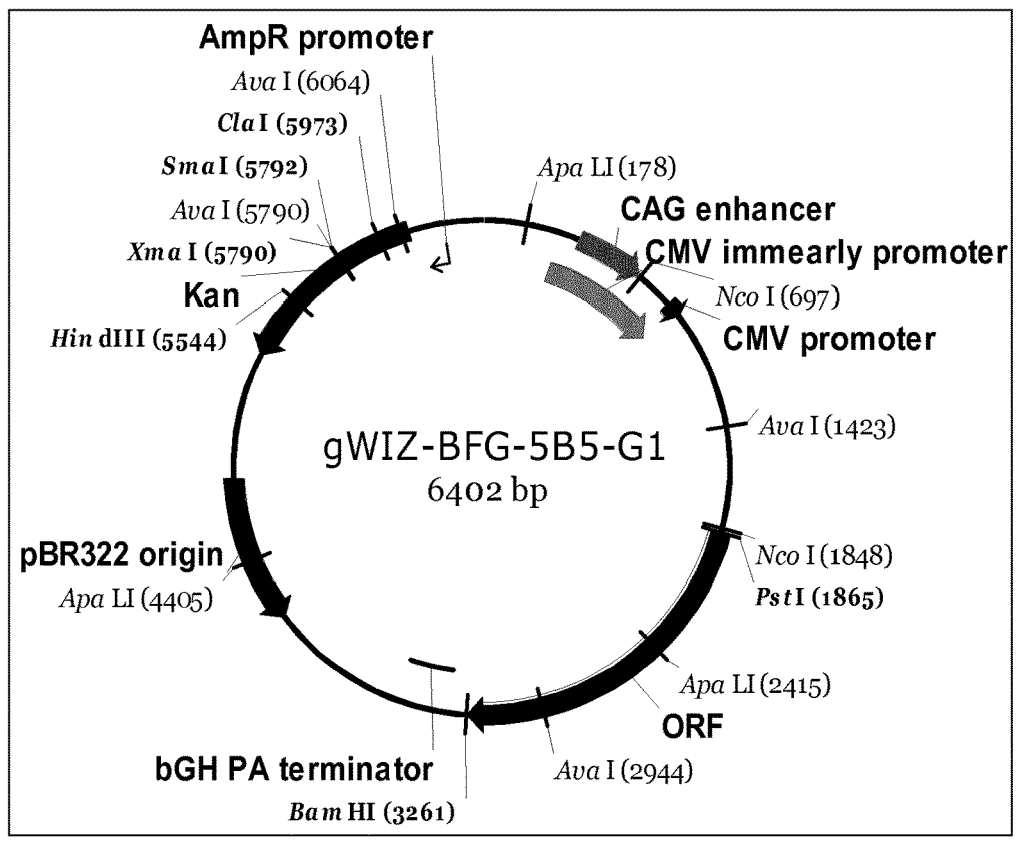
Figure 15B:
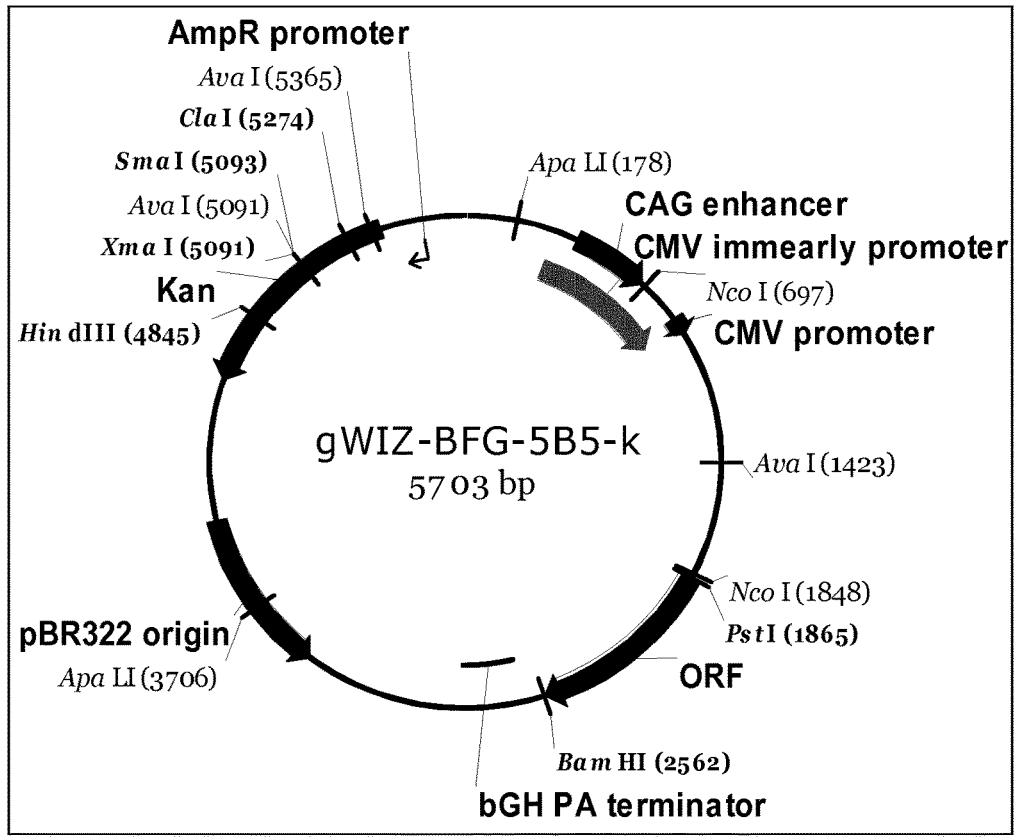
Figure 15C:
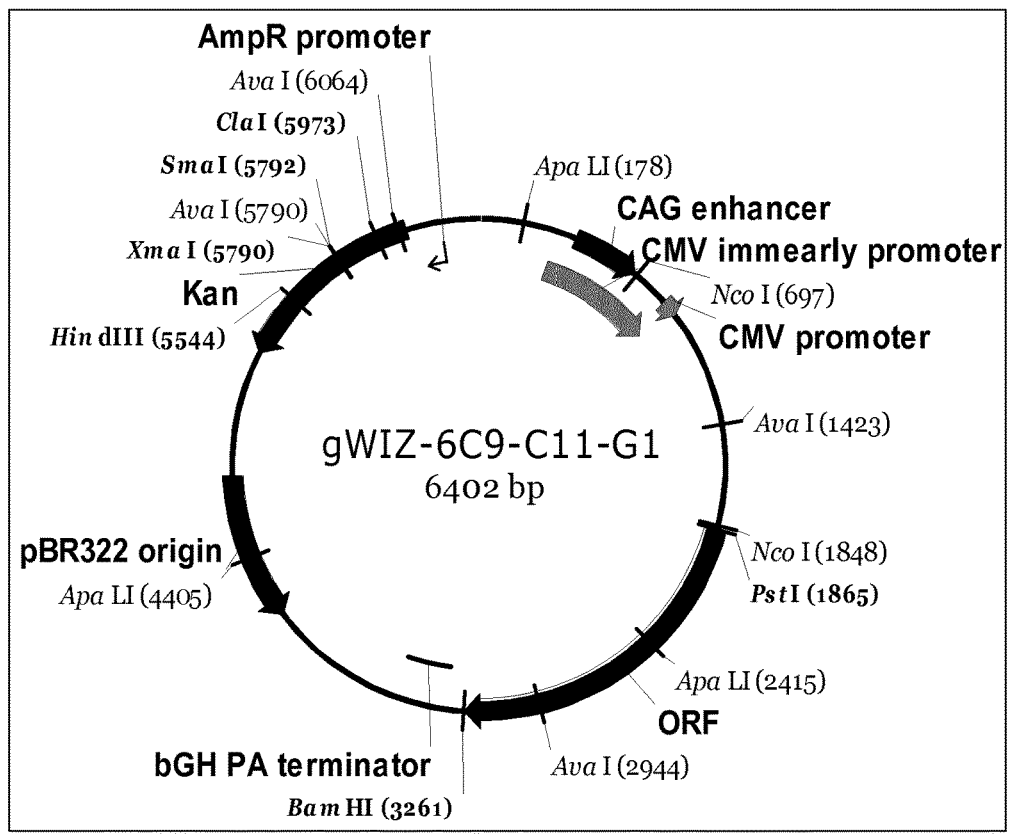
Figure 15C:
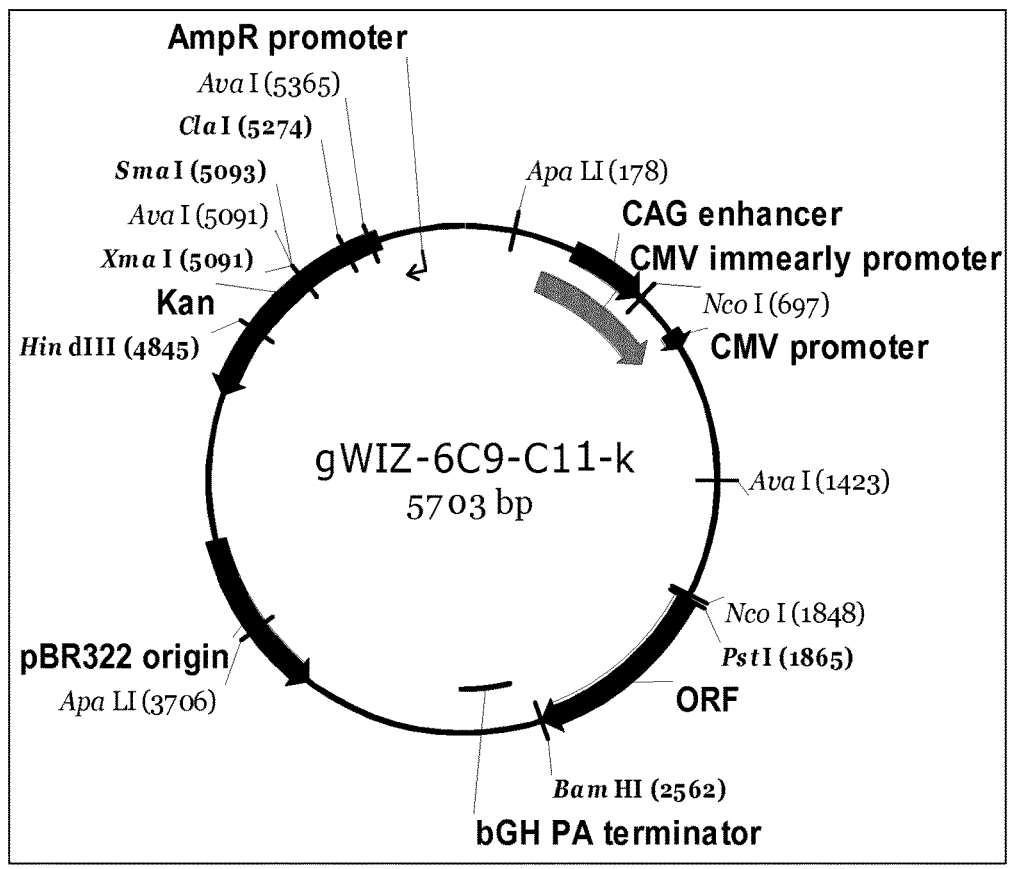

Representative results are shown in FIG. 14. The continuous treatment of Huh7 cells with all antibodies, as well as with BFG-5B5-G7, caused a decrease of the number of colonies with respect to control, albeit to different extents. The anti-proliferative effects shown by BMK-3B6-E4, BMK-5H9-D1, BMK-6C9-C11, BMK-8D4-E2 and BMK-8E3-E4, as well as by the reference antibody BFG-5B5-G7, at concentrations of 50-100 ug/mL (0.3-0.6 uM), were comparable to or higher than those observed with similar concentrations of the FGFR4 inhibitor BLU9931.

In conclusion, based on their immunological and functional properties, three anti-FGFR4 monoclonal antibodies were selected for further characterization, namely BMK-3B6-E4, BFG-5B5-G7 and BMK-6C9-C11 that satisfied all the three following conditions: i. binding to the receptor expressed on the surface of colon CSCs and HCC cells, with dissociation constants in the low nanomolar range; ii. FGFR4 signalling pathway inhibition in cells expressing high receptor levels; iii. anti-proliferative activity on FGFR4 positive cells at concentrations compatible with standard therapeutic doses of antibody drugs.

Example 10

Production and Characterization of Anti-FGFR4 Human-Rat Chimeric Antibodies

VH and VL regions of the immunoglobulin genes expressed by rats hybridomas BFG-5B5-G7, BMK-1E7-C4, BMK-3B6-E4, BMK-5H9-D1, BMK-6C9-C11, BMK-8D4-E2, BMK-8E3-E4, and BMK-10G11-F3 were amplified with a set of Aldevron's (Freiburg, Germany) proprietary primers from cDNA generated from the hybridoma cells using standard RT-PCR protocols. After sequencing using a standard dye-terminator capillary sequencing method, the cDNAs encoding for the VH regions were cloned in frame with the coding sequence for the human IgGI constant regions into the gWIZ expression vector (Aldevron), while the cDNAs encoding for the VL regions were cloned in frame with the coding sequence for the human kappa chain constant region into the same expression vector (FIG. 15).

Figure 16:
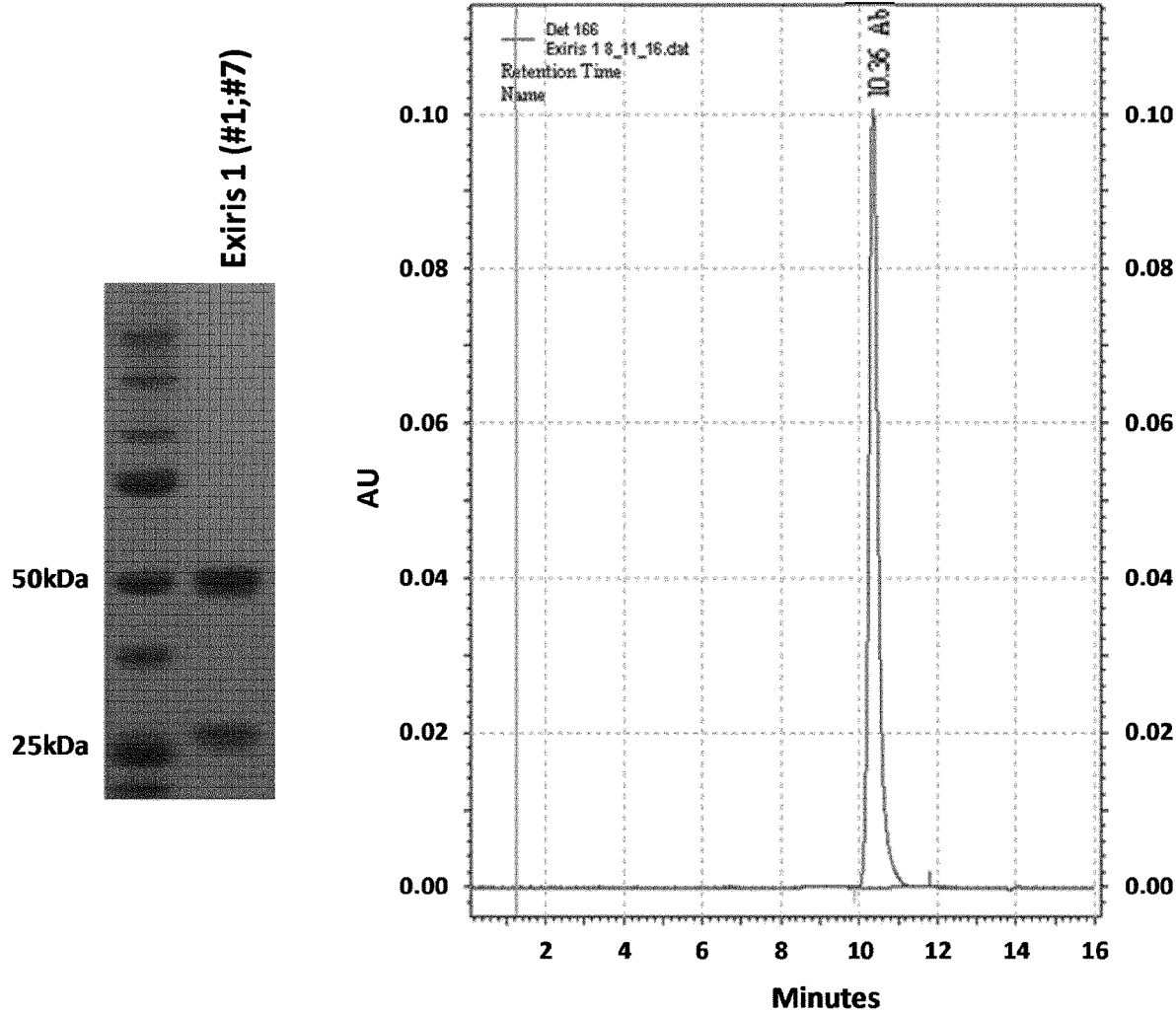
FIG. 16. Quality controls for the antibody ch3B6. Left: SDS-PAGE; right: HPLC-SEC. Similar results were obtained for the antibodies ch6C9 and ch5B5.

The expression vectors encoding the heavy and light chains of each of the three chimeric antibodies BFG-5B5-G7, BMK-3B6-E4 and BMK-6C9-C11, defined for simplicity ch3B6, ch6C9 and ch5B5, were transiently cotransfected into the cell line 293F and the antibodies were purified in PBS pH 7.2 by Protein-A Sepharose affinity chromatography from >2 L of cellular supernatant at a final concentration of 2-3 mg/mL. Yields were from 20 and 30 mg/liter of supernatant, depending on the antibody and the preparation. Quality controls confirmed the purity and the monomeric state of the recombinant antibodies (FIG. 16).

The chimeric antibodies were controlled by FACS for their ability of binding FGFR4 expressed on the surface of HepG2 and Huh7 hepatocellular carcinoma cells. ch3B6 was also tested on the breast cancer cell line MDA-MB453, described to express high levels of the FGFR4 Y367C mutant variant (Roidl et al., 2010). The assay has been performed as described in the Example 7, but an anti-human fluorescent secondary antibody (Goat Anti-Human IgG R-phycoerythrin [R-PE] Conjugate, Southern Biotech) was used in this case.

Figure 17A:
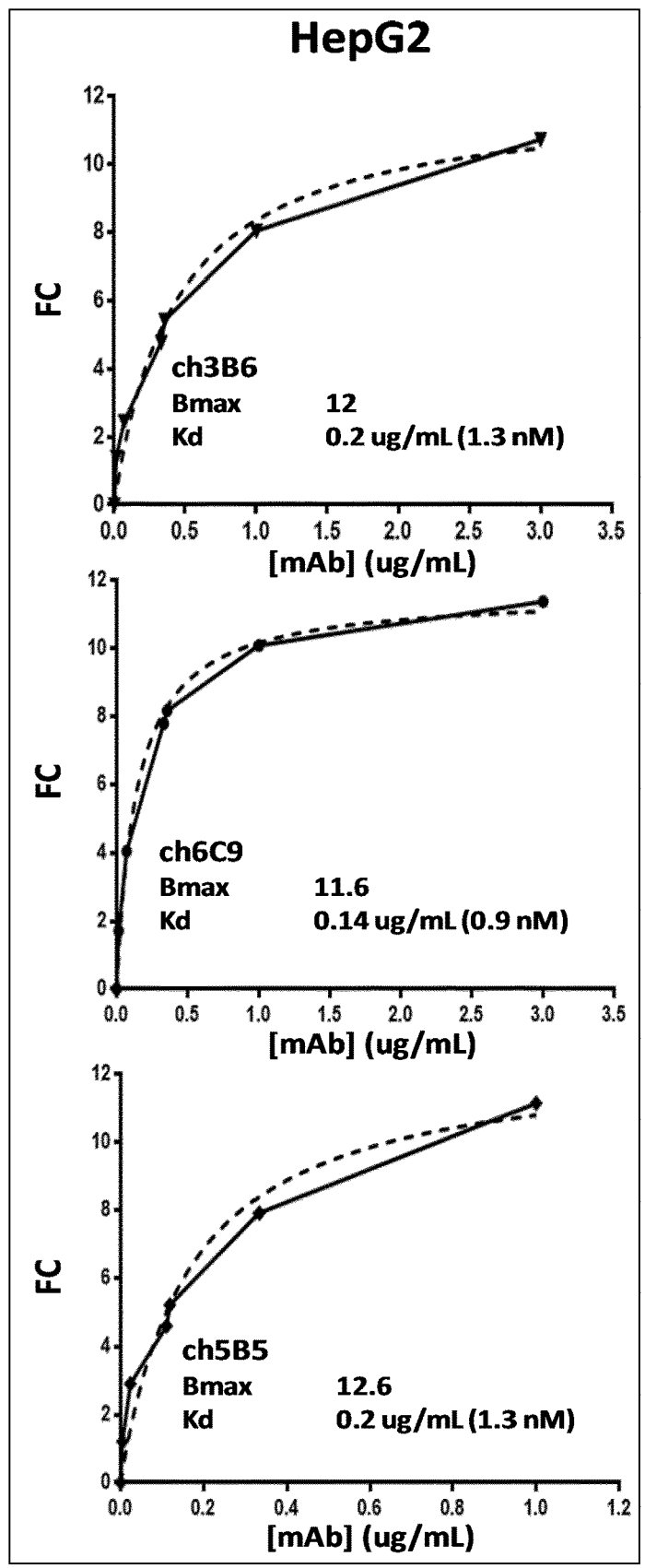
FIG. 17. Graphs of the FC values as a function of the antibody concentration, obtained by FACS analysis of the chimeric mAbs ch3B6, ch6C9 and ch5B5 on the HCC cell lines HepG2 and Huh7 and on the breast cancer cell line MDA-MB453. Continuous lines are the experimental ones while dashed lines are those obtained by fitting experimental data to the "one site binding" equation.
Figure 17B:
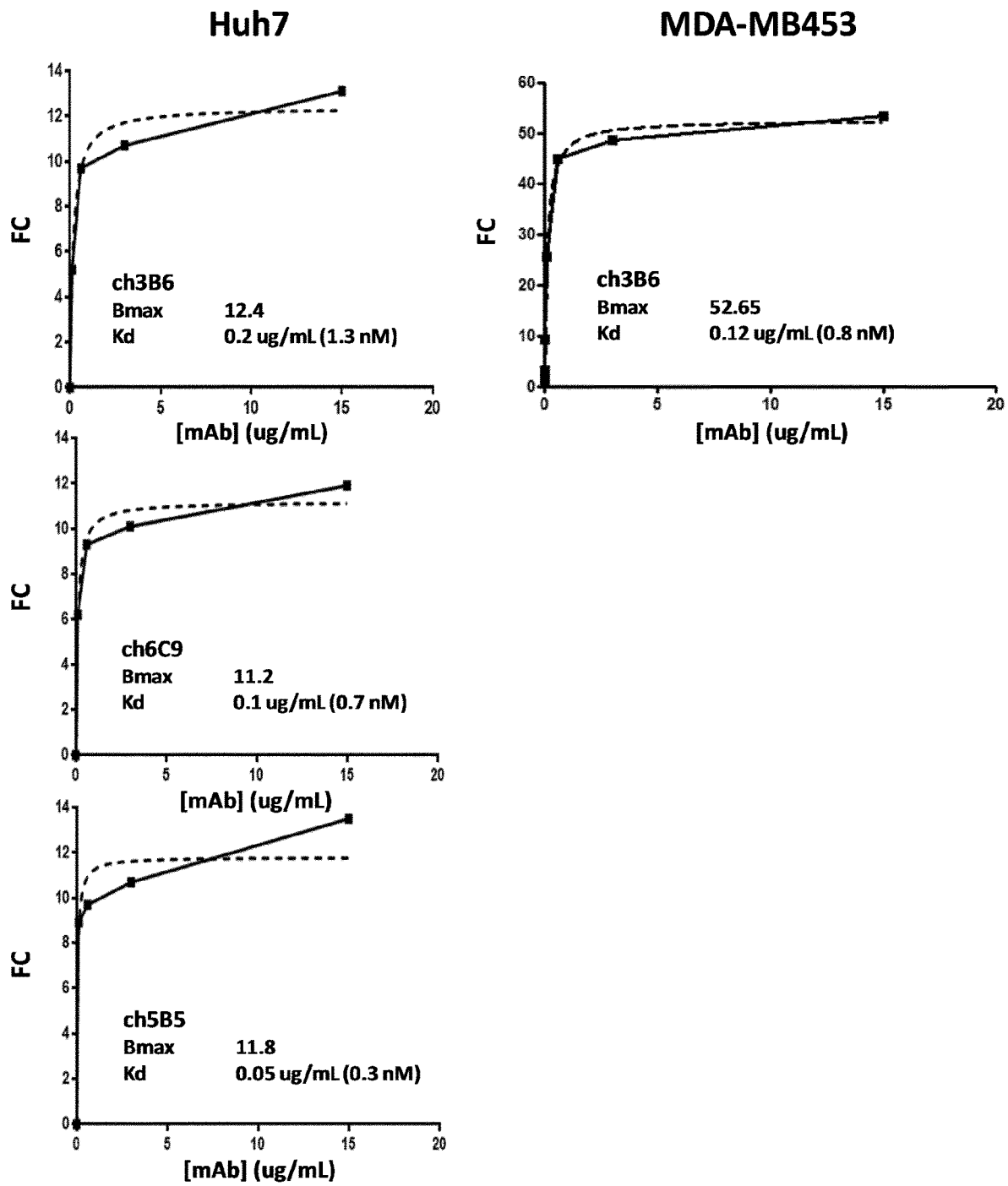

Representative data are reported in FIG. 17.

The chimeric antibodies confirmed to retain the binding activity of the corresponding rat mAbs with similar dissociation constants in the low nM range. In addition, ch3B6 was shown to bind efficiently also to the FGFR4 Y367C mutant overexpressed in the MDA-MB453 cells. This mutant receptor was described as a dominant, ligand-independent, constitutive activated variant, insensitive to the inhibition with a known antagonistic antibody (Roidl et al., 2010).

The binding affinity and specificity of the chimeric antibodies for FGFR4 with respect to the other members of the FGF receptor family was then measured in vitro using the solid phase receptor binding assay and the human chimeric receptors FGFRI-Fc, FGFR2-Fc, FGFR3-Fc and FGFR4-Fc (R&D Systems). For FGFR1 and FGFR2 both alpha and beta splicing variants were tested. In addition, for each of the two FGFR2 variants, the two additional alternative splicing variants IIIb and IIIc that differ in the Ig III domain were tested. This and the other solid phase binding assays described below were performed essentially as described in the Example 7, with the following modifications. 96 well-microplates were directly coated with the human chimeric receptors FGFR-Fc in PBS at 2 ug/mL overnight at 4° C. After incubation with increasing antibody concentrations, a HRP-conjugated goat anti-human IgG, Fab specific, secondary antibody (Sigma Aldrich) was used for detection at a 1:2500 dilution.

Figure 18:
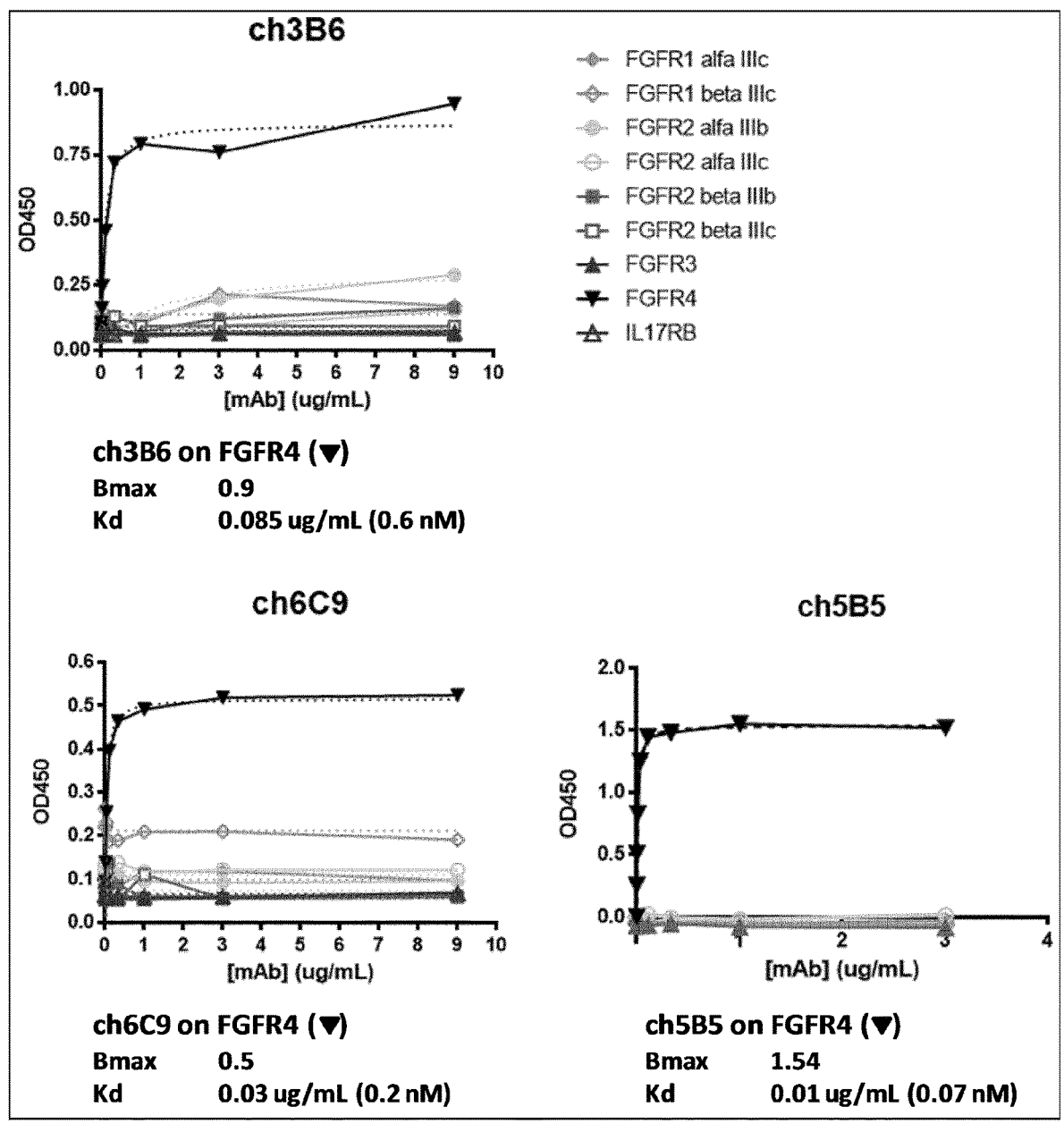
FIG. 18. Graphs of the absorbance values at 450 nm obtained from a FGFR-Fc-dependent solid phase binding assay, as a function of the concentration of the anti-FGFR4 antibodies. Serial 1:3 dilutions of each antibody (9 experimental points from 0.0014 ug/mL to 9 ug/mL) were tested in triplicate on the extracellular regions of FGFRIa IIIc, FGFRI IIIc, FGFR2a IIIb, FGFR2a IIIc, FGFR2 IIIb, FGFR2 IIIc, FGFR3 and FGFR4 fused with human Fc. As a negative control, the extracellular region of the IL17B receptor fused to human Fc was included. Continuous lines are the experimental ones while dashed lines are those obtained by fitting experimental data to the "one site binding" equation.

Representative dose-response binding curves are shown in FIG. 18.

In this assay the chimeric antibodies confirmed a sub-nanomolar affinity for FGFR4, while no significant binding was measured on the other FGF receptors.

Next we confirmed the efficiency of the chimeric antibodies in preventing/competing the binding of FGF19 to FGFR4-Fc in the solid phase assay performed as in the Example 8 by adding, after the incubation with increasing antibody concentrations, FGF19/heparin at the equimolar concentration of 23 nM.

Figure 19:
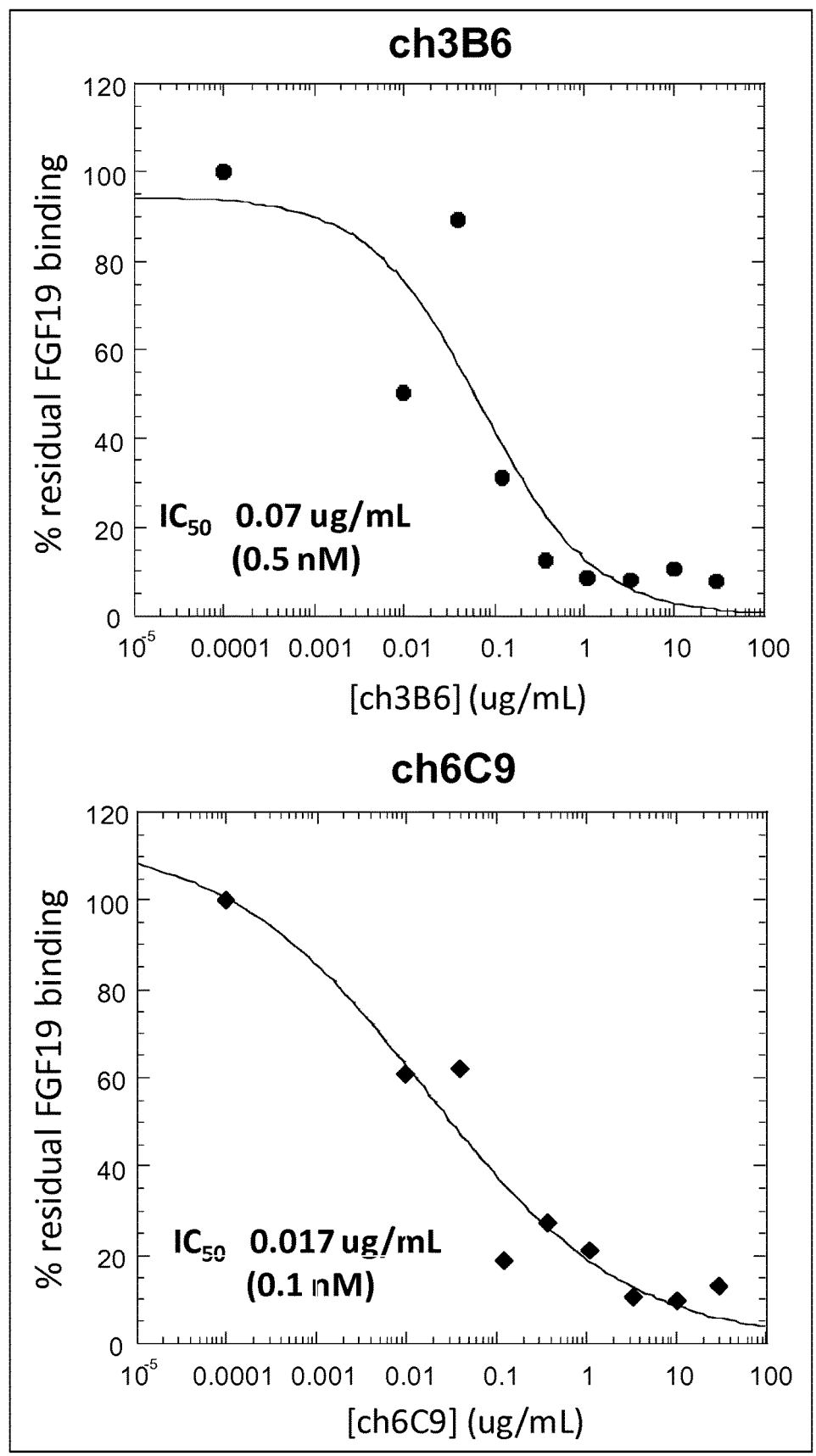
FIG. 19. Dose-response curves of the residual binding of FGF19 to FGFR4 as a function of the concentration of ch3B6 and ch6C9, derived from the absorbance values at 450 nm obtained from a solid phase FGF19-FGFR4 binding assay (n=3). Inhibition curves were derived by 4P logistic fitting of the experimental data with the KaleidaGraph software, based on the residual absorbance at 450 nm (% of PBS control) at increasing antibody concentrations (1:3 serial dilutions from 0.014 to 30 ug/mL).

Representative dose-response inhibition curves are shown in FIG. 19.

The anti-proliferative activity of the chimeric antibodies on the HCC cell line Huh7 was then evaluated in a clonogenic assay in liquid. The FGFR4 inhibitor BLU9931 was included as reference at increasing concentrations from 0.2 uM to 5 uM.

Figure 20:
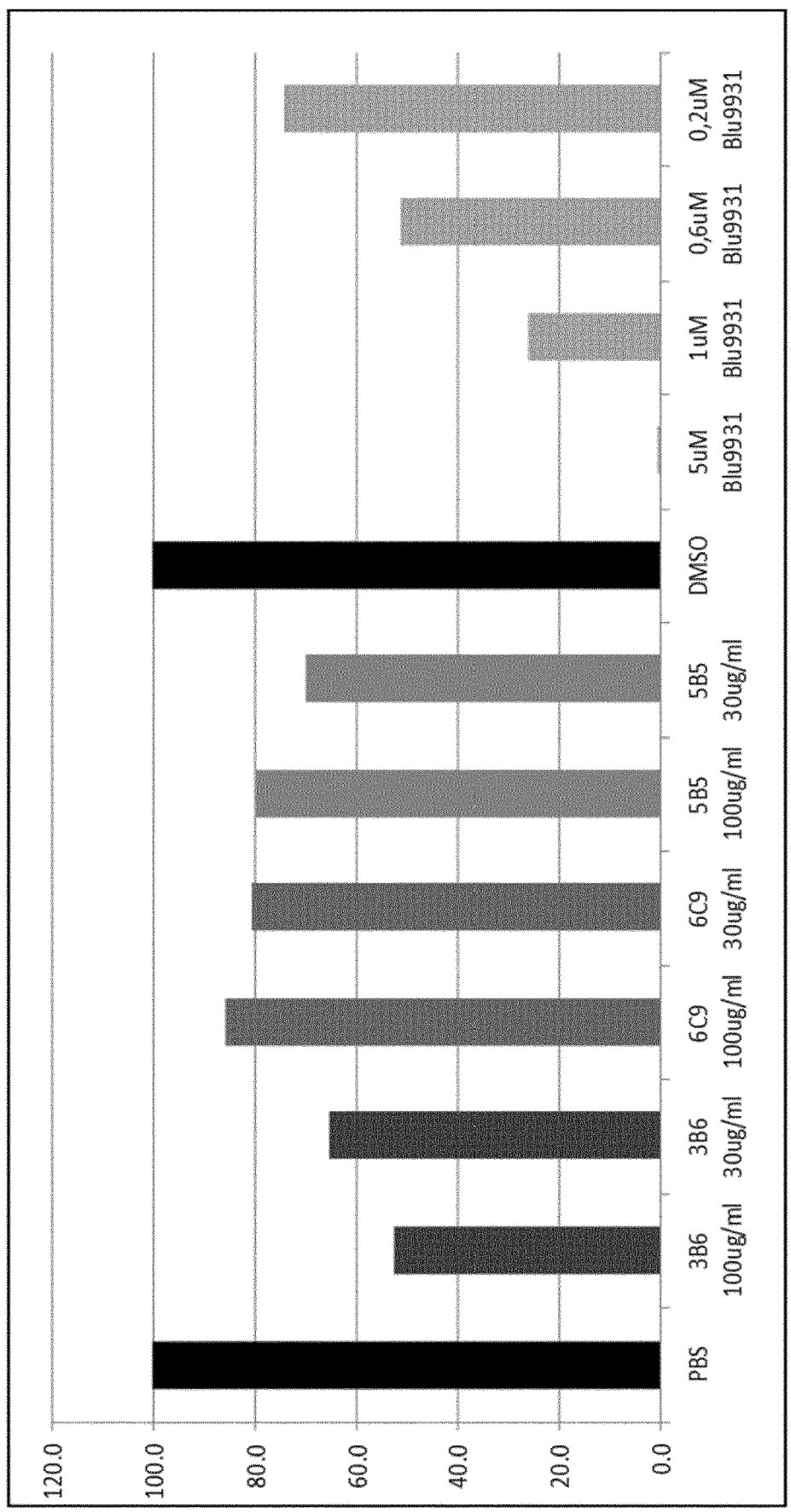
FIG. 20. Inhibitory effects of the anti-FGFR4 chimeric antibodies on the colony formation efficiency by HCC Huh7 cells. 600 cells/well of a 24-well plate were incubated at 37° C., 5% C02 for ten days in the presence or absence (negative controls in PBS or DMSO) of the indicated antibodies at concentrations of 30 ug/mL and 100 ug/mL, or with the compound BLU9931 at the indicated increasing concentrations. Cultures were supplemented with fresh medium containing antibodies, BLU9931, or vehicles every two days. Colonies were monitored under an inverted light microscope and at the end of the experiment were stained with a 0.5% Crystal Violet solution in 20% methanol. The number of colonies in each of the experimental quadruplicates was determined and the replicate means were expressed as percentage of those of the vehicle controls (PBS for the antibodies and DMSO for BLU9931).

Representative results are shown in FIG. 20.

The continuous treatment of Huh7 cells with the three antibodies, caused a decrease of the number of colonies with respect to control, albeit to different extents. The antiproliferative effects shown by the antibody ch3B6, at concentrations of 30 and 100 ug/mL (0.2 uM and 0.6 uM, respectively), were comparable to those observed with the compound BLU9931 at the same concentrations. The other two antibodies showed less significant inhibitory effects.

Figure 21:
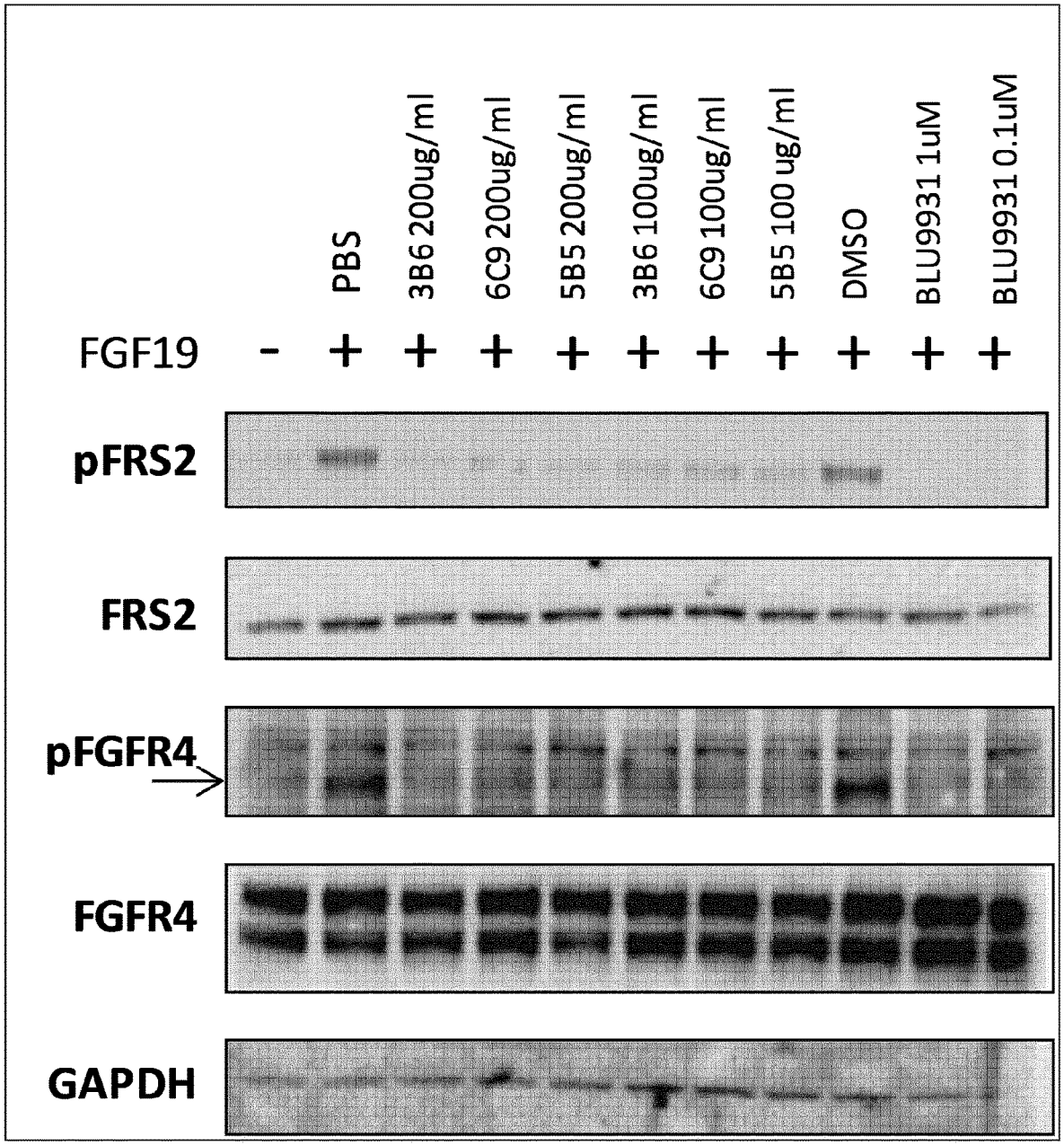
FIG. 21. Inhibition of FGF19-dependent FGFR4 and FRS2 phosphorylation in Huh7 cells treated with the anti-FGFR4 chimeric antibodies analyzed by Western Blot. Cells were treated with 100 or 200 ug/mL of each antibody, with 0.1 uM or 1 uM BLU9931, or with PBS prior of the addition of FGF19/heparin under the experimental conditions described in the Example 8. Western blot analysis was performed using an anti-phospho-FRS2 antibody (Tyr196, Cell Signalling), an anti-FRS2 antibody (LSBio), an anti-phospho-FGFR4 antibody (FGFR4 [phospho-Tyr642] antibody, Biorbyt), the anti-FGFR4 antibody BFG-2F7-B9, and an anti-GAPDH antibody (Sigma-Aldrich).

To confirm the specificity of the observed anti-proliferative effects, the three anti-FGFR4 chimeric antibodies were evaluated for their ability of interfering with the FGFR4 signalling pathway activation in the sensitive HCC cell line Huh7. To this aim, the inhibitory effects on the phosphorylation of FGFR4 and of the adaptor protein FRS2 induced by cell treatment with FGF19 were analyzed by Western blot (FIG. 21).

All three antibodies, as well as the positive control BLU9931, could inhibit FGF19-induced FGFR4 and FRS2 phosphorylation in Huh7 cells.

On the basis of the in vitro experimental evidence, potential therapeutic antitumor effects of the three chimeric antibodies were evaluated in an in vivo model, using immunodeficient mice transplanted with the HCC cell line Huh7. A suspension of $5 \times 10^6$ Huh7 cells in 50% Matrigel (Corning) was inoculated subcutaneously in the flank of each of 35 athymic nude mice (Envigo) of 5-6 weeks of age. Twelve days after the transplant, mice that showed measurable tumors were randomly assigned to four groups, namely BMK-3B6-E4, BMK-6C9-C11, BFG-5B5-G7 (n=8) and control (n=7) groups, with mean tumor volumes of 107 mm, in all groups. Mice were treated via IP injection with 25 mg/Kg of each antibody in PBS administered twice a week for three weeks. The control group received corresponding volumes of blank injection (PBS). Mice weight was controlled twice a week and tumor size (major and minor axis) was measured with a vernier caliper twice a week. Tumor volumes were calculated using the formula: TV (mm$^3$)=d2× D/2 where d and D refer to the shortest and the longest diameter, respectively.

Figure 22:
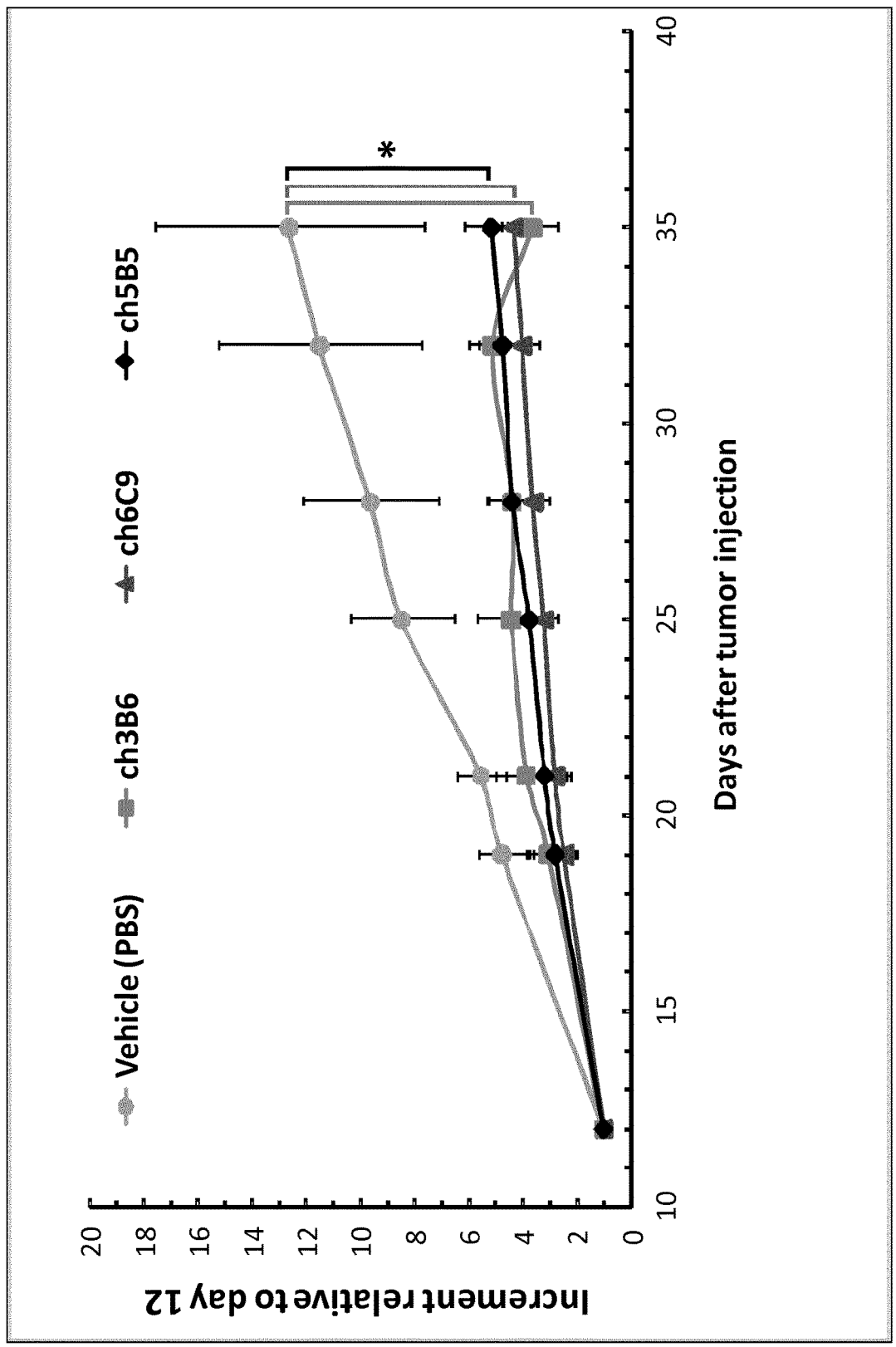
FIG. 22. Anti-tumor effects by the three anti-FGFR4 chimeric antibody on xenografts of Huh7 liver tumor cells. Data are expressed as increment of the mean tumor volume relative to day 11±StDev; (*) p<0.05 with respect to the vehicle control.

A reduction of the tumor volume was observed in mice treated with each antibody relative to the control group, a difference that became statistically significant starting from the 16th day of treatment (FIG. 22). On the contrary, body weight loss or clinical adverse effects were not observed (not shown).

At the end of the study surviving mice were sacrificed and residual tumor masses were collected and divided into three fragments for the evaluation of specific biomarkers by qRT-PCR, Western Blot and immunohistochemistry, respectively.

First we evaluated the capacity of the antibodies of modulating, in treated mice tumors, the transcription of two FGFR4- and liver-specific biomarkers, namely CYP7A1 and CTGF that are regulated, at the mRNA level, by FGF19-dependent activation of the FGFR4 signalling pathway both in normal and tumor liver cells, as described in detail in the Example 8. We have previously shown that the treatment of hepatocellular carcinoma cell cultures with the corresponding rat anti-FGFR4 antibodies partially reverted the FGF19-dependent modulation of the expression of these two genes (Examples 8 and 9).

In this ex vivo study, qRT-PCR assays were performed with total RNA extracted from tumor samples collected from mice treated with each of the three anti-FGFR4 chimeric antibodies or with PBS, using the experimental procedure described in details in the Example 8.

Figure 23:
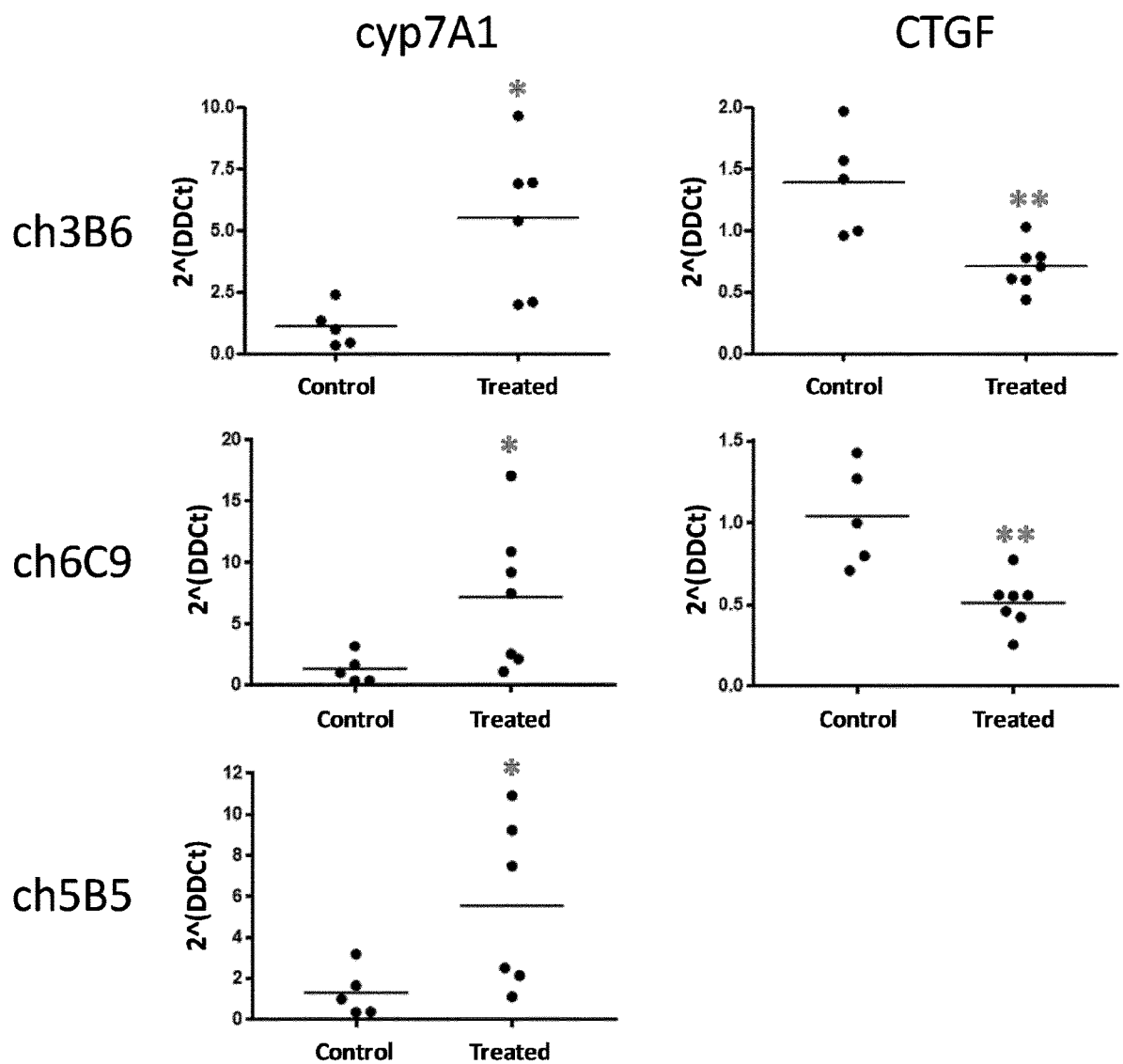
FIG. 23. In vivo treatment of Huh7 xenografts with the anti-FGFR4 chimeric antibodies derepressed CYP7A1 expression (left panels) and inhibited CTGF expression (right panels) with respect to vehicle-treated tumors. Dot plots where the mRNA levels in single tumors are expressed as 2^(-AAc-t) are shown. The human gene for the beta glucuronidase (GUS) was used as normalizer and the ΔΔΩ value corresponding to one of the control group mice was chosen as a relative reference and set equal to 1. Statistically significant differences between treated and control mice resulted from t-test analysis of both CYP7A1 (*p<0.05) and CTGF (**p=0.003) data.

The results of this analysis are shown in FIG. 23.

The therapeutic administration of the chimeric anti-FGFR4 antibodies caused a modulation of the analyzed biomarkers in the tumors, consistent with an antagonistic effect on FGFR4 signal transduction pathway activation in this liver xenograft model.

Figure 24:
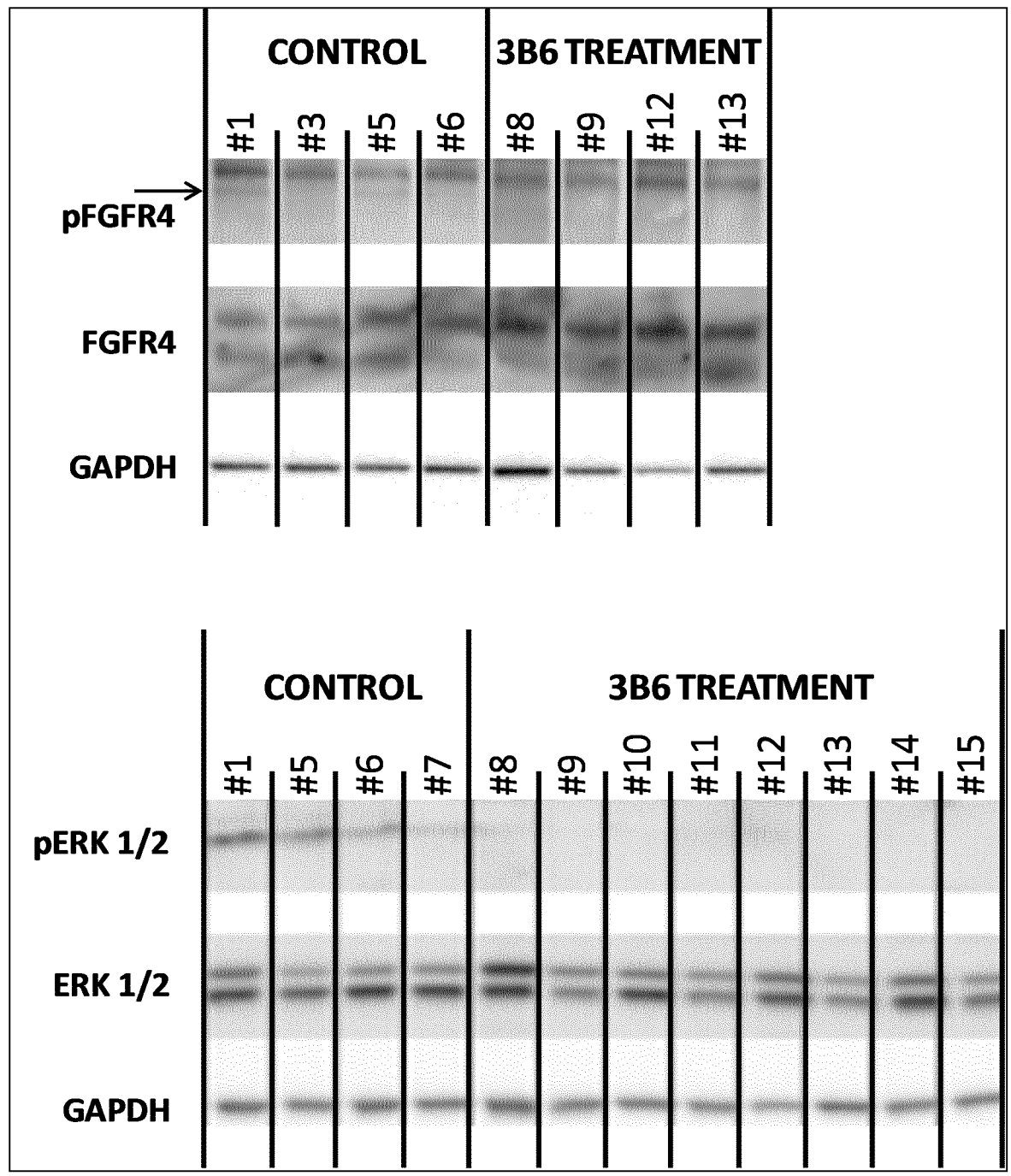
FIG. 24. Inhibition of FGFR4 (upper panel) and ERK1/2 phosphorylation in Huh7 xenografts treated with the antibody ch3B6 or with PBS. Western blot analysis of tumor protein extracts was performed using an anti-phospho-FGFR4 antibody (FGFR4 [phospho-Tyr642] antibody, Biorbyt), the anti-FGFR4 antibody BFG-2F7-B9, an anti-phospho-p44/42 MAPK (Erkl/2) (Thr202/Tyr204) antibody (Cell Signalling), an anti-p44/42 MAPK (Erkl/2) antibody (Cell Signalling), and an anti-GAPDH antibody (Sigma-Aldrich).

To further confirm the specificity of the observed antitumor activity, the antibody inhibitory effects on the phosphorylation of FGFR4 and of MAP kinase ERK1/2 (Extracellular Regulated Kinase 1 and 2) in treated tumors were evaluated. Protein extracts prepared from tumor samples collected from treated and control mice were analyzed by Western blot (FIG. 24).

The antibody ch3B6 was shown to significantly decrease, in tumors from treated mice, the FGFR4 and ERK1/2 phosphorylation levels measured in the control tumors.

Overall, the ex vivo experimental evidence indicates that the therapeutic treatment with the anti-FGFR4 chimeric antibodies modulated different components of the FGFR4 signalling in Huh7 tumors on which they have shown growth inhibition effects.

The receptor-mediated intracellular internalization of the antibodies was then evaluated in Huh7. Cells were treated for 1 hour at 4° C. with each of the three anti-FGFR4 chimeric antibodies or with the unrelated antibody 1H4 to promote binding to the cell surface receptor. Samples were collected at the end of the incubation (time 0), and then cells were transferred at 37° C. to foster the internalization of the antibody-receptor complexes and were collected at different times for FACS analysis performed as previously described. Results are summarized in Table 16.

TABLE 16

FGFR4-dependent internalization of the three chimeric antibodies in Huh7 cells. Cells were treated with the anti-FGFR4 antibodies or with the unrelated antibody 1H4 for 1h at 4° C. (time 0) and then incubated at 37° C. Samples were collected at the indicated time-points and subjected to FACS analysis. Data are expressed as percentage of the geometric mean fluorescence values measured at time 0.

| time @ 37° C. | % FGFR4 on cell surface | | | |
| --- | --- | --- | --- | --- |
| | 3B6 | 6C9 | 5B5 | 1H4 |
| 0' | 100.0 | 100.0 | 100.0 | 100.0 |
| 15' | 57.3 | 54.2 | 52.6 | 90.1 |
| 30' | 44.2 | 41.2 | 41.6 | 87.0 |
| 60' | 38.6 | 36.0 | 41.4 | 89.4 |

The analysis showed a time-dependent decrease of the membrane signal in the samples treated with the anti-FGFR4 antibodies, but not with the negative control antibody, thus suggesting a specific, receptor-mediated cell internalization.

Figure 25:
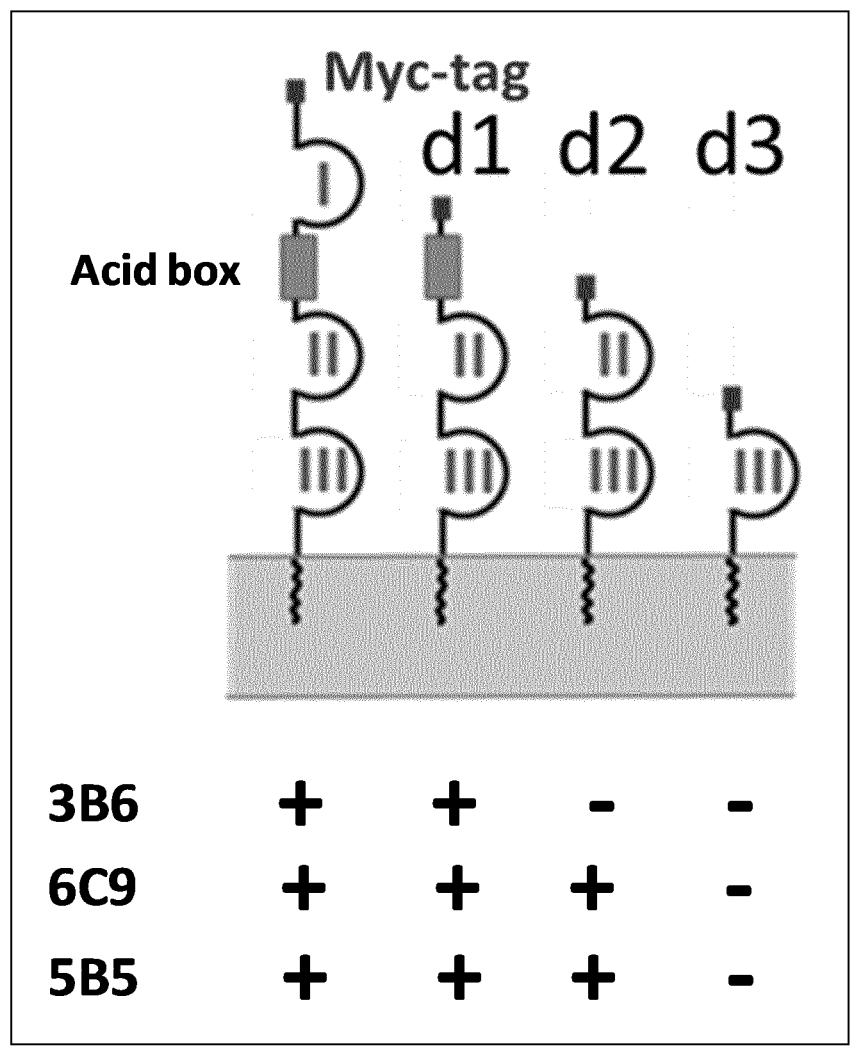
FIG. 25. Reactivity of the chimeric antibodies towards FL FGFR4 and the FGFR4 deletion mutants d I, d2 and d3, measured in BOSC23 reporter cells by FACS analysis. The assay was performed as described in the Example 8.

Next we proceeded with the identification of the antigen binding sites of the three antibodies within the FGFR4 extracellular region. To this aim, BOSC23 reporter cells ectopically expressing FL FGFR4 or the three FGFR4 deletion mutants (d I, d2, d3) described in detail in Example 8 were treated with each antibody and analyzed by FACS as previously described. Results are schematically reported in FIG. 25.

All three antibodies confirmed their reactivity on the full-length receptor and resulted positive also on the d I mutant, thus showing to not interact with the Ig I domain. The antibody ch3B6 completely lost positivity on the d2 mutant, thus showing a binding specificity for the acid box. The other two antibodies that retained reactivity towards the d2 mutant, resulted negative on d3, thus showing a binding specificity for the Ig II domain and, in the case of ch5B5, confirming the binding data obtained with the corresponding rat antibody.

The identification of the antigen binding sites was confirmed using the epitope mapping ELISA technology based on scanning with the antibodies of interest a library of overlapping synthetic peptides covering the complete target protein amino acid sequence.

To this aim, twenty three and twenty two 15-amino acid peptides, with a sequence overlapping of 11 amino acids, were synthesized based on the sequences of FGFR4 domains Ig I (aa 22-118) and Ig II (aa 157-241), respectively. Twenty six additional 15-amino acid peptides, with a sequence overlapping of 13 amino acids, were synthesized based on the sequence of the FGFR4 acid box domain (aa 119-156) (JPT Peptide Technologies). All peptides were conjugated at the N-terminus to biotin through a chemical spacer to allow binding to streptavidin-coated microplates. The binding specificity of the three chimeric antibodies was evaluated by ELISA, on the three peptide libraries corresponding to the Ig I, Ig II and acid box domains, including, as positive control, a chimeric anti-myc antibody (Absolute Antibody) and the corresponding synthetic biotinylated peptide epitope (JPT Peptide Technologies). Each well of streptavidin-coated high binding capacity 96-well white microplates (Pierce/Thermo Fisher Scientific) was washed three times with 200 uL of blocking buffer (PBS containing 0.1% BSA and 0.5% Tween-20). Then wells were coated with 100 uL of each peptide, suspended in blocking buffer at a concentration of 50 uM, for 2 h shaking at RT. After three washes with 200 uL of blocking buffer, 100 uL of each antibody diluted in blocking buffer at a concentration of 150 ug/mL were added and incubated for 1.5 h shaking at RT. After three washes with 200 uL of blocking buffer, 100 uL of a HRP-conjugated goat anti-human IgG, Fab specific secondary antibody (Sigma Aldrich) was added at a 1:10000 dilution in blocking buffer and incubated for 1 h shaking at RT. After four washes with 200 uL of blocking buffer, 100 uL of a chemiluminescent HRP substrate (SuperSignal ELISA Pico Chemiluminescent Substrate, Pierce/Thermo Fisher Scientific) were added and after 1 min, luminescence was measured using the microplate reader Multimode Detector DTX 880 (Beckman Coulter).

As expected from the FGFR4 deletion analysis, none of the chimeric antibodies showed a specific reactivity on peptides corresponding to the Ig I domain (not shown) and the antibodies ch6C9 and ch5B5 resulted negative also on peptides corresponding to the acid box. ch6C9 showed a low reactivity, distributed in multiple peaks on peptides corresponding to the Ig II domain, suggesting that it recognizes a discontinuous/conformational epitope in this region. On the contrary, ch5B5 showed a high and specific reactivity on three overlapping peptides within domain Ig II, thus defining a linear epitope of 23 amino acids (FIG. 26A).

Different from the other antibodies, ch3B6 showed a clear positivity on specific peptides corresponding to the acid box, thus confirming the FGFR4 deletion data. Although also in this case the reactivity was distributed within a discrete number of peaks, it was however possible to define for this antibody a discontinuous binding site within the acid box comprising amino acids between 127 and 154 (FIG. 26B). The alignment of the human FGFR4 protein sequence and the mouse orthologous sequence depicted in FIG. 26C shows that the residues that contribute to the binding within the experimentally identified ch3B6 epitope are conserved in the corresponding mouse sequence, thus supporting the observed cross-reactivity of the antibody for the murine receptor.

Example 11

Humanization of the Anti-FGFR4 Antibody ch3B6

Figure 27A:
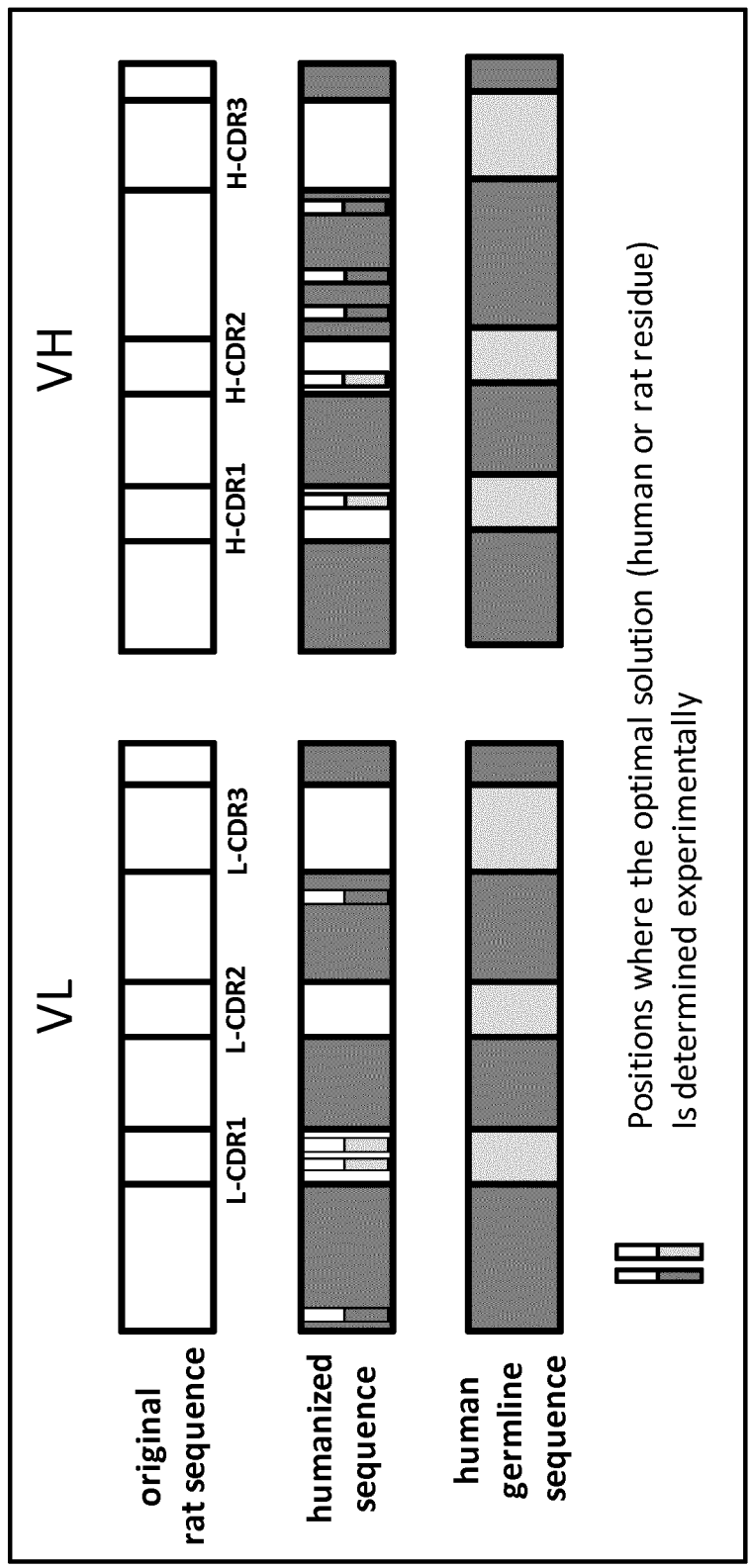
FIG. 27. Anti-FGFR4 antibody 3B6 humanization. (A) Scheme of the strategy of the humanization of 3B6. (B) 3D model of the selected human germline IgG. Germline residues substituted by the rat residues are indicated in the left panel, while positions where optimal solutions (human or rat amino acid) needed to be determined experimentally are indicated in the right panel.
Figure 27B:
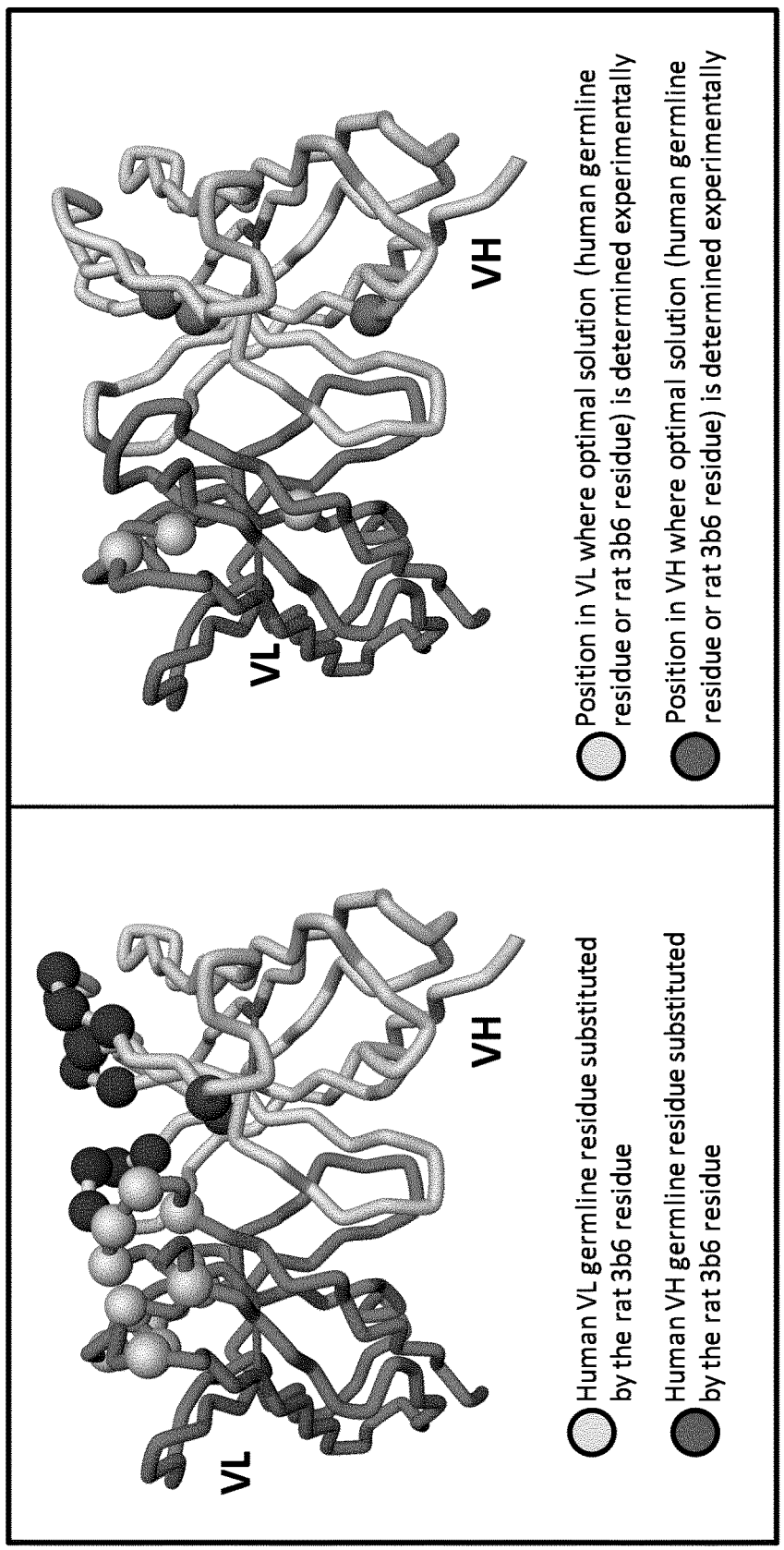

We then proceeded to the humanization of the antibody ch3B6 by grafting the original hybridoma rat CDR sequences into selected human immunoglobulin variable regions. To optimize the humanized variants, the human germline immunoglobulin variable sequences most similar to those of the original rat antibody 3B6 were identified and selected. Based on the homology with known immunoglobulin crystal structures, a 3D model of the selected human germline variable regions was generated both for the heavy chain variable region (VH), and for the light chain variable region (VL). Each amino acid position within the 3D model has been evaluated in order to decide which additional amino acid residues within the human frameworks needed to be substituted by the corresponding original murine residues, with particular attention for the amino acids potentially affecting the antigen binding or the VH/VL orientation. For few positions the theoretically optimal choice between human or rat amino acid was not trivial and had therefore to be tested experimentally. For this reason, slightly different versions of the humanized sequences were designed, three for VH and two for VL, respectively, whose combination produces six different antibodies. This process is schematized in FIG. 27.

In addition, we selected a known humanized anti-FGFR4 antibody (hI_DI.v22 Genentech, U.S. Pat. No. 9,266,955B2) to be included as benchmark in our experiments and the unrelated antibody Bezlotoxumab (Merck & Co) to be used as isotypic control. The amino acid sequences of the 3B6 humanized VH and VL variants are listed in Table 17.

TABLE 17

Humanized variable sequences, 3 variants for VH and 2 for VL, are shown. Amino acid changes relative to the original rat 3B6 sequence are indicated in bold, while changes relative to the human germline sequence selected for grafting are underlined. Table 17 discloses SEQ ID NOS 2-4 and 12-13, respectively, in order of appearance.

Variant Sequence
VH_3B6_um1
EVQLVESGGGLVQPGGSLRLSCAASGFTFSNYYMSVWRQAPGKGLEWVATINPSGTRTYYPDSVK
GRFTIS (SEQ ID N. 2)

RDNAKNSLYLQMNSLRAEDTAVYYCARm AFDYWGQGTLVTVSS

VH_3B6_um2
EVQLVESGGGLVQPGGSLRLSCAASGFTFSNYYMSWVRQAPGKGLEVWANIJ\LESGTRTYYPDSV
KGRFTIS (SEQ ID N. 3)

RDNAKNSLYLQMNSLRAEDTAVYYCARm AFDYWGQGTLVTVSS

TABLE 17-continued

Humanized variable sequences, 3 variants for VH and 2 for VL, are shown.
Amino acid changes relative to the original rat 3B6 sequence are
indicated in bold, while changes relative to the human germline sequence
selected for grafting are underlined. Table 17 discloses SEQ ID NOS 2-4
and 12-13, respectively, in order of appearance.

VH_3B6_um3
EVQLVESGGGLVQPGGSLRLSCAASGFTFSNYYMSWWRQAPGKGLEWWATIJ/U$^3$/$_4$GTRIYYPDSVK
GRFTIS (SEQ ID N. 4)

RDSAKSSLYLQMNSLRAEDTAVYYCARIJmNYAFDYWGQGTLVTVSS

Vk_3B6_umi
DIQMTQSPSSLSASVGDRVTITCRASESISTLLHWYQQKPGKAPKLLIYGTSNLESGVPSRFSGSGS
GTDF (SEQ ID N. 12)

TLTISSLQPEDFATYYCQQSWNDPPTFGGGTKVEIK

VK_3B6_um2
DIQMTQSPSSLSASVGDRVTITCRASESVSTIJIHWYQQKPGKAPKLLIYGTSNLESGVPSRFSGSGS
GTDF (SEQ ID N. 13)

TLTISSLQPEDFATYYCQQSWNDPPTFGGGTKVEIK

The DNA sequences encoding the five amino acid variants proposed for the antibody 3B6 were determined based on the nucleotide sequences of the human germline immunoglobulin variable regions selected for grafting and introducing, where necessary, codons for the rat amino acids. For the control antibodies, the DNA sequences were instead determined with the help of a codon optimization method available online (http://eu.idtdna.com/CodonOpt).

Figure 28A:
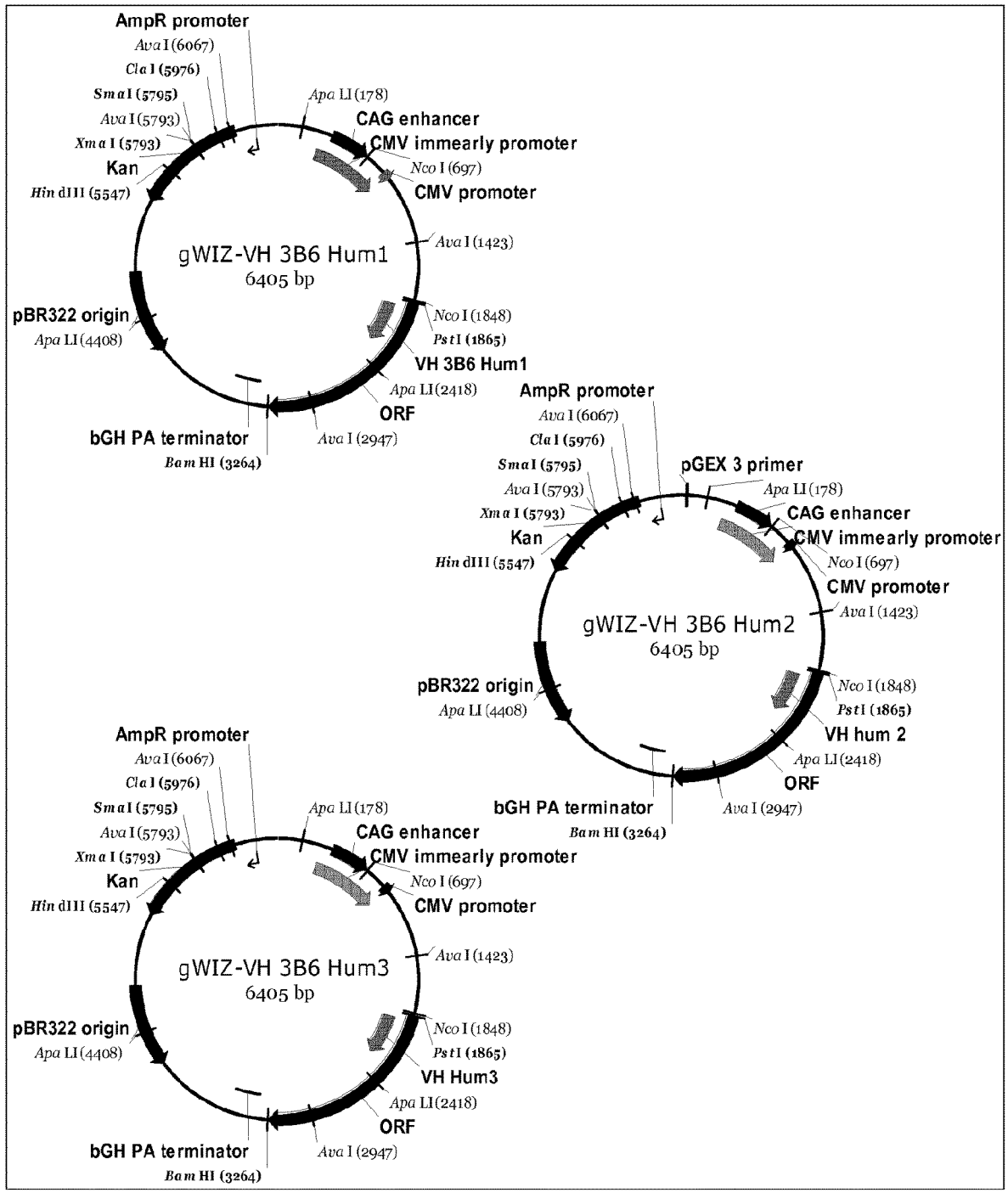
FIG. 28. Expression vectors encoding the 3B6 humanized heavy and light chain variants.
Figure 28B:
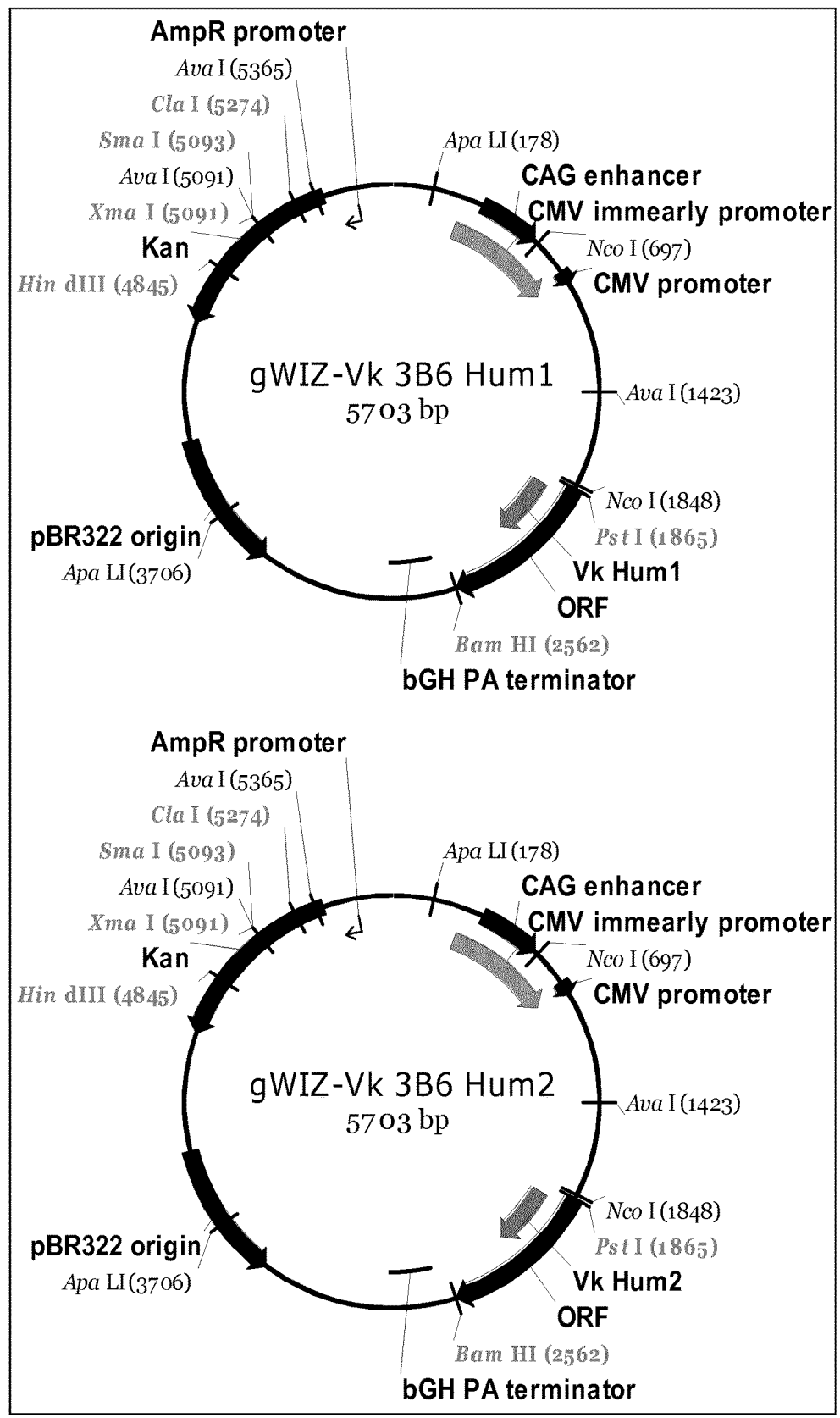

Synthetic DNA fragments for the five 3B6 variants and for the control antibodies were produced, bearing at the ends unique restriction enzyme recognition sites suitable for cloning each of these fragments into the ch3B6 heavy and light chain expression vectors (Example 10). Fully humanized expression vectors were generated by replacing the original rat VH coding sequence, in the expression vector gWiz-3B6-E4-GI, with each of the three humanized 3B6 VH coding sequences and by replacing the original rat VL coding sequence, in the expression vector gWiz-3B6-E4-k, with each of the two humanized 3B6 VL coding sequences (FIG. 28). An identical cloning strategy was used to generate the expression vectors encoding the heavy and light chains of the control antibodies. All DNA constructs were controlled by sequencing.

The expression vectors encoding the heavy and light chains of each of the six 3B6 humanized variants (Table 18) and of the positive and negative control antibodies were transiently co-transfected into the cell line 293F as well as the vectors expressing ch3B6 heavy and light chains.

TABLE 18

The VH and VL sequence combinations, as well as
the corresponding CDRH and CDRL sequence
combinations generating the six humanized antibody variants
are listed . Numbers correspond to the SEQ. ID numbers.

VH VL CDRH 1 CDRH2 CDRH3 CDRL1 CDRL2 CDRL3
Hu3B6a 2 12 6 7 9 15 16 17
Hu3B6b 3 12 6 8 9 15 16 17
Hu3B6c 4 12 6 7 9 15 16 17
Hu3B6d 2 13 6 7 9 14 16 17
Hu3B6e 3 13 6 8 9 14 16 17
Hu3B6f 4 13 6 7 9 14 16 17

Figure 29:
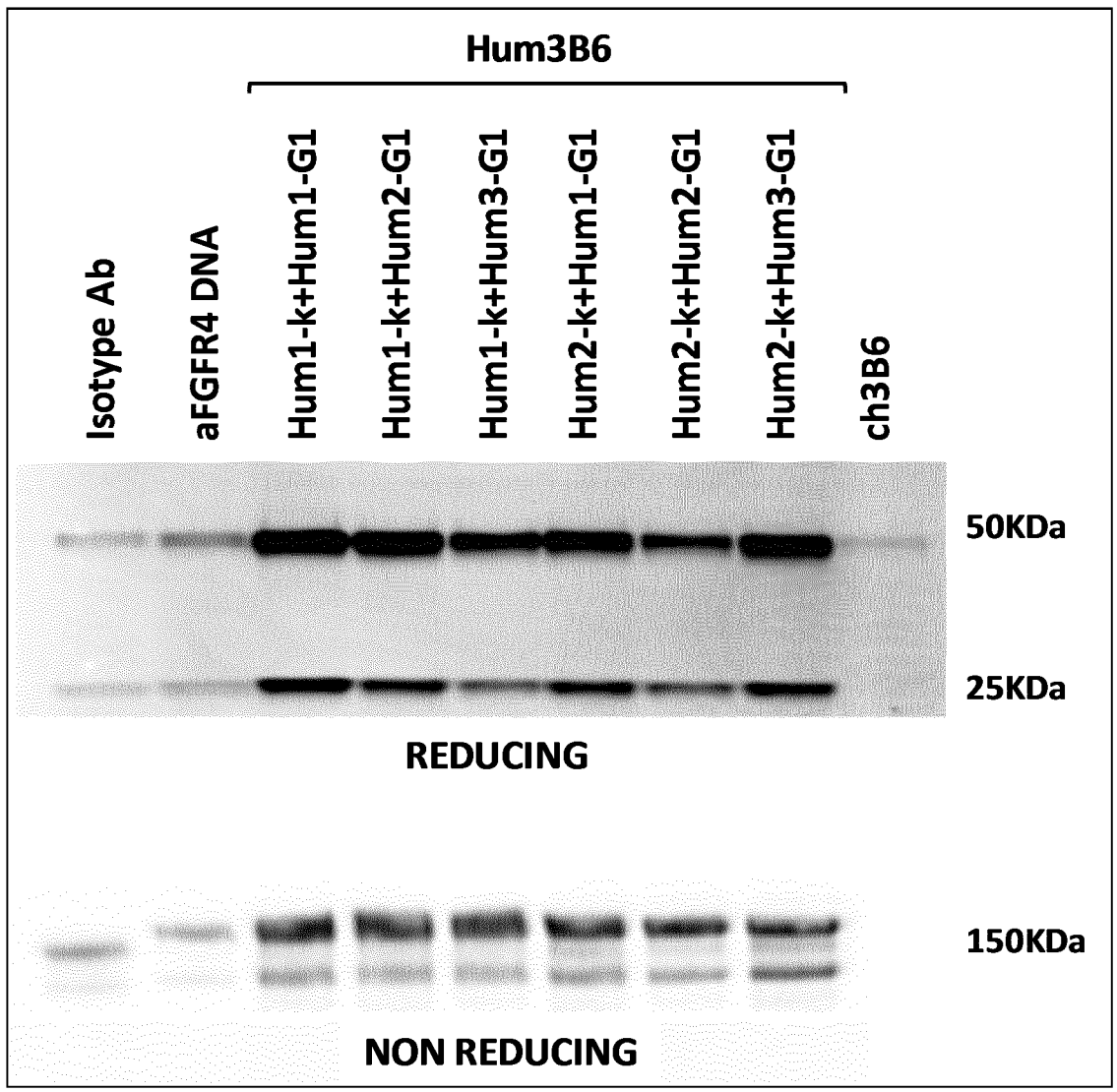
FIG. 29. Western blot analysis under reducing (top) and non reducing (bottom) conditions of the supernatants of 293F cell transfected with the indicated expression vectors.

Western blot analysis of the cell supernatants showed that all different 3B6 humanized variants were expressed at higher levels than the chimeric 3B6 antibody (FIG. 29).

Example 12

Characterization of the Six 3B6 Humanized Variants

The six 3B6 humanized variants listed in Table 18 were evaluated in dose-response experiments for their ability of inhibiting the binding of FGF19 to the immobilized receptor in the previously described solid phase assay performed as in the Example 8.

Immobilized FGFR4-Fc was pre-incubated with increasing concentrations of each antibody prior of the addition of FGF19 and heparin. The chimeric ch3B6 antibody and the hI_DI.v22 antibody described in the example 11 were included as positive controls, while the unrelated antibody Bezlotoxumab was used as isotype control.

Figure 30:
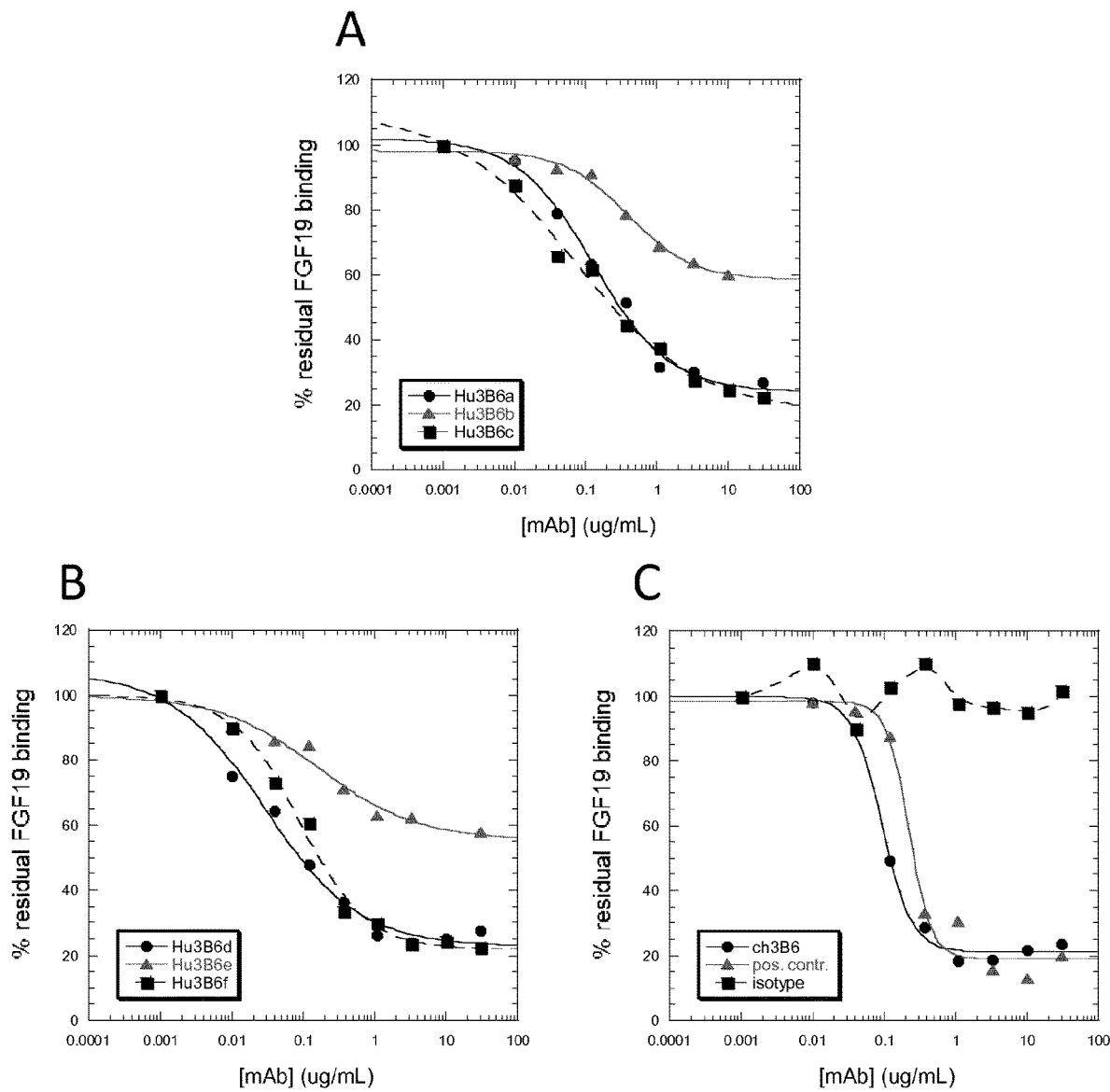
FIG. 30. Dose-response curves of the residual binding of FGF19 to FGFR4 as a function of the concentration of the six humanized 3B6 variants, derived from the absorbance values at 450 nm obtained from a solid phase FGF19-FGFR4 binding assay (n=3). Inhibition curves were derived by 4P logistic fitting of the experimental data with the KaleidaGraph software, based on the residual absorbance at 450 nm (% of PBS control) at increasing antibody concentrations (1:3 serial dilutions from 0.01 to 30 ug/mL). (A) From the corresponding inhibition curves, IC values of 0.13 ug/mL (0.87 nM), 0.4 ug/mL (2.7 nM), and 0.07 ug/mL (0.47 nM) were inferred for Hu3B6a, Hu3B6b, and Hu3B6c, respectively. (B) From the corresponding inhibition curves, $IC_t$ values of 0.03 ug/mL (0.2 nM), 0.16 ug/mL (1 nM), and 0.09 ug/mL (0.6 nM) were inferred for Hu3B6d, Hu3B6e, and Hu3B6f, respectively. (C) From the corresponding inhibition curves, IC values of 0.09 ug/mL (0.6 nM) and 0.2 ug/mL (1.3 nM) were inferred for ch3B6 and the positive control antibody hI_DI.v22, respectively. No inhibition curve was obtained with the isotype control.

As shown in FIG. 30, all tested antibodies, with the exception of the isotype control, caused a clear dose-dependent inhibition of the FGF19-FGFR4 binding with $IC_{50}$ values in the sub/low nM range, very similar to those calculated for ch3B6 and the positive control antibody.

Example 13

Comparative Analysis of ch3B6 and the Commercial Antibody Ab41948

A rabbit polyclonal antibody, ab41948, commercialized by Abcam, was raised against a synthetic peptide of undisclosed sequence derived from within residues 100-200 of human FGFR4, according to the online available datasheet. This antibody is described as specifically reacting with the human receptor and to be suitable for WB, ICC/IF and IHC applications. Based on the available data, different from ch3B6, ab41948 does not cross-react with the murine receptor.

To assess whether ab41948 shares any biological property with ch3B6, we performed a comparative analysis of the two antibodies.

First we controlled that the commercial antibody ab41948 could bind to the hFGFR4-Fc recombinant protein in our solid phase receptor binding assay. The assay was performed essentially as described in the Example 10. After incubation with increasing antibody concentrations, a Goat Anti-Rabbit IgG (HL)-HRP Conjugate secondary antibody (Pierce) was used for detection at a 1:2000 dilution.

Figure 31:
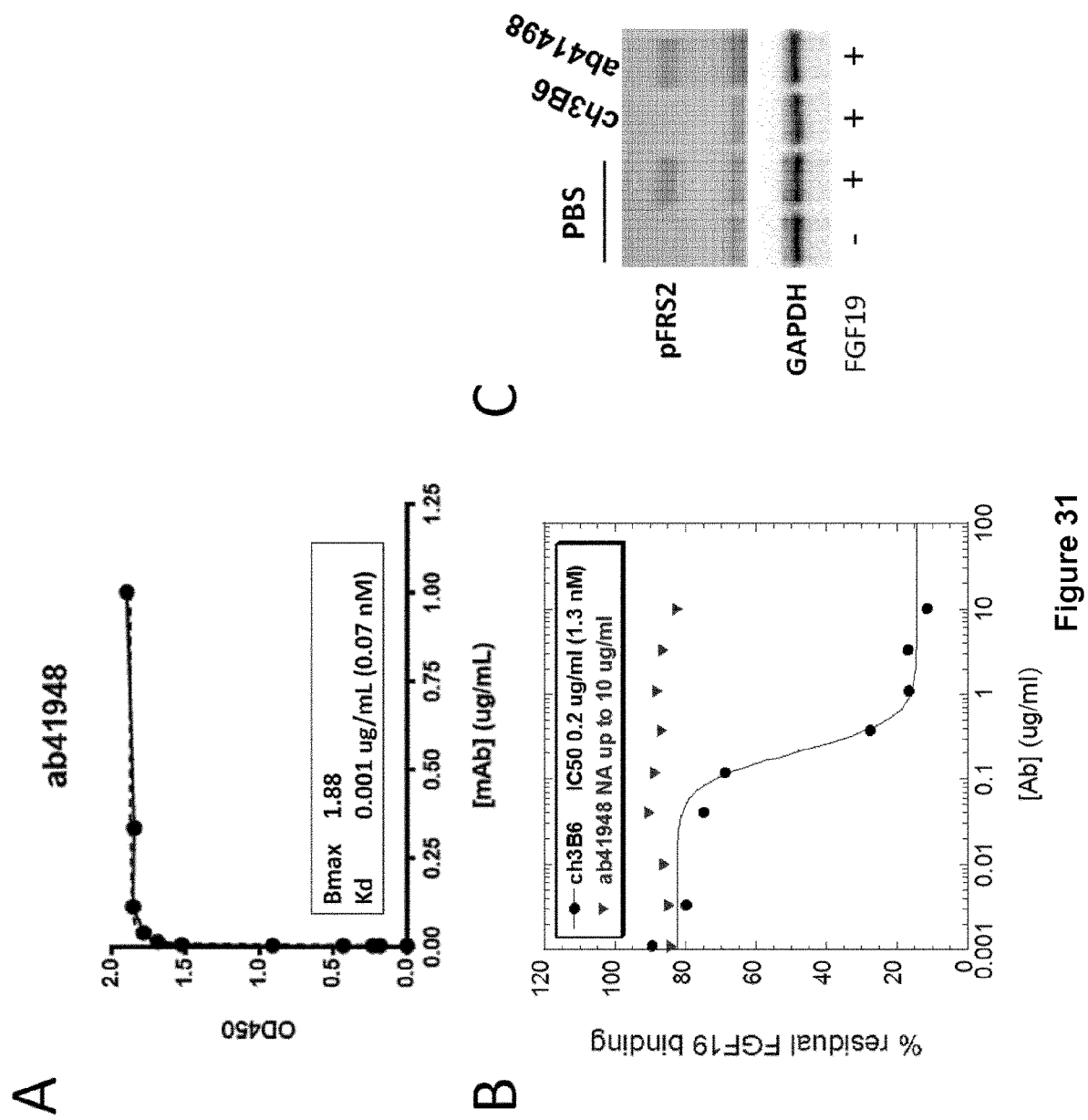
FIG. 31. Comparative analysis of ch3B6 and the commercially available antibody ab41948. (A) Graph of the absorbance values at 450 nm obtained from a FGFR4-Fc-dependent solid phase binding assay, as a function of the concentration of ab41948. Serial 1:3 dilutions (10 experimental points from 0.00005 ug/mL to 1 ug/mL) were tested in triplicate on the extracellular regions of FGFR4 fused with human Fc. The continuous line is the experimental one while the dashed line is that obtained by fitting experimental data to the "one site binding" equation. (B) Dose-response curves of the residual binding of FGF19 to FGFR4 as a function of the concentration of ch3B6 and ab41948, derived from the absorbance values at 450 nm obtained from a solid phase FGF19-FGFR4 binding assay (n=3). Inhibition curves were derived by 4P logistic fitting of the experimental data with the KaleidaGraph software, based on the residual absorbance at 450 nm (% of PBS control) at increasing antibody concentrations (1:3 serial dilutions from 0.001 to 10 ug/mL). (C) Inhibition of FGF19-dependent FRS2 phosphorylation in Huh7 cells treated with ch3B6 or ab41948 analyzed by Western Blot. Cells were treated with 100 ug/mL of each antibody or with PBS prior of the addition of FGF19/heparin under the experimental conditions described in the Example 8. Western blot analysis was performed using an anti-phospho-FRS2 antibody (Tyr-436, Cell Signalling) and an anti-GAPDH antibody (Sigma-Aldrich).

As shown by the representative dose-response binding curve in FIG. 31a, ab41948 could efficiently bind to the receptor with subnanomolar affinity.

Next we assessed the capability of ab41948 of preventing/competing the binding of FGF19 to FGFR4-Fc in the solid phase assay performed as in the Example 8 by adding, after the incubation with increasing antibody concentrations, FGF19/heparin at the equimolar concentration of 23 nM. ch3B6 was retested in parallel as a positive control.

Representative dose-response inhibition curves are shown in FIG. 31b. While ch3B6 confirmed to efficiently inhibit FGF19 binding to the receptor with an IC50 value of 0.2 ug/mL (1.3 nM), ab41948 resulted completely inactive.

Finally, the ab41948 antibody was evaluated, alongside with ch3B6, for its ability of interfering with the FGFR4 signalling pathway activation in the sensitive HCC cell line Huh7. To this aim, the inhibitory effect on the phosphorylation of the downstream effector protein FRS2 induced by cell treatment with FGF19 was analyzed by Western blot (FIG. 31c).

Contrary to ch3B6, ab41948 resulted unable to inhibit FGF19-induced FRS2 phosphorylation in Huh7 cells.

In conclusion, based on the lack of biological activity shown by the ab41948 antibody in key functional assays, it can be concluded that the two antibodies do not bind to the same epitope within the FGFR4 Acid Box region.

Example 14 ch3B6 Anti-Tumor Activity on Colon CSC-Derived Xenograft Models

We assayed the effect of the antibody ch3B6 on subcutaneous tumors generated by injection of colon CSCs in immunodeficient mice.

CTSC85 cells were resuspended in cold PBS and the suspension mixed with an equal volume of cold Matrigel (Becton Dickinson) at a final cell concentration of $5 \times 10^6$ cells/mL Twenty six NOD/SCID mice (Charles River) were injected subcutaneously with 0.2 mL of the cell/Matrigel suspension. Three weeks after the transplant, mice that showed measurable tumors were randomly assigned to two treatment groups (n=9), namely the anti-FGFR4 antibody ch3B6 and the vehicle control groups, with mean tumor volumes of 65 mm³ in each group.

Mice were treated via IP injection with 25 mg/Kg of ch3B6 antibody in PBS, administered twice a week for two weeks. The control group received corresponding volumes of blank injection (PBS). Mice weight was controlled twice a week and tumor size (major and minor axis) was measured with a vernier caliper twice a week. Tumor volumes were calculated using the formula: TV (mm3)=d2×D/2 where d and D refer to the shortest and the longest diameter, respectively.

Figure 32:
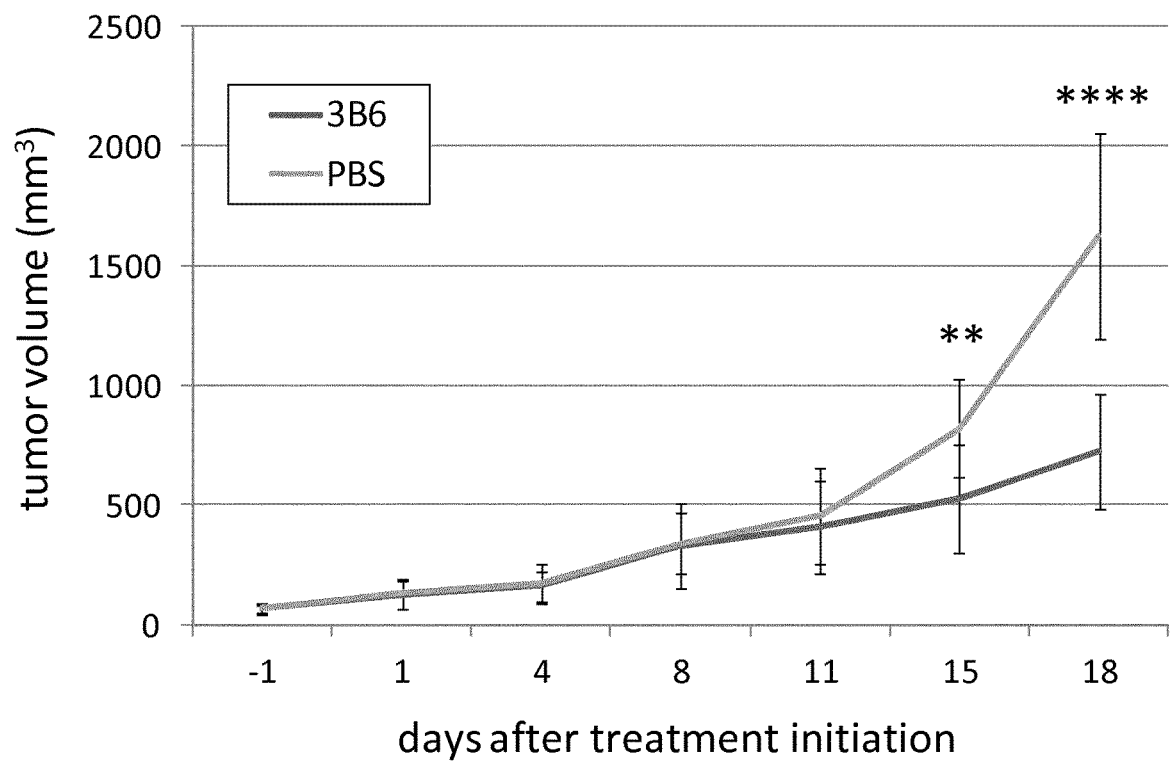
FIG. 32. Anti-tumor effects by the ch3B6 antibody on xenografts of colon CTSC85. In the upper panel, curves represent the increase of the mean tumor volumes±StDev during the treatment; in the lower panel, the increment of the mean tumor volumes relative to day −1 is shown ±StDev. () p<0.01; (*) p<0.005; (****) p<0.0005 with respect to the vehicle control.
Figure 32:
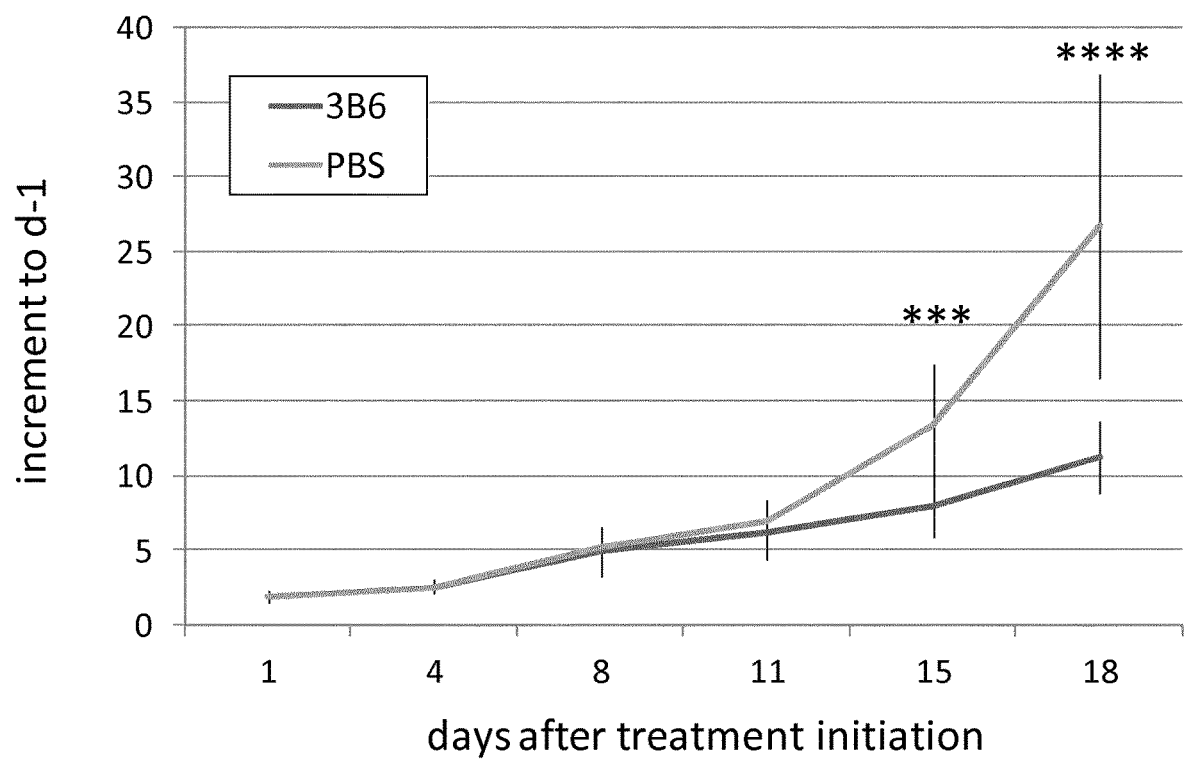

Compared to vehicle-treated controls, ch3B6 significantly reduced the growth rate of the tumors (FIG. 32). Body weight loss or clinical adverse effects were not observed during the treatment.

Example 15 ch3B6 and ch6C9 Anti-Tumor Activity on Colon CSC-Derived Hepatic Metastasis Model We assayed the effect of the antibodies ch3B6 and ch6C9 on hepatic metastasis generated by injection of colon CSCs in the liver of immunodeficient mice.

To this aim a reporter CTSC85 LUC-GFP cell line was used. CTSC85 LUC-GFP cells were generated by lentiviral infection using the pRRLsin-cPPT-hCMV-hPGK-GFP-Wpre vector (Ricci-Vitiani et al., 2004). The Luciferase cDNA was cloned into the GFP lentiviral vector (Ricci-Vitiani et al., 2004). Lentiviral particles were produced by the calcium phosphate transfection protocol in the packaging human embryonic kidney cell line 293T as previously described (Ricci-Vitiani et al., 2004). Viral supernatants were collected 48 h post-transfection, filtered through a 0.45μm pore size filter and added to cells in the presence of 8 μg/ml polybrene. Cells were centrifuged for 30 minutes at 1800 rpm. After infection, the fluorescence of transduced cells was evaluated by FACSCanto (Becton Dickinson).

CTSC85 LUC-GFP cells were resuspended in cold PBS and the suspension mixed with an equal volume of cold Matrigel (Becton Dickinson) at a final cell concentration of $1.25 \times 10^7$ cells/mL 20 uL of the cell/Matrigel suspension (250000 cells) were injected into the hepatic parenchyma of each of thirty NOD/SCID mice (Charles River). Tumor growth was monitored by bioluminescence imaging of luciferase-labeled cancer cells using an IVIS Spectrum imager (PerkinElmer). Ten days after the transplant, mice were randomly assigned to three groups (n=7), namely the ch3B6, the ch6C9 and the control groups with similar mean photons/second values in all groups. Mice were treated via IP injection with 25 mg/Kg of each antibody in PBS administered twice a week for four weeks. The control group received corresponding volumes of blank injection (PBS). Mice body weight and tumor growth were measured once a week. Treated mice were maintained up to 2 weeks without any further treatment, except for measurement of tumor signal and body weight, then sacrificed by cervical dislocation.

Figure 33:
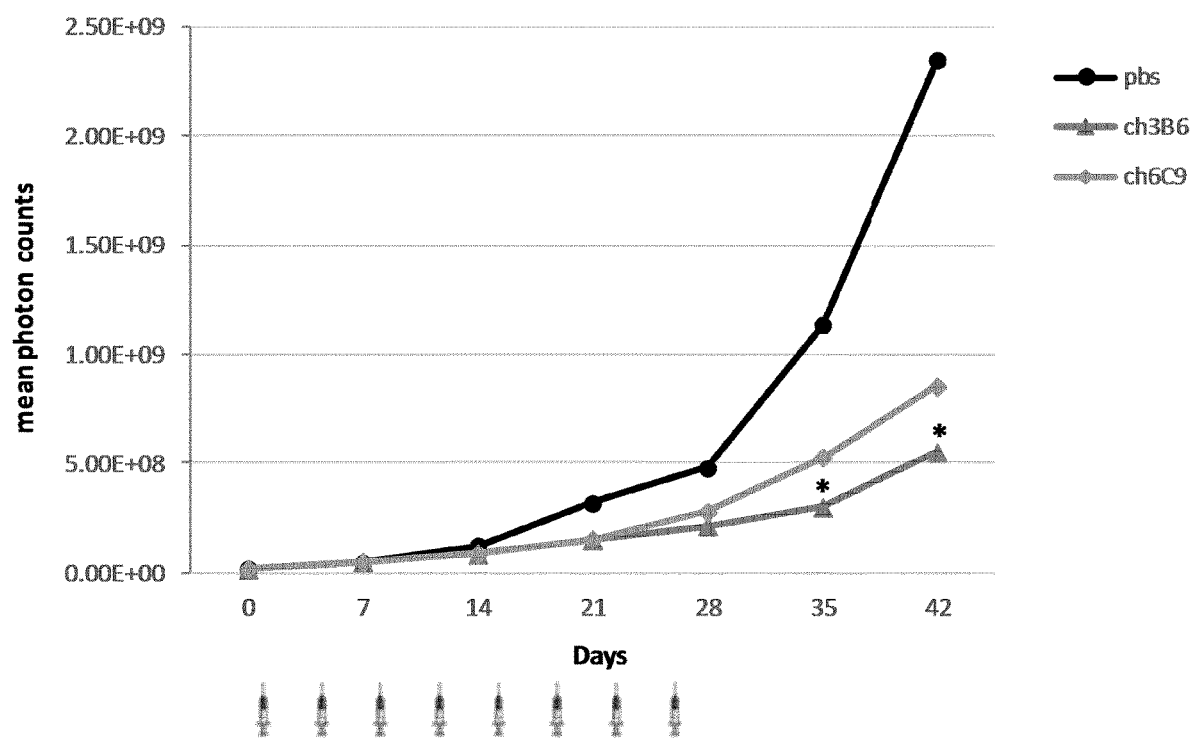
FIG. 33. Anti-tumor effects by the ch3B6 and the ch6C9 antibodies on colon CTSC85-derived hepatic metastasis. Curves represent the increase of the mean photon counts

Compared to vehicle-treated controls, both ch3B6 and ch6C9 were able to reduce the growth rate of the tumors (FIG. 33). In particular, the anti-tumor effect shown by ch3B6 reached statistical significance.

Body weight loss or clinical adverse effects were not observed during the treatment.

REFERENCES

Abbass S A, Asa S L, Ezzat S. (1997) Altered expression of fibroblast growth factor receptors in human pituitary adenomas. J Clin Endocrinol Metall 82, 1160-1166

Al-Hajj M, Wicha M S, Benito-Hernandez A, Morrison S J, Clarke M F. (2003) Prospective identification of tumorigenic breast cancer cells. Proc. Natl. Acad. Sci. USA. 100, 3983-3988

American Cancer Society: Colorectal Cancer Facts and Figures: 2017-2019. http://www.cancer.org/Research/Cancer-Facts-statistics/Colorectal-CancerFactsFigures/colorectal-cancer-facts-figures-2017-2019

Andre F, Cortes J. (2015) Rationale for targeting fibroblast growth factor receptor signalling in breast cancer. Breast Cancer Res Treat, 150, 1-8

Arnold M, Sierra M S, Laversanne M, Soerjomataram I, Jemal A, Bray F. (2017) Global patterns and trends in colorectal cancer incidence and mortality. Gut 66, 683-691

Baiocchi M, Biffoni M, Ricci-Vitiani L, Pilozzi E, De Maria R. (2010) New models for cancer research: human cancer stem cell xenografts. Curr Opin Pharmacol. 10, 380-384.

Bao S, Wu Q, McLendon R E, Hao Y, Shi Q, Hjelmeland A B, Dewhirst M W, Bigner D D, Rich J N. (2006) Glioma stem cells promote radioresistance by preferential activation of the DNA damage response. Nature AAA, 756-760

Barker N, van Es J H, Kuipers J, Kujala P, van den Born M, Cozijnsen M, Haegebarth A, Korving J, Begthel H, Peters P J, Clevers H. (2007) Identification of stem cells in small intestine and colon by marker gene Lgr5. Nature 449, 1003-1007

Bartz R, Fukuchi K, Lange T, Gruner K, Ohtsuka T, Watanabe I, Hayashi S, Redondo-Muller M, Takahashi M, Agatsuma T, Bange J, Abraham R. (2016) Abstract 3852; U3-1784, a human anti-FGFR4 antibody for the treatment of cancer. In: Proceedings of the 107th Annual Meeting of the American Association for Cancer Research; 2016 Apr. 16-20: New Orleans, La. Philadelphia (Pa.): AACR; Cancer Res 2016: 76(14 Suppl): Abstract nr 3852

Beenken A, Mohammadi M. (2009) The FGF family: biology, pathophysiology and therapy. Nat Rev Drug Discov. 8, 235-253

Bonnet D, Dick J E (1997) Human acute myeloid leukemia is organized as a hierarchy that originates from a primitive hematopoietic cell. Nature Med. 3, 730-737

Brittan M, Wright N A. (2004). The gastrointestinal stem cell, Cell Prolif. 37, 35-53 • Bruix J, Sherman M. (2005) Management of hepatocellular carcinoma. Hepatology 42, 1208-1236

Bumbaca D, Wong A, Drake E, Arthur E. Reyes II AE, Lin B C, Stephan J-P, Desnoyers L, Ben-Quan Shen B-Q, Dennis M S. (2011) Highly specific off-target binding identified and eliminated during the humanization of an antibody against FGF receptor 4. mAbs 3, 376-386

Chen C, Wang G. (2015) Mechanisms of hepatocellular arcinoma and challenges and opportunities for molecular targeted therapy. World J Hepatol. 7, 1964-1970

Chen H, Shen D P, Zhang Z-Z, Liu J-H, Shen Y-Y, Ni X-Z, (2015) Fibroblast growth factor receptor 4 protein expression and clinicopathological features in gastric cancer. World J Gastroenterol, 21, 1838-1844

Chiang J Y. (2009) Bile acids: regulation of synthesis. J Lipid Res. 50, 1955-1966 Cho S H, Hong C S, Kim H N, Shin M H, Kim K R, Shim H J, Hwang J E, Bae W K, Chung IJ. (2016) FGFR4 Arg388 is Correlated with Poor Survival in Resected Colon Cancer Promoting Epithelial to Mesenchymal Transition. Cancer Res Treat. November 9 doi: 10.4143/crt.2016.457.

Crose L E, Etheridge K T, Chen C, Belyea B, Talbot L J, Bentley R C, Linardic C M. (2012) FGFR4 blockade exerts distinct antitumorigenic effects in human embryonal versus alveolar rhabdomyosarcoma. Olin Cancer Res. 18, 3780-3790

Dalerba P, Dylla S J, Park 1K, Liu R, Wang X, Cho R W, Hoey T, Gurney A, Huang E H, Simeone D M, Shelton A A, Parmiani G, Castelli C, Clarke M F. (2007) Phenotypic characterization of human colorectal cancer stem cells. Proc. Natl. Acad. Sci. USA 104, 10158-10163

Desnoyers L R, Pai R, Ferrando R E, Hotzel K, Le T, Ross J, Carano R, D'Souza A, Qing J, Mohtashemi I, Ashkenazi A, French D M (2008) Targeting FGF19 inhibits tumor growth in colon cancer xenograft and FGF19 transgenic hepatocellular carcinoma models. Oncogene 27, 85-97

Diehn M, Cho R W. Lobo N A, Kalisky T, Dorie M J, Kulp A N, Qian D, Lam J S, Allies L E, Wong M, Joshua B, Kaplan M J, Wapnir I, Dirbas F M, Somlo G, Garberoglio C, Paz B, Shen J, Lau S K, Quake S R, Brown J M, Weissman I L, Clarke M F. (2009) Association of reactive oxygen species levels and radioresistance in cancer stem cells. Nature 458, 780-783

Dienstmann R, Rodon J, Prat A, Perez-Garcia J, Adamo B, Felip E, Cortes J, Iafrate AJ, Nuciforo P, Tabernero J. (2014) Genomic aberrations in the FGFR pathway: opportunities for targeted therapies in solid tumors. Ann Oncol. 25, 552-563

El-Serag H B, Rudolph K L. (2007) Hepatocellular carcinoma: epidemiology and molecular carcinogenesis. Gastroenterology 132, 2557-2576

Enguita-German M, Fortes P. (2014) Targeting the insulin-like growth factor pathway in hepatocellular carcinoma. World J Hepatol, 6, 716-737

Ferlay J., Soerjomataram I, Dikshit R, Eser S, Mathers C, Rebelo M, Parkin D M, Forman D, Bray F. (2015) Cancer incidence and mortality worldwide: Sources, methods and major patterns in GLOBOCAN. Int. J. Cancer. 136, E359-E386

Feng S, Shao L, Yu W, Gavine P, Ittmann M. (2012) Targeting fibroblast growth factor receptor signalling inhibits prostate cancer progression. Clin Cancer Res. 18, 3880-3888.

Fong Y, Kemeny N, Lawrence T. Cancer of the Liver and Biliary Tree. (2001) In: DeVita V, Hellman S, Rosenberg S, editors. Cancer: Principles & Practice of Oncology, pp. 1162-1199. Lippincott, Williams & Wilkins French D M, Lin B C, Wang M, Adams C, Shek T, Hotzel K, Bolon B, Ferrando R, Blackmore C, Schroeder K, Rodriguez L A, Hristopoulos M, Venook R, Ashkenazi A, Desnoyers L R. (2012) Targeting FGFR4 inhibits hepatocellular carcinoma in preclinical mouse models. PLoS One. 7:e36713

Frullanti E, Berking C, Harbeck N, Jezequel P, Haugen A, Mawrin C, Parise O Jr, Sasaki H, Tsuchiya N, Dragani T A. (2011) Meta and pooled analyses of FGFR4 Gly388Arg polymorphism as a cancer prognostic factor. Eur J Cancer Prev. 20, 340-347.

Goetz R, Mohammadi M. (2013) Exploring mechanisms of FGF signalling through the lens of structural biology. Nat Rev Mol Cell Biol. 14, 166-180

Gregorieff A, Clevers H. (2005) Wnt signalling in the intestinal epithelium: from endoderm to cancer. Genes Dev. 19, 877-890

Hagel M, Miduturu C, Sheets M, Rubin N, Weng W, Stransky N, Bifulco N, Kim J L, Hodous B, Brooijmans N, Shutes A, Winter C, Lengauer C, Kohl N E, Guzi T. (2015) First Selective Small Molecule Inhibitor of FGFR4 for the Treatment of Hepatocellular Carcinomas with an Activated FGFR4 Signalling Pathway. Cancer Discov. 5, 424-437

Hierro C, Rodon J, Tabernero J. (2015) Fibroblast Growth Factor (FGF) Receptor/FGF Inhibitors: Novel Targets and Strategies for Optimization of Response of Solid Tumors. Semin Oncol. 42, 801-819

Ho H K, Pok S, Streit S, Ruhe J E, Hart S, Lim K S, Loo H L, Aung M O, Lim S G, Ullrich A. (2009) Fibroblast growth factor receptor 4 regulates proliferation, anti-apoptosis and alpha-fetoprotein secretion during hepatocellular carcinoma progression and represents a potential target for therapeutic intervention. J Hepatol. 50, 118-127

Hoofnagle J R (2004) Hepatocellular carcinoma: summary and recommendations. Gastroenterology 127, S319-S323

Hopfner M, Schuppan D, Scherubl H. (2008) Growth factor receptors and related signalling pathways as targets for novel treatment strategies of hepatocellular cancer. World J Gastroenterol. 14, 1-14

Huang E H, Hynes M J, Zhang T, Ginestier C, Dontu G, Appelman H, Fields J Z, Wicha M S, Boman B M. (2009) Colon cancer stem cells hydrogenase 1 is a marker for normal and malignant human colonic stem cells (SC) and tracks SC overpopulation during colon tumorigenesis. Cancer Res. 69, 3382-3389

Huang H P, Feng H I, Qiao H B1, Ren Z X1, Zhu G D I. (2015) The prognostic significance of fibroblast growth factor receptor 4 in non-small-cell lung cancer. Onco Targets Ther. 8, 1157-1164.

Igawa T, Tsunoda H, Kuramochi T, Sampei Z, Ishii S, Hattori K. MAbs. 2011 May-June; 3(3): 243-52. Engineering the variable region of therapeutic IgG antibodies.

Inagaki T, Choi M, Moschetta A, Peng L, Cummins C L, McDonald J G, Luo G, Jones, S A, Goodwin B, Richardson J A, et al. (2005). Fibroblast growth factor 15 functions as an enterohepatic signal to regulate bile acid homeostasis. Cell Metab. 2, 217-225

Ito S, Fujimori T, Furuya A, Satoh J, and Nabeshima Y. (2005) Impaired negative feedback suppression of bile acid synthesis in mice lacking betaKlotho. J. Clin. Invest. 115, 2202-2208

Kalinina J, Dutta K, Ilghari D, Beenken A, Goetz R, Eliseenkova A V, Cowburn D, Mohammadi M. (2012) The alternatively spliced acid box region plays a key role in FGF receptor autoinhibition. Structure 20, 77-88

Kan M, Wu X, Wang F, McKeehan W L. (1999) Specificity for Fibroblast Growth Factors Determined by Heparan Sulfate in a Binary Complex with the Receptor Kinase. J. Biol Chem. 274, 15947-15952

Katoh M, Nakagama H (2014). FGF receptors: cancer biology and therapeutics. Med Res Rev. 34, 280-300

Lapidot T, C. Sirard C, Vormoor J, Murdoch B, Hoang T, Caceres-Cortes J, Minden M, Paterson B, Caligiuri M A, Dick J E, (1994) A cell initiating human acute myeloid leukaemia after transplantation into SCID mice. Nature 367, 645-648

Li C S, Zhang S X, Liu H J, Shi Y L, Li L P, Guo X B, Zhang Z H, (2014) Fibroblast growth factor receptor 4 as a potential prognostic and therapeutic marker in colorectal cancer. Biomarkers 19, 81-85

Lin B C, Wang M, Blackmore C, Desnoyers L R. (2007) Liver-specific activities of FGF19 require Klotho beta. J Biol Chem 282: 27277-27284

Lin B C, Desnoyers L R. (2012) FGF19 and cancer. Adv Exp Med Biol. 728, 183-194 • Liu R, Li J, Xie K, Zhang T, Lei Y, Chen Y, Zhang L, Huang K, Wang K, WU H, Wu M, Nice E C, Huang C, Wei Y. (2013) FGFR4 promotes stroma-induced epithelial-to-mesenchymal transition in colorectal cancer. Cancer Res. 73, 5926-5935

Llovet J M, Villanueva A, Lachenmayer A, et al. Advances in targeted therapies for hepatocellular carcinoma in the genomic era (2015) Nat Rev Olin Oncol. 12: 408-424 • Maugeri-Sacca M, Vigneri P, De Maria R. (2011) Cancer Stem Cells and Chemosensitivity. Clin Cancer Res. 17:4942-4947

Olsen S K, Ibrahimi O A, Raucci A, Zhang F, Eliseenkova A V, Yayon A, Basilica J, Robert J. Linhardt R J, Schlessinger J, and Moosa Mohammadi M. (2004) Insights into the molecular basis for fibroblast growth factor receptor autoinhibition and ligand-binding promiscuity PNAS 101: 935-940

Onwuazor O N, Wen X Y, Wang D Y, Zhuang L, Masih-Khan E, Claudio J, Barlogie, B, Shaughnessy J D Jr, and Stewart A K (2003) Mutation, SNP, and isoform analysis of fibroblast growth factor receptor 3 (FGFR3) in 150 newly diagnosed multiple myeloma patients. Blood 102: 772-773.

Pai R, Dunlap D, Qing J, Mohtashemi I, Hotzel K, French D M. (2008) Inhibition of fibroblast growth factor 19 reduces tumor growth by modulating beta-catenin signalling. Cancer Res. 68: 5086-5095

Pai R, French D, Ma N, Hotzel K, Plise E, Salphati L, Setchell K D R, Ware J, Lauriault V, Schutt L, Hartley D, Dambach, D. (2012) Antibody-Mediated Inhibition of Fibroblast Growth Factor 19 Results in Increased Bile Acids Synthesis and Heal Malabsorption of Bile Adds in Cynomolgus Monkeys. Toxicol Sci 126: 446-456

Pelaez-Garcia A, Barderas R, Torres S, Hernandez-Varas P, Teixido J, Bonilla F, de Herreros A G, Casal J I. (2013) FGFR4 role in epithelial-mesenchymal transition and its therapeutic value in colorectal cancer. PLoS One. 8(5): e63695

Reya T, Morrison S J, Clarke M F, Weissman I L (2001) Stem cells, cancer, and cancer stem cells Nature 414, 105-111

Ricci-Vitiani L, Lombardi D G, Pilozzi E, Biffoni M, Todaro M, Peschle C, De Maria R (2007) Identification and expansion of human colon-cancer-initiating cells. Nature 445, 111-115

Ricci-Vitiani L, Pedini F, Mollinari C, Condorelli G, Bonci D, Bez A, Colombo A, Parati E, Peschle C, De Maria R. (2004) Absence of caspase 8 and high expression of PED protect primitive neural cells from cell death. J Exp Med. 200, 1257-1266.

Roidl A, Berger H J, Kumar S, Bange J, Knyazev P, Ullrich A. (2009) Resistance to chemotherapy is associated with fibroblast growth factor receptor 4 up-regulation. Clin Cancer Res. 15, 2058-2066

Roidl A, Foo P, Wong W, Mann C, Bechtold S, Berger H J, Streit S, Ruhe J E, Hart S, Ullrich A, Ho H K. (2010) The FGFR4 Y3670 mutant is a dominant oncogene in MDA-MB453 breast cancer cells. Oncogene 29, 1543-1552

Sahadevan K, Darby 5, Leung H Y, Mathers M E, Robson O N, Gnanapragasam V J. (2007) Selective over-expression of fibroblast growth factor receptors 1 and 4 in clinical prostate cancer. J Pathol. 213, 82-90

Shmelkov S V, Butler J M, Hooper A T, Hormigo A, Kushner J, Milde T, St Clair R, Baljevic M, White I, Jin D K, Chadburn A, Murphy A J, Valenzuela D M, Gale N W, Thurston G, Yancopoulos G D, D'Angelica M, Kemeny N, Lyden D, Rafii S. (2008) CD133 expression is not restricted to stem cells, and both CD133+ and CD133− metastatic colon cancer cells initiate tumors. J. Clin. Invest. 118, 2111-2120

Signore M, Buccarelli M, Pilozzi E, De Luca G, Cappellari M, Maurizio Fanciulli M, Frauke Goeman F, Melucci E, Biffoni M, Ricci-Vitiani L. (2016) UCN-01 enhances cytotoxicity of irinotecan in colorectal cancer stem-like cells by impairing DNA damage response. Oncotarget. 7, 44113-44128.

Singh S K, Clarke I D, Terasaki M, Bonn V E, Hawkins C, Squire J, Dirks P B. (2003) Identification of a cancer stem cell in human brain tumors Cancer Res. 63, 5821-5828

Spinola M, Leoni V P, Tanuma J, Pettinicchio A, Frattini M, Signoroni S, Agresti R, Giovanazzi R, Pilotti S, Bertario L, Ravagnani F, Dragani T A. (2005a) FGFR4 Gly388Arg polymorphism and prognosis of breast and colorectal cancer. Oncol Rep. 14, 415-419 • Spinola M, Leoni V, Pignatiello C, Conti B, Ravagnani F, Pastorino U, Dragani T A. (2005b) Functional FGFR4 Gly388Arg polymorphism predicts prognosis in lung adenocarcinoma patients. J Clin Oncol. 23, 7307-7311

Streit 3, Bange J, Fichtner A, Ihrler S, Issing Ullrich A. (2004) Involvement of the FGFR4 Arg388 allele in head and neck squamous cell carcinoma. Int J Cancer 111, 213-217

Taylor J G, Cheuk A T, Tsang P S, Chung J Y, Song Y K, Desai K, Yu Y, Chen Q R, Shah K, Youngblood V, Fang J, Kim S Y, Yeung C, Heiman L J, Mendoza A, Ngo V, Staudt L M, Wei J S, Khanna C, Catchpoole D, Qualman S J, Hewitt S M, Merlino G, Chanock S J, Khan J. (2009) Identification of FGFR4-activating mutations in human rhabdomyosarcomas that promote metastasis in xenotransplanted models. J Clin Invest. 119, 3395-3407

Thorgeirsson S S, Grisham J W. (2002) Molecular pathogenesis of human hepatocellular carcinoma. Nature Genet. 31, 339-346

Todaro M, Gaggianesi M, Catalano V, Benfante A, Iovino F, Biffoni M, Apuzzo T, Sperduti I, Volpe S, Cocorullo G, Gulotta G, Dieli F, De Maria R, Stassi G (2014) CD44v6 Is a Marker of Constitutive and Reprogrammed Cancer Stem Cells Driving Colon Cancer Metastasis. Cell Stem Cell 14, 342-356

Todaro M, Alea M P, Di Stefano A B, Cammareri P, Vermeulen L, Iovino F, Tripodo C, Russo A, Gulotta G, Medema J P, Stassi G. (2007) Colon cancer stem cells dictate tumor growth and resist cell death by production of interleukin-4. Cell Stem Cell. 1, 389-402

Trovato F M, Tognarelli J M, Crossey M M, Catalano D, Taylor-Robinson S D, Trovato G M. (2015) Challenges of liver cancer: Future emerging tools in imaging and urinary biomarkers. World J Hepatol. 7, 2664-2675

Turkington R C, Longley D B, Allen W L, Stevenson L, McLaughlin K, Dunne P D, Blayney J K, Salto-Tellez M, Van Schaeybroeck S, Johnston P G. (2014) Fibroblast growth factor receptor 4 (FGFR4): a targetable regulator of drug resistance in colorectal cancer. Cell Death Dis. 5:e1046

Uriarte I, Latasa M U, Carotti 3, Fernandez-Barrena M G, Garcia-Irigoyen O, Elizalde M, Urtasun R, Vespasiani-Gentilucci U, Morini S, de Mingo A, Mari M, Corrales F J, Prieto J, Berasain C, Avila M A. (2015) Ileal FGF15 contributes to fibrosis-associated hepatocellular carcinoma development. Int J Cancer. 136, 2469-2475

Valent P, Bonnet D, De Maria R, Lapidot T, Copland M, Melo J V, Chomienne C, Ishikawa F, Schuringa J J, Stassi G, Huntly B, Herrmann H, Soulier J, Roesch A, Schuurhuis G J, VVohrer S, Arock M, Zuber J, Cemy-Reiterer S, Johnsen H E, Andreeff M, Eaves C. (2012) Cancer stem cell definitions and terminology: the devil is in the details. Nat Rev Cancer. 12, 767-75 van der Flier L G, Haegebarth A, Stange D E, van de Wetering M, Clevers H. (2009) OLFM4 is a robust marker for stem cells in human intestine and marks a subset of colorectal cancer cells. Gastroenterology 137, 15-17

Worns M A, Galle P R. (2014) HCC therapies-lessons learned. Nat Rev Gastroenterol Hepatol. 11, 447-452

Wu X, Ge H, Lemon B, Vonderfecht S, Weiszmann J, Hecht R, Gupte J, Hager T, Wang Z, Lindberg R, Li Y. (2010) FGF19-induced hepatocyte proliferation is mediated through FGFR4 activation. J Biol Chem: 285, 5165-5170

Wu X, Li Y. (2012) Understanding the structure-function relationship between FGF19 and its mitogenic and metabolic activities. Adv Exp Med Biol. 728, 195-213

Xie, M. H Holcomb, I., Deuel, B., Dowd, P., Huang, A., Vagts, A., Foster, J., Liang, J., Brush, J., Gu, Q., et al, (1999) FGF-19, a novel fibroblast growth factor with unique specificity for FGFR4. Cytokine 11, 729-735

Xu B, Tong N, Chen S Q, Hua L X, Wang Z J, Zhang Z D, Chen M. (2011) FGFR4 Gly388Arg polymorphism contributes to prostate cancer development and progression: a meta-analysis of 2618 cases and 2305 controls. BMC Cancer February 24; 11: 84

Yang Y, Zhou Y, Lu M, An Y, Li R, Chen Y, Lu D R, Jin L, Zhou W P, Qian J, Wang H Y. (2012) Association between fibroblast growth factor receptor 4 polymorphisms and risk of hepatocellular carcinoma. Mol Carcinog. 51, 515-521.

Ye Y W, Hu S, Shi Y Q, Zhang X F, Zhou Y, Zhao C L, Wang G J, Wen J G, Zong H. (2013) Combination of the FGFR4 inhibitor PD173074 and 5-fluorouracil reduces proliferation and promotes apoptosis in gastric cancer. Oncol Rep. 30, 2777-2784

Yoshida K, Murata M, Yamaguchi T, Matsuzaki K. (2014) TGF-beta/Smad signalling during hepatic fibro-carcinogenesis. Int J Oncol. 45, 1363-1371

Yu C, Wang F, Kan M, Jin C, Jones R B, Weinstein M, Deng C X, McKeehan W L. (2000) Elevated cholesterol metabolism and bile acid synthesis in mice lacking membrane tyrosine kinase receptor FGFR4. J. Biol. Chem. 275, 15482-15489

Yu W Feng S, Dakhova O, Creighton C J, Cai Y, Wang J, Li R, Frolov A, Ayala G, Ittmann M. (2011) FGFR4 Arg$^{388}$ enhances prostate cancer progression via extracellular signal-related kinase and serum response factor signalling. Clin Cancer Res. 17, 4355-4366

Zaid T M, Yeung T L, Thompson M S, Leung C S, Harding T, Co N N, Schmandt R S, Kwan S Y, Rodriguez-Agway C, Lopez-Berestein G, Seed A K, Wong K K, Birrer M J, Mok S C. (2013) Identification of FGFR4 as a potential therapeutic target for advanced-stage, high-grade serous ovarian cancer. Clin Cancer Res. 19, 809-820

Zeuner A, Todaro M, Stassi G, De Maria, R. (2014) Colorectal cancer stem cells: From the crypt to the clinic. Cell Stem Cell 15, 692-705

Zhang X, Ibrahimi O A, SK, Umemori H, Mohammadi M, David M. Ornitz D M. (2006) Receptor Specificity of the Fibroblast Growth Factor Family. J. Biol. Chem. 281, 15694-15700.

Zhou S K, Schuetz J D, Bunting K D, Colapietro A-M, Sampath J, Morris J J, Lagutina I, Grosveld G C, Osawa M, Nakauchi H, Sorrentino B P. (2001) The ABC transporter Bcrpl/ABCG2 is expressed in a wide variety of stem cells and is a molecular determinant of the side-population phenotype. Nature Med. 7, 1028-1034.

The invention claimed is:

1. A monoclonal antibody, or antigen-binding fragment thereof, wherein the antibody binds to the human tyrosine kinase fibroblast growth factor receptor 4 (FGFR4) or precursor thereof, and the monoclonal antibody or antigen-binding fragment thereof comprises:
   (a) a heavy chain comprising:
      (i) a heavy chain CDR1 comprising the amino acid sequence of SEQ ID NO:5 or SEQ ID NO:6,
      (ii) a heavy chain CDR2 comprising the amino acid sequence of SEQ ID NO:7 or SEQ ID NO:8,
      (iii) a heavy chain CDR3 comprising the amino acid sequence of SEQ ID NO:9, and
   (b) a light chain comprising:
      (i) a light chain CDR1 comprising the amino acid sequence of SEQ ID NO: 14 or SEQ ID NO:15,
      (ii) a light chain CDR2 comprising the amino acid sequence of SEQ ID NO:16, and
      (iii) a light chain CDR3 comprising the amino acid sequence of SEQ ID NO:17.

2. The monoclonal antibody, or antigen-binding fragment thereof, of claim 1,
   wherein the monoclonal antibody, or antigen-binding fragment thereof comprises:
   (a) a heavy chain comprising:
      (i) heavy chain complementarity-determining regions comprising the amino acid sequences of SEQ ID NO:5, SEQ ID NO:7 and SEQ ID NO:9,
      (ii) heavy chain complementarity-determining regions comprising the amino acid sequences of SEQ ID NO:6, SEQ ID NO: 7 and SEQ ID NO:9, or
      (iii) heavy chain complementarity-determining regions comprising the amino acid sequences of SEQ ID NO:6, SEQ ID NO:8 and SEQ ID NO:9, and
   (b) a light chain comprising:
      (i) a light chain complementarity-determining region-1 (CDR1) comprising the amino acid sequence of SEQ ID NO: 14 or SEQ ID NO: 15,
      (ii) a light chain complementarity-determining region-2 (CDR2) comprising the amino acid sequence of SEQ ID NO: 16, and
      (iii) a light chain complementarity-determining region-3 (CDR3) comprising the amino acid sequence of SEQ ID NO: 17.

3. The monoclonal antibody, or antigen-binding fragment thereof, of claim 2, wherein
   (a) the variable region of its heavy chain is coded by a nucleotide sequence having at least 80% identity with any of the sequences as set forth in SEQ ID NO: 18-22 or SEQ ID NO: 92-96, provided that the antibody keeps its binding specificity, and
   (b) the variable region of its light chain is coded by a nucleotide sequence having at least 80% identity with any of the sequences as set forth in SEQ ID NO: 23-26 or SEQ ID NO: 97-99, provided that the antibody keeps its binding specificity.

4. The monoclonal antibody, or antigen-binding fragment thereof, of claim 2, wherein the monoclonal antibody, or antigen-binding fragment thereof, comprises:
   (a) a heavy chain variable region comprising an amino acid sequence as set forth in any one of SEQ ID NO:1, SEQ ID NO:2, SEQ ID NO:3, SEQ ID NO:4, 1-4 or as set forth in any one of SEQ ID NO:84, SEQ ID NO:85, SEQ ID NO:86, SEQ ID NO:87, SEQ ID NO:88, or a sequence having at least 85% identity with any of said sequences, and
   (b) a light chain variable region comprising an amino acid sequence of any one of SEQ ID NO:10, SEQ ID NO:12 and SEQ ID NO:13, or SEQ ID NO:89, SEQ ID NO:90 and SEQ ID NO:91, or a sequence having at least 85% identity with any of said sequences.

5. The monoclonal antibody, or antigen-binding fragment thereof, of claim 2, which is a humanized antibody comprising:
   (a) a heavy chain comprising:
      (i) a complementarity-determining region (CDR) heavy chain-1 (CDRH1) having a sequence as set forth in SEQ ID NO: 6,
      (ii) a complementarity-determining region (CDR) heavy chain-2 (CDRH2) having a sequence as set forth in SEQ ID NO: 7, and
      (iii) a complementarity-determining region (CDR) heavy chain-3 (CDRH3) having a sequence as set forth in SEQ ID NO: 9, and
   (b) a light chain comprising:
      (i) a complementarity-determining region (CDR) light chain-1 (CDRL1) having a sequence as set forth in SEQ ID NO: 14,
      (ii) a complementarity-determining region (CDR) light chain-2 (CDRL2) having a sequence as set forth in SEQ ID NO: 16, and
      (iii) a complementarity-determining region (CDR) light chain-3 (CDRL3) having a sequence as set forth in SEQ ID NO: 17.

6. The monoclonal antibody, or antigen-binding fragment thereof, of claim 2, which is a humanized antibody comprising:
   (a) a heavy chain comprising:
      (i) a CDRH 1 as set forth in SEQ ID NO: 6,
      (ii) a CDRH2 as set forth in SEQ ID NO: 7 and
      (iii) a CDRH3 as set forth in SEQ ID NO: 9, and
   (b) a light chain comprising:
      (i) a CDRL1 as set forth in SEQ ID NO: 15,
      (ii) a CDRL2 as set forth in SEQ ID NO: 16, and
      (iii) a CDRL3 as set forth in SEQ ID NO: 17.

7. The monoclonal antibody, or antigen-binding fragment thereof, of claim 2, which is a humanized antibody comprising:
(a) a heavy chain comprising:
  (i) a CDRH 1 as set forth in in SEQ ID NO:6,
  (ii) a CDRH2 as set forth in SEQ ID NO:8, and
  (iii) a CDRH3 as set forth in SEQ ID NO:9, and
(b) a light chain comprising:
  (i) a CDRL1 as set forth in SEQ ID NO:14,
  (ii) a CDRL2 as set forth in SEQ ID NO:16, and
  (iii) a CDRL3 as set forth in SEQ ID NO:17.

8. The monoclonal antibody, or antigen-binding fragment thereof, of claim 2, which is a humanized antibody comprising:
(a) a heavy chain comprising a CDRH 1 as set forth in SEQ ID NO: 6, a CDRH2 as set forth in SEQ ID NO: 8 and a CDRH3 as set forth in SEQ ID NO: 9, and
(b) a light chain comprising a CDRL1 as set forth in SEQ ID NO: 15, a CDRL2 as set forth in SEQ ID NO: 16 and a CDRL3 as set forth in SEQ ID NO: 17.

9. The monoclonal antibody, or antigen-binding fragment thereof, of claim 2, which is a rat or a chimeric monoclonal antibody comprising:
(a) a heavy chain comprising a CDRH 1 as set forth in SEQ ID NO: 5, a CDRH2 as set forth in SEQ ID NO: 7 and a CDRH3 as set forth in SEQ ID NO: 9, and
(b) a light chain comprising a CDRL1 as set forth in SEQ ID NO: 14, a CDRL2 as set forth in SEQ ID NO: 16 and a CDRL3 as set forth in SEQ ID NO: 17.

10. A pharmaceutical composition comprising a monoclonal antibody, or antigen-binding fragment thereof, of claim 1, and at least one pharmaceutically acceptable vehicle or excipient.

11. The pharmaceutical composition of claim 10, wherein the pharmaceutical composition further comprises an anticancer agent.

12. An antibody-drug conjugate (ADC) comprising a monoclonal antibody, or antigen-binding fragment thereof, of claim 1, and a drug attached to the monoclonal antibody or antigen-binding fragment thereof.

13. The antibody-drug conjugate (ADC) according to claim 12, wherein:
(a) the drug comprises a toxin selected from the group consisting of: auristatins, maytansinoids, calicheamycins, tubulysins, duocarmycins, camptothecin analogs, benzodiazepines, doxorubicins, a-amanitin derivatives, anthracyclins, rhizoxins, thailanstatins, spliceostatins, cryptophycins and histone deacetylase inhibitors; or
(b) said conjugate has the following formula (I)

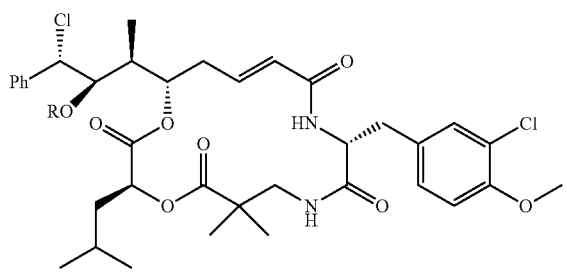

wherein R is —CO—CH2-X-(A)n-B wherein X is selected from the group consisting of NRa, wherein Ra is selected from a group consisting of H and C1-C10 alkyl, and O; A, which can be present or absent, is a self-immolative linker, n is 0 or 1; B is the monoclonal antibody of claim 1; or
(c) the antibody-drug conjugate (ADC) further comprises a pharmaceutically acceptable salt thereof.

* * * * *